United States Patent
Zhi

(10) Patent No.: US 10,730,831 B2
(45) Date of Patent: *Aug. 4, 2020

(54) SELECTIVE ANDROGEN RECEPTOR MODULATORS (SARMS) AND USES THEREOF

(71) Applicant: Ligand Pharmaceuticals Incorporated, San Diego, CA (US)

(72) Inventor: Lin Zhi, San Diego, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/148,798

(22) Filed: Oct. 1, 2018

(65) Prior Publication Data

US 2019/0040006 A1 Feb. 7, 2019

Related U.S. Application Data

(60) Continuation of application No. 15/590,884, filed on May 9, 2017, now Pat. No. 10,106,500, which is a continuation of application No. 14/827,228, filed on Aug. 14, 2015, now Pat. No. 9,675,583, which is a division of application No. 14/263,237, filed on Apr. 28, 2014, now Pat. No. 9,139,520, which is a division of application No. 13/694,063, filed on Oct. 23, 2012, now Pat. No. 8,748,633, which is a division of application No. 12/734,993, filed as application No. PCT/US2008/013657 on Dec. 12, 2008, now Pat. No. 8,354,446.

(60) Provisional application No. 61/008,731, filed on Dec. 21, 2007.

(51) Int. Cl.

| *C07D 207/08* | (2006.01) |
|---|---|
| *C07D 207/09* | (2006.01) |
| *C07D 498/04* | (2006.01) |
| *A61K 31/402* | (2006.01) |
| *A61K 31/5383* | (2006.01) |
| *A61K 45/06* | (2006.01) |
| *C07D 207/16* | (2006.01) |
| *A61K 31/401* | (2006.01) |

(52) U.S. Cl.
CPC .......... *C07D 207/09* (2013.01); *A61K 31/401* (2013.01); *A61K 31/402* (2013.01); *A61K 31/5383* (2013.01); *A61K 45/06* (2013.01); *C07D 207/08* (2013.01); *C07D 207/16* (2013.01); *C07D 498/04* (2013.01); *Y02A 50/401* (2018.01)

(58) Field of Classification Search
CPC .................................................. C07D 207/08
See application file for complete search history.

(56) References Cited

U.S. PATENT DOCUMENTS

| 3,710,795 A | 1/1973 | Higuchi et al. |
|---|---|---|
| RE28,819 E | 5/1976 | Thompson |
| 4,044,126 A | 8/1977 | Cook et al. |
| 4,231,938 A | 11/1980 | Monaghan et al. |
| 4,294,926 A | 10/1981 | Monaghan et al. |
| 4,319,039 A | 3/1982 | Albers-Schonberg |
| 4,328,245 A | 5/1982 | Yu et al. |
| 4,346,227 A | 8/1982 | Terahara et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,410,629 A | 10/1983 | Terahara et al. |
| 4,414,209 A | 11/1983 | Cook et al. |
| 4,444,784 A | 4/1984 | Hoffman et al. |
| 4,522,811 A | 6/1985 | Eppstein et al. |
| 4,537,859 A | 8/1985 | Terahara et al. |
| 4,681,893 A | 7/1987 | Roth |
| 4,729,999 A | 3/1988 | Young |
| 4,761,406 A | 8/1988 | Flora et al. |
| 4,782,084 A | 11/1988 | Vyas et al. |
| 4,820,850 A | 4/1989 | Verhoeven et al. |

(Continued)

FOREIGN PATENT DOCUMENTS

| CL | 3237-2005 | 4/2006 |
|---|---|---|
| CL | 1709-2007 | 11/2007 |

(Continued)

OTHER PUBLICATIONS

Adams et al., "Time course of myosin heavy chain transitions in neonatal rats: importance of innervation and thyroid state," Am. J. Physiol. 276(4 Pt 2): R954-961 (1999).

Adesanya et al., "Sex steroid induced changes on the morphology of prostate of sprague-dawley rats," Sci. Res. Essays 2(8):309-314 (2007).

(Continued)

*Primary Examiner* — Brian E McDowell
(74) *Attorney, Agent, or Firm* — Knobbe Martens Olson & Bear LLP

(57) ABSTRACT

Provided herein are compounds, such as compounds of Formula I, that bind to androgen receptors and/or modulate activity of androgen receptors. Also provided are methods for making and using such compounds. Also provided are compositions including such compounds and methods for making and using such compositions.

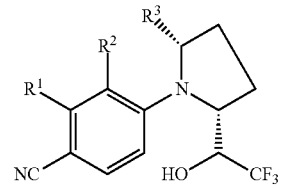

13 Claims, No Drawings

(56) References Cited

U.S. PATENT DOCUMENTS

| | | |
|---|---|---|
| 4,876,248 A | 10/1989 | Breliere et al. |
| 4,885,314 A | 12/1989 | Vyas et al. |
| 4,894,373 A | 1/1990 | Young |
| 4,911,165 A | 3/1990 | Lennard et al. |
| 4,916,239 A | 4/1990 | Treiber |
| 4,927,814 A | 5/1990 | Gall et al. |
| 4,929,437 A | 5/1990 | Tobert |
| 4,970,335 A | 11/1990 | Isomura et al. |
| 4,981,784 A | 1/1991 | Evans et al. |
| 5,030,447 A | 7/1991 | Joshi et al. |
| 5,033,252 A | 7/1991 | Carter |
| 5,052,558 A | 10/1991 | Carter |
| 5,071,773 A | 12/1991 | Evans et al. |
| 5,118,853 A | 6/1992 | Lee et al. |
| 5,177,080 A | 1/1993 | Angerbauer et al. |
| 5,180,589 A | 1/1993 | Joshi et al. |
| 5,189,164 A | 2/1993 | Kapa et al. |
| 5,204,350 A | 4/1993 | Egbertson et al. |
| 5,217,994 A | 6/1993 | Egbertson et al. |
| 5,273,995 A | 12/1993 | Roth |
| 5,290,946 A | 3/1994 | Lee et al. |
| 5,323,907 A | 6/1994 | Kalvelage |
| 5,342,952 A | 8/1994 | Butler et al. |
| 5,354,772 A | 10/1994 | Kathawala |
| 5,356,896 A | 10/1994 | Kabadi et al. |
| 5,393,763 A | 2/1995 | Black et al. |
| 5,489,691 A | 2/1996 | Butler et al. |
| 5,501,969 A | 3/1996 | Hastings et al. |
| 5,510,517 A | 4/1996 | Dauer et al. |
| 5,576,324 A | 11/1996 | Kyotani et al. |
| 5,639,754 A | 6/1997 | Heeres et al. |
| 5,648,491 A | 7/1997 | Dauer et al. |
| 5,696,130 A | 12/1997 | Jones et al. |
| 5,710,159 A | 1/1998 | Voss et al. |
| 5,723,480 A | 3/1998 | Gante et al. |
| 5,736,357 A | 4/1998 | Bromme et al. |
| 5,741,796 A | 4/1998 | Hartman et al. |
| 5,760,028 A | 6/1998 | Jadhav et al. |
| 5,773,644 A | 6/1998 | Chen et al. |
| 5,773,646 A | 6/1998 | Chandrakumar et al. |
| 5,780,426 A | 7/1998 | Palladino et al. |
| 5,843,906 A | 12/1998 | Chandrakumar et al. |
| 5,852,210 A | 12/1998 | Chen et al. |
| 5,919,792 A | 7/1999 | Duggan et al. |
| 5,925,655 A | 7/1999 | Duggan et al. |
| 5,929,120 A | 7/1999 | Hartman et al. |
| 5,952,281 A | 9/1999 | Mondin et al. |
| 5,952,341 A | 9/1999 | Duggan et al. |
| 5,981,546 A | 11/1999 | Duggan et al. |
| 6,008,213 A | 12/1999 | Bondinell et al. |
| 6,017,924 A | 1/2000 | Edwards et al. |
| 6,017,925 A | 1/2000 | Duggan |
| 6,017,926 A | 1/2000 | Askew et al. |
| 6,028,223 A | 2/2000 | Ruminski et al. |
| 6,040,311 A | 3/2000 | Duggan et al. |
| 6,048,861 A | 4/2000 | Askew et al. |
| 6,066,648 A | 5/2000 | Duggan et al. |
| 6,069,158 A | 5/2000 | Miller et al. |
| 6,159,964 A | 12/2000 | Ali et al. |
| 6,444,642 B1 | 9/2002 | Sklar et al. |
| 6,489,333 B2 | 12/2002 | Pitts et al. |
| 6,492,554 B2 | 12/2002 | Dalton et al. |
| 6,566,372 B1 | 5/2003 | Zhi et al. |
| 6,569,896 B2 | 5/2003 | Dalton et al. |
| 6,596,298 B2 | 7/2003 | Leung et al. |
| 6,622,729 B1 | 9/2003 | Peyman |
| 6,630,128 B1 | 10/2003 | Love et al. |
| 6,710,066 B2 | 3/2004 | Kennedy et al. |
| 6,723,750 B2 | 4/2004 | Voet |
| 6,784,190 B2 | 8/2004 | Askew et al. |
| 6,806,284 B1 | 10/2004 | Moser |
| 6,838,484 B2 | 1/2005 | Steiner et al. |
| 6,899,888 B2 | 5/2005 | Steiner et al. |
| 6,960,474 B2 | 11/2005 | Salvati et al. |
| 6,964,973 B2 | 11/2005 | Zhi et al. |
| 6,995,284 B2 | 2/2006 | Dalton et al. |
| 6,998,500 B2 | 2/2006 | Dalton et al. |
| 7,011,812 B1 | 3/2006 | Griffiths |
| 7,012,075 B2 | 3/2006 | Prasit et al. |
| 7,018,395 B2 | 3/2006 | Chen |
| 7,018,993 B2 | 3/2006 | Ohta |
| 7,022,870 B2 | 4/2006 | Dalton et al. |
| 7,026,484 B2 | 4/2006 | Zhi et al. |
| 7,026,500 B2 | 4/2006 | Dalton et al. |
| 7,037,888 B1 | 5/2006 | Sklar et al. |
| 7,053,263 B2 | 5/2006 | Sawyers et al. |
| 7,056,909 B2 | 6/2006 | Wang |
| 7,067,116 B1 | 6/2006 | Bess et al. |
| 7,074,930 B2 | 7/2006 | Wells et al. |
| 7,112,589 B2 | 9/2006 | Altmann et al. |
| 7,138,426 B2 | 11/2006 | DiNinno et al. |
| 7,151,196 B2 | 12/2006 | Wilkening et al. |
| 7,153,862 B2 | 12/2006 | Askew et al. |
| 7,157,604 B2 | 1/2007 | Meng et al. |
| 7,182,964 B2 | 2/2007 | Kupper et al. |
| 7,186,838 B2 | 3/2007 | Meissner et al. |
| 7,196,076 B2 | 3/2007 | Coleman et al. |
| 7,205,437 B2 | 4/2007 | Dalton et al. |
| 7,214,690 B2 | 5/2007 | Higuchi et al. |
| 7,214,693 B2 | 5/2007 | Dalton et al. |
| 7,214,804 B2 | 5/2007 | Zhai et al. |
| 7,217,720 B2 | 5/2007 | Meissner et al. |
| 7,241,411 B2 | 7/2007 | Berry et al. |
| 7,241,753 B2 | 7/2007 | Loria |
| 7,253,210 B2 | 8/2007 | Dalton et al. |
| 7,268,153 B2 | 9/2007 | Hanney et al. |
| 7,268,232 B2 | 9/2007 | Schlienger et al. |
| 7,279,472 B2 | 10/2007 | Emmanuel et al. |
| 7,279,478 B2 | 10/2007 | Boyd et al. |
| 7,288,553 B2 | 10/2007 | Lanter et al. |
| 7,291,673 B2 | 11/2007 | Hubbell et al. |
| 7,301,026 B2 | 11/2007 | Tan et al. |
| 7,696,246 B2 | 4/2010 | Zhi et al. |
| 7,727,980 B2 | 6/2010 | Zhi et al. |
| 8,354,446 B2 | 1/2013 | Zhi |
| 8,748,633 B2 | 6/2014 | Zhi |
| 8,865,918 B2 | 10/2014 | Zhi et al. |
| 2002/0022621 A1 | 2/2002 | Chaturvedula et al. |
| 2002/0025955 A1 | 2/2002 | Han et al. |
| 2002/0183314 A1 | 12/2002 | Higuchi et al. |
| 2002/0183346 A1 | 12/2002 | Zhi et al. |
| 2003/0114496 A1 | 6/2003 | Churcher et al. |
| 2003/0130505 A1 | 7/2003 | Zhi et al. |
| 2003/0149268 A1 | 8/2003 | Hamann et al. |
| 2003/0186970 A1 | 10/2003 | Higuchi et al. |
| 2005/0288350 A1 | 12/2005 | Zhi et al. |
| 2006/0111441 A1 | 5/2006 | Dalton et al. |
| 2007/0066650 A1 | 3/2007 | Zhi et al. |
| 2007/0254875 A1 | 11/2007 | Zhi et al. |
| 2007/0293528 A9 | 12/2007 | Zhi et al. |
| 2008/0300241 A9 | 12/2008 | Higuchi et al. |
| 2009/0203725 A1 | 8/2009 | Van Oeveren et al. |
| 2009/0227571 A1 | 9/2009 | Loren et al. |
| 2009/0264455 A9 | 10/2009 | Pedram et al. |
| 2010/0069379 A1 | 3/2010 | Zhi et al. |
| 2010/0152236 A1 | 6/2010 | Yamamoto et al. |
| 2010/0210678 A1 | 8/2010 | Zhi et al. |
| 2010/0256129 A1 | 10/2010 | Zhi |
| 2013/0184206 A1 | 6/2013 | Zhi |
| 2014/0005186 A1 | 1/2014 | Zhi et al. |
| 2014/0350065 A1 | 11/2014 | Zhi |
| 2015/0099720 A1 | 4/2015 | Zhi et al. |

FOREIGN PATENT DOCUMENTS

| | | |
|---|---|---|
| EP | 2222636 B1 | 9/2010 |
| EP | 2489656 A1 | 8/2012 |
| JP | 2002-88073 | 3/2002 |
| JP | A-2004-524317 | 8/2004 |
| JP | A-2005-529883 | 10/2005 |
| WO | WO 98/28268 | 7/1998 |
| WO | WO 99/67221 | 12/1998 |
| WO | WO 00/07995 | 2/2000 |
| WO | WO 00/38618 | 7/2000 |

(56) References Cited

FOREIGN PATENT DOCUMENTS

| | | |
|---|---|---|
| WO | WO 00/44777 | 8/2000 |
| WO | WO 00/50391 | 8/2000 |
| WO | WO 00/61186 | 10/2000 |
| WO | WO 01/16108 | 3/2001 |
| WO | WO 01/19797 | 3/2001 |
| WO | WO 01/27091 | 4/2001 |
| WO | WO 01/27108 | 4/2001 |
| WO | WO 01/34571 | 5/2001 |
| WO | WO 01/34639 | 5/2001 |
| WO | WO 01/49288 | 7/2001 |
| WO | WO 01/53255 | 7/2001 |
| WO | WO 01/60826 | 8/2001 |
| WO | WO 01/66564 | 9/2001 |
| WO | WO 01/70677 | 9/2001 |
| WO | WO 01/74783 | 10/2001 |
| WO | WO 01/74784 | 10/2001 |
| WO | WO 01/74796 | 10/2001 |
| WO | WO 01/77073 | 10/2001 |
| WO | WO 01/77086 | 10/2001 |
| WO | WO 01/77144 | 10/2001 |
| WO | WO 01/90084 | 11/2001 |
| WO | WO 01/92235 | 12/2001 |
| WO | WO 02/36555 | 3/2002 |
| WO | WO 02/30912 | 4/2002 |
| WO | WO 02/47671 | 6/2002 |
| WO | WO 02/057252 | 7/2002 |
| WO | WO 02/066475 | 8/2002 |
| WO | WO 02/068427 | 9/2002 |
| WO | WO 02/081433 | 10/2002 |
| WO | WO 02/081435 | 10/2002 |
| WO | WO 03/018543 | 3/2003 |
| WO | WO 03/049675 | 6/2003 |
| WO | WO 03/090672 | 11/2003 |
| WO | WO 2005/000795 | 1/2005 |
| WO | WO 2005/090282 | 9/2005 |
| WO | WO 2005/108351 | 11/2005 |
| WO | WO 2006/064944 | 6/2006 |
| WO | WO 2006/124447 | 11/2006 |
| WO | WO 2006/138347 | 12/2006 |
| WO | WO 2007/015567 | 2/2007 |
| WO | WO 2007/075884 | 7/2007 |
| WO | WO 2007/145349 | 12/2007 |
| WO | WO 2009/082437 | 7/2009 |

OTHER PUBLICATIONS

Allan et al. "A selective androgen receptor modulator with minimal prostate hypertrophic activity enhances lean body mass in male rats and stimulates sexual behavior in female rats," Endocrine 32(1):41-51 (2007).
Allegretto et al., "Transactivation properties of retinoic acid and retinoid X receptors in mammalian cells and yeast. Correlation with hormone binding and effects of metabolism," J. Biol. Chem. 268(35):26625-26633 (1993).
American Society for Reproductive Medicine, "Sexual Dysfunction—Patients Fact Sheet," 1 page (1998).
Ames et al., "Methods for detecting carcinogens and mutagens with the Salmonella/mammalian-microsome mutagenicity test," Mutation Res. 31(6):347-364 (1975).
Anderson et al., "Androgen supplementation in eugonadal men with osteoporosis-effects of 6 months of treatment on bone mineral density and cardiovascular risk factors," Bone 18(2):171-177 (1996).
Ansel, "Introduction to Pharmaceutical Dosage Forms," Fourth Edition, Lea and Febiger, Philadelphia, PA, p. 126 (1985).
Antonio et al., "Effects of castration and androgen treatment on androgen-receptor levels in rat skeletal muscles," J. Appl. Physiol. 87(6):2016-2019 (1999).
Arlt, "Dehydroepiandrosterone replacement in women with adrenal insufficiency," N. Engl. J. Med. 341(14):1013-1020 (1999).
Arlt, W., "Androgen therapy in women," Eur. J. Endocrinol. 154(1):1-11 (2006).
Arriza et al., "Cloning of human mineralocorticoid receptor complementary DNA: structural and functional kinship with the glucocorticoid receptor," Science 237(4812):268-275 (1987).
Ashby et al., "The peripubertal male rat assay as an alternative to the Hershberger castrated male rat assay for the detection of anti-androgens, oestrogens and metabolic modulators," J. Appl. Tox. 20(1):35-47 (2000).
Bandeen-Roche et al., "Phenotype of frailty: characterization in the women's health and aging studies," J. Gerontol. A: Biol. 61A(3):262-266 (2006).
Beers et al., Eds., "Chapter 52: Osteoarthritis and neurogenic arthropathy," in Merck Manual, 17th Edition, pp. 449-452 (1999).
Behre et al., "Long-term effect of testosterone therapy on bone mineral density in hypogonadal men," J. Clin. Endocrinol. Metabol. 82(8):2386-2390 (1997).
Bellido et al., "Regulation of interleukin-6, osteoclastogenesis, and bone mass by androgens. The role of the androgen receptor," J. Clin. Invest. 95(6):2886-2895 (1995).
Ben-Av et al., "Induction of vascular endothelial growth factor expression in synovial fibroblasts by prostaglandin E and interleukin-1: a potential mechanism for inflammatory angiogenesis," FEBS Lett. 372(1):83-87 (1995).
BenEzra et al., "In vivo angiogenic activity of interleukins," Arch. Ophthalmol. 108:573-576 (1990).
Bentel et al., "Androgen receptor expression in primary prostate cancers of Lobund-Wistar rats and in tumor-derived cell lines," In Vitro Cell Dev. Biol. 35(10):655-662 (1999).
Beresford et al., "Formation of mineralized nodules by bone derived cells in vitro: a model of bone formation?" 45(2):163-178 (2005).
Berge et al., "Pharmaceutical salts," J. Pharm. Sci. 66(1):1-19 (1977).
Berger et al., "Interaction of glucocorticoid analogues with the human glucocorticoid receptor," J. Steroid Biochem. Mol. Biol. 41(3-8):733-738 (1992).
Bhasin et al., "Testosterone replacement increases fat-free mass and muscle size in hypogonadal men," J. Clin. Endocrinol. Metabol. 82(2):407-413 (1997).
Bhasin et al., "Drug Insight: testosterone and selective androgen receptor modulators as anabolic therapies for chronic illness and aging," Nat. Clin. Pract. Endocrin. Metabol. 2(3):146-159 (2006).
Bhasin et al., "Proof of the effect of testosterone on skeletal muscle," J. Endocrinol. 170(1):27-38 (2001).
Bhasin et al., "The effects of supraphysiologic doses of testosterone on muscle size and strength in normal men," N. Engl. J. Med. 335(1):1-7 (1996).
Bijlsma et al., "Estrogens and rheumatoid arthritis," Am. J. Reprod. Immunol. 28(3-4):231-234 (1992).
Bissonnette et al., "9-cis Retinoic acid inhibition of activation-induced apoptosis is mediated via regulation of Fas ligand and requires retinoic acid receptor and retinoid X receptor activation," Mol. Cell Biol. 15(10):5576-5585 (1995).
Boehm et al., "Synthesis and structure-activity relationships of novel retinoid X receptor-selective retinoids," J. Med. Chem. 37(18):2930-2941 (1994).
Boudou et al., "Effect of oral isotretinoin treatment on skin androgen receptor levels in male acneic patients," J. Clin. Endocrinol. Metabol. 80(4):1158-1161 (1995).
Bouma et al., "Thrombin-activatable fibrinolysis inhibitor (TAFI, plasma procarboxypeptidase B, procarboxypeptidase R, procarboxypeptidase U)," Thromb. Res. 101(5):329-354 (2001).
Box et al., "Correcting inhomogeneity of variance with power transformation weighting," Technometrics 16:385-389 (1974).
Box, G. and D. Cox, "An analysis of transformations," J. Roy. Stat. Soc. B 26:211-252 (1964).
Brady et al., "Depot testosterone with etonogestrel implants result in induction of azoospermia in all men for long-term contraception," Hum. Reprod. 19(11):2658-2667 (2004).
Broulik, P. and L. Starka, "Effect of antiandrogens casodex and epitestosterone on bone composition in mice," Bone 20(5):473-475 (1997).
Brower, V., "Tumor angiogenesis: new drugs on the block," Nature Biotechnol. 17(10):963-968 (1999).
Brown, T., "Nonsteroidal selective androgen receptor modulators (SARMs): designer androgens with flexible structures provide clinical promise," Endocrinol. 145(12):5417-5419 (2004).

(56) References Cited

OTHER PUBLICATIONS

Buhler et al., "Intermittent androgen suppression in the LuCaP 23.12 prostate cancer xenograft model," The Prostate 43(1):63-70 (2000).
Buijsman et al., "Non-steroidal steroid receptor modulators," Curr. Med. Chem. 12(9):1017-1075 (2005).
Bundgaard et al., "A novel solution-stable, water-soluble prodrug type for drugs containing a hydroxyl or an NH-acidic group," J. Med. Chem. 32(12):2503-2507 (1989).
Cadilla et al., "Selective androgen receptor modulators in drug discovery: medicinal chemistry and therapeutic potential," Curr. Top. Med. Chem. 6(3):245-270 (2006).
Carmina. "Ovarian and andrenal hyperandrogenism" Ann NY Acad Sci (2006) 1092:130-137.
Carnahan, R. and P. Perry, "Depression in aging men: the role of testosterone," Drugs Aging 21(6): 361-376 (2004).
Cesario et al., "The rexinoid LG100754 is a novel RXR:P-PARgamma agonist and decreases glucose levels in vivo," Mol. Endocrinol. 15(8):1360-1369 (2001).
Chakraborty et al., "Developmental expression of the cyclo-oxygenase-1 and cyclo-oxegenase-2 genes in the peri-implantation mouse uterus and their differential regulation by the blastocyst and ovarian steroids," J. Mol. Endocrinol. 16:107-122 (1996).
Chan, S., "A review of selective estrogen receptor modulators in the treatment of breast and endometrial cancer," Semin Oncol. 29(3 Suppl 11):129-133 (2002).
Chen et al., "A selective androgen receptor modulator (SARM) for hormonal male contraception," JPET Fast Forward, JPET #75424, 46 pages (2004).
Chen et al., "A selective androgen receptor modulator for hormonal male contraception," J. Pharmacol. Exp. Ther. 312(2):546-553 (2005).
Chen et al., "Androgen-dependent and -independent human prostate xenograft tumors as models for drug activity evaluation," Cancer Res. 58(13):2777-2783 (1998).
Chen et al., "Discovery and therapeutic promise of selective androgen receptor modulators," Mol. Interv. 5(3):173-188 (2005).
Chen et al., "Testosterone inhibits osteoclast formation stimulated by parathyroid hormone through androgen receptor," FEBS Lett. 491(1-2):91-93 (2001).
Cheng, Y. and W. Prusoff, "Relationship between the inhibition constant (K1) and the concentration of inhibitor which causes 50 per cent inhibition (I50) of an enzymatic reaction," Biochem. Pharmacol. 22(23):3099-3108 (1973).
Chiarugi et al., "Cox-2, iNOS and p53 as play-makers of tumor angiogenesis (review)," Int. J. Mol. Med. 2(6):715-719 (1998).
Chung, L., "LNCaP human prostate cancer progression model," Urol. Oncol. 2(4): 126-128 (1996).
Corbould, A., "Chronic testosterone treatment induces selective insulin resistance in subcutaneous adipocytes of women," J. Endocrinol. 192(3):585-594 (2007).
Coxam et al., "Effects of dihydrotestosterone alone and combined with estrogen on bone mineral density, bone growth, and formation rates in ovariectomized rats," Bone 19(2):107-114 (1996).
Craft et al., "Evidence for clonal outgrowth of androgen-independent prostate cancer cells from androgen-dependent tumors through a two-step process," Cancer Res. 59(19):5030-5036 (1999).
Cutolo et al., "Androgens and estrogens modulate the immune and inflammatory responses in rheumatoid arthritis," Ann. N.Y. Acad. Sci. 966:131-142 (2002).
Cutolo, M., "Sex hormone adjuvant therapy in rheumatoid arthritis," Rheum. Dis. Clin. N. Am. 26(4):881-895 (2000).
Davis, S., "Androgen replacement in women: a commentary," Clin. Endocrinol. Metab. 84:1886-1891 (1999).
Deaton, D. and F. Tavares, "Design of cathepsin K inhibitors for osteoporosis," Curr. Top. Med. Chem. 5(16):1639-1675 (2005).
Dei et al., "Synthesis and cholinergic affinity of diastereomeric and enantiomeric isomers of 1-methyl-2(2-methyl-1,3-dioxolan-4-yl)-pyrrolidine, 1-methyl-2-(2-methyl-1,3-oxathiolan-5-yl)pyrrolidine and of their iodomethylates," Bioorg. Med. Chem. 11(14):3153-3164 (2003).
Deplewski et al., "Preputial sebocyte 5-reductase isoform specificity," Endocrinol. 138(10):4416-4420 (1997).
Devogelaer et al., "Low bone mass in hypogonadal males. Effect of testosterone substitution therapy, a densitometric study," Maturitas 15(1):17-23 (1992).
Eagleson et al., "Polycystic ovarian syndrome: evidence that flutamide restores sensitivity of the gonadotropin-releasing hormone pulse generator to inhibition by estradiol and progesterone," J. Clin. Endocrinol. Metab. 85(11): 4047-4052 (2000).
Edwards et al., "New nonsteroidal androgen receptor modulators based on 4-(trifluoromethyl)-2(1H)-pyrrolidino[3,2-g]quinolinone," Bioorg. Med. Chem. Lett. 8:745-750 (1998).
Eisenberg, E. and G. Gordan, "The levator ani muscle of the rat as an index of myotrophic activity of steroidal hormones," J. Pharmacol. Exp. Ther. 99(1):38-44 (1950).
Etreby et al., "Antitumor activity of mifepristone in the human LNCaP, LNCaP-C4, and LNCaP-C4-2 prostate cancer models in nude mice," The Prostate 42(2): 99-106 (2000).
Evans, "The steroid and thyroid hormone receptor superfamily," Science 240:889-95 (1988).
Evans et al., "Ostarine increases lean body mass and improves physical performance in healthy elderly subjects: Implications for cancer cachexia patients," J. Clin. Oncol., 2007 ASCO Annual Meeting Proceedings (Post-Meeting Edition) vol. 25, No. 18S (Jun. 20 Supplement), Abstract #9119 (2007).
Fernandez et al., "Neovascularization produced by angiotensin II," J. Lab. Clin. Med. 105(2):141-145 (1985).
Ferrando et al, "Testosterone administration to older men improves muscle function: molecular and physiological mechanisms," Am. J. Physiol. Endocrinol. Metabol. 282(3):E601-E607 (2002).
Fine, S., "Erectile dysfunction and comorbid diseases, androgen deficiency, and diminished libido in men," J. Am. Osteopath. Assoc. 104(1 Supplement 1):S9-S15 (2004).
Fingl et al., "The Pharmacological Basis of Therapeutics," Ch.1 pp. 1-46 (1975).
Finkelstein et al., "Increases in bone density during treatment of men with idiopathic hypogonadotropic hypogonadism," J. Clin. Endocrinol. Metab. 69(4):776-783 (1989).
Food and Drug Administration, "International conference on harmonization; guidance on specific aspects of regulatory genotoxicity tests for pharmaceuticals; availability; notice," Federal Register 61(80):18198-18202 (Apr. 24, 1996).
Food and Drug Administration, "International conference on harmonization; draft guideline on genotoxicity: a standard battery for genotoxicity testing of pharmaceuticals; notice," Federal Register 62(64):16026-16030 (Apr. 3, 1997).
Forman et al., "Identification of a nuclear receptor that is activated by farnesol metabolites," Cell 81(5):687-693 (1995).
Fujisaki et al., "Halogenation using N-halogenocompounds. I. Effect of amines on ortho bromination of phenols with NBS," Bull. Chem. Soc. Jpn. 66:1576-1579 (1993).
Fuller et al., "Androgens in the etiology of Alzheimer's disease in aging men and possible therapeutic interventions," J. Alzheimers Dis. 12(2):129-142 (2007).
Furr, "The development of Casodex (bicalutamide): preclinical studies," Eur. Urol. 29:83-95 (1996).
Furr, B. and H. Tucker, "The preclinical development of bicalutamide: pharmacodynamics and mechanism of action," Urology 47 (Suppl. 1A): 13-25 (1996).
Galloway et al., "Report from working group on in vitro tests for chromosomal aberrations," Mutat. Res. 312(3):241-261 (1994).
Gao et al., "Selective androgen receptor modulator treatment improves muscle strength and body composition and prevents bone loss in orchidectomized rats," Endocrinol. 146(11):4887-4897 (2005).
Gao et al., "Pharmacokinetics and pharmacodynamics of nonsteroidal androgen receptor ligands," Pharm. Res. 23(8):1641-1658 (2006).
Gao, W. and J. Dalton, "Expanding the therapeutic use of androgens via selective androgen receptor modulators (SARMs)," Drug Discov. Today 12(5-6):241-248 (2007).

(56) References Cited

OTHER PUBLICATIONS

Gerdes et al., "Transforming growth factor-beta1 induces nuclear to cytoplasmic distribution of androgen receptor and inhibits androgen response in prostate smooth muscle cells," Endocrinol. 139(8):3569-3577 (1998).
Ghosh et al., "A global model to define the behavior of partial agonists (bell-shaped dose-response inducers) in pharmacological evaluation of activity in the presence of the full agonist," J. Biopharm. Stat. 8(4):645-665 (1998).
Giguere et al., "Functional domains of the human glucocorticoid receptor," Cell 46:645-652 (1986).
Goldstein et al., "A pharmacological review of selective oestrogen receptor modulators," Hum. Reprod. Update 6(3):212-224 (2000).
Gonzalez-Cadavid et al., "Up-regulation of the levels of androgen receptor and its mRNA by androgens in smooth-muscle cells from rat penis," Mol. Cell. Endocrinol. 90(2):219-229 (1993).
Gooren et al., "Recent insights into androgen action on the anatomical and physiological substrate of penile erection," Asian J. Androl. 8(1):3-9 (2006).
Gouras et al., "Testosterone reduces neuronal secretion of Alzheimer's .beta.-amyloid peptides," Proc. Nat. Acad. Sci. U.S.A. 97(3):1202-1205 (2000).
Gowen et al., "Antagonizing the parathyroid calcium receptor stimulates parathyroid hormone secretion and bone formation in osteopenic rats," J. Clin. Invest. 105(11):1595-1604 (2000).
Green et al., "Mutagen testing using TRP+ reversion in *Escherichia coli*," Mutat. Res. 38(1):3-32 (1976).
Gregory et al., "Androgen Receptor Stabilization in Recurrent Prostate Cancer Is Associated with Hypersensitivity to Low Androgen" Cancer Research (2001) 61:2892-2898.
Hamann et al., "Synthesis and biological activity of a novel series of nonsteroidal, peripherally selective androgen receptor antagonists derived from 1,2-dihydropyridono[5,6-g]quinolines," J. Med. Chem. 41(4):623-639 (1998).
Hammond et al., "Testosterone-mediated neuroprotection through the androgen receptor in human primary neurons," J. Neurochem. 77(5):1319-1326 (2001).
Hannon, R. and R. Eastell, "Bone markers and current laboratory assays," Cancer Treat. Rev. 32(Suppl 1):7-14 (2006).
Harada et al., "Expression and regulation of vascular endothelial growth factor in osteoblasts," Clin. Orthop. Relat. Res. 313:76-80 (1995).
Harris et al., "Nilutamide. A review of its pharmacodynamic and pharmacokinetic properties, and therapeutic efficacy in prostate cancer," Drugs and Aging 3:9-25 (1993).
Harris, K. and E. Small, "Hormonal treatment for prostate cancer," Expert Opin. Investig. Drugs 10(3):493-510 (2001).
Hasselgren et al., "Muscle wasting: current progress and future aims," Intl. J. Biochem. Cell Biol. 37:1932 (2005).
Hershberger et al., "Myotrophic activity of 19-nortestosterone and other steroids determined by modified levator ani muscle method," Proc. Soc. Exptl. Biol. Med. 83:175-178 (1953).
Higuchi et al., "Potent, nonsteroidal selective androgen receptor modulators (SARMs) based on 8H-[1,4]oxazino[2,3-f]quinolin-8-ones," Bioorg. Med. Chem. Lett. 17:5442-5446 (2007).
Hla et al., "Human cyclooxygenase-2 cDNA," Proc. Natl. Acad. Sci. U.S.A. 89:7384-7388 (1992).
Hofbauer, L. and S. Khosla, "Androgen effects on bone metabolism: recent progress and controversies," Eur. J. Endocrinol. 140:271-286 (1999).
Hunter et al., "*Biochemical markers of bone turnover and their association with bone marrow lesions*," Arthritis Res. Ther. 10(4):R102, 8 pages (2008).
Ilio et al., "The primary culture of rat prostate basal cells," J. Androl. 19(6):718-724 (1998).
Ivaska et al., "Release of intact and fragmented osteocalcin molecules from bone matrix during bone resorption in vitro," J. Biol. Chem. 279(18):18361-18369 (2004).
Jackson et al., "Suppression of androgen receptor expression by dibenzoylmethane as a therapeutic objective in advanced prostate cancer," Anticancer Res. 27(36):1483-1488 (2007).
Jansson, L. and R. Holmdahl, "Enhancement of collagen-induced arthritis in female mice by estrogen receptor blockage," Arthritis Rheum. 44(9):2168-2175 (2001).
Jasuja et al., "Delta-4-androstene-3,17-dione binds androgen receptor, promotes myogenesis in vitro, and increases serum testosterone levels, fat-free mass, and muscle strength in hypogonadal men," J. Clin. Endocrinol. Metabol. 90(2):855-863 (2005).
Jasuja et al., "Tetrahydrogestrinone is an androgenic steroid that stimulates androgen receptor-mediated, myogenic differentiation in C3H10T1/2 multipotent mesenchymal cells and promotes muscle accretion in orchidectomized male rats," Endocrinology 146(10):4472-4478 (2005).
Jilka et al, "Increased osteoclast development after estrogen loss: mediation by interleukin-6," Science 257(5066):88-91 (1992).
Johnson, S., "Premenstrual syndrome therapy," Clin. Obstet. Gynecol. 41(2):405-421 (1998).
Jones, "The structure, reactions, synthesis and uses of heterocyclic compounds," Comprehensive Heterocyclic Chemistry, vol. 2, Ch. 2, p. 421-426 (1984).
Jongsma et al., "Androgen deprivation of the prohormone convertase-310 human prostate cancer model system induces neuroendocrine differentiation," Cancer Res. 60:741-748 (2000).
Jongsma et al., "Kinetics of neuroendocrine differentiation in an androgen-dependent human prostate xenograft model," Amer. J. Path. 154(2):543-551 (1999).
Jordan, V., "Selective estrogen receptor modulation: A personal perspective," Cancer Res. 61:5683-5687 (2001).
Joseph et al., "Role of endocrine-immune dysregulation in osteoporosis, sarcopenia, frailty and fracture risk," Mol. Aspects Med. 26(3):181-201 (2005).
Kang et al., "Mechanisms and Clinical Relevance of Androgens and Androgen Receptor Actions" Chang Gung Med J (2003) 26(6):388-402.
Kapil et al., "Phase I clinical trial of LGD-4033, a novel selective androgen receptor modulator (SARM)," 14th International Congress of Endocrinology, Kyoto, Japan, Mar. 26-30, 2010 [poster presentation].
Katznelson et al., "Increase in bone density and lean body mass during testosterone administration in men with acquired hypogonadism," J. Clin. Endocrinol. Metabol. 81(12):4358-4365 (1996).
Kazmin et al., "Linking ligand-induced alterations in androgen receptor structure to differential gene expression: a first step in the rational design of selective androgen receptor modulators," Mol Endocrinol. 20(6):1201-1217 (2006).
Keller et al., "Inhibition of NFkappaB activity through maintenance of IkappaBalpha levels contributes to dihydrotestosterone-mediated repression of the interleukin-6 promoter," J. Biol. Chem. 271(42):26267-26275 (1996).
Kilbourne et al., "Selective androgen receptor modulators for frailty and osteoporosis," Curr. Opin. Investig. Drugs 8(10):821-829 (2007).
Kim et al., "Inhibition of vascular endothelial growth factor-induced angiogenesis suppresses tumour growth in vivo," Nature 362(6423):841-844 (1993).
Kingsberg, S., "Testosterone treatment for hypoactive sexual desire disorder in postmenopausal women," J. Sex Med. 4 Suppl 3: 227-234 (2007).
Kliewer et al., "Retinoid X receptor interacts with nuclear receptors in retinoic acid, thyroid hormone and vitamin D3 signalling," Nature 355(6359):446-449 (1992).
Kolvenbag, G. and G. Blackledge, "Worldwide activity and safety of bicalutamide: a summary review," Urology 47 (Suppl. 1A):70-79 (1996).
Korte, W., "Changes of the coagulation and fibrinolysis system in malignancy: their possible impact on future diagnostic and therapeutic procedures," Clin. Chem. Lab Med. 38(8):679-692 (2000).
Koyama et al., "A one step sandwich enzyme immunoassay for gamma-carboxylated osteocalcin using monoclonal antibodies," J. Immunol. Methods 139(1):17-23 (1991).

(56) References Cited

OTHER PUBLICATIONS

Kurokouchi et al., "TNF-alpha increases expression of IL-6 and ICAM-1 genes through activation of NF-kappaB in osteoblast-like ROS17/2.8 cells," J. Bone Mineral Res. 13(8):1290-1299 (1998).
Laaksonen et al., "Sex hormones, inflammation and the metabolic syndrome: a population-based study," Euro. J. Endocrinol. 149(6):601-608 (2003).
Laaksonen et al., "Testosterone and sex hormone-binding globulin predict the metabolic syndrome and diabetes in middle-aged men," Diabetes Care 27(5):1036-1041 (2004).
Labrie et al., "Tetrahydrogestrinone induces a genomic signature typical of a potent anabolic steroid," J. Endocrinol. 184(2):427-433 (2005).
Lapointe et al., "Androgens down-regulate bcl-2 protooncogene expression in ZR-75-1 human breast cancer cells," Endocrinology 140(1): 416-421 (1999).
Lemus et al., "5alpha-reduction of norethisterone enhances its binding affinity for androgen receptors but diminishes its androgenic potency," J. Steroid Biochem. Mol. Biol. 60(1-2):121-129 (1997).
Lin et al., "Insulin and leptin resistance with hyperleptinemia in mice lacking androgen receptor," Diabetes 54(6): 1717-1725 (2005).
Long et al., "Selective androgen receptor modulators based on a series of 7H-[1,4]oxazino[3,2-g]quinolin-7-ones with improved in vivo activity," Bioorg. Med. Chem. Lett. 18(9):2967-2671 (2008).
Lovejoy et al., "Exogenous androgens influence body composition and regional body fat distribution in obese postmenopausal women—a clinical research center study," J. Clin. Endocrinol. Metabol. 81(6):2198-2203 (1996).
Lovejoy et al., "Oral anabolic steroid treatment, but not parenteral androgen treatment, decreases abdominal fat in obese, older men," Int. J. Obesity 19(9):614-624 (1995).
Lufkin et al., The role of selective estrogen receptor modulators in the prevention and treatment of osteoporosis, Rheum. Dis. Clin. N. Am. 27(1):163-185 (2001).
Ly et al., "Rates of suppression and recovery of human sperm output in testosterone-based hormonal contraceptive regimens," Hum. Reprod. 20(6):1733-1740 (2005).
Lynch et al., "Therapeutic approaches for muscle wasting disorders," Pharmacol. Therapeut. 113(3):461-487 (2007).
Lynch, G., "Emerging drugs for sarcopenia: age-related muscle wasting," Expert Opin. Emerg. Drugs 9(2):345-361 (2004).
Mahfouz et al., "Synthesis, chemical and enzymatic hydrolysis, and bioavailability evaluation in rabbits of metronidazole amino acid ester prodrugs with enhanced water solubility," J. Pharm. Pharmacol. 53(6):841-848 (2001).
Majumdar et al., "Studies on the amine oxide rearrangements: regioselective synthesis of pyrrolo[3,2-f]quinolin-7-ones," J. Chem. Res. S. 9:310-311 (1997).
Mangelsdorf et al., "A direct repeat in the cellular retinol-binding protein type II gene confers differential regulation by RXR and RAR," Cell 66:555-561 (1991).
Marhefka et al., "Design, synthesis, and biological characterization of metabolically stable selective androgen receptor modulators," J. Med. Chem. 47(4):993-998 (2004).
Marin et al., "Androgen treatment of abdominally obese men," Obesity Res. 1(4):245-251 (1993).
Maron et al., "Revised methods for the Salmonella mutagenicity test," Mutat. Res. 113(3-4):173-215 (1983).
Martinborough et al., "Substituted 6-(1-pyrrolidine)quinolin-2(1H)-ones as novel selective androgen receptor modulators," J. Med. Chem. 50(21):5049-5052 (2007).
Marynick et al., "Androgen Excess in Cystic Acne" N Engl J Med (1983) 308:981-986.
Maucher, A. and E. von Angerer, "Antiproliferative activity of Casodex (ICI 176.334) in hormone-dependent tumours," J. Cancer Res. Clin. Oncol. 119(11):669-674 (1993).
Max et al., "Cytosolic androgen receptor in regenerating rat levator ani muscle," Biochem. J. 200(1): 77-82 (1981).
McDonnell et al., "RU486 exerts antiestrogenic activities through a novel progesterone receptor A form-mediated mechanism," J. Biol. Chem. 269(16):11945-11949 (1994).
Miller, C., and B. Komm, "Section IV: Immunology, endriconology and metabolic diseases. Chapter 15: Targeting the Estrogen Receptor with SERMs," Ann. Rep. Med. Chem. 36:149-158 (2001).
Miller, K., "Androgen deficiency in women," Clin. Endocrinol. Metabol. 86:2395-2401 (2001).
Miner et al., "An orally active selective androgen receptor modulator is efficacious on bone, muscle, and sex function with reduced impact on prostate," Endocrinology 148(1):363-373 (2007).
Miyake et al., "Androgen receptor expression in the preputial gland and its sebocytes," J. Invest. Dermatol. 103(5):721-725 (1994).
Mooradian et al., "Biological action of androgens," Endocr. Rev. 8(1):1-28 (1987).
Morrissey et al., "Changes in hormone sensitivity in the ventral prostate of aging Sprague-Dawley rats," J. Androl. 23(3):341-351 (2002).
Navone et al., "Establishment of two human prostate cancer cell lines derived from a single bone metastasis," Clin. Cancer Res. 3:2493-2500 (1997).
Navone et al., "TabBO: A model reflecting common molecular features of androgen-independent prostate cancer," Clin. Cancer Res. 6:1190-1197 (2000).
Negro-Vilar, "Selective androgen receptor modulators (SARMs) a novel approach to androgentherapy for the new millennium," J. Clin. Endocrinol. Metabol. 84(10):3459-3462 (1999).
Neri et al., "Complete androgen blockade as treatment for advanced prostate cancer: clinical response and side-effects," Anticancer Res. 9(1):13-16 (1989).
Neri, R. and E. Peets, "Biological aspects of antiandrogens," J. Steroid Biochem. 6(6):815-819 (1975).
Neri, R., "Pharmacology and pharmacokinetics of flutamide," Urology 34(4 Suppl.):19-21 (1989).
Neri, R., "Pharmacology and pharmacokinetics of flutamide," Urology 34(4 Suppl.):46-56 (1989).
Ng et al., "Differential induction of the interleukin-6 gene by tumor necrosis factor and interleukin-1," J. Biol. Chem. 269(29):19021-19027 (1994).
Nickerson et al., "Effect of testosterone propionate on the ultrastructure of the preputial gland in the rat," Acta Anat. (Basel) 94:481-489 (1976).
Niikura et al., "A novel inhibitor of vacuolar ATPase, FR167356, which can discriminate between osteoclast vacuolar ATPase and lysosomal vacuolar ATPase," Br. J. Pharmacol. 142:558-566 (2004).
Niikura, K., "Vacuolar ATPase as a drug discovery target," Drug News Perspect. 19(3):139-144 (2006).
Nogrady, "Medicinal Chemistry: A Biochemical Approach," Oxford University Press, New York, NY, pp. 388-392 (1985).
Notelovitz, M., "Hot flashes and androgens: a biological rationale for clinical practice," 05/*/o Clin. Proc. 79(4 Suppl):S8-S13 (2004).
O'Reilly et al., "Regulation of expression of a baculovirus ecdysteroid UDP glucosyltransferase gene," in Baculovirus Expression Vectors, WH Freeman:NY, 139-179 (1992).
Okazaki et al., "Thiazolidinediones inhibit osteoclast-like cell formation and bone resorption in vitro," Endocrinology 140:5060-5065 (1999).
Omwancha, J. and T. Brown, "Selective androgen receptor modulators: in pursuit of tissue-selective androgens," Curr. Opin. Investig. Drugs 7(10):873-881 (2006).
Papasozomenos et al., "Testosterone prevents the heat shock-induced overactivation of glycogen synthase kinase-3.beta. but not of cyclin-dependent kinase 5 and c-Jun NH2-terminal kinase and concomitantly abolishes hyperphosphorylation of .GAMMA.: Implications for Alzheimer's disease," Proc. Nat. Acad. Sci. U.S.A. 99:1140-1145 (2002).
Pasquali, R., "Obesity and androgens: facts and perspectives," Fertil. Steril. 85(5):1319-1340 (2006).
Pasqualotto et al., "Trends in male contraception," Rev. Hosp. Clin. Fac. Med. Sao Paulo 58(5):275-283 (2003).
Pathirana et al., "Nonsteroidal human progesterone receptor modulators from the marine alga Cymopolia barbata," Mol. Pharmacol. 47(3):630-635 (1995).

(56) References Cited

OTHER PUBLICATIONS

Peehl, D., "Human prostatic epithelial and stromal cell lines and strains," Urol. Oncol. 2(4):100-102 (1996).
Peltier et al., "Technical note: application of the box-cox data transformation to animal science experiments," J. Anim. Sci. 76: 847-849 (1998).
Petrangolini et al., "Effect of a novel vacuolar-H+-ATPase inhibitor on cell and tumor response to camptothecins," J. Pharmacol. Exp. Ther. 318 (3):939-946 (2006).
Pfankuch et al., "Role of circulating androgen levels in effects of apoE4 on cognitive function," Brain Res. 1053(1-2): 88-96 (2005).
Pietschmann et al., "Bone structure and metabolism in a rodent model of male senile osteoporosis," Exp. Gerontol. 42(11): 1099-1108 (2007).
Prakash et al., "Synthetic methods and reactions. 141. Fluorine-induced trifluoromethylation of carbonyl compounds withtrifluoromethyltrimethylsilane (TMS-CF3). A trifluoromethide equivalent," J. Am. Chem. Soc. 111(1):393-395 (1989).
Preston et al., "Mammalian in vivo and in vitro cytogenetic assays: a report of the U.S. EPA's gene-tox program," Mutat. Res. 87(2):143-188 (1981).
Purdie, D., "Consequences of long-term hormone replacement therapy," Br. Med. Bull. 56(3):809-823 (2000).
Quimby et al., "Tetrasodium carbonyldiphosphonate. Synthesis, reactions, and spectral properties," J. Org. Chem. 32(12):4111-4114 (1967).
Raber et al., "Androgens protect against Apolipoprotein E-4 induced cognitive deficits," J. Neurosci. 22(12):5204-5209 (2002).
Reid et al., "Antiandrogens in prostate cancer," Investig. New Drugs 17:271-284 (1999).
Remington, "The Science and Practice of Pharmacy, 19th Ed.," Mack Publishing Co., Easton, Pa., pp. 1399-1404 (1995).
Ricciardelli et al., "Effects of oestradiol-17.beta. and 5-dihydrotestosterone on guinea-pig prostate smooth muscle cell proliferation and steroid receptor expression in vitro," J. Endocrinol. 140(3):373-383 (1994).
Rivera-Woll et al., "Androgen insufficiency in women: diagnostic and therapeutic implications," Hum. Reproduct. Update 10(5):421-432 (2004).
Roche, E. ed., "Bioreversible carriers in drug design: theory and application," Pergamon Press: New York, pp. 14-21 (1987).
Sadeghi-Nejad et al., "Preliminary report on the development and characterization of rabbit clitoral smooth muscle cell culture," Int. J. Impotence Res. 10(3):165-169 (1998).
Salm et al., "Transforming growth factor-beta is an autocrine mitogen for a novel androgen-responsive murine prostatic smooth muscle cell line, PSMC1," J. Cell. Physiol. 185(3):416-424 (2000).
Sastry et al., "Synthesis and antibacterial activity of 1,4-oxazinoquinolone carboxylic acids," Indian J. Chem. Section B 27:649-652 (1988).
Seed et al., "The inhibition of colon-26 adenocarcinoma development and angiogenesis by topical diclofenac in 2.5% hyaluronan," Cancer Res. 57:1625-1629 (1997).
Segal et al., "Therapeutic potential of the SARMs: revisiting the androgen receptor for drug discovery," Expert Opin. Investig. Drugs 15(4):377-387 (2006).
Sharifi et al., "Androgen Receptor as a Therapeutic Target for Androgen Independent Prostate Cancer" American Journal of Therapeutics (2006) 13(2):166-170.
Sharma, P. and N. Schreiber-Agus, "Mouse models of prostate cancer," Oncogene 18(38):5349-5355 (1999).
Shayeganpour et al., "Determination of the enzyme(s) involved in the metabolism of amiodarone in liver and intestine of rat: the contribution of cytochrome P450 3A isoforms," Drug Metab. Dispos. 34 (1):43-50 (2006).
Shen et al., "Androgen-induced growth inhibition of androgen receptor expressing androgen-independent prostate cancer cells is mediated by increased levels of neutral endopeptidase," Endocrinology 141(5):1699-1704 (2000).

Simental et al., "Transcriptional activation and nuclear targeting signals of the human androgen receptor," J. Biol. Chem. 266(1):510-518 (1991).
Sinclair, Rodney, "Male pattern androgeneticalopecia," BMJ (1998), vol. 317, pp. 854-869.
Sit et al., "Relationship between bone mineral density and biochemical markers of bone turnover in hemodialysis patients," Adv. Ther. 24(5):987-995 (2007).
Smith et al., "03/*/'s Advanced Organic Chemistry, 6th ed.," Wiley, NJ, pp. 1053-1062 (2007).
Smith et al., "03/*/'s Advanced Organic Chemistry, 6th ed.," Wiley, NJ, pp. 1300-1309 (2007).
Smith et al., "03/*/'s Advanced Organic Chemistry, 6th ed.," Wiley, NJ, pp. 1715-1728 (2007).
Smith et al., "03/*/'s Advanced Organic Chemistry, 6th ed.," Wiley, NJ, pp. 1805-1806 (2007).
Srinivasan, G. and E. Thompson, "Overexpression of full-length human glucocorticoid receptor in Spodoptera frugiperda cells using the baculovirus expression vector system," Mol. Endo. 4(2):209-216 (1990).
Srivastava et al., "Development and application of a serum C-telopeptide and osteocalcin assay to measure bone turnover in an ovariectomized rat model," Calcified Tissue Int. 66(6):435-442 (2000).
Stoch et al., "Bone loss in men with prostate cancer treated with gonadotropin-releasing hormone agonists," J. Clin. Endocrinol. Metabol. 86(6):2787-2791 (2001).
Sulak, P., "Ovulation suppression of premenstrual symptoms using oral contraceptives," Am. J. Manag. Care 11:S492-S497 (2005).
Suzuki et al., "Effects of antiandrogens on growth of androgen-dependent mouse mammary tumor (Shionogi carcinoma 115) in vivo and in vitro," J. Steroid Biochem. Mol. Biol. 37(4):559-567 (1990).
Svartberg, J., "Androgen and chronic obstructive pulmonary disease" Current Opinion in Endocrinology, Diabetes and Obesity (2010) 17(3):257-261.
Szulc et al., "Biochemical assessment of bone turnover and bone fragility in men," Osteoporos Int. 18(11):1451-1461 (2007).
Tajana et al., "Synthesis of a testosterone-dependent secretory protein by rat seminal vesicle-derived cell lines," EMBO J. 3(3):637-644 (1984).
Thevis et al., "Screening for 2-quinolinone-derived selective androgen receptor agonists in doping control analysis," Rapid Commun. Mass Spectrom. 21(21):3477-3486 (2007).
Tobias et al., "5 alpha-Dihydrotestosterone partially restores cancellous bone volume in osteopenic ovariectomized rats," Am. J. Physiol. 267(6 Pt 1): E853-E859 (1994).
Tsujii et al., "Cyclooxygenase regulates angiogenesis induced by colon cancer cells," Cell 93(5):705-716 (1998).
Turner et al., "Contraceptive efficacy of a depot progestin and androgen combination in men," J. Clin. Endocrinol. Metabol. 88(10):4659-4667 (2003).
Turner, C. and D. Burr, "Basic biomedical measurements of bone: a tutorial," Bone 14:595-608 (1993).
Umesono et al., "Retinoic acid and thyroid hormone induce gene expression through a common responsive element," Nature 336:262-265 (1988).
Vadja et al., "LGD-4033 builds muscle and bone with reduced prostate activity and 05/*/ be beneficial in age-related frailty," Gerontological Society of America 62nd Annual Scientific Meeting, Atlanta, Georgia, Nov. 18-22, 2009 [poster presentation].
Van Oeveren et al., "Discovery of 6-N,N-bis(2,2,2-trifluoroethyl)amino-4-trifluoromethylquinolin-2(1H)-one as a novel selective androgen receptor modulator," J. Med. Chem. 49(21):6143-6146 (2006).
Van Oeveren et al., "Discovery of an androgen receptor modulator pharmacophore based on 2-quinolinones," Bioorg. Med. Chem. Lett. 17(6):1523-1526 (2007).
Van Oeveren et al., "Novel selective androgen receptor modulators: SAR studies on 6-bisalkylamino-2-quinolinones," Bioorg. Med. Chem. Lett. 17(6):1527-1531 (2007).
Van Weerden et al., "Human prostate tumor xenografts as representative models for clinical prostate cancer," Urol. Oncol. 2: 122-125 (1996).

(56) References Cited

OTHER PUBLICATIONS

Vandenput et al., "The estrogen receptor ligand ICI 182,780 does not impair the bone-sparing effects of testosterone in the young orchidectomized rat model," Calcified Tissue Int. 70(3):170-175 (2002).
Vanderschueren et al., "Time-related increase of biochemical markers of bone turnover in androgen-deficient male rats," Bone Miner. 26(2): 123-131 (1994).
Vanderschueren et al., "An aged rat model of partial androgen deficiency: prevention of both loss of bone and lean body mass by low-dose androgen replacement," Endocrinology 141(5):1642-1647 (2000).
Vanderschueren et al., "Androgens and bone," Endocrine Rev. 25(3):389-425 (2004).
Vegeto et al., "The mechanism of RU486 antagonism is dependent on the conformation of the carboxy-terminal tail of the human progesterone receptor," Cell 69(4):703-713 (1992).
Visentin et al., "A selective inhibitor of the osteoclastic V-H(+)-ATPase prevents bone loss in both thyroparathyroidectomized and ovariectomized rats," J. Clin. Invest. 106(2):309-318 (2000).
Wagaw et al., "Palladium-catalyzyed coupling of optically active amines with aryl bromides," J. Am. Chem. Soc. 119(12):8451-8458 (1997).
Wakley et al., "Androgen treatment prevents loss of cancellous bone in the orchidectomized rat," J. Bone Min. Res. 6(4):325-330 (1991).
Wang et al, "Male rodent model of age-related bone loss in men," Bone 29(2):141-148 (2001).
Willy et al., "LXR, a nuclear receptor that defines a distinct retinoid response pathway," Genes Dev. 9(9):1033-1045 (1995).
Wright et al., "Analysis of myosin heavy chain mRNA expression by RT-PCR," J. Appl. Physiol. 83(4):1389-1396 (1997).
Wuts et al., "Green's Protective Groups in Organic Synthesis, 4th ed.," Wiley, NJ, pp. 725-727 (2007).
Wuts et al., "Green's Protective Groups in Organic Synthesis, 4th ed.," Wiley, NJ, pp. 727-735 (2007).
Xin et al., "Peroxisome proliferator-activated receptor .gamma. ligands are potent inhibitors of angiogenesis in vitro and in vivo," J. Biol. Chem. 274(13):9116-9121 (1999).
Yalpani, "Cholesterol Lowering Drugs," Chem. Ind. 3:85-89 (1996).
Yamada et al., "Comparative evaluation of a 5-day hershberger assay utilizing mature male rats and a pubertal male assay for detection of flutamide's antiandrogenic activity," Tox. Sciences 53: 289-296 (2000).
Yassin et al., "Treatment of sexual dysfunction of hypogonadal patients with long-acting testosterone undecanoate (Nebido)," World J. Urol. 24:6:639-644 (2006).
Ye et al., "Androgen and epidermal growth factor down-regulate cyclin-dependent kinase inhibitor p27Kipl and costimulate proliferation of MDA PCa 2a and MDA PCa 2b prostate cancer cells," Clin. Cancer Res. 5(8):2171-2177 (1999).
Yeap et al., "Differential posttranscriptional regulation of androgen receptor gene expression by androgen in prostate and breast cancer cells," Endocrinology 140:3282-3291 (1999).
Yin et al., "Pharmacodynamics of selective androgen receptor modulators," J. Pharmacol. Exp. Ther. 304(3):1334-1340 (2003).
Yki-Jarvinen, H., "Thiazolidinediones," N. Eng. J. Med. 351(11):1106-1118 (2004).
Zacharski, L. and D. Orenstein, "Heparin and cancer," Thromb. Haemost. 80(1):10-23 (1998).
Zhang et al., "Human prostatic smooth muscle cells in culture: estradiol enhances expression of smooth muscle cell-specific markers," Prostate 30(2):117-129 (1997).
Zhang et al., "Design, synthesis, and in vivo SAR of a novel series of pyrazolines as potent selective androgen receptor modulators," J. Med. Chem. 50(16):3857-3869 (2007).
Zhi et al., "Chapter 17: Selective androgen receptor modulators (SARMs)," Ann. Rep. Med. Chem. 36:169-180 (2001).
Zhi et al., "Switching androgen receptor antagonists to agonists by modifying C-ring substituents on piperidino[3,2-g]quinolinone," Bioorg. Med. Chem. Lett. 9(7):1009-1012 (1999).

Zhuang et al., "Subcellular location of androgen receptor in rat prostate, seminal vesicle and human osteosarcoma MG-63 cells," J. Steroid Biochem. Mol. Biol. 41(3-8):693-696 (1992).
International Preliminary Report on Patentability, dated Jun. 22, 2010, in connection with corresponding International Patent Application No. PCT/US2008/013657, 9 pages.
Examination Report, dated Jun. 10, 2011, in connection with corresponding European Patent Application No. 08865188.0, 3 pages.
Response to Examination Report, submitted Oct. 7, 2011, in connection with corresponding European Patent Application No. 08865188.0, 11 pages.
Examination Report, dated Nov. 4, 2011, in connection with corresponding European Patent Application No. 08865188.0, 3 pages.
Official Action, dated Feb. 13, 2012, in connection with corresponding Chinese Patent Application No. 200880127182.1, 8 pages.
Official Action dated Feb. 21, 2012, in connection with corresponding Chilean Patent Application No. 3825-2008, 3 pages.
Response to Examination Report, submitted Apr. 25, 2012, in connection with corresponding European Patent Application No. 08865188.0, 51 pages.
Instructions for Response to Office Action, submitted Jun. 27, 2012, in connection with corresponding Chile Patent Application No. 03825-2008, 60 pages.
Extended European Search Report, dated Jul. 17, 2012, in connection with corresponding European Patent Application No. 12168231.4-2101, 8 pages.
Instructions for Response to Office Action, submitted Jul. 27, 2012, in connection with corresponding Chinese Patent Application No. 200880127182.1, 18 pages.
Notice of Preliminary Rejection dated Mar. 30, 2015 for the Korean Patent Application No. 10-2010-7015852, filed Jul. 16, 2010.
Canadian Office Action dated Jan. 13, 2015 for Canadian Application No. 2,709,677, filed Jun. 16, 2010.
Canadian Office Action dated Oct. 16, 2015 for Canadian Application No. 2,709,677, filed Jun. 16, 2010.
Chinese Office Action dated Jan. 29, 2013 for Chinese Application No. 200880127182.1, filed Dec. 19, 2008.
Chinese Office Action dated Jul. 25, 2013 for Chinese Application No. 200880127182.1, filed Dec. 19, 2008.
Chinese Office Action dated Feb. 7, 2014 for Chinese Application No. 200880127182.1, filed Dec. 19, 2008.
Chinese Office Action dated Dec. 17, 2015 for Chinese Application No. 201410347302.6, filed Jul. 21, 2014.
European Office Action dated Mar. 18, 2013 for European Application No. 12168231.4, filed Dec. 12, 2008.
Japanese Office Action dated May 7, 2013 for Japanese Application No. 2010-539438, filed Dec. 12, 2008.
Japanese Office Action dated Mar. 10, 2015 for Japanese Application No. 2014-093514, filed Apr. 30, 2014.
Taiwanese Office Action dated Jun. 6, 2013 for Taiwanese Application No. 097148899, filed Dec. 16, 2008.
Office Action dated Oct. 9, 2013 for U.S. Appl. No. 13/694,063, filed Oct. 23, 2012.
Office Action dated Jan. 23, 2015 for U.S. Appl. No. 14/263,237, filed Apr. 28, 2014.
Chilean Office Action dated Jan. 16, 2012 for Chilean Application No. 3825-2008, filed Dec. 19, 2008.
Mexican Office Action dated Aug. 20, 2013 for Mexican Application No. MX/a/2010/006972, filed Jun. 21, 2010.
Mexican Office Action dated Jan. 24, 2014 for Mexican Application No. MX/a/2010/006972, filed Jun. 21, 2010.
Chinese Office Action dated Aug. 29, 2016 for Chinese Application No. 201410347302.6, filed Jul. 21, 2014.
Office Action dated Sep. 2, 2016 for U.S. Appl. No. 14/827,228, filed Aug. 14, 2015.
Argentine Office Action dated Nov. 22, 2017 for Argentine Application No. 080105633, filed Dec. 19, 2008.
Office Action dated Jun. 14, 2018 for Argentine Application No. 080105633, filed Dec. 19, 2008.

SELECTIVE ANDROGEN RECEPTOR MODULATORS (SARMS) AND USES THEREOF

RELATED APPLICATIONS

This application is a continuation of Ser. No. 15/590,884, filed May 9, 2017, which is a continuation of U.S. application Ser. No. 14/827,228, filed Aug. 14, 2015, now U.S. Pat. No. 9,675,583, which is a divisional of U.S. application Ser. No. 14/263,237, filed Apr. 28, 2014, now U.S. Pat. No. 9,139,520, which is a divisional of U.S. application Ser. No. 13/694,063, filed Oct. 23, 2012, now U.S. Pat. No. 8,748,633, which is a divisional of U.S. patent application Ser. No. 12/734,993, filed Jun. 7, 2010, now U.S. Pat. No. 8,354,446, which is the U.S. National Stage application of PCT/US2008/013657, filed Dec. 12, 2008, and entitled "SELECTIVE ANDROGEN RECEPTOR MODULATORS (SARMs) AND USES THEREOF," which claims benefit of priority to U.S. Provisional Patent Application Ser. No. 61/008,731, to Lin Zhi, filed on Dec. 21, 2007, entitled "SELECTIVE ANDROGEN RECEPTOR MODULATORS (SARMs) AND USES THEREOF." Where permitted, the subject matter of each of the-above mentioned applications is incorporated by reference in its entirety.

FIELD

Provided herein are selective androgen receptor modulator (SARM) compounds that bind to androgen receptors and/or modulate activity of androgen receptors, and to methods for making and using such compounds. Also provided are compositions including such compounds and methods for making and using such compositions. Also provided are methods for the treatment of androgen receptor mediated diseases.

BACKGROUND

Certain intracellular receptors (IRs) have been shown to regulate transcription of certain genes (e.g., see R. M. Evans, Science 240: 889 (1988)). Certain of such IRs are steroid receptors, such as androgen receptors, estrogen receptors, mineralo-corticoid receptors, and progesterone receptors. Gene regulation by such receptors typically involves binding of an IR by a ligand.

In certain instances, a ligand binds to an IR, forming a receptor/ligand complex. Such a receptor/ligand complex can then translocate to the nucleus of a cell, where it binds to the DNA of one or more gene regulatory regions. Once bound to the DNA of a particular gene regulatory region, a receptor/ligand complex can modulate the production of the protein encoded by that particular gene. In certain instances, an androgen receptor/ligand complex regulates expression of certain proteins. In certain instances, an androgen receptor/ligand complex can interact directly with the DNA of a particular gene regulatory region or with other transcription factors. In certain instances, such interactions result in modulation of transcriptional activation.

Androgen therapy has been used to treat a variety of male disorders such as reproductive disorders and primary or secondary male hypogonadism. A number of natural or synthetic AR agonists have been investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, are used to treat prostate cancer. The effectiveness of known modulators of steroid receptors is often tempered by their undesired side-effect profile, particularly during long-term administration. For example, potential side effects of androgen therapy for women include acne, weight gain, excess facial and body hair, permanent lowering of the voice, and adverse lipid changes. In men, adverse effects can include disordered sleep and breathing, polycythemia, and repression of high density lipoprotein. Thus there is a need for compounds that do not exhibit the adverse side-effects. It is among the objects herein to provide such compounds that modulate the activity of androgen receptor.

SUMMARY

Compounds for use in compositions and methods for modulating the activity of androgen receptor are provided. The compounds provided herein are non-steroidal Selective Androgen Receptor Modulators or SARMs. In particular, non-steroidal SARMs display therapeutic benefit but generally do not display adverse androgenic effects, such as prostate enlargement, acne, hirsutism, virilization and masculinization. The compounds selectively modulate (agonize or antagonize) the function of the AR, such as in a tissue-selective manner, to produce the effects of androgens without or with reduced negative or undesired androgenic properties. Among the compounds provided herein are agonists of androgen receptor. Among the compounds provided herein are antagonists of androgen receptor. Among the compounds provided herein are androgen receptor partial agonists.

Among the compounds provided herein are tissue specific selective androgen receptor modulators. They can be used for oral testosterone replacement therapy. Compounds provided herein display agonist activity with $EC_{50}$ values generally less than 1 micromolar. Compounds provided herein display antagonist activity with $IC_{50}$ values generally less than 2 micromolar. SARMs provided herein generally target anabolic tissue, such as connective tissue, including bone and muscle, and can be used to increase the mass of a connective tissue in a subject and to reverse connective tissue loss in a subject. Among the disorders that can be treated are muscle wasting, cachexia, frailty and osteoporosis and other muscle and bone disorders, including those enumerated below.

Compounds provided herein have a structure of Formula I or Formula II or Formula III:

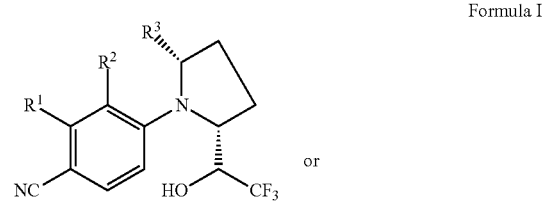

Formula I

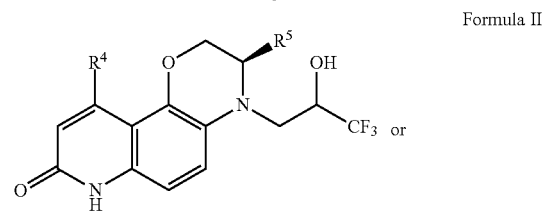

Formula II

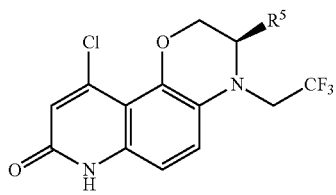

Formula III where R¹ is halogen, pseudohalogen, optionally substituted lower alkyl, optionally substituted haloalkyl or NO$_2$, particularly lower haloalkyl or halogen, and in particular is CF$_3$, F, or Cl; R² is hydrogen, halogen, pseudohalogen, optionally substituted lower alkyl or optionally substituted lower haloalkyl, particularly hydrogen or methyl; R³ is hydrogen, halogen, pseudohalogen, optionally substituted lower alkyl or optionally substituted lower haloalkyl, particularly hydrogen or lower alkyl, and in particular hydrogen or methyl; R⁴ is halogen or lower haloalkyl, particularly CF$_3$ or halogen, and in particular Cl or CF$_3$; and R⁵ is lower alkyl or lower haloalkyl, particularly C$_1$ to C$_4$ alkyl or C$_1$ to C$_4$ haloalkyl, and in particular methyl, ethyl or CF$_3$. Also provided are pharmaceutically acceptable salts, esters and prodrugs of compounds of Formula I or Formula II or Formula III.

In some embodiments, the compounds provided herein exhibit tissue selective androgen receptor agonist activity. In some embodiments, the compounds provided herein exhibit tissue selective androgen receptor antagonist activity. In some embodiments, the compounds provided herein are androgen receptor selective binding compounds.

Compounds provided herein are effective for treating one or more androgen receptor mediated diseases or conditions. Such conditions and diseases include those caused by androgen deficiency and/or those that can be ameliorated by androgen administration. In certain embodiments, compounds provided herein are effective for treating one or more diseases or conditions responsive to an androgen receptor agonist. In certain embodiments, compounds provided herein are effective in treating one or more conditions whose etiology involves hypoactivity or subsensitivity of androgen receptor. In other embodiments, compounds provided herein are effective for treating one or more diseases or conditions responsive to an androgen receptor antagonist. In other embodiments, compounds provided herein are effective in treating one or more conditions whose etiology involves hyperactivity of androgen receptor.

In some tissues, the compounds provided herein can exhibit AR agonist activity and can be used to treat conditions that are caused by androgen deficiency or hypoactivity or subsensitivity of androgen receptor, or that can be ameliorated by androgen replacement or are responsive to treatment with an AR agonist. Such conditions, include, but not limited to, aging skin; Alzheimer's disease; anemias, such as for example, aplastic anemia; anorexia; arthritis, including inflammatory arthritis, rheumatoid arthritis, osteoarthritis and gout; arteriosclerosis; atherosclerosis; bone disease, including metastatic bone disease; bone damage or fracture, such as by accelerating bone fracture repair and/or stimulation of osteoblasts and/or stimulation of bone remodeling and/or stimulation of cartilage growth; distraction osteogenesis; reduced bone mass, density or growth; bone weakening, such as induced by glucocorticoid administration; musculoskeletal impairment (e.g., in the elderly); cachexia; cancer, including breast cancer and osteosarcoma; cardiac dysfunction (e.g., associated with valvular disease, myocardial infarction, cardiac hypertrophy or congestive heart failure); cardiomyopathy; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; contraception (male and female); chronic obstructive pulmonary disease (COPD); chronic bronchitis; decreased pulmonary function; emphysema; decreased libido in both men and women; depression; nervousness, irritability and/or stress; reduced mental energy and low self-esteem (e.g., motivation/assertiveness); dyslipidemia; erectile dysfunction; frailty; age-related functional decline ("ARFD") in the elderly; growth hormone deficiency; hematopoietic disorders; hormone replacement (male and female); hypercholesterolemia; hyperinsulinemia; hyperlipidemia; hypertension; hyperandrogenemia; hypogonadism (including primary and secondary); hypothermia (including hypothermia following anesthesia); impotence; insulin resistance; type 2 diabetes; lipodystrophy (including in subjects taking HIV or AIDS therapies such as protease inhibitors); male menopause; metabolic syndrome (syndrome X); loss of muscle strength and/or function (e.g., in the elderly); muscular dystrophies; muscle loss following surgery (e.g., post-surgical rehabilitation); muscular atrophy (e.g., due to physical inactivity, bed rest or reduced weight-bearing conditions such as microgravity); neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction (e.g., erectile dysfunction, decreased sex drive, sexual well-being, decreased libido); physiological short stature, including growth hormone deficient children and short stature associated with chronic illness and growth retardation associated with obesity; tooth damage (such as by acceleration of tooth repair or growth); thrombocytopenia; vaginal dryness; atrophic vaginitis; ventricular dysfunction; wasting, including wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia), chemotherapy, multiple sclerosis or other neurodegenerative disorders.

In some tissues, the compounds provided herein exhibit AR agonist activity and can be used to stimulate pulsatile growth hormone release; in hormone replacement therapy, such as female androgen deficiency and male androgen decline; to improve bone strength, muscle strength and tone; to reduce subcutaneous fat in a subject; to enhance bone and muscle performance/strength; to increase athletic performance; to attenuate or reverse protein catabolic responses following trauma (e.g., reversal of the catabolic state associated with surgery, congestive heart failure, cardiac myopathy, burns, cancer, COPD); to improve sleep quality and/or correct the relative hyposomatotropism of senescence due to high increase in REM sleep and a decrease in REM latency; and to treat age related decreased testosterone levels in men.

In some tissues, the compounds provided herein can exhibit AR antagonist activity and can be used to treat conditions whose etiology involves hyperactivity of androgen receptor or that are responsive to treatment with an AR antagonist. Such conditions include, but are not limited to, acanthosis nigricans, acne, adrenal hyper-androgenism, androgenetic alopecia (male-pattern baldness), adenomas and neoplasias of the prostate (e.g., advanced metastatic prostate cancer), benign prostate hyperplasia, cancer (e.g., cancer of the breast, bladder, endometrium, lung (non-small cell lung cancer), pancreas, prostate, including androgen dependent prostate cancer, and skin); bulimia nervosa; chronic fatigue syndrome (CFS); chronic myalgia; acute fatigue syndrome; contraception; counteracting preeclampsia, eclampsia of pregnancy and preterm labor; delayed wound healing; erythrocytosis; gestational diabetes; hirsutism; hyperinsulinemia including nesidioblastosis; hyperandrogenism; hypercortisolism; Cushing's syndrome; hyperpilosity; infertility; malignant tumor cells containing the androgen receptor, such as is the case for breast, brain, skin, ovarian, bladder, lymphatic, liver and kidney cancers; menstrual irregularity; ovarian hyperandrogenism; polycystic ovarian syndrome; seborrhea; sleep disorders; sleep apnea; and visceral adiposity.

In certain embodiments, compounds provided herein are effective for treating prostate cancer. In certain embodiments, compounds provided herein are effective for treating androgen dependant prostate cancer. In certain embodiments, compounds provided herein are effective for treating androgen independent prostate cancer. In certain embodiments, compounds provided herein are effective for treating androgen independent androgen receptor dependent prostate cancer.

The methods of treatment are practiced by administering to the subject a compound provided herein. In certain embodiments, provided herein are methods for treating a condition responsive to androgen receptor modulation in a subject by identifying a subject in need of such treatment and administering to the subject a compound provided herein. In certain embodiments, the methods provided herein are for treating a disease or condition responsive to an androgen receptor agonist. In certain embodiments, the methods provided herein are for treating a condition responsive to an androgen receptor antagonist.

In certain embodiments, provided herein are methods for modulating an activity of an androgen receptor by contacting an androgen receptor with at least one compound provided herein. In certain such embodiments, the androgen receptor is in a cell. In some embodiments, the modulation is agonizing the receptor. In some embodiments, the modulation is antagonizing the receptor.

In certain embodiments, provided herein are methods for identifying a compound that is capable of modulating an activity of an androgen receptor by contacting a cell expressing an androgen receptor with a compound provided herein and monitoring an effect of the compound upon the cell.

In certain embodiments, provided herein are methods of contraception in a subject. The methods include administering to the subject a compound of Formula I, II or III or pharmaceutically acceptable salts or prodrugs thereof, in an amount effective to provide contraception. In some embodiments, the compound is co-administered with an androgen selected from among testosterone, 19-nortestosterone, 7α-methyl-19-nortestosterone and 5α-dihydro-testosterone. In one embodiment, the subject is male and a compound of formula I, II or III is administered in an amount effective to suppress sperm production in the subject, thereby effecting contraception in the subject. In one embodiment, the compounds provided herein inhibit spermatogenesis in a subject. In one embodiment, the subject is female and a compound of formula I, II or III is administered in an amount effective to provide contraception in the subject.

In certain embodiments, provided herein are methods for providing hormone therapy. The methods include administering to the subject a compound of formula I, II or III, in an amount effective to modulate androgen receptor activity, and thereby effect a change in an androgen-dependent condition. In some tissues, the compound is an androgen receptor agonist. In some tissues, the compound is an androgen receptor antagonist.

In certain embodiments, provided herein are methods for treating cancer in a subject, comprising administering to the subject a compound of Formula I, II or III or pharmaceutically acceptable salts or prodrugs thereof, in an amount effective to treat cancer in the subject. In certain embodiments, the cancer is selected from among breast cancer, colorectal cancer, gastric carcinoma, glioma, head and neck squamous cell carcinoma, skin cancer, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer. In some embodiments, the compound is administered in an amount effective to kill the cancerous cells. In some embodiments, the compound is administered in an amount effective to inhibit growth and/or metastasis of the cancer. In some embodiments, the compound is co-administered with one or more other therapeutic agents selected from among anti-proliferative agents, anti-tumor agents, adrenocorticosteroids, progestins, estrogens, antiestrogens, radionuclides, toxins and cytotoxic drugs, chemotherapy agents, photodynamic therapy dyes and antibiotics or combinations thereof.

In certain embodiments, provided herein are methods of treating prostate cancer in a subject. The methods include administering to the subject a compound of Formula I, II or III or pharmaceutically acceptable salts or prodrugs thereof, in an amount effective to treat prostate cancer in the subject. In some embodiments, the prostate cancer is androgen dependant prostate cancer. In some embodiments, the prostate cancer is androgen independent prostate cancer. In some embodiments, the prostate cancer is androgen independent, but androgen receptor dependant prostate cancer. In some embodiments, the compound is administered to the subject in an amount effective to kill the cancerous cells. In some embodiments, the compound is administered to the subject in an amount effective to inhibit the growth and/or metastasis of the prostate cancer cells. In some embodiments, the compound is co-administered with another therapeutic agent selected from among flutamide, a toxin, bicalutamide, nilutamide, an anti-tumor agent, a cytotoxic drug, a radionuclide and combinations thereof. In some embodiments, the compound and/or another therapeutic agent, if present, is selectively targeted to react with prostate cancer cells by conjugating the compound and/or therapeutic agent to a prostate tumor antigen.

In certain embodiments, provided herein are methods of delaying the progression of prostate cancer in a subject. The methods include administering to the subject a compound of Formula I, II or III or pharmaceutically acceptable salts or prodrugs thereof, in an amount effective to delay the progression of prostate cancer in the subject.

In certain embodiments, provided herein are methods of improving athletic performance in a subject. The methods include administering to the subject a compound of Formula I, II or III or pharmaceutically acceptable salts or prodrugs thereof in an amount effective to improve athletic performance in the subject.

In certain embodiments, provided herein are methods of increasing muscle performance, muscle size and/or muscle strength in a subject. The methods include administering to the subject a compound of Formula I, II or III or pharmaceutically acceptable salts or prodrugs thereof in an amount effective to increase muscle performance, muscle size and/or muscle strength in a subject.

In certain embodiments, provided herein are methods of treating, preventing, suppressing, inhibiting or reducing the incidence of muscle wasting in a subject. The methods include administering to the subject a compound of Formula I, II or III or pharmaceutically acceptable salts or prodrugs thereof in an amount effective to treat, prevent, suppress, inhibit or reduce the incidence of a muscle wasting in the subject. In some embodiments, the muscle wasting is caused by a condition selected from among andropause, spinal muscular atrophies, muscular dystrophies (e.g., Duchenne, Myotonic and Becker), myasthenia gravis, cachexias such as AIDS cachexia, cardiac cachexia, and cancer cachexia, cancer, Chronic Obstructive Pulmonary Disease (COPD), emphysema, diabetes, HIV infection, acquired immunodeficiency syndrome (AIDS), sepsis, tuberculosis, renal failure, heart failure, cardiomyopathy, bed rest, disuse, inactivity, microgravity, malnutrition, sarcopenia, aging and frailty (e.g., see Lynch et al., Pharmacology & Therapeutics 113(3): 461-487 (2007)).

In certain embodiments, provided herein are methods of treating a neuro-degenerative disease or disorder in a subject. The methods include administering to the subject a compound of Formula I, II or III or pharmaceutically acceptable salts or prodrugs thereof in an amount effective to treat the neurodegenerative disease or disorder in the subject. In some embodiments, the neurodegenerative disorder is Alzheimer's disease.

In certain embodiments, provided herein are methods for preventing the onset or delaying the progression of Alzheimer's disease in a subject. The methods include administering to the subject a compound of Formula I, II or III or pharmaceutically acceptable salts or prodrugs thereof in an amount effective to prevent the onset or delay the progression of Alzheimer's disease in the subject. In some embodiments, the compound is co-administered with an effective amount of a compound that inhibits the formation or release of β-amyloid.

In certain embodiments, provided herein are methods for treating cognitive impairment in a subject. The methods include administering to the subject a compound of Formula I, II or III or pharmaceutically acceptable salts or prodrugs thereof in an amount effective to treat cognitive impairment in the subject.

In certain embodiments, provided herein are methods for treating depression in a subject. The methods include administering to the subject a compound of Formula I, II or III or pharmaceutically acceptable salts or prodrugs thereof in an amount effective to treat depression in the subject.

In certain embodiments, provided herein are methods for treating one or more postmenopausal conditions in a subject. The methods include administering to the subject a compound of Formula I, II or III or pharmaceutically acceptable salts or prodrugs thereof in an amount effective to treat one or more postmenopausal conditions in the subject. In some embodiments, the postmenopausal condition is selected from among loss of libido, decreased sexual activity, diminished feelings of physical well-being, fatigue and hot flashes. In some embodiments, the compound is co-administered with another therapeutic agent selected from among estrone, 2-hydroxyestrone, 2-methoxyestrone, 4-hydroxyestrone, 15-α-hydroxy-estrone, 16-α-hydroxyestrone, 16-β-hydroxyestone, estradiol (17-β-estradiol), 2-hydroxy-estradiol, 2-methoxy-estradiol, 4-hydroxy-estradiol, 16-oxo-estradiol, estriol, 16-epiestriol and 17-epiestriol and combinations thereof. In some embodiments, the compound is co-administered with another therapeutic agent selected from among estradiol valerate, estrone, estrone sulfate, an estrone sulfate piperazine salt or an ester thereof, a synthetic estrogen and combinations thereof. In some embodiments, the compound is co-administered with another therapeutic agent selected from among alendronate, calcitonin, clodronate, clomiphene, clomiphene citrate, clonidine, conjugated estrogen, natural or synthetic estrogen, ethinyl estradiol, estradiol, enclomiphene, enclomiphene citrate, etidronate, ibandronate, medroxy-progesterone acetate, megestrol acetate, norethindrone acetate, pamidronate, progesterone, risedronate, tiludronate, zuclomiphene, zuclomiphene citrate and combinations thereof.

In certain embodiments, provided herein are methods of improving the lipid profile in a subject. The methods include administering to the subject a compound of Formula I, II or III or pharmaceutically acceptable salts or prodrugs thereof, in an amount effective to affect the lipid profile in the subject.

In certain embodiments, provided herein are methods of reducing circulating lipid levels in a subject. The methods include administering to the subject a compound of Formula I, II or III or pharmaceutically acceptable salts or prodrugs thereof, in an amount effective to reduce circulating lipid levels in the subject. In some embodiments, the compound is co-administered with a therapeutic agent selected from among β-hydroxy-β-methylbutyric acid, lactoferrin, cholestyramine, colestipol, colesevelam, nicotinic acid, one or more fibric acids (e.g., gemfibrozil, fenofibrate and clofibrate) and one or more HMG-CoA reductase inhibitors (lovastatin, pravastatin, simvastatin, fluvastatin, atorvastatin and cerivastatin) and combinations thereof.

In certain embodiments, provided herein are methods of treating atherosclerosis, a cardiovascular disorder, a cerebrovascular disorder, a peripheral vascular disorder, and/or an intestinal vascular disorder in a subject. The methods include administering to the subject a compound of Formula I, II or III or pharmaceutically acceptable salts or prodrugs thereof, in an amount effective to treat the atherosclerosis, cardiovascular disorder, cerebrovascular disorder, peripheral vascular disorder, and/or intestinal vascular disorder in the subject. In some embodiments, the compound is co-administered with a selective estrogen receptor modulator (SERM) compound.

In certain embodiments, provided herein are methods of treating osteoporosis, osteopenia, glucocorticoid-induced osteoporosis or bone fracture in a subject. The methods include administering to the subject a compound of Formula I, II or III or pharmaceutically acceptable salts or prodrugs thereof, in an amount effective to treat the osteoporosis, osteopenia, glucocorticoid-induced osteoporosis or bone fracture in the subject. In some embodiments, the compound is co-administered with an effective amount of at least one other therapeutic agent selected from among estrogen, estrogen derivatives, progestin, progestin derivatives, a bisphosphonate, an anti-estrogen, a selective estrogen receptor modulator (SERM), an $\alpha_v\beta_3$ integrin receptor antagonist, a cathepsin inhibitor, a proton pump inhibitor, a PPARγ inhibitor, calcitonin, osteoprotegerin and combinations thereof.

In certain embodiments, provided herein are methods of increasing the strength or mass of bone of a subject. The methods include administering to the subject a compound of Formula I, II or III or pharmaceutically acceptable salts or prodrugs thereof, in an amount effective to increase the strength or mass of a bone in the subject.

In certain embodiments, provided herein are methods of promoting bone formation in a subject. The methods include administering to the subject a compound of Formula I, II or III or pharmaceutically acceptable salts or prodrugs thereof, in an amount effective to promote bone formation in the subject.

In certain embodiments, provided herein are methods of treating a hematopoietic disorder in a subject. The methods include administering to the subject a compound of Formula I, II or III or pharmaceutically acceptable salts or prodrugs thereof, in an amount effective to treat the hematopoietic disorder in the subject. In some embodiments, the hematopoietic disorder is selected from among anemia, leukemia, and hematopoietic conditions caused by bone marrow transplantation or chemotherapy or radiation therapy.

In certain embodiments, provided herein are methods of increasing the number of red blood cells in a subject. The methods include administering to the subject a compound of Formula I, II or III or pharmaceutically acceptable salts or prodrugs thereof, in an amount effective to increase the number of red blood cells in the subject.

In certain embodiments, provided herein are methods of treating anemia, thrombocytopenia or neutropenia in a subject. The methods include administering to the subject a compound of Formula I, II or III or pharmaceutically acceptable salts or prodrugs thereof, in an amount effective to treat anemia, thrombocytopenia or neutropenia in the subject. In some embodiments, the compound is co-administered with a therapeutically effective amount of at least one hematopoietic cytokine. In some embodiments, the hematopoietic cytokine is selected from among erythropoietin, granulocyte-colony stimulating factor, granulocyte-macrophage-colony stimulating factor, interleukin-1, interleukin-3, interleukin-4, interleukin-5, interleukin-7, interleukin-9, interleukin-11, macrophage-colony stimulating factor, stem cell factor and thrombopoietin.

In certain embodiments, provided herein are methods of increasing serum erythropoietin (EPO) levels in a subject. The methods include administering to the subject a compound of Formula I, II or III or pharmaceutically acceptable salts or prodrugs thereof, in an amount effective to increasing serum EPO levels in the subject.

In certain embodiments, provided herein are methods of preventing and/or treating obesity or an obesity-related condition or disease in a subject. The methods include administering to the subject a compound of Formula I, II or III or pharmaceutically acceptable salts or prodrugs thereof, in an amount effective to prevent and/or treat obesity or an obesity-related condition or disease in the subject.

In certain embodiments, provided herein are methods of treating abdominal adiposity in a subject. The methods include administering to the subject a compound of Formula I, II or III or pharmaceutically acceptable salts or prodrugs thereof that is an AR agonist, in an amount effective to treat abdominal adiposity in the subject.

In certain embodiments, provided herein are methods of treating abdominal obesity in a subject. The methods include administering to the subject a compound of Formula I, II or III or pharmaceutically acceptable salts or prodrugs thereof that is an AR antagonist, in an amount effective to treat abdominal obesity in the subject.

In certain embodiments, provided herein are methods of treating insulin resistance in a subject. The methods include administering to the subject a compound of Formula I, II or III or pharmaceutically acceptable salts or prodrugs thereof, in an amount effective to treat insulin resistance in the subject.

In certain embodiments, provided herein are methods of treating type 2 diabetes in a subject. The methods include administering to the subject a compound of Formula I, II or III or pharmaceutically acceptable salts or prodrugs thereof, in an amount effective to treat type 2 diabetes in the subject. In some embodiments, the compound is co-administered with an effective amount of an anti-diabetic drug, such as, but not limited to, thiazolidinedione-type drugs such as pioglitazone or rosiglitazone, sulfonylurea-type drugs, such as chlorpropamide, glimepiride, glipizide, glyburide or tolbutamide, a biguanide-type drug such as metformin, exenatide, acarbose, repaglinide, nateglinide, tolazamide or combinations thereof.

In certain embodiments, provided herein are methods of treating arterial hypertension, hyper-insulinaemia, hyperglycemia or dyslipidemia in a subject. The methods include administering to the subject a compound of Formula I, II or III or pharmaceutically acceptable salts or prodrugs thereof, in an amount effective to treat arterial hypertension, hyper-insulinaemia, hyperglycemia or dyslipidemia in the subject.

In certain embodiments, provided herein are methods for the treatment or prevention of an arthritic condition or inflammatory disorder in a subject. The methods include administering to the subject a compound of Formula I, II or III or pharmaceutically acceptable salts or prodrugs thereof, in an amount effective to treat or prevent the arthritic condition or inflammatory disorder in the subject. In some embodiments, the arthritic condition or inflammatory disorder is selected from among osteoarthritis, Behcet's disease, bursitis, tendonitis, CPPD deposition disease, carpal tunnel syndrome, Ehlers-Danlos syndrome, fibromyalgia, gout, infectious arthritis, inflammatory bowel disease, juvenile arthritis, lupus erythematosus, Lyme disease, Marfan syndrome, myositis, osteoarthritis, osteogenesis imperfecta, osteonecrosis, polyarteritis, polymyalgia rheumatica, psoriatic arthritis, Raynaud's phenomenon, reflex sympathetic dystrophy syndrome, Reiter's syndrome, rheumatoid arthritis, scleroderma and Sjogren's syndrome.

In certain embodiments, provided herein are methods for the treatment or prevention of osteoarthritis in a subject. The methods include administering to the subject a compound of Formula I, II or III or pharmaceutically acceptable salts or prodrugs thereof, in an amount effective to treat or prevent osteoarthritis in the subject. In some embodiments, the compound is co-administered with corticosteroids, gold treatment, methotrexate, aspirin, NSAIDs, COX-2 inhibitors and DMARDs (Disease-Modifying Anti-Rheumatic Drugs).

In certain embodiments, provided herein are methods of treating sexual dysfunction in a subject. The methods include administering to the subject a compound of Formula I, II or III or pharmaceutically acceptable salts or prodrugs thereof, in an amount effective to treat sexual dysfunction in the subject. In some embodiments, the sexual dysfunction is male erectile dysfunction. In some embodiments, the sexual dysfunction is impotence.

In certain embodiments, provided herein are methods of increasing the libido of a subject. The methods include administering to the subject a compound of Formula I, II or III or pharmaceutically acceptable salts or prodrugs thereof, in an amount effective to increase the libido of the subject.

In certain embodiments, provided herein are methods of treating a condition related to androgen decline in a male subject. The methods include administering to the subject a compound of Formula I, II or III or pharmaceutically acceptable salts or prodrugs thereof, in an amount effective to treat the condition related to androgen decline in the subject. In some embodiments, the condition is selected from among fatigue, depression, decreased libido, sexual dysfunction, erectile dysfunction, hypogonadism, osteoporosis, hair loss, obesity, sarcopenia, osteopenia, benign prostate hyperplasia, anemia, alterations in mood and cognition, and prostate cancer. In certain embodiments, provided are methods of treating sarcopenia in a subject.

In certain embodiments, provided herein are methods of treating a condition related to androgen deficiency in a female subject. The methods include administering to the subject a compound of Formula I, II or III or pharmaceutically acceptable salts or prodrugs thereof, in an amount effective to treat the condition related to androgen decline in the subject. In some embodiments, the condition is selected from among sexual dysfunction, decreased sexual libido, sarcopenia, osteopenia, osteoporosis, alterations in cognition and mood, depression, anemia, hair loss, obesity, endometriosis, breast cancer, uterine cancer and ovarian cancer.

In certain embodiments, provided herein are methods of treating a disease in a subject. The methods include administering to the subject a compound of Formula I, II or III or pharmaceutically acceptable salts or prodrugs thereof, in an amount effective to treat the disease, wherein the disease is selected from among angina, coronary artery disease, arteriosclerosis, atherosclerosis, obesity, diabetes, syndrome X, glucose intolerance, insulin resistance, hypercholesterolemia, hyperlipoproteinemia, hyper-glycemia, hyperinsulinemia, hyperlipidemia, glaucoma, hypertension, hypertriglyceridemia, renal disease, thrombosis, peripheral vascular disease, vascular wall damage, stroke, dyslipidemia, diabetic dyslipidemia, mixed dyslipidemia and nonalcoholic fatty liver disease.

Pharmaceutical compositions formulated for administration by an appropriate route and means including effective concentrations of one or more than one compound of Formula I, II or III or pharmaceutically acceptable salts or prodrugs thereof, or pharmaceutically acceptable derivatives thereof, that deliver amounts effective for the treatment, prevention, or amelioration of one or more symptoms of diseases or disorders that are modulated or otherwise affected by androgen receptor activity, or in which androgen receptor activity is implicated, also are provided. The effective amounts and concentrations are effective for ameliorating any of the symptoms of any of the diseases or disorders.

In certain embodiments, provided herein is a pharmaceutical composition including: i) a physiologically acceptable carrier, diluent, and/or excipient; and ii) one or more than one compound of Formula I, II or III or pharmaceutically acceptable salts or prodrugs thereof.

In certain embodiments, compounds provided herein are used to detect the presence, quantity and/or state of androgen receptors in a sample, such as a cell, cell homogenates and lysates. In some embodiments, samples are obtained from a subject. In certain embodiments, compounds are radio- or isotopically-labeled.

Also provided are articles of manufacture that include packaging material, within the packaging material one or more than one compound of Formula I, II or III or pharmaceutically acceptable salts or prodrugs thereof, or composition that includes one or more than one compound of Formula I, II or III or pharmaceutically acceptable salts or prodrugs thereof, that is effective for modulating the activity of androgen receptor, or for treatment, prevention or amelioration of one or more symptoms of androgen receptor mediated diseases or disorders, or diseases or disorders in which androgen receptor activity is implicated, and a label that indicates that the compound or composition is used for modulating the activity of androgen receptor, or for treatment, prevention or amelioration of one or more symptoms of androgen receptor mediated diseases or disorders, or diseases or disorders in which androgen receptor activity is implicated.

Provided herein also are kits, which contain the compositions including the compounds described herein, a device for administration of the composition and, optionally, instructions for administration.

DETAILED DESCRIPTION

A. Definitions
B. Compounds
C. Preparation of the Compounds
1. Scheme I—Preparation of Compounds of Formula I
2. Scheme II and III—Preparation of Compounds of Formula II
3. Scheme IV—Preparation of Compounds of Formula III
D. Certain Indications
1. Muscle Wasting
2. Muscle Tone and Strength
3. Osteoporosis
4. Prostate Disease and Prostate Cancer
5. Hematopoietic Conditions and Disorders
6. Neurodegenerative Diseases and Disorders
7. Obesity
8. Insulin Disorders and Diabetes
9. Sexual Dysfunction
10. Arthritic Conditions and Inflammatory Disorders
11. Modifying Lipid Profile
12. Contraception
13. Postmenopausal Conditions
E. Formulation of Pharmaceutical Compositions
1. Compositions for Oral Administration
2. Injectables, Solutions and Emulsions
3. Lyophilized Powders
4. Topical Administration
5. Compositions for Other Routes of Administration
F. Articles of Manufacture
G. Kits
H. Evaluation of the Activity of the Compounds
1. Effect on muscle
2. Effect on bone
3. Antagonist activity against hormone-dependent tumors
4. Efficacy and toxicity
5. Receptor Binding Assays
6. In vivo assay—Sprague-Dawley Rat Models
I. Methods of Use of the Compounds and Compositions
1. Methods of Treating Muscle Wasting
2. Methods for Improving Muscle Performance, Size and/or Strength
3. Methods of Improving Athletic Performance
4. Methods of Treating Bone-related conditions
5. Methods of Treating Cancer
6. Methods of Treating Prostate Cancer
7. Methods of Contraception
8. Methods of Providing Hormone Therapy
9. Methods of Treating Postmenopausal Conditions
10. Methods of Treating Hematopoietic Disorders
11. Methods of Treating Neurodegenerative Diseases and Disorders
12. Methods of Treating Cognitive Impairment
13. Methods of Treating Depression 14. Methods of Treating Obesity
15. Methods of Treating Insulin Resistance and Diabetes
16. Methods of Treating Sexual Dysfunction
17. Methods of Treating Arthritic Conditions and Inflammatory Disorders
18. Methods of Improving Lipid Profile
19. Methods of Treating Atherosclerosis
20. Methods of Treating Conditions Related to Androgen Decline
21. Methods of Treating Conditions Related to Androgen Deficiency J. Combination Therapies K. Examples The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Unless specific definitions are provided, the nomenclatures used in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of subjects. Reactions and purification techniques can be performed e.g., using kits according to manufacturer's specifications or as commonly accomplished in the art or as described herein. The foregoing techniques and procedures can be generally performed according to conventional methods well known in the art and as described in various general and more specific references that are cited and discussed herein. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

A. DEFINITIONS

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

As used herein, the term "target receptor" refers to a molecule or a portion of a receptor capable of being bound by a selective binding compound. In certain embodiments, a target receptor is a androgen receptor.

As used herein, the term "selective binding compound" refers to a compound that selectively binds to any portion of one or more target receptors.

As used herein, the term "selectively binds" refers to the ability of a selective binding compound to bind to a target receptor with greater affinity than it binds to a non-target receptor. In certain embodiments, specific binding refers to binding to a target with an affinity that is at least 2, 5, 10, 25, 50, 75, 100, 150, 200, 250, 500, 1000 or more times greater than the affinity for a non-target.

As used herein, the term "androgen receptor selective binding compound" refers to a compound that selectively interacts with an androgen receptor with a greater affinity than it with a non-androgen receptor, such as, but not limited to, a progesterone receptor (PR), estrogen receptor (ER), glucocorticoid receptor (GR), mineralocorticoid receptor (MR), retinoic acid receptor (RAR), rexinoid receptor (RXR), or peroxisome proliferator-activated receptor (PPAR). In certain embodiments, an androgen receptor selective binding compound binds to an androgen receptor with an affinity that is at least 5, 10, 25, 50, 75, 100, 150, 200, 250, 500, 1000 or more times greater than the affinity for a non-androgen receptor. In some embodiments, the compounds provided herein are androgen receptor selective binding compounds.

As used herein, "treating a subject having a disease or condition" means that a compound, composition or other product provided herein is administered to the subject.

As used herein, the terms "treat" and "treating" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms. The term treatment also is intended to include prophylactic treatment.

As used herein, the term "treatment" means any manner in which the symptoms of a condition, disorder or disease are ameliorated or otherwise beneficially altered. Hence, treatment encompasses prophylaxis, therapy and/or cure. Treatment also encompasses any pharmaceutical use of the compositions herein.

As used herein, the term "therapeutic agent" refers to conventional drugs and drug therapies, including vaccines, which are known to those skilled in the art.

As used herein, amelioration of the symptoms of a particular disease or disorder by a treatment, such as by administration of a compound provided herein or a pharmaceutical composition thereof or other therapeutic agent, refers to any lessening, whether permanent or temporary, lasting or transient, of the symptoms that can be attributed to or associated with administration of the composition or therapeutic.

As used herein, prevention or prophylaxis refers to methods in which the risk of developing disease or condition is reduced. Prophylaxis includes reduction in the risk of developing a disease or condition and/or a prevention of worsening of symptoms or progression of a disease or reduction in the risk of worsening of symptoms or progression of a disease.

As used herein, an effective amount of a compound or composition for treating a particular disease is an amount that is sufficient to ameliorate, or in some manner reduce the symptoms associated with the disease. Such amount can be administered as a single dosage or can be administered according to a regimen, whereby it is effective. The amount can cure the disease but, typically, is administered in order to ameliorate the symptoms of the disease. Typically, repeated administration is required to achieve a desired amelioration of symptoms.

As used herein, "therapeutically effective amount" or "therapeutically effective dose" refers to an agent, compound, material, or composition containing a compound that is at least sufficient to produce a therapeutic effect. An effective amount is the quantity of a therapeutic agent necessary for preventing, curing, ameliorating, arresting or partially arresting a symptom of a disease or disorder.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient, that can be attributed to or associated with administration of the compound or composition.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments, the presence of a modulator results in an activity that does not occur in the absence of the modulator.

As used herein, the term "selective modulator" refers to a compound that selectively modulates a target activity.

As used herein, "selective androgen receptor modulator" or "SARM" is a compound that mimics the action of a natural androgen receptor ligand in some tissues but not in others. SARMs are compounds that elicit androgen agonism in one or more target tissues (e.g., muscle and/or bone) and antagonism and/or minimal agonism or no effect in other tissues (e.g., skin, prostate). SARMs exhibit tissue selective androgen agonism. Among the compounds provided herein, are those that are SARMs that exhibit agonistic anabolic properties and antagonistic androgenic properties in selected tissues. Others of the compounds are SARMs that are AR agonists in some tissues and cause increased transcription of AR-responsive genes (e.g., muscle anabolic effect). In other tissues, compounds are competitive inhibitors of androgens such as testosterone on the AR and thereby prevent agonistic effects of the native androgens. For example, compounds provided herein are SARMs that have agonist activity in muscle and demonstrate antagonist activity in a gonad of a subject. SARMs that demonstrate such activity can increase muscle mass and decrease fat in subjects without causing androgenic side effects, such as sebaceous gland stimulation.

As used herein, "tissue selective androgen receptor agonism" refers to the ability of a SARMs compound to agonize an androgen receptor of one (or more than one) target tissue with greater affinity than it agonizes an androgen receptor of a non-target tissue.

In certain embodiments, tissue selective androgen receptor agonism refers to agonism of an AR of a target tissue that is at least about or 2 fold up to more than about or 500 fold, greater than the androgen receptor agonism of an androgen receptor of a non-target tissue.

In certain embodiments, tissue selective androgen receptor agonism refers to agonism of an AR of a target tissue that is at least 2, 5, 10, 15, 20, 25, 30, 50, 60, 75, 100, 125, 150, 175, 200, 225, 250, 275, 300, 350, 400, 450, 500, 600, 700, 800, 900 or 1000 or more times greater than the androgen receptor agonism of an androgen receptor of a non-target tissue. For example, SARMs can exhibit agonism of an AR receptor in muscle tissue and antagonism of the AR in prostate tissue.

As used herein, "tissue selective androgen receptor antagonism" refers to the ability of a SARMs compound to antagonize an androgen receptor of one (or more than one) target tissue with greater affinity than it antagonizes an androgen receptor of a non-target tissue. In certain embodiments, tissue selective androgen receptor antagonism refers to antagonism of an AR of a target tissue that is at least about or 2 fold up to more than about or 500 fold, greater than the androgen receptor agonism of an androgen receptor of a non-target tissue. In certain embodiments, tissue selective androgen receptor antagonism refers to antagonism of an AR of a target tissue that is at least 2, 5, 10, 15, 20, 25, 30, 50, 60, 75, 100, 125, 150, 175, 200, 225, 250, 275, 300, 350, 400, 450, 500, 600, 700, 800, 900 or 1000 or more times greater than the androgen receptor antagonism of an androgen receptor of a non-target tissue. For example, SARMs can exhibit antagonist activity against hormone-dependent tumors while exhibiting no activity, or in some instances agonist activity, against other non-tumor tissues containing the androgen receptor.

As used herein, the term "selectively modulates" refers to the ability of a selective modulator to modulate a target activity to a greater extent than it modulates a non-target activity. In certain embodiments the target activity is selectively modulated by, for example about or 2 fold up to more than about or 500 fold, in some embodiments, about or 2, 5, 10, 25, 50, 75, 100, 150, 200, 250, 300, 350, 400, 450 or more than 500 fold.

As used herein, an "activity" of a SARMS compound provided herein refers to any activity exhibited by a selective androgen modulator. Such activities can be tested in vitro and/or in vivo and include, but are not limited to, agonism or antagonism of an androgen receptor. Activity can be assessed in vitro or in vivo using recognized assays, for example, by using the co-transfection assay. The results of such assays that indicate that a compound exhibits an activity can be correlated to activity of the compound in vivo, in which in vivo activity can be referred to as biological activity. Assays to determine functionality or activity of androgen receptor modulators, including selective androgen receptor modulator compounds, are known to those of skill in the art. Exemplary assays include, but are not limited to, fluorescence polarization assay, luciferase assay and co-transfection assay. In certain embodiments, the compounds provided herein are capable of modulating activity of androgen receptor in a "co-transfection" assay (also called a "cis-trans" assay), which is known in the art (see e.g., Evans et al., Science 240: 889-895 (1988); U.S. Pat. Nos. 4,981,784 and 5,071,773; and Pathirana et al., "Nonsteroidal Human Progesterone Receptor Modulators from the Marie Alga Cymopolia Barbata,"*Mol. Pharm.* 47: 630-35 (1995)).

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein a biological activity of a selective androgen receptor modulator encompasses the agonism or antagonism of an androgen receptor.

As used herein, the term "assess" and grammatical variations thereof, is intended to include quantitative and qualitative determination in the sense of obtaining an absolute value for the activity of a compound, and also of obtaining an index, ratio, percentage, visual or other value indicative of the level of the activity. Assessment can be direct or indirect.

As used herein, the term "targeting agent" refers to any moiety, such as a protein or effective portion thereof, that provides specific binding to a cell surface molecule, such a cell surface receptor, which in some instances can internalize a bound conjugate or portion thereof. A targeting agent also can be one that promotes or facilitates, for example, affinity isolation or purification of the conjugate; attachment of the conjugate to a surface; or detection of the conjugate or complexes containing the conjugate.

As used herein, derivative or analog of a molecule refers to a portion derived from or a modified version of the molecule. In some embodiments, a derivative includes, but is not limited, to acid derivatives, amide derivatives, ester derivatives and ether derivatives. In other embodiment, the SARM compounds provided herein are hydrates, including hemihydrate, monohydrate, dehydrate and trihydrate.

As used herein, the term "disease" or "disorder" refers to a pathological condition in an organism resulting from cause or condition including, but not limited to, infections, acquired conditions, genetic conditions, and characterized by identifiable symptoms. Diseases and disorders also include those that are caused by the absence of a compound, such as an androgen agonist.

As used herein, "patient" or "subject" to be treated includes humans and or non-human animals, including mammals. Mammals include primates, such as humans, chimpanzees, gorillas and monkeys; domesticated animals, such as dogs, horses, cats, pigs, goats, cows; and rodents such as mice, rats, hamsters and gerbils.

As used herein, "animal" includes any animal, such as, but not limited to; primates including humans, gorillas and monkeys; rodents, such as mice and rats; fowl, such as chickens; ruminants, such as goats, cows, deer, sheep; ovine, such as pigs and other animals. Non-human animals exclude humans as the contemplated animal.

As used herein, a "combination" refers to any association between two or among more items. The association can be spatial or refer to the use of the two or more items for a common purpose.

As used herein, a "composition" refers to any mixture of two or more products or compounds (e.g., agents, modulators, regulators, etc.). It can be a solution, a suspension, liquid, powder, a paste, aqueous or non-aqueous formulations or any combination thereof.

As used herein, a "fluid" refers to any composition that can flow. Fluids thus encompass compositions that are in the form of semi-solids, pastes, solutions, aqueous mixtures, gels, lotions, creams and other such compositions.

As used herein, a "kit" refers to a packaged combination, optionally including reagents and other products and/or components for practicing methods using the elements of the combination. For example, kits containing a compound provided herein and another item for a purpose including, but not limited to, administration, diagnosis, and assessment of a biological activity or property are provided. Kits optionally include instructions for use.

As used herein, an "article of manufacture" is a product that is made and sold. As used throughout this application, the term is intended to encompass compounds of formulae I, II or III contained in articles of packaging.

As used herein, the term "target activity" refers to a target activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "mediate" means affect or influence. Thus, for example, conditions mediated by an androgen receptor are those in which an androgen receptor plays a role. Androgen receptors are known to play a role in conditions including, for example, acne, aging skin, male-pattern baldness, sexual dysfunction, impotence, depression, wasting diseases, HIV-wasting, frailty, cognitive decline, Alzheimer's disease, sleep apnea, hirsutism, hypogonadism, premature ovarian failure, inflammatory arthritis and joint repair, osteopenia, osteoporosis, glucocorticoid-induced osteoporosis, bone fracture, bone damage following bone reconstructive surgery, atherosclerosis, hypercholesterolemia, hyperlipidemia, aplastic anemia and other hematopoietic disorders, obesity, abdominal adiposity, metabolic syndrome, type II diabetes, muscular dystrophies, periodontal disease, sarcopenia, postmenopausal symptoms in women, prostatic hyperplasia, prostate cancer, benign prostatic hyperplasia (BPH), cancer cachexia, and hormone-dependent cancers.

As used herein, the term "receptor mediated activity" refers any biological activity that results, either directly or indirectly, from binding of a ligand to a receptor.

As used herein, the term "agonist" refers to a compound, the presence of which results in an activity of a receptor that is the same as the activity resulting from the presence of a naturally occurring ligand for the receptor. An agonist of the androgen receptor can bind to the androgen receptor and initiate a physiological or a pharmacological response characteristic of that receptor. A "full agonist" induces full activation of the androgen receptor population at a given concentration.

As used herein, the term "partial agonist" refers to a compound the presence of which results in a biological activity of a receptor that is of the same type as that resulting from the presence of a naturally occurring ligand for the receptor, but of a lower magnitude. A "partial agonist" is an agonist that is unable to induce maximal activation of the receptor population, regardless of the amount of compound applied.

As used herein, the term "antagonist" refers to a compound, the presence of which results in a decrease in the magnitude of an activity of a receptor. In certain embodiments, the presence of an antagonist results in complete inhibition of an activity of a receptor. In another embodiment, the compound binds to androgen receptor and blocks or inhibits the androgen-associated responses normally induced by a natural androgen receptor ligand.

As used herein, the $IC_{50}$ refers to an amount, concentration or dosage of a particular test compound that achieves a 50% inhibition of a maximal response, such as modulation of androgen receptor activity, in an assay that measures such response. $IC_{50}$ also refers to the concentration of test compound required to decrease specific binding by 50%. $IC_{50}$ values can be determined using the log-logit (Hill) method.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, $K_i$ values can be determined using the Cheng-Prusoff equation using a previously determined $K_d$ value for the steroid, such as dihydrotestosterone:

$$K_i = IC_{50}/(1+[L]/K_d)$$

where [L]=concentration of labeled steroid and $K_d$=dissociation constant of labeled steroid. For a discussion of the calculation of $K_i$, see e.g., Cheng, Y. C. and Prusoff, W. H. *Biochem. Pharmacol.* 22: 3099 (1973).

As used herein, the term "carrier" refers to a compound that facilitates the incorporation of another compound into cells or tissues. For example, dimethyl sulfoxide (DMSO) is a carrier commonly used for improving incorporation of certain organic compounds into cells or tissues.

As used herein, the term "pharmaceutical composition" refers to a chemical compound or composition capable of inducing a desired therapeutic effect in a subject. In certain embodiments, a pharmaceutical composition includes an active agent, which is the agent that induces the desired therapeutic effect. In certain embodiments, a pharmaceutical composition includes a prodrug. In certain embodiments, a pharmaceutical composition includes inactive ingredients such as carriers and excipients.

As used herein, a "prodrug" refers to a compound that is converted from a less active form into a corresponding more active form in vivo. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady, *Medicinal Chemistry A Biochemical Approach*, Oxford University Press, New York, pages 388-392 (1985)). Conventional procedures for the selection and preparation of suitable prodrug derivatives are described, for example, in *Design of Prodrugs*, (ed. H. Bundgaard, Elsevier, 1985), which is hereby incorporated herein by reference in its entirety. A non-limiting example of a prodrug for use herein includes those that promote the solubility of alcohols such as by the procedures described in Mahfous, N. H. et al, J. Pharm. Pharmacol. 53: 841-848 (2001) and Bundgaard, H. et al., J. Med. Chem. 32: 2503-2507 (1989), both of which are incorporated herein by reference in their entirety. Prodrugs include compounds where hydroxy, ester, amine or sulfhydryl groups are bonded to any group that, when administered to a mammalian subject, cleaves to form a free hydroxyl, ester, amino, or sulfhydryl group, respectively. Examples of prodrugs include, but are not limited to, acetate, formate and benzoate derivatives of alcohol functional groups within the compounds provided herein.

As used herein, the term "ester" refers to a chemical moiety with formula $—(R)_n—COOR'$, where R and R' are independently selected from the group consisting of alkyl, cycloalkyl, aryl, heteroaryl (bonded through a ring carbon), a non-aromatic heterocycle, arylalkyl or heteroarylalkyl, and where n is 0 or 1.

Any hydroxy side chain on the compounds described herein can be esterified. The procedures and specific groups to be used to achieve this end are known to those of skill in the art and can readily be found in reference sources such as Greene and Wuts, *Protective Groups in Organic Synthesis* (3rd ed., John Wiley & Sons, New York, N.Y. (1999)).

An example of a prodrug is a "prodrug ester" or "ester derivative" of the compounds disclosed herein, which are formed by the addition of any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in, for example, T. Higuchi and V. Stella, in "*Prodrugs as Novel Delivery Systems*", Vol. 14, A.C.S. Symposium Series, American Chemical Society (1975); and "*Bioreversible Carriers in Drug Design: Theory and Application*", edited by E. B. Roche, Pergamon Press: New York, 14-21 (1987).

As used herein, the term "pharmaceutically acceptable formulation" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, "pharmaceutically acceptable derivative" refers to derivatives of a compound that does not significantly abrogate the biological activity, a pharmacological activity and/or other properties of the compound when the formulated compound is administered to a subject, and include, but are not limited to, salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs.

As used herein, the term "pharmaceutically acceptable salt" is intended to include all salts known and used in the art of pharmaceuticals. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzyl-phenethylamine, 1-para-chloro-benzyl-2-pyrrolidin-1'-ylmethyl-benzimidazole, diethylamine and other alkylamines, piperazine and tris(hydroxy-methyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Exemplary pharmaceutically acceptable salts include acetate, lactobionate, benzenesulfonate, laurate, benzoate, malate, bicarbonate, maleate, bisulfate, mandelate, bitartrate, mesylate, borate, methylbromide, methylnitrate, calcium edetate, methylsulfate, camsylate, mucate, carbonate, napsylate, bromide, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate and valerate, which can be used as a dosage form for modifying the solubility or hydrolysis characteristics or can be used in sustained release or prodrug formulations. The preparation of the pharmaceutically acceptable salts described above and other typical pharmaceutically acceptable salts is more fully described by Berg et al., "Pharmaceutical Salts," J. Pharm. Sci. 66: 1-19 (1977).

Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about or 100, or 1 to about or 10, or one to about or 2, 3 or 4, solvent or water molecules.

As used herein, the term "alkyl" refers to straight or branched chain substituted or unsubstituted hydrocarbon groups, in one embodiment 1 to 40 carbon atoms, in another embodiment, 1 to 20 carbon atoms, in another embodiment, 1 to 10 carbon atoms. The expression "lower alkyl" refers to an alkyl group of 1 to 6 carbon atoms. An alkyl group can be a "saturated alkyl," meaning that it does not contain any alkene or alkyne groups and in certain embodiments, alkyl groups are optionally substituted. An alkyl group can be an "unsaturated alkyl," meaning that it contains at least one alkene or alkyne group. An alkyl group that includes at least one carbon-carbon double bond (C=C) also is referred to by the term "alkenyl," and in certain embodiments, alkenyl groups are optionally substituted. An alkyl group that includes at least one carbon-carbon triple bond (C≡C) also is referred to by the term "alkynyl," and in certain embodiments, alkynyl groups are optionally substituted.

In certain embodiments, an alkyl contains 1 to 20 carbon atoms (whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated). An alkyl can be designated as "$C_1$-$C_4$ alkyl" or by similar designations. By way of example only, "$C_1$-$C_4$ alkyl" indicates an alkyl having one, two, three, or four carbon atoms, i.e., the alkyl is selected from among methyl, ethyl, propyl, iso-propyl, n-butyl, iso-butyl, sec-butyl and t-butyl. Thus "$C_1$-$C_4$" includes $C_1$-$C_2$, $C_1$-$C_3$, $C_2$-$C_3$ and $C_2$-$C_4$ alkyl. Alkyls include, but are not limited to, methyl, ethyl, propyl, isopropyl, butyl, isobutyl, tertiary butyl, pentyl, hexyl, ethenyl, propenyl, butenyl, hexenyl, ethynyl, propynyl, butynyl and hexynyl.

As used herein, the term "haloalkyl" alone or in combination refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another. Certain haloalkyls are saturated haloalkyls, which do not include any carbon-carbon double bonds or any carbon-carbon triple bonds. Certain haloalkyls are haloalkenes, which include one or more carbon-carbon double bonds. Certain haloalkyls are haloalkynes, which include one or more carbon-carbon triple bonds. In certain embodiments, haloalkyls are optionally substituted.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

As used herein, "pseudohalogen" refers to compounds that behave substantially similar to halides/halogens. Such compounds can be used in the same manner and treated in the same manner as halides/halogens (X-, in which X is a halogen, such as Cl, F or Br). Pseudohalogens include, but are not limited to, cyanide, cyanate, thiocyanate, selenocyanate, trifluoromethoxy, trifluoromethyl and azide.

As used herein, "cycloalkyl" refers to a saturated mono- or multicyclic ring system where each of the atoms forming a ring is a carbon atom. Cycloalkyls can be formed by three, four, five, six, seven, eight, nine, or more than nine carbon atoms. In one embodiment, the ring system includes 3 to 12 carbon atoms. In another embodiment, they ring system includes 3 to 6 carbon atoms. The term "cycloalkyl" includes rings that contain one or more unsaturated bonds. As used herein, the terms "cycloalkenyl" and "cycloalkynyl" are unsaturated cycloalkyl ring system. Cycloalkyls can be optionally substituted. In certain embodiments, a cycloalkyl contains one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane and cycloheptene.

As used herein, the term "aryl" refers to a monocyclic, bicyclic or tricyclic aromatic system that contains no ring heteroatoms. Where the systems are not monocyclic, the term aryl includes for each additional ring the saturated form (perhydro form) or the partially unsaturated form (for example the dihydro form or tetrahydro form) or the maximally unsaturated (nonaromatic) form. In some embodiments, the term aryl refers to bicyclic radicals in which the two rings are aromatic and bicyclic radicals in which only one ring is aromatic. Examples of aryl include phenyl, naphthyl, anthracyl, indanyl, 1,2-dihydro-naphthyl, 1,4-dihydronaphthyl, indenyl, 1,4-naphthoquinonyl and 1,2,3,4-tetrahydronaphthyl.

Aryl rings can be formed by three, four, five, six, seven, eight, nine, or more than nine carbon atoms. In some embodiments, aryl refers to a 3-, 4-, 5-, 6-, 7-, 8-, 9-, 10-, 11-, 12-, 13- or 14-membered, aromatic mono-, bi- or tricyclic system. In some embodiments, aryl refers to an aromatic $C_3$-$C_9$ ring. In some embodiments, aryl refers to an aromatic $C_4$-$C_8$ ring. Aryl groups can be optionally substituted.

As used herein, the term "heteroaryl" refers to an aromatic ring in which at least one atom forming the aromatic ring is a heteroatom. Heteroaryl rings can be formed by three, four, five, six, seven, eight, nine and more than nine atoms. Heteroaryl groups can be optionally substituted. Examples of heteroaryl groups include, but are not limited to, aromatic $C_{3-8}$ heterocyclic groups containing one oxygen or sulfur atom, or two oxygen atoms, or two sulfur atoms or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl is selected from among oxazolyl, isoxazolyl, oxadiazolyl, thiazolyl, isothiazolyl, pyridinyl, pyridazinyl, pyrimidinal, pyrazinyl, indolyl, benzimidazolyl, quinolinyl, isoquinolinyl, quinazolinyl or quinoxalinyl.

In some embodiments, a heteroaryl group is selected from among pyrrolyl, furanyl (furyl), thiophenyl (thienyl), imidazolyl, pyrazolyl, 1,2,3-triazolyl, 1,2,4-triazolyl, 1,3-oxazolyl (oxazolyl), 1,2-oxazolyl (isoxazolyl), oxadiazolyl, 1,3-thiazolyl (thiazolyl), 1,2-thiazolyl (isothiazolyl), tetrazolyl, pyridinyl (pyridyl) pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, benzodioxolyl, acridinyl, quinolinyl, isoquinolinyl, quinazolinyl, quinoxalinyl, phthalazinyl, thienothiophenyl, 1,8-naphthyridinyl, other naphthyridinyls, pteridinyl or phenothiazine. Where the heteroaryl group includes more than one ring, each additional ring is the saturated form (perhydro form) or the partially unsaturated form (for example the dihydro form or tetrahydro form) or the maximally unsaturated (nonaromatic) form. The term heteroaryl thus includes bicyclic radicals in which the two rings are aromatic and bicyclic radicals in which only one ring is aromatic. Such examples of heteroaryl are include 3H-indolinyl, 2(1H)-quinolinonyl, 4-oxo-1,4-dihydroquinolinyl, 2H-1-oxoisoquinolyl, 1,2-dihydroquinolinyl, (2H)quinolinyl N-oxide, 3,4-dihydroquinolinyl, 1,2-dihydroiso-quinolinyl, 3,4-dihydro-isoquinolinyl, chromonyl, 3,4-dihydroiso-quinoxalinyl, 4-(3H)quinazolinonyl, 4H-chromenyl, 4-chromanonyl, oxindolyl, 1,2,3,4-tetrahydro-isoquinolinyl, 1,2,3,4-tetrahydro-quinolinyl, 1H-2,3-dihydroisoindolyl, 2,3-dihydrobenzosoindolyl, 1,2,3,4-tetrahydro-benzo[g]isoquinolinyl, 1,2,3,4-tetrahydro-benzo[g]isoquinolinyl, chromanyl, isochromanonyl, 2,3-dihydro-chromonyl, 1,4-benzo-dioxanyl, 1,2,3,4-tetrahydro-quinoxalinyl, 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, 1,4-naphthoquinolyl, 5,6,7,8-tetrahydro-quinolinyl, 5,6,7,8-tetrahydro-isoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydro-benzoxazolyl, 1H-4-oxa-1,5-diazanaphthalen-2-onyl, 1,3-dihydro-imidizolo-[4,5]-pyridin-2-onyl, 2,3-dihydro-1,4-dinaphthoquinonyl, 2,3-dihydro-1H-pyrrol[3,4-b]quinolinyl, 1,2,3,4-tetrahydrobenzo[b]-[1,7]naphthyridinyl, 1,2,3,4-tetra-hydrobenz-[b][1,6]-naphthyridinyl, 1,2,3,4-tetrahydro-9H-pyrido[3,4-b]indolyl, 1,2,3,4-tetrahydro-9H-pyrido[4,3-b]indolyl, 2,3-dihydro-1H-pyrrolo-[3,4-b]indolyl, 1H-2,3,4,5-tetrahydro-azepino[3,4-b]indolyl, 1H-2,3,4,5-tetrahydroazepino-[4,3-b]indolyl, 1H-2,3,4,5-tetrahydroazepino[4,5-b]indolyl, 5,6,7,8-tetrahydro-[1,7]-napthyridinyl, 1,2,3,4-tetrahydro-[2,7]-naphthyridyl, 2,3-dihydro[1,4]dioxino[2,3-b]pyridyl, 2,3-dihydro[1,4]-dioxino[2,3-b]pyridyl, 3,4-dihydro-2H-1-oxa[4,6]-diazanaphthalenyl, 4,5,6,7-tetrahydro-3H-imidazo[4,5-c]pyridyl, 6,7-dihydro[5,8]-diazanaphthalenyl, 1,2,3,4-tetrahydro[1,5]-napthyridinyl, 1,2,3,4-tetrahydro[1,6]-napthyridinyl, 1,2,3,4-tetrahydro[1,7]-napthyridinyl, 1,2,3,4-tetrahydro-[1,8]-napthyridinyl or 1,2,3,4-tetrahydro[2,6]-napthyridinyl. In some embodiments, heteroaryl groups are optionally substituted. In one embodiment, the one or more substituents are each independently selected from among halo, hydroxy, amino, cyano, nitro, alkylamido, acyl, $C_{1-6}$-alkoxy, $C_{1-6}$-alkyl, $C_{1-6}$-haloalkyl, $C_{1-6}$-hydroxyalkyl, $C_{1-6}$-aminoalkyl, $C_{1-6}$-alkylamino, alkylsulfenyl, alkylsulfinyl, alkyl sulfonyl, sulfamoyl, or trifluoromethyl.

Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline and quinoxaline. In some embodiments, the substituents are halo, hydroxy, cyano, O—$C_{1-6}$-alkyl, $C_{1-6}$-alkyl, hydroxy-$C_{1-6}$-alkyl and amino-$C_{1-6}$-alkyl.

As used herein, the term "arylalkyl" alone or in combination, refers to an alkyl substituted with an aryl that can be optionally substituted.

As used herein, the term "heteroarylalkyl" alone or in combination, refers to an alkyl substituted with a heteroaryl that is optionally substituted.

As used herein, the term "optionally substituted," refers to a group in which none, one, or more than one of the hydrogen atoms has been replaced with one or more group(s) individually and independently selected from among alkyl, cycloalkyl, heteroalkyl, aryl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, C-amido, N-thiocarbamyl, N-amido, S-sulfonamido, N-sulfonamido, C-carboxy, O-carboxy, isocyanato, thiocyanato, isothiocyanato, nitro, silyl, trihalomethanesulfonyl, and amino, including mono and di substituted amino groups, and the protected derivatives of amino groups. Such protective derivatives (and protecting groups that can form such protective derivatives) are known to those of skill in the art and can be found in references such as Greene and Wuts (*Protective Groups in Organic Synthesis*, 3$^{rd}$ ed., John Wiley & Sons, New York, N.Y., 1999), which is incorporated herein in its entirety. In embodiments in which two or more hydrogen atoms have been substituted, the substituent groups can together form a ring.

As used herein, the term "non-aromatic heterocycle" refers to a non-aromatic ring wherein one or more atoms forming the ring is a heteroatom. Non-aromatic heterocyclic rings can be formed by three, four, five, six, seven, eight, nine, or more than nine atoms. Non-aromatic heterocycles can be optionally substituted. In certain embodiments, non-aromatic heterocycles contain one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiine, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidi one, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine and 1,3-oxathiolane.

Throughout the specification, groups and substituents thereof can be chosen by one skilled in the field to provide stable moieties and compounds.

It is to be understood that the compounds provided herein can contain chiral centers. Such chiral centers can be of either the (R) or (S) configuration, or can be a mixture thereof. Thus, the compounds provided herein can be enantiomerically pure or be stereoisomeric or diastereomeric mixtures.

As used herein, "enantiomer" refers to one of a pair of molecular entities that are mirror images of each other and non-superimposable. Enantiomeric excess (ee) can be calculated for a mixture of (R) and (S)-enantiomers. The ee can be defined as the absolute value of the mole fractions of $F_{(R)}$ minus the mole fraction of $F_{(S)}$. The percent ee then is the absolute value of the mole fractions of $F_{(R)}$ minus the mole fraction of $F_{(S)}$ multiplied by 100.

As used herein, the term "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Thus, substantially pure object species (e.g., compound) is the predominant species present (i.e., on a molar basis it is more abundant than any other individual species in the composition). In certain embodiments, a substantially purified fraction is a composition wherein the object species includes at least about 50 percent (on a molar basis) of all species present. In certain embodiments, a substantially pure composition will include more than about or 50%, 60%, 70%, 80%, 85%, 90%, 95%, or 99% of all species present in the composition. In certain embodiments, a substantially pure composition will include more than about or 80%, 85%, 90%, 95%, or 99% of all species present in the composition. Methods for purification of the compounds to produce substantially chemically pure compounds are known to those of skill in the art. A substantially chemically pure compound can, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers can be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms also are intended to be included.

The compounds described herein can be administered alone or in combination with one or more than one other active ingredient or drug or agent. The individual components of the combination can be administered separately at different times during the course of therapy or concurrently in divided or single combination forms. As used herein, the term "co-administer" refers to administering more than one pharmaceutical agent to a subject. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times. The methods disclosed herein therefore are to be understood as embracing all such regimes of simultaneous or alternating treatment.

As used herein, "PO" refers to Per Os, meaning by mouth or orally.

As used herein, the term "subject" is an animal, typically a mammal, including human.

As used herein, the term "patient" includes human and animal subjects.

As used herein, the term "tissue-selective" refers to the ability of a compound to modulate a biological activity in one tissue to a greater or lesser degree than it modulates a biological activity in another tissue. The biological activities in the different tissues can be the same or they can be different. The biological activities in the different tissues can be mediated by the same type of target receptor. In certain embodiments, e.g., a tissue-selective compound can modulate an androgen receptor mediated biological activity in one tissue and fail to modulate, or modulate to a lesser degree, an androgen receptor mediated biological activity in another tissue type.

As used herein, the term "monitoring" refers to observing an effect or absence of any effect. In certain embodiments, one monitors cells after contacting those cells with a compound provided herein. Examples of effects that can be monitored include, but are not limited to, changes in cell phenotype, cell proliferation, androgen receptor activity, or the interaction between an androgen receptor and a natural binding partner.

As used herein, the term "cell phenotype" refers to physical or biological characteristics. Examples of characteristics that constitute phenotype included, but are not limited to, cell size, cell proliferation, cell differentiation, cell survival, apoptosis, or the utilization of a metabolic nutrient (e.g., glucose uptake). Certain changes or the absence of changes in cell phenotype are readily monitored using techniques known in the art.

As used herein, the term "contacting" refers to bringing two or more materials into close enough proximity whereby they can interact. In certain embodiments, contacting can be accomplished in a vessel such as a test tube, a petri dish, or the like. In certain embodiments, contacting can be performed in the presence of additional materials. In certain embodiments, contacting can be performed in the presence of cells. In certain of such embodiments, one or more of the materials that are being contacted can be inside a cell. Cells can be alive or can be dead. Cells can or can not be intact.

As used herein, "arthritic condition" or "arthritis" refers to a disease whose underlying etiology is inflammation of a joint, usually accompanied by pain, such as osteoarthritis and rheumatoid arthritis (Taber's Cyclopedic Medical Dictionary; 14$^{th}$ edition, 1983). The compounds disclosed herein are useful, alone or in combination, to treat or prevent arthritic conditions. Exemplary arthritic conditions include Behcet's disease; bursitis and tendinitis; CPPD deposition disease; carpal tunnel syndrome; Ehlers-Danlos syndrome; fibromyalgia; gout; infectious arthritis; inflammatory bowel disease; juvenile arthritis; lupus erythematosus; Lyme disease; Marfan syndrome; myositis; osteoarthritis; osteogenesis imperfecta; osteonecrosis; polyarteritis; polymyalgia rheumatica; psoriatic arthritis; Raynaud's phenomenon; reflex sympathetic dystrophy syndrome; Reiter's syndrome; rheumatoid arthritis; scleroderma; and Sjogren's syndrome. (Bijlsma et al., Am J Reprod Immunol 28(34): 231-234 (1992); Cutolo et al., Ann. N.Y. Acad. Sci. 966: 131-142 (2002); Cutolo, Rheum Dis Clin North Am 26(4): 881-895 (2000); Jansson et al., Arthritis Rheum 44(9): 2168-2175 (2001); Merck Manual (17$^{th}$ edition, pp. 449-451) and Purdie, Br Med Bull 56(3): 809-823 (2000)).

As used herein, "NSAIDs" refer to non-steroidal anti-inflammatory drugs. These drugs exhibit anti-inflammatory and analgesic effects and are commonly used to reduce inflammation and pain, including by decreasing prostaglandin production. Exemplary NSAIDs include, but are not limited to, aspirin, diclofenac/misoprostol, diclofenac potassium, diclofenac, diflunisal, etodolac, fenoprofen, flurbiprofen, ibuprofen, indomethacin, ketoprofen, meclofenamate, mefanamic acid, meloxicam, nabumetone, naproxen and naproxen sodium, oxaprozin, piroxicam, sodium sulindac and tolmetin.

As used herein, "COX-2 inhibitors" refers to drugs that inhibit only the inducible form of the Cyclooxygenase (COX) enzyme (EC 1.14.99.1), which is referred to as COX-2. These compounds are well known in the art (e.g., see PNAS, 89: 7384 (1992); Arch. Opthalmol. 108: 573 (1990); FEBS Letters 372: 83 (1995); Clin. Orthop. 313: 76 (1995); J. Mol. Endocrinol. 16: 107 (1996); Cancer Res. 57: 1625 (1997); Cell 93: 705 (1998); Intl. J. Mol. Med. 2: 715 (1998) and J. Biol. Chem. 274: 9116 (1999)). Exemplary COX-2 inhibitors include, but are not limited to, celecoxib, rofecoxib and valdecoxib.

As used herein, "DMARDs (Disease-Modifying Anti-Rheumatic Drugs)" refer to drugs that function by acting upon the immune system of a subject to slow or stop the underlying processes that cause certain forms of inflammatory arthritis, including rheumatoid arthritis (RA), ankylosing spondylitis, and psoriatic arthritis. DMARDs have been shown to be effective in the treatment of rheumatoid arthritis, psoriatic arthritis, and ankylosing spondylitis and, for some subjects, these drugs can stop progression of the disease. Exemplary DMARDs include, but are not limited to, adalimumab, leflunomide, auranofin, sodium aurothiomalate, chloroquine, etanercept, infliximab, sulfasalazine, mycophenolate, myochrysine, cyclosporine, cyclophosphamide, azathioprine, chlorambucil, methotrexate, minocycline, penicillamine and hydroxychloroquine.

As used herein, "photodynamic therapy dyes" refers to any of the conjugated or unconjugated dyes or pigments used in photodynamic therapy. The photodynamic therapy dyes include porphyrins, chlorines, purpurins, benzoporphyrins and other dyes and pigments that absorb light of a particular wavelength, thereby initiating tumor necrosis presumably through formation of singlet oxygen or other destructive chemical species. Photodynamic therapy for the treatment of cancer is well known in the art (e.g., see U.S. Pat. Nos. 7,018,395, 7,011,812, 6,806,284, 6,723,750, 6,710,066 and 6,630,128).

As used herein, "toxins and cytotoxic drugs" refers to chemical molecules that are known to affect the growth and action of some cells, and in some instances leads to the death of the cell when the cells are exposed to the chemical molecules. Exemplary toxins and cytotoxic agents include, but are not limited to, adrenocortical suppressants, such as mitotane; alkyl sulfonates, such as busulfan; ethylenimine derivatives, such as thiotepa; nitrosoureas, such as carmustine, lomustine, semustine and streptozocin; folic acid analogs, such as methotrexate; methyl hydrazine derivatives, such as procarbazine; nitrogen mustards, such as mechlorethamine, cyclophosphamide, melphalan, uracil mustard and chlorambucil; purine analogs, such as mercaptopurine and thioguanine; pyrimidine analogs, such as fluorouracil, cytarabine and azaribine; substituted urea compounds, such as hydroxyurea; taxol; triazenes, such as dacarbazine; and *vinca* alkaloids, such as vinblastine and vincristine.

As used herein, an "anti-proliferative agent" refers to any agent that reduces the rate or level of cellular proliferation. The agent can reduce proliferation by inducing apoptosis, modulating cellular microtubule structure (e.g., promoting microtubule polymerization), inhibiting tyrosine kinase mediated signaling, antagonizing cell surface receptor binding (e.g., EGFR and VEGFR inhibitors), modulating glucocorticoid receptor functioning, down-regulating angiogenesis (e.g., inhibiting VEGF functioning) or inducing cell death.

As used herein, an "anti-tumor agent" refers to any agent that limits the growth of or destroys a tumor, and includes the following classes of compounds: angiogenesis inhibitors, DNA intercalators/cross-linkers, DNA synthesis inhibitors, DNA-RNA transcription regulators, enzyme inhibitors, gene regulators and microtubule inhibitors.

As used herein, "angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclo-oxygenase-2 inhibitors like celecoxib and rofecoxib, steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetyl-carbonyl)-fumagillol, thalidomide, angiostatin, troponin-1, angiotensin II antagonists (see Fernandez et al., J. Lab. Clin. Med. 105: 141-145 (1985)), and antibodies to VEGF (see, Nature Biotechnology 17: 963-968 (October 1999); Kim et al., Nature 362: 841-844 (1993), WO 00/44777 and WO 00/61186). Other therapeutic agents that modulate or inhibit angiogenesis include agents that modulate or inhibit the coagulation and fibrinolysis systems (see review in Clin. Chem. La. Med. 38: 679-692 (2000)). Examples of such agents that modulate or inhibit the coagulation and fibrinolysis pathways include, but are not limited to, heparin (see Thromb. Haemost. 80: 10-23 (1998)), low molecular weight heparins and carboxypeptidase U inhibitors (also known as inhibitors of active thrombin activatable fibrinolysis inhibitor [TAFIa]) (see Thrombosis Res. 101: 329-354 (2001)).

As used herein, "HMG-CoA reductase inhibitors" refers to inhibitors of 3-hydroxy-3-methylglutaryl-CoA reductase. Exemplary HMG-CoA reductase inhibitors include, but are not limited to, lovastatin (see U.S. Pat. Nos. 4,231,938, 4,294,926 and 4,319,039), simvastatin (see U.S. Pat. Nos. 4,444,784, 4,820,850 and 4,916,239), pravastatin (see U.S. Pat. Nos. 4,346,227, 4,537,859, 4,410,629, 5,030,447 and 5,180,589), fluvastatin (see U.S. Pat. Nos. 5,354,772, 4,911,165, 4,929,437, 5,189,164, 5,118,853, 5,290,946 and 5,356,896), atorvastatin (see U.S. Pat. Nos. 5,273,995, 4,681,893, 5,489,691 and 5,342,952) and cerivastatin, also known as rivastatin (see U.S. Pat. No. 5,177,080). The structural formulas of these and additional HMG-CoA reductase inhibitors are described at page 87 of M. Yalpani, "Cholesterol Lowering Drugs," Chemistry & Industry, pp. 85-89 and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds that have HMG-CoA reductase inhibitory activity.

As used herein, a "synthetic estrogen" refers to non-naturally occurring compounds that exhibit at least some of the properties of 17β-estradiol when administered to a subject. Exemplary synthetic estrogens include ethinyl estradiol, diethylstilbestrol (DES), chlorotrianisene, dienestrol, ethinyl estradiol and ethinyl estradiol 3-cyclopentyl ether.

As used herein, the term "estrogen receptor agonist" refers to a compound that acts at an estrogen receptor and has at least some of the same biological effects as 17β-estradiol. Compounds that act at an estrogen receptor to block the effects of 17β-estradiol are called "estrogen receptor antagonists." Compounds exhibiting such selectivity are termed "selective estrogen receptor modulators" or "SERMs." Exemplary SERMs include bazedoxifene, clomifene, fulvestrant, lasofoxifene, raloxifene, tamoxifen and toremifene.

As used herein, the term "osteoporosis" refers to the condition characterized by reduced bone mass and disruption of bone architecture, resulting in increased bone fragility and increased fracture risk, and decreased calcification or density of bone. Osteoporosis is a thinning of the bones with reduction in bone mass due to depletion of calcium and bone protein. In osteoporotic patients, bone strength is abnormal, with a resulting increase in the risk of fracture. The fracture can be in the form of cracking (as in a hip fracture) or collapsing (as in a compression fracture of the spine). The spine, hips, and wrists are common areas of osteoporosis-induced bone fractures, although fractures also can occur in other skeletal areas. Unchecked osteoporosis can lead to changes in posture, physical abnormality and decreased mobility. Osteoporosis can be identified by bone mineral density measurements.

As used herein, "osteopenia" refers to decreased calcification or density of bone.

As used herein, a "cathepsin inhibitor" refers to an inhibitor of cysteine protease. Cysteine proteases, such as cathepsins, are linked to a number of disease conditions, including arthritis, bone remodeling, inflammation and tumor metastasis. Cathepsin protease inhibitors can inhibit osteoclastic bone resorption by inhibiting the degradation of collagen fibers and thus are useful in the treatment of bone resorption diseases, such as osteoporosis. Examples of cathepsin inhibitors are described in Deaton, Current Topics in Medicinal Chemistry 5(16): 1639-1675 (2005), in U.S. Pat. Nos. 7,279,478, 7,279,472, 7,112,589 and 7,012,075, and in WO 01/49288 and WO 01/77073.

As used herein, a "proton pump inhibitor" refers to osteoclast vacuolar ATPase inhibitors. The proton ATPase found on the apical membrane of the osteoclast has been reported to play a significant role in the bone resorption process and is a target for the design of inhibitors of bone resorption, thereby useful for the treatment and prevention of osteoporosis and related metabolic diseases (e.g., see Niikura, Drug News Perspect. 19(3): 139-44 (2006), Visentin et al., J Clin Invest 106(2): 309-318 (2000) and Niikura et al., Br J of Pharmacology 142: 558-566 (2004)). Exemplary inhibitors include bafilomycin A1, SB242784, FR167356, FR177995, FR202126, FR133605 and NiK-12192 [4-(5,6-dichloro-1H-indol-2-yl)-3-ethoxy-N-(2,2,6,6-tetramethyl-piperidin-4-yl)-benzamide] (Petrangolini et al., J Pharmacol Exp Ther 318 (3): 939-946 (2006).

As used herein, "PPARγ activators" refers to activators of the peroxisome proliferator-activated receptor gamma (PPARγ), which are known in the art to inhibit osteoclast-like cell formation and bone resorption (e.g., see Okazaki et al., Endocrinology 140: 5060-5065 (1999)). Exemplary PPARγ activators include the glitazones, such as ciglitazone, darglitazone, englitazone, troglitazone, pioglitazone, rosiglitazone, the thiazolidinediones (see, e.g., Yki-Jarvinen, New Eng J Med 351(11): 1106-1118 (2004), netoglitazone, 15 deoxy-$\Delta_{12,14}$-prostaglandin $J_2$ and analogs, derivatives, and pharmaceutically acceptable salts thereof.

As used herein, "muscle wasting" refers to atrophy or loss of muscle tissue, which can result from disease or disuse (lack of exercise). As used herein, muscle wasting also includes loss of muscle tone and neurogenic atrophy. Muscle wasting is characterized by a weakening, shrinking, and loss of muscle tissue, often caused by degradation of the contractile myofibrillar proteins actin and myosin (e.g., see Hasselgren et al., Int'l J of Biochemistry & Cell Biology 37(10): 1932 (225); Lynch et al., Pharmacology & Therapeutics 113, (3): 461-487 (2007)).

As used herein, "chronic muscle wasting" refers to chronic (i.e., persisting over a long period of time) progressive loss of muscle mass and/or to the chronic progressive weakening and degeneration of muscle.

As used herein, "cachexia" refers to weakness and a loss of weight caused by a disease or as a side effect of illness. Cardiac cachexia, which includes muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass. Cachexia also occurs in acquired immunodeficiency syndrome (AIDS). Human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

As used herein, "sarcopenia" refers to a debilitating disease that afflicts the elderly and chronically ill patients and is characterized by loss of muscle mass and function.

As used herein, the term "obesity" refers to the state of being well above one's normal weight. Traditionally, a person is considered to be obese if they are more than 20 percent over their ideal weight. Obesity has been defined by the National Institute of Health (NIH) as a Body to Mass Index (BMI) of 30 or above. Overweight due to obesity is a significant contributor to health problems. It increases the risk of developing a number of diseases including, for example, type 2 diabetes, high blood pressure (hypertension), stroke, heart attack (myocardial infarction), heart failure, certain forms of cancer, such as prostate cancer and colon cancer, gallstones and gallbladder disease (cholecystitis), gout and gout-related arthritis, osteoarthritis (degenerative arthritis) of the knees, hips, and the lower back, sleep apnea and Pickwickian syndrome (obesity, red face, underventilation and drowsiness). As used herein, the term "obesity" includes any one of the above-listed obesity-related conditions and diseases.

As used herein, the term "cancer" or "neoplastic disease" refers to a broad group of malignant neoplasms, growth or tumor caused by abnormal and uncontrolled cell division, and includes carcinomas and sarcomas (*Taber's Cyclopedic Medical Dictionary*, 14$^{th}$ edition, 1983). In additional to their uncontrolled growth, cancer cells invade and destroy adjacent tissues and often metastasize to new sites within the body.

As used herein, the term "treating cancer" or "treatment of cancer" refers to administration of a treatment to a mammal afflicted with a cancerous condition and refers to an effect that alleviates the cancerous condition by killing the cancerous cells, as well as an effect that results in the inhibition of growth and/or metastasis of the cancer.

As used herein, the term "lipid profile" refers to total cholesterol, low density lipoprotein (LDL), high density lipoprotein (HDL), very low density lipoprotein (VLDL), and triglycerides in a subject. LDL, HDL and VLDL are the three types of lipoproteins found in the blood, and they usually represent the types of cholesterol found in the blood (cholesterol combined with a protein and triglyceride).

As used herein, the term "anemia" refers to the condition of having less than the normal number of red blood cells or less than the normal quantity of hemoglobin in the blood. Because of the decreased number of red blood cells or reduced quantity of hemoglobin, the oxygen-carrying capacity of the blood is decreased. A subject with anemia may feel tired and fatigue easily, appear pale, develop palpitations and become usually short of breath. There are many forms of anemia, including aplastic anemia, Fanconi anemia, hereditary spherocytosis, iron deficiency anemia, osteopetrosis, pernicious anemia, sickle cell disease, thalassemia, myelodysplastic syndrome, and a variety of bone marrow diseases.

As used herein, the term "depression" refers to an illness that involves the body, mood and thoughts, that affects the way a person eats and/or sleeps and the way one feels about oneself and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

As used herein, the term "sexual dysfunction" refers to impairment of the emotional or physical responses associated with sexual activity, including sexual desire disorders, sexual arousal disorders, orgasm disorders, and sexual pain disorders, which can prevent an individual from engaging in sexual activity or result in inadequate sexual functioning. Sexual dysfunction includes lack of sexual desire, anxiety about sexual performance, difficulty in becoming aroused, inability to achieve orgasm (anorgasmia), premature ejaculation, erectile dysfunction, impotence, frigidity, dyspareunia, vaginismus and dyspareunia (e.g., see American Society for Reproductive Medicine, "Sexual Dysfunction—Patient's Fact Sheet" (1998)).

As used herein, the term "male sexual dysfunction" includes impotence, loss of libido, orgasm dysfunction (e.g., premature ejaculation or retrograde ejaculation) and erectile dysfunction.

As used herein, the term "erectile dysfunction" refers to a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

As used herein, the term "female sexual dysfunction" includes dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an SARM compound provided herein can result in improved blood flow, improved lubrication, improved sensation, facilitation of reaching orgasm, reduction in the refractory period between orgasms, and improvements in arousal and desire.

As used herein, the term "libido" refers to sexual desire.

As used herein, the term "hypogonadism" refers to a condition resulting from or characterized by abnormally decreased functional activity of the gonads, with retardation of growth and sexual development.

As used herein, the term "cognition" refers to the process of knowing, specifically the process of being aware, knowing, thinking, learning and judging. As used herein, the term "mood" refers to a temper or state of the mind. As used herein, the term "alteration" or "alterations" refers to any change for the positive or negative, in cognition and/or mood.

As used herein, the term "hair loss" refers to alopecia, or baldness, such as in the common type of male-pattern baldness. Hair loss affects both males and females.

As used herein, "frailty" refers to an adverse, primarily gerontologic, health condition, characterized by low functional reserve, accelerated osteoporosis, easy tiring, decreased muscle strength, high susceptibility to disease and decreased libido (e.g., see Bandeen-Roche et al., The Journals of Gerontology Series A: Biological Sciences and Medical Sciences 61: 262-266 (2006)).

As used herein, "bioavailability" refers to the rate and extent to which the active substance or therapeutic moiety is absorbed from a pharmaceutical form and becomes available at the site of action or reaches systemic circulation. The "absolute bioavailability" of a given pharmaceutical form is compared to that following intravenous administration, which is by definition 100%. Administration by a route other than intravenous administration generally is less than 100%, due to slow or incomplete absorption, or metabolic destruction. "Good bioavailability" generally is >50% and "poor bioavailability" generally is <20%.

As used herein, "androgenic activity" refers to androgen receptor (AR) agonist activity in androgenic target tissues, such as prostate and seminal vesicles. Androgenic activity is typically demonstrated by increases in the weights of the prostate and seminal vesicles, which are accepted in the art as indicators of androgenic activity (e.g., see Lemus et al., J Steroid Biochem Mol Biol 60(1-2): 121-129 (1997)).

As used herein, "androgenic effect" or "androgenic effects" refers to producing or enhancing male traits, and includes producing side effects associated with administration of steroidal androgens such as testosterone. These adverse androgenic effects include manifestations such as prostate enlargement, acne, repression of high density lipoprotein cholesterol (HDL), hirsutism, virilization and masculinization.

As used herein, "anabolic activity" refers to increasing the mass and/or strength of a tissue, such as a connective tissue. Increases in the weight of the levator ani muscle are indicative of anabolic activity, and are accepted in the art as a reliable index of anabolic activity (e.g., see Antonio et al., J Appl Physiol 87: 2016-2019 (1999)). Anabolic activity in bone and muscle decreases bone fracture rates in a subject. Anabolic activity of the compounds provided herein on muscle can be tested by assessing expression of MHC subtypes in skeletal muscle (e.g., see Wright et al., J Appl Physiol. 83(4): 1389-96 (1997)). Bone formation rate, another indication of anabolic activity, can be assessed by osteocalcin level measurement. Plasma osteocalcin levels can be determined using any method known in the art (e.g., see Koyama et al., J Immunol Methods 139(1): 17-23 (1991)). A rat osteocalcin EIA kit is commercially available from Biomedical Technologies Inc. (Stoughton, Mass.).

As used herein, "connective tissue" refers to tissue generally of mesodermal origin that is characterized by a highly vascular matrix and which forms the supporting and connecting structures of the body. Connective tissue includes collagenous, elastic, and reticular fibers, muscle, adipose tissue, cartilage, and bone. Exemplary connective tissue includes adipose tissue, areolar tissue, blood, bone (including cancellous bone, compact bone, cortical bone, spongy bone and trabecular bone), bone marrow, cartilage, collagen, cutis, elastic tissue, endoneurium, fascia, ligament, mesenchymal connective tissue, mucous connective tissue, muscle, osseous tissue, perineurium, perimysium, submucosa and tendon.

As used herein, "bone mineral density" or "BMD" refers to the density of minerals (such as calcium) in bone. BMD is determined using a special X-ray, computed tomography (CT) scan, or ultrasound. This information is used to estimate the strength of bones. Increasing mineral content of bone increases the density of the bone and its strength. The denser the bone, the less likely it is to break.

As used herein, "unit dosage forms" refers to physically discrete units suitable for human and animal subjects. Each unit dosage includes a predetermined quantity of the therapeutically active compound sufficient to produce the desired therapeutic effect, in association with, when required, a pharmaceutical carrier, vehicle or diluent. Examples of unit dosage forms include tablets, capsules, pills, powders, granules, sterile parenteral solutions or suspensions, ampoules and syringes, and oral solutions or suspensions, and oil-water emulsions. Unit dosage forms can be individually packaged as is known in the art, such as in blister packs. Unit dosage forms can be administered in fractions or multiples thereof.

As used herein, "multiple dosage forms" refers to a plurality of identical unit dosage forms packaged in a single container to be administered in segregated unit dosage form. Examples of multiple dosage forms include vials, bottles of tablets or capsules or bottles of pints or gallons of liquid containing the active compound. Hence, a multiple dosage form is a multiple of unit dosages which are not segregated in packaging.

As used herein, "non-specific binding" refers to that binding remaining in the presence of an excess of unlabeled specific ligand (i.e., in the case of androgen receptor, 1000 nM of unlabeled dihydrotestosterone).

As used herein, "potency" refers to the dose of drug required to produce a specific effect of given intensity as compared to a standard reference.

As used herein, the term "AUC" refers to the area under the plasma concentration-time curve and can be used as a metric for extent of exposure of a pharmaceutical.

As used herein, the term "exposure" refers to AUC and the term "total exposure" refers to $AUC_{0-\infty}$.

As used herein, the term "$AUC_{0-\infty}$" or "$AUC_{0-inf}$" refers to the area under the concentration-time curve from time zero to infinity (extrapolated). $AUC_{0-\infty}$ can be calculated as $AUC_{0-t}+(C_t/K_{el})$ where $C_t$ is the calculation at time t.

As used herein, the term "$AUC_{0-t}$" refers to the area under the concentration-time curve from time zero to time of last non-zero (last measurable) concentration. The linear trapezoidal rule can be used to calculate $AUC_{0-t}$.

As used herein, the term "$AUC_x$" refers to the area under the concentration-time curve from time zero to x hours post dose. Thus, $AUC_6$ refers to the area under the concentration-time curve from time zero to 6 hours post-administration and $AUC_{24}$ refers to the area under the concentration-time curve from time zero to 24 hours post-administration.

As used herein, the term "$C_{MAX}$" refers to the maximum (peak) observed plasma concentration.

As used herein, the term "$C_{MIN}$" refers to the minimum observed plasma concentration, which also can be referred to as the trough concentration.

As used herein, the term "$T_{MAX}$" refers to the time to reach the maximum (peak) observed plasma concentration $C_{MAX}$.

As used herein, the term "apparent half-life" or "$t_{1/2}$" refers to the apparent time required for half the quantity of a drug or other substance administered to an organism to be metabolized or eliminated.

B. COMPOUNDS

Provided herein are compounds that have a structure of Formula I or Formula II or Formula III:

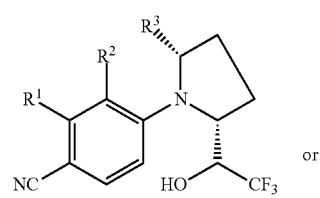

Formula I or

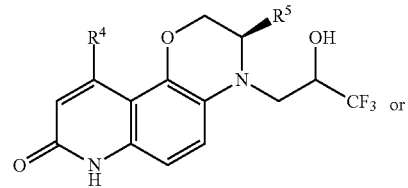

Formula II or

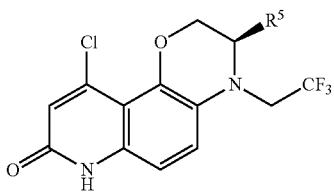

Formula III where R¹ is halogen, pseudohalogen, optionally substituted lower alkyl, optionally substituted haloalkyl or NO₂; R² is hydrogen, halogen, pseudohalogen, optionally substituted lower alkyl or optionally substituted lower haloalkyl; R³ is hydrogen, halogen, pseudohalogen, optionally substituted lower alkyl or optionally substituted lower haloalkyl; R⁴ is halogen or lower haloalkyl; and R⁵ is lower alkyl or lower haloalkyl; and pharmaceutically acceptable salts, esters and prodrugs thereof.

In one embodiment, R¹ is lower haloalkyl or halogen; R² is hydrogen or lower alkyl; R³ is hydrogen or lower alkyl; R⁴ is CF₃ or halogen; and R⁵ is C₁ to C₄ alkyl or C₁ to C₄ haloalkyl; and pharmaceutically acceptable salts, esters and prodrugs thereof. In one embodiment, R¹ is CF₃, F, or Cl; R² is H or methyl; R³ is H or methyl; R⁴ is Cl or CF₃; and R⁵ is methyl, ethyl or CF₃; and pharmaceutically acceptable salts, esters and prodrugs thereof.

For any and all of the embodiments, substituents can be selected from among a subset of the listed alternatives.

In certain embodiments, R¹ is CF₃. In certain embodiments, R¹ is F or Cl. In certain embodiments, R¹ is F. In certain embodiments, R¹ is Cl.

In certain embodiments, R² is H. In certain embodiments, R² is methyl.

In certain embodiments, R³ is H. In certain embodiments, R³ is methyl.

In certain embodiments, R⁴ is Cl. In certain embodiments, R⁴ is CF₃.

In certain embodiments, R⁵ is methyl or ethyl. In certain embodiments, R⁵ is methyl. In certain embodiments, R⁵ is ethyl. In certain embodiments, R⁵ is CF₃.

The compounds provided herein include:
R,R-4-(2-(1-Hydroxyl-2,2,2-trifluoroethyl)pyrrolidinyl)-2-trifluoromethylbenzonitrile;
4-(2(R)-(1(S)-hydroxyl-2,2,2-trifluoroethyl)pyrrolidinyl)-2-trifluoromethyl-benzonitrile;
R,R,R-4-(2-(1-Hydroxyl-2,2,2-trifluoroethyl)-5-methylpyrrolidinyl)-2-trifluoromethyl-benzonitrile;
R,R,R-4-(2-(1-Hydroxyl-2,2,2-trifluoroethyl)-5-methylpyrrolidinyl)-2-chlorobenzonitrile;
4-(2(R)-(1(S)-hydroxyl-2,2,2-trifluoroethyl)-5(R)-methyl-pyrrolidinyl)-2-trifluoro-methylbenzonitrile;
4-(2(R)-(1(S)-hydroxyl-2,2,2-trifluoroethyl)-5(R)-methyl-pyrrolidinyl)-2-chlorobenzonitrile;
R,R-4-(2-(1-Hydroxyl-2,2,2-trifluoroethyl)pyrrolidinyl)-2-chlorobenzonitrile;
R,R-4-(2-(1-Hydroxyl-2,2,2-trifluoroethyl)pyrrolidinyl)-2-chloro-3-methyl-benzonitrile;
4-(2(R)-(1(S)-hydroxyl-2,2,2-trifluoroethyl)pyrrolidinyl)-2-chlorobenzonitrile; 4-(2(R)-(1(S)-hydroxyl-2,2,2-trifluoroethyl)pyrrolidinyl)-2-chloro-3-methyl-benzonitrile;
3-methyl-4-((R)-2-((R)-2,2,2-trifluoro-1-hydroxyethyl)pyrrolidin-1-yl)-2-(trifluoro-methyl)benzonitrile;
3-methyl-4-((R)-2-((S)-2,2,2-trifluoro-1-hydroxyethyl)pyrrolidin-1-yl)-2-(trifluoro-methyl)benzonitrile;
3-methyl-4-((2R,5R)-2-methyl-5-((S)-2,2,2-trifluoro-1-hydroxyethyl)pyrrolidin-1-yl)-2-(trifluoromethyl)benzonitrile;
2-fluoro-4-((2R,5R)-2-methyl-5-((S)-2,2,2-trifluoro-1-hydroxyethyl)pyrrolidin-1-yl)benzonitrile;
2-fluoro-3-methyl-4-((2R,5R)-2-methyl-5-((S)-2,2,2-trifluoro-1-hydroxyethyl)-pyrrolidin-1-yl)benzonitrile;
2-fluoro-3-methyl-4-((R)-2-((S)-2,2,2-trifluoro-1-hydroxyethyl)pyrrolidin-1-yl)-benzonitrile;
2-fluoro-4-((R)-2-((S)-2,2,2-trifluoro-1-hydroxyethyl)pyrrolidin-1-yl)benzonitrile;
2-chloro-4-((2R,5R)-2-methyl-5-((S)-2,2,2-trifluoro-1-hydroxy ethyl)pyrrolidin-1-yl)benzonitrile;
2-chloro-3-methyl-4-((2R,5R)-2-methyl-5-((S)-2,2,2-trifluoro-1-hydroxyethyl)-pyrrolidin-1-yl)benzonitrile;
2-chloro-3-methyl-4-((R)-2-((S)-2,2,2-trifluoro-1-hydroxy ethyl)pyrrolidin-1-yl)-benzonitrile;
2-chloro-4-((R)-2-((S)-2,2,2-trifluoro-1-hydroxy ethyl)pyrrolidin-1-yl)benzonitrile;
(3R)-10-chloro-3-methyl-4-(3,3,3-trifluoro-2(R)-hydroxypropyl)-3,4-dihydro-2H-[1,4]oxazino[2,3-f]quinolin-8(7H)-one;
(3R)-10-chloro-3-ethyl-4-(3,3,3-trifluoro-2(R)-hydroxypropyl)-3,4-dihydro-2H-[1,4]oxazino[2,3-f]quinolin-8(7H)-one;
(3R)-10-chloro-4-(3,3,3-trifluoro-2(R)-hydroxypropyl)-3-(trifluoromethyl)-3,4-dihydro-2H-[1,4]oxazino[2,3-f]quinolin-8(7H)-one;
(3R)-10-chloro-3-methyl-4-(3,3,3-trifluoro-2 (S)-hydroxypropyl)-3,4-dihydro-2H-[1,4]oxazino[2,3-f]quinolin-8(7H)-one;
(3R)-10-chloro-3-ethyl-4-(3,3,3-trifluoro-2(S)-hydroxypropyl)-3,4-dihydro-2H-[1,4]oxazino[2,3-f]quinolin-8(7H)-one;
(3R)-10-chloro-4-(3,3,3-trifluoro-2(S)-hydroxypropyl)-3-(trifluoromethyl)-3,4-dihydro-2H-[1,4]oxazino[2,3-f]quinolin-8(7H)-one;
(3R)-3-ethyl-4-(3,3,3-trifluoro-2(R)-hydroxypropyl)-10-(trifluoromethyl)-3,4-dihydro-2H-[1,4]oxazino[2,3-f]quinolin-8(7H)-one;
(3R)-3-methyl-4-(3,3,3-trifluoro-2(R)-hydroxypropyl)-10-(trifluoromethyl)-3,4-dihydro-2H-[1,4]oxazino[2,3-f]quinolin-8(7H)-one;
(3R)-4-(3,3,3-trifluoro-2(R)-hydroxypropyl)-3,10-bis(trifluoromethyl)-3,4-dihydro-2H-[1,4]oxazino[2,3-f]quinolin-8(7H)-one;
(3R)-3-ethyl-4-(3,3,3-trifluoro-2(S)-hydroxypropyl)-10-(trifluoromethyl)-3,4-dihydro-2H-[1,4]oxazino[2,3-f]quinolin-8(7H)-one;
(3R)-3-methyl-4-(3,3,3-trifluoro-2(S)-hydroxypropyl)-10-(trifluoromethyl)-3,4-dihydro-2H-[1,4]oxazino[2,3-f]quinolin-8(7H)-one;
(3R)-4-(3,3,3-trifluoro-2(S)-hydroxypropyl)-3,10-bis(trifluoromethyl)-3,4-dihydro-2H-[1,4]oxazino[2,3-f]quinolin-8(7H)-one;
(R)-10-chloro-3-methyl-4-(2,2,2-trifluoroethyl)-3,4-dihydro-2H-[1,4]oxazino-[2,3-f]-quinolin-8(7H)-one;
(R)-10-chloro-3-ethyl-4-(2,2,2-trifluoroethyl)-3,4-dihydro-2H-[1,4]oxazino[2,3-f]-quinolin-8(7H)-one; and
(R)-10-chloro-4-(2,2,2-trifluoroethyl)-3-(trifluoromethyl)-3,4-dihydro-2H-[1,4]-oxazino[2,3-f]quinolin-8(7H)-one;
and pharmaceutically acceptable salts, esters and/or prodrugs thereof.

These compounds are SARMs in that they exhibit tissue selectivity. In some embodiments, the target tissue is connective tissue. In some embodiments, the target tissue is muscle. In some embodiments, the target tissue is bone. In some embodiments, the compounds provided herein have anabolic activity and promote tissue formation and/or growth. In some embodiments, the compounds provided herein can demonstrate full agonist activity in connective tissue without adverse androgenic effects. In some embodiments, the compounds provided herein can demonstrate full agonist activity in muscle, resulting in increased or improved muscle mass and muscle strength without adverse androgenic effects. In some embodiments, the compounds provided herein can demonstrate full agonist activity in bone, resulting in increased or improved bone density and strength without adverse androgenic effects. Thus, in some embodiments, the SARM compounds provided herein have utility in treating conditions that are remediated by anabolic activity (e.g., reversing connective tissue loss).

The compounds provided herein also are androgen receptor selective binding compounds, in that they bind to any portion of an androgen receptor with a greater affinity than they bind to a non-androgen receptor, such as, but not limited to, a progesterone receptor (PR), estrogen receptor (ER), glucocorticoid receptor (GR), mineralocorticoid receptor (MR), retinoic acid receptor (RAR), rexinoid receptor (RXR), or peroxisome proliferator-activated receptor (PPAR). The high selectivity for the androgen receptor means that the compounds are unlikely to have non-target receptor activity.

For example, compound 4-(2(R)-(1(S)-hydroxyl-2,2,2-trifluoroethyl)-pyrrolidinyl)-2-trifluoromethylbenzonitrile (Compound 102) is a potent AR agonist with tissue selectivity and is highly selective for the AR receptor. It has been shown to be orally bioavailable in multiple animal species, including monkeys, indicating good bioavailability in humans. Based on its plasma half-life it can be formulated for administration as a once or twice a day drug. It has shown good tolerance and safety in a multiple dose toxicology study. It is negative for genotoxicity in in vitro assays.

Certain compounds provided herein can exist as stereoisomers, including optical isomers. The present disclosure is intended to include all stereoisomers and the racemic mixtures of such stereoisomers as well as the individual enantiomers that can be separated according to any of a number of conventional methods that are known in the art. These methods include chiral chromatography, derivatization with a chiral auxiliary followed by separation by chromatography or crystallization, and fractional crystallization of diastereomeric salts.

C. PREPARATION OF THE COMPOUNDS

Provided herein are methods of making androgen receptor modulators of formulae I, II and III. In certain embodiments, the compounds provided herein can be synthesized using the following synthesis schemes. In each of the Schemes, the R groups correspond to the definitions described above.

1. Scheme I—Preparation of Compounds of Formula I

Scheme I describes the preparation of compounds of Formula I (shown as Structure 3 in Scheme I).

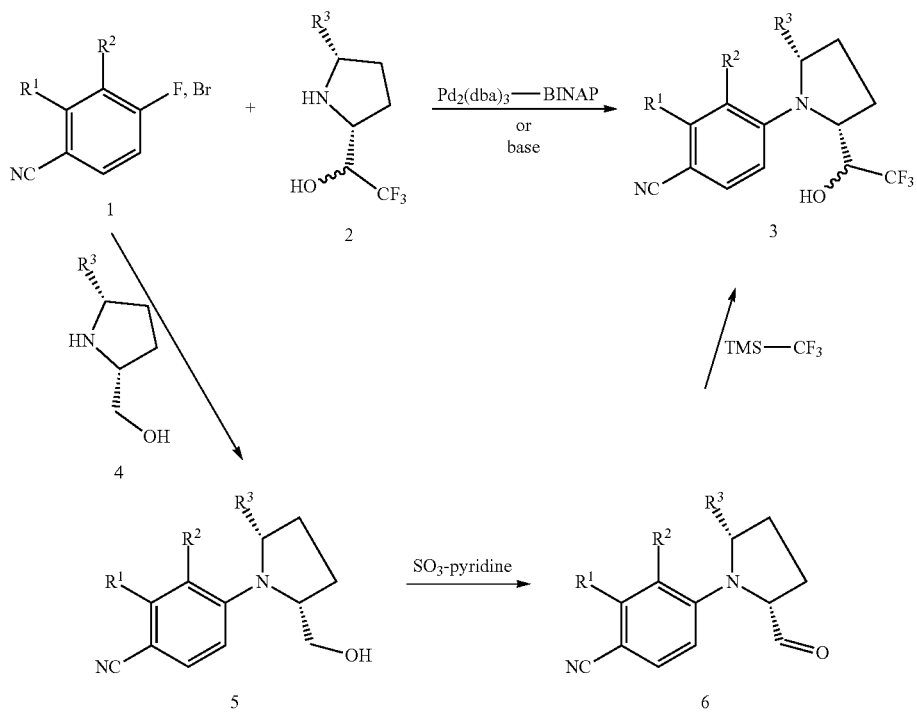

In Scheme I, compounds of Structure 1 are either commercially available or easily prepared by known methods. For example, 4-fluoro-2-(trifluoromethyl)-benzonitrile (Alfa Aesar, Ward Hill, Mass., Cat. No. B20617), 2,4-difluorobenzonitrile (Alfa Aesar, Ward Hill, Mass., Cat. No. A14113) 2-chloro-4-fluorobenzonitrile (Alfa Aesar, Ward Hill, Mass., Cat. No. A15478) and 2,4-difluoro-3-methylbenzonitrile (Fluorochem Ltd—Wesley Street, Old Glossop, Derbyshire SK13 7RY, Cat. No. 033815) are commercially available.

2-Chloro-4-fluoro-3-methylbenzonitrile can be prepared using methods known in the art. For example, 2-Chloro-4- fluorobenzonitrile (1 g) and TMEDA (1.13 mL) in THF (10 mL) were cooled to −78° C., under nitrogen. Sec-butyllithium (1.3M in cyclo-hexane, 8.54 mL) was added over 20 min, keeping the temperature below −70° C. The mixture was then stirred at −78° C. for 2.5 h. Methyl iodide (0.5 mL) was added and the mixture allowed to warm to 15° C., over 35 min. The reaction was quenched with a saturated aqueous solution of ammonium chloride and the product was extracted with ethyl acetate. The ethyl acetate was washed with brine, dried ($MgSO_4$), filtered and concentrated under reduced pressure to give crude product (1.28 g).

2-Chloro-4-fluoro-3-methylbenzonitrile also can be synthesized by adding 3-bromo-2-chloro-6-fluorotoluene (173 mg, 0.78 mmol), zinc cyanide (91 mg, 0.78 mmol), tetrakis-(triphenylphosphine)palladium(0) (27 mg, 23 Tmol) and DMF (1 mL) to a vial, and after sealing the vial, irradiating the mixture at 200° C. in a microwave oven. Diethyl ether (30 ml) is then added and the reaction mixture washed with magnesium sulphate (4% solution, 3×20 mL) followed by brine (20 mL). The organic layer is dried and evaporated. The product is further purified by column chromatography on silica gel using n-heptane/ethyl acetate (9:1) giving a white solid.

4-Fluoro-3-methyl-2-(trifluoromethyl)benzonitrile (Compound 1 of Scheme I with fluoro at position 4) is synthesized by methods known in the art. For example, 4-fluoro-2-(trifluoromethyl)benzonitrile (1.22 g, available from Alfa Aesar, Ward Hill, Mass., Cat. No. B20617) and TMEDA (1.13 mL) in THF (10 mL) are cooled to −78° C., under nitrogen. Sec-butyllithium (1.3M in cyclohexane, 8.54 mL) is added over 20 min., keeping the temperature below −70° C. The mixture is stirred at −78° C. for 2.5 h. Methyl iodide (0.5 mL) is added and the mixture allowed to warm to 15° C., over 35 min. The reaction is quenched with a saturated aqueous solution of ammonium chloride and the product is extracted with ethyl acetate. The ethyl acetate is washed with brine, dried ($MgSO_4$), filtered and concentrated under reduced pressure to give the crude product, which is further purified by column chromatography on silica gel using n-heptane/ethyl acetate (9:1) giving a white solid.

Compounds of Structures 2 and 4 are prepared from D-proline or D-pyroglutamic acid. For example, (R)-2,2,2-trifluoro-1-(pyrrolidin-2-yl)ethanol (Compound 2, Scheme I, $R^3$=hydrogen) is prepared by oxidation of D-prolinol (Compound 4, Scheme I, $R^3$=hydrogen) to afford D-prolinaldehyde (see e.g., Smith et al., March's Advanced Organic Chemistry, 6$^{th}$ ed., Wiley, N J, 2007, p. 1715-1728). The resulting D-prolinaldehyde is reacted with $CF_3$-TMS (trimethyl(trifluoromethyl)-silane) to afford the (R)-2,2,2-trifluoro-1-(pyrrolidin-2-yl)ethanol (see e.g., Prakash et al., J. Am. Chem. Soc. 111: 393, 1989).

2,2,2-trifluoro-1-((2R,5R)-5-methylpyrrolidin-2-yl)ethanol (Compound 2, Scheme I, $R^3$=methyl) is prepared by oxidation of ((2R,5R)-5-methylpyrrolidin-2-yl)methanol (Compound 4, Scheme I, $R^3$=methyl) to afford the resulting aldehyde, (2R,5R)-5-methylpyrrolidine-2-carbaldehyde (see e.g., Smith et al., March's Advanced Organic Chemistry, 6$^{th}$ ed., Wiley, N J, 2007, p. 1715-1728). The resulting aldehyde is reacted with $CF_3$-TMS (trimethyl(trifluoromethyl)silane) to afford 2,2,2-trifluoro-1-((2R,5R)-5-methylpyrrolidin-2-yl)ethanol (see e.g., Prakash et al., J. Am. Chem. Soc. 111: 393, 1989).

(R)-pyrrolidin-2-ylmethanol (Compound 4, Scheme I, $R^3$=hydrogen) also is known as D-prolinol, which is available from Sigma-Aldrich, Milwaukee, Wis., Cat. No. 81744. (R)-pyrrolidin-2-ylmethanol is prepared by reducing D-proline with $LiAlH_4$ (see, Smith et al., March's Advanced Organic Chemistry, 6$^{th}$ ed., Wiley, N J, 2007, p. 1805-1806; see also, Dei et al., Bioorg. Med. Chem. 11: 3153-3164 (2003)).

((2R,5R)-5-methylpyrrolidin-2-yl)methanol (Compound 4, Scheme I, $R^3$=methyl) is prepared by protecting (R)-(−)-5-(hydroxymethyl)-2-pyrrolidinone (available from Sigma Aldrich, Milwaukee, Wis., Cat. No. 366358) at the nitrogen atom with a suitable protecting group, such as a Boc protecting group, to afford, for example, (2R,5R)-tert-butyl-2-formyl-5-methylpyrrolidine-1-carboxylate (see e.g., Wuts et al., Green's Protective Groups in Organic Synthesis, 4$^{th}$ ed., Wiley, N J, 2007, p. 725-727). The resulting compound is treated with MeLi or MeMgX, where X is Cl or Br (see e.g., Smith et al., March's Advanced Organic Chemistry, 6$^{th}$ ed., Wiley, N J, 2007, p. 1300-1309), followed by hydrogenation (see e.g., Smith et al., *March's Advanced Organic Chemistry*, 6$^{th}$ ed., Wiley, N J, 2007, p. 1053-1062) and cleavage of the nitrogen protecting group (see e.g., Wuts et al., *Green's Protective Groups in Organic Synthesis*, 4$^{th}$ ed., Wiley, N J, 2007, p. 727-735) to afford ((2R,5R)-5-methylpyrrolidin-2-yl)-methanol.

Palladium catalyzed coupling reaction or base-mediated displacement reaction of compounds of Structure 1 and pyrrolidine derivatives of Structure 2 provide products of Structure 3 in a mixture of two diastereomers that are separated to give final products. Alternatively, intermediates of Structure 5 are obtained in the similar reaction conditions using Structure 4 and are oxidized to the aldehydes of Structure 6. Treatment of the aldehydes with TMS-$CF_3$ followed by separation of the diastereomers leads to final products of Formula I (shown as Structure 3 in Scheme I).

2. Preparation of Compounds of Formula II a. Scheme II—Compounds of Formula II where $R^4$ is $CF_3$ Scheme II describes the preparation of compounds of Formula II where $R^4$ is $CF_3$ (shown as Structure 15 in Scheme II). In Scheme II, intermediates of Structure 14 ($R^5$=Me, Et) are prepared from compound 12 by a known method described in U.S. Pat. No. 7,214,690, which is incorporated herein in its entirety.

Scheme II

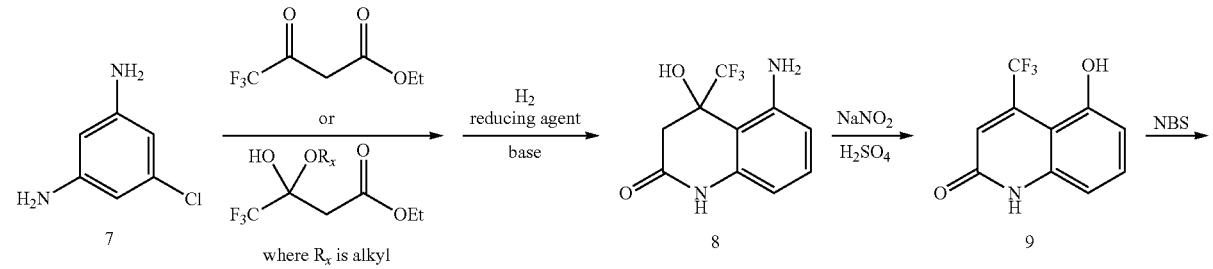

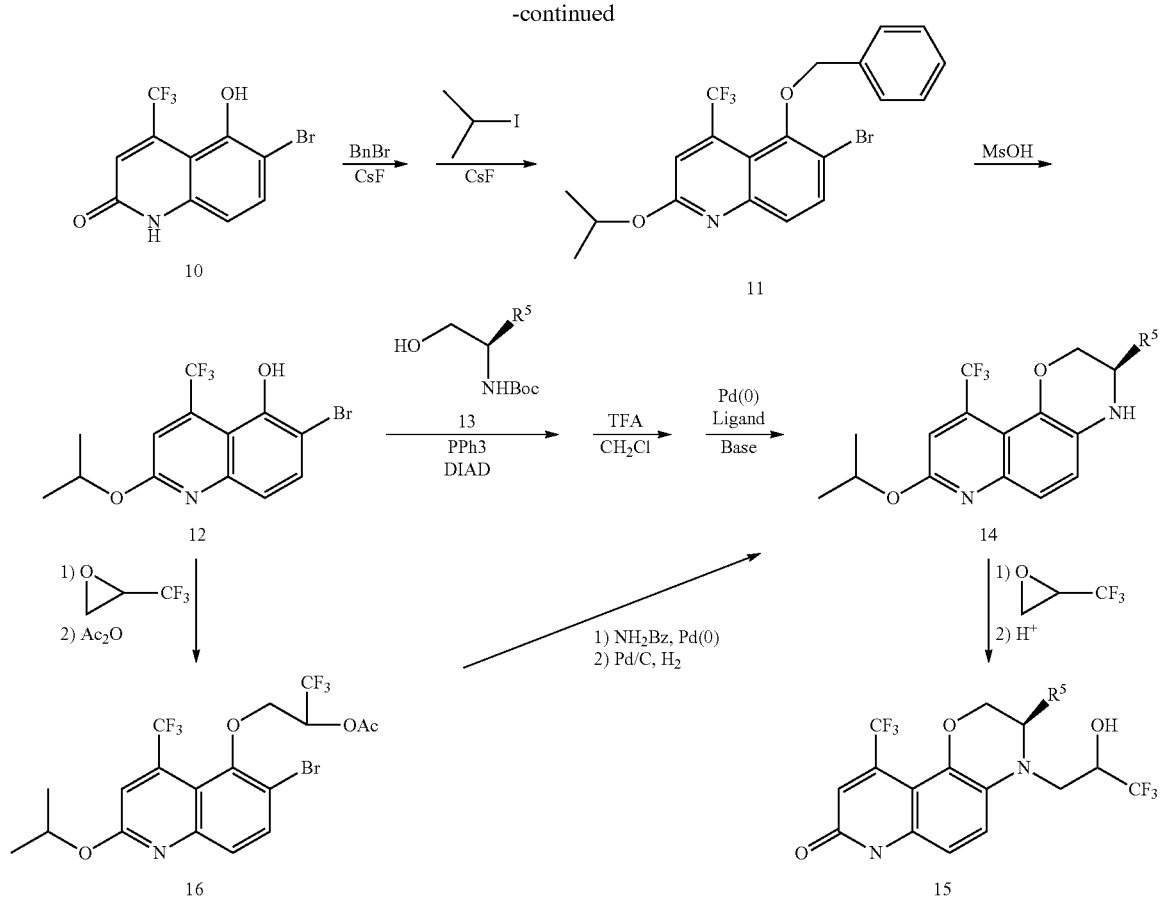

The process depicted in Scheme II begins with the Knorr cyclization of a phenylenediamine derivative, for example, 5-chloro-1,3-phenylenediamine (Structure 7), with a β-ketoester, or its corresponding hydrate or hemiacetal, for example ethyl 4,4,4-trifluoroacetoacetate, to afford the corresponding (1H)-quinolin-2-one (see Jones, *Comprehensive Heterocyclic Chemistry* (Katritzky & Rees, eds., Pergamon, N.Y., Vol. 2, chap. 2.08, pp 421-426 (1984), the disclosure of which is herein incorporated by reference). Reduction of the halide group can be achieved by chemical reduction, with, for example, a metal catalyst, for example, 10% Pd—C, in a hydrogen atmosphere, to afford a compound of Structure 8. Conversion of the aniline ring to a phenol ring can be effected by treatment of Structure 8 with a diazotizing agent, for example, sodium nitrite in sulfuric acid, to afford a compound of Structure 9. Bromination of the phenol ring with a brominating reagent, for example, N-bromosuccinimide, in the presence of a base, for example, diisopropylamine, affords a compound of Structure 10 (see, e.g., Fujisaki et al., Bull. Chem. Soc. Jpn. 66: 1576-1579 (1993), the disclosure of which is herein incorporated by reference.

Selective protection of the phenolic oxygen can be achieved by treatment of Structure 10 with an alkyl halide, for example, benzyl bromide, in the presence of a base, for example, cesium fluoride, to afford the corresponding ether. Protection of the pyridone ring, with, for example isopropyl iodide, mediated by a base, for example, cesium fluoride, affords the corresponding imino ether (Structure 11). Selective hydrolysis of the phenolic ether can be accomplished by acidic hydrolysis, with, for example, a 1:1 mixture of methanesulfonic acid and acetic acid, to afford a compound of Structure 12.

The compound of Structure 14 is prepared by alkylation of the phenolic oxygen of Structure 12 by treatment with a protected amino alcohol 13. For example, (R)—N-t-boc-2-aminoalkan-1-ol (13, $R^5$=Me or Et), is reacted with the compound of Structure 12 under Mitsunobu conditions, for example, triphenylphosphine and diisopropyl azodicarboxylate, in the presence of a base, for example, N-methylmorpholine, to afford the corresponding Mitsunobu product. Removal of the t-butoxycarbonyl protecting group can be accomplished by acidic hydrolysis, with, for example, trifluoroacetic acid. Closure of the amine to the aromatic halide can be achieved by treatment with a transition metal, for example $Pd_2(dba)_3$ in the presence of a ligand, for example, BINAP, and a base, for example, sodium t-butoxide, to afford a compound of Structure 14 (see, Wagaw et al., J. Am. Chem. Soc. 119: 8451-8458 (1997)).

Alternatively, intermediate 14 is prepared by O-alkylation of compound 12 with a chiral trifluoromethyl epoxide followed by acetate formation to give intermediate 16. Palladium catalyzed amination of the bromoaryl 16 followed by an intramolecular cyclization yield intermediate 14. N-Alkylation of intermediates of Structure 14 with a chiral trifluoromethyl epoxide followed by acid hydrolysis gives final products of Formula II (Structure 15 in Scheme II) in a stereoselective fashion.

b. Scheme III—compounds of Formula II where $R^4$ is Cl

Scheme III describes the preparation of compounds of Formula II where $R^4$ is Cl (shown as Structure 20 in Scheme III). In Scheme III, treatment of 5-chloro-1,3-diaminobenzene (Alfa Aesar, Ward Hill, Mass., Cat. No. L06485) with ethyl malonate followed by hydrogenation to remove the 5-chlorine and chloronation with $POCl_3$ provide intermediate 17. Diazotization followed by hydrolysis, bromination, and isopropyl ether formation give intermediate 18. O-Alkylation of compound 18 followed by an intramolecular amino coupling reaction yields intermediates of Structure 19. N-alkylation with a chiral epoxide followed by an acid hydrolysis gives final products of Formula II where $R^4$ is Cl (Structure 20 in Scheme III).

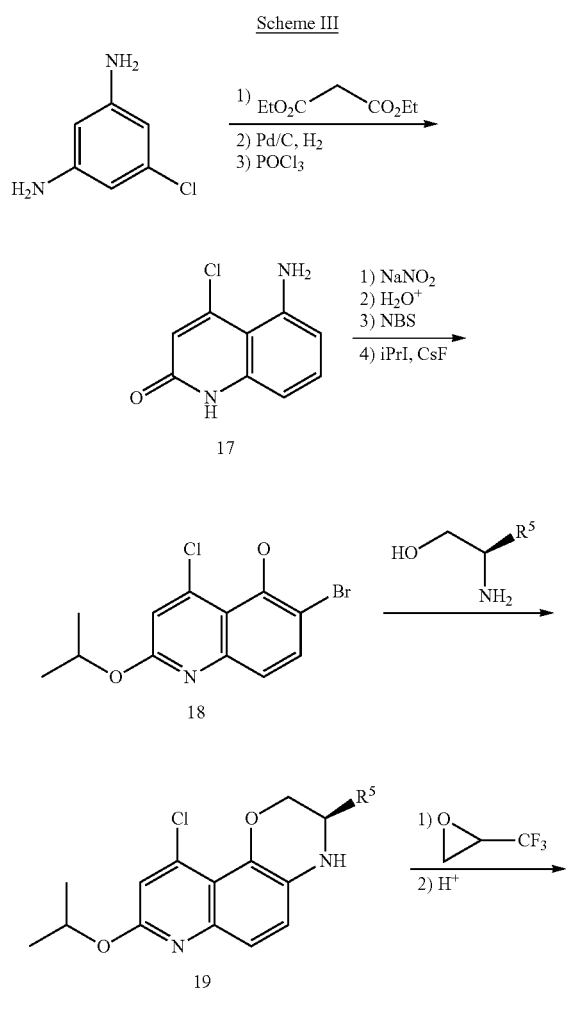

3. Scheme IV—Preparation of Compounds of Formula III

Scheme IV describes the preparation of compounds of Formula III (shown as Structure 20 is Scheme IV).

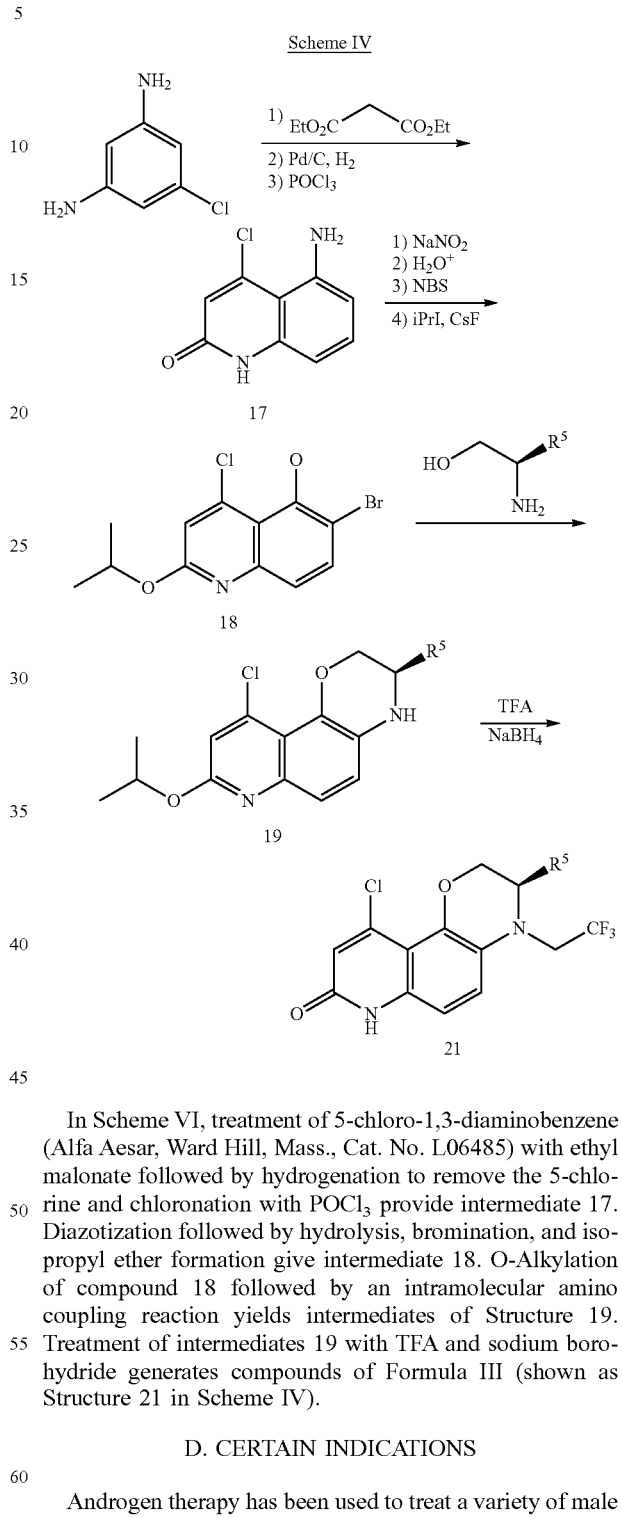

In Scheme VI, treatment of 5-chloro-1,3-diaminobenzene (Alfa Aesar, Ward Hill, Mass., Cat. No. L06485) with ethyl malonate followed by hydrogenation to remove the 5-chlorine and chloronation with $POCl_3$ provide intermediate 17. Diazotization followed by hydrolysis, bromination, and isopropyl ether formation give intermediate 18. O-Alkylation of compound 18 followed by an intramolecular amino coupling reaction yields intermediates of Structure 19. Treatment of intermediates 19 with TFA and sodium borohydride generates compounds of Formula III (shown as Structure 21 in Scheme IV).

D. CERTAIN INDICATIONS

Androgen therapy has been used to treat a variety of male disorders such as reproductive disorders and primary or secondary male hypogonadism. A number of natural or synthetic AR agonists have been investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, are used to treat prostate cancer.

Progress of androgen therapy has been limited by the inability to separate desirable androgenic activities from undesirable or dose-limiting side effects. Recent advances in the development of selective androgen receptor modulators (SARMs) that exhibit tissue selectivity in targeting the androgen receptor while eliminating undesired side effects (e.g., see Negro-Vilar, A. JCE&M 54(10): 3459-62 (1999); Reid et al., Investigational New Drugs 17: 271-284 (1999)). For example, the compound LG120907, a non-steroidal AR antagonist, has been shown, in rats, to have reduced antagonist effects on the hypothalamic axis and on libido (reproductive rate) as compared to other clinically used AR antagonists, such as Casodex, and has been characterized as a selective androgen receptor modulator for the treatment of prostate cancer (e.g., see Gao et al., Pharmaceutical Research 23(8): 1641-1658 (2006)). Other SARMs and uses thereof have been identified in the art (e.g., see U.S. Pat. Appl. No. US2007254875 and U.S. Pat. Nos. 7,301,026; 7,291,673; 7,288,553; 7,268,232; 7,268,153; 7,253,210; 7,217,720; 7,214,804; 7,214,693; 7,214,690; 7,205,437; 7,186,838; 7,026,500; 7,022,870; 6,998,500; 6,995,284; 6,960,474; 6,899,888; 6,838,484; 6,569,896 and 6,492,554; Thevis et al., Rapid Commun Mass Spectrom. 21(21): 3477-3486 (2007); Kilbourne et al., Curr Opin Investig Drugs. 8(10): 821-829 (2007); Higuchi et al., Bioorg Med Chem Lett. 17(19): 5442-5446 (2007); Zhang et al., J Med Chem. 50(16): 3857-3869 (2007); Gao et al; Drug Discov Today. 12(5-6): 241-248 (2007); Omwancha et al., Curr Opin Investig Drugs. 7(10): 873-881 (2006); Kazmin et al., Mol Endocrinol. 20(6): 1201-1217 (2006); Segal et al., Expert Opin Investig Drugs. 15(4): 377-387 (2006); Cadilla et al., Curr Top Med Chem. 6(3): 245-270 (2006); Chen et al., Mol Interv. 5(3): 173-188 (2005); Buijsman et al., Curr Med Chem. 12(9): 1017-1075 (2005); Brown et al., Endocrinology 145(12): 5417-5419 (2004); Chen et al., J Pharmacol Exp Ther. 312(2): 546-553 (2005); Marhefka et al; J Med Chem. 47(4): 993-998 (2004); and Yin et al., J Pharmacol Exp Ther. 304(3): 1334-1340 (2003)).

This class of ligands demonstrates better pharmacokinetic and specificity profiles than other steroidal therapies. In particular, non-steroidal SARMs display therapeutic benefit but do not display the androgenic effects associated with other steroidal therapies. These adverse androgenic effects include manifestations such as prostate enlargement, acne, repression of high density lipoprotein cholesterol (HDL), hirsutism, virilization and masculinization.

The compounds provided herein are SARMs. Compounds provided herein demonstrate the ability to exhibit their activity on the androgen receptor in a tissue-selective manner. This tissue selectivity allows the compounds provided herein to function as an agonist in some tissues, while having no effect or even an antagonist effect in other tissues. The molecular basis for this tissue selective activity is not completely understood. Without being limited to any particular explanation, particular ligands put nuclear receptors in different conformational states. These states dictate the ability of co-activators, co-repressors, and other proteins to be recruited by the nuclear receptor. The combination of the nuclear receptor different co-activators, co-repressors, and other proteins are the gene transcription factors that are thought to modulate tissue-selective effects. Some of the SARMs exhibit agonistic anabolic properties and antagonistic androgenic properties. Compounds provided herein have anabolic building activity, such as in muscle and bone, without unwanted androgenic side effects on most other tissues, such as prostate and skin sebaceous glands.

Compounds provided herein are tissue-selective modulators of the androgen receptor. In one aspect, the compounds provided herein can be used to activate the function of the androgen receptor in a subject, and in particular to activate the function of the androgen receptor in bone and/or muscle tissue and block or inhibit (antagonize) the function of the androgen receptor in the prostate of a male individual or in the uterus of a female individual.

In some embodiments, compounds provided herein exhibit antagonist activity in hormone-dependent tumors while exhibiting no activity, or in some embodiments agonist activity, against other non-tumor tissues containing the androgen receptor. As described below, these SARMs can be used to treat a number of androgen receptor-mediated conditions, including treatment of hormone-dependent tumors containing AR, such as prostate cancer, in patients by inhibiting the growth of the tumor while mitigating side effects such as muscle wasting, cachexia, sexual dysfunction such as loss of libido, osteoporosis and gynecomastia.

The compounds provided herein typically display micromolar or submicro-molar binding affinity for the androgen receptor. The compounds provided herein demonstrate AR agonist or antagonist activity, as evidenced by their activity in standard AR agonist and antagonist assays, such as the co-transfection assay described herein. For example, compounds provided herein demonstrate a potency ($EC_{50}$) of 1 µM or less in the co-transfection assay described herein. In some embodiments, compounds provided herein demonstrate a potency ($EC_{50}$) of 100 nM or less. In some embodiments, compounds provided herein demonstrate a potency ($EC_{50}$) of 50 nM or less. In some embodiments, compounds provided herein demonstrate a potency ($EC_{50}$) of 10 nM or less. Compounds provided herein also demonstrate an efficacy of 50% or greater in a standard AR agonist assay. The compounds provided herein are therefore useful in treating mammals suffering from disorders related to androgen receptor function. Therapeutically effective amounts of one or more of the compounds provided herein, or any of the pharmaceutically acceptable salts thereof, are administered to the subject, to treat disorders related to androgen receptor function, such as, androgen deficiency, disorders that can be ameliorated by androgen replacement, or that can be improved by androgen replacement, or to treat disorders that are responsive to treatment with an anti-androgen. Treatment is effected by administration of a therapeutically effective amount of one or more than one of the compounds provided herein to a subject in need of such treatment. In addition, these compounds are useful as ingredients in pharmaceutical compositions alone or in combination with other active agents.

In certain embodiments, compounds and/or compositions provided herein are used for the prevention, treatment, or amelioration of one or more of the symptoms of diseases or disorders associated with androgen receptor activity. The diseases and disorders that are treated include those caused by androgen deficiency and/or those that can be ameliorated by androgen administration, as well as those whose etiology involves hyperactivity of androgen receptor and/or those that can be ameliorated by anti-androgen administration.

Disorders, diseases or conditions that are caused by androgen deficiency or hypoactivity or subsensitivity of androgen receptor, or that can be ameliorated by androgen replacement or are responsive to treatment with an AR agonist, include, but are not limited to, aging skin; Alzheimer's disease; anemias, such as for example, aplastic anemia;

anorexia; arthritis, including inflammatory arthritis, rheumatoid arthritis, osteoarthritis and gout; arteriosclerosis; atherosclerosis; bone disease, including metastatic bone disease; bone damage or fracture, such as by accelerating bone fracture repair and/or stimulation of osteoblasts and/or stimulation of bone remodeling and/or stimulation of cartilage growth; distraction osteogenesis; reduced bone mass, density or growth; bone weakening, such as induced by glucocorticoid administration; musculoskeletal impairment (e.g., in the elderly); cachexia; cancer, including breast cancer and osteosarcoma; cardiac dysfunction (e.g., associated with valvular disease, myocardial infarction, cardiac hypertrophy or congestive heart failure); cardiomyopathy; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; contraception (male and female); chronic obstructive pulmonary disease (COPD); chronic bronchitis; decreased pulmonary function; emphysema; decreased libido in both men and women; depression; nervousness, irritability and/or stress; reduced mental energy and low self-esteem (e.g., motivation/assertiveness); dyslipidemia; erectile dysfunction; frailty; age-related functional decline ("ARFD") in the elderly; growth hormone deficiency; hematopoietic disorders; hormone replacement (male and female); hyper-cholesterolemia; hyperinsulinemia; hyperlipidemia; hypertension; hyperandrogenemia; hypogonadism (including primary and secondary); hypothermia (including hypothermia following anesthesia); impotence; insulin resistance; type 2 diabetes; lipodystrophy (including in subjects taking HIV or AIDS therapies such as protease inhibitors); male menopause; metabolic syndrome (syndrome X); loss of muscle strength and/or function (e.g., in the elderly); muscular dystrophies; muscle loss following surgery (e.g., post-surgical rehabilitation); muscular atrophy (e.g., due to physical inactivity, bed rest or reduced weight-bearing conditions such as microgravity); neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction (e.g., erectile dysfunction, decreased sex drive, sexual well-being, decreased libido); physiological short stature, including growth hormone deficient children and short stature associated with chronic illness and growth retardation associated with obesity; tooth damage (such as by acceleration of tooth repair or growth); thrombocytopenia; vaginal dryness; atrophic vaginitis; ventricular dysfunction; wasting, including wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia), chemotherapy, multiple sclerosis or other neurodegenerative disorders.

The compounds provided herein that demonstrate AR agonist activity also can be used to stimulate pulsatile growth hormone release; to improve bone strength, muscle strength and tone; to reduce subcutaneous fat in a subject; to enhance bone and muscle performance/strength; to increase athletic performance; to attenuate or reverse protein catabolic responses following trauma (e.g., reversal of the catabolic state associated with surgery, congestive heart failure, cardiac myopathy, burns, cancer, COPD); to improve sleep quality and/or correct the relative hyposomatotropism of senescence due to high increase in REM sleep and a decrease in REM latency; to treat age related decreased testosterone levels in men; to modifying lipid profile; and for hormone replacement therapy, such as female androgen deficiency and male androgen decline.

SARMs can act as antagonists in specific tissues, and thus also are useful in treating conditions where elevated androgen concentration or activity causes symptoms. The compounds provided herein that demonstrate AR antagonism can be used to treat conditions whose etiology involves hyperactivity of androgen receptor or that are responsive to treatment with an AR antagonist. Such conditions, include, but are not limited to, acanthosis nigricans, acne, adrenal hyperandrogenism, androgenetic alopecia (male-pattern baldness), adenomas and neoplasias of the prostate (e.g., advanced metastatic prostate cancer), benign prostate hyperplasia, cancer (e.g., cancer of the breast, bladder, endometrium, lung (non-small cell lung cancer), pancreas, prostate, including androgen dependent prostate cancer, and skin); bulimia nervosa; chronic fatigue syndrome (CFS); chronic myalgia; acute fatigue syndrome; contraception; counteracting preeclampsia, eclampsia of pregnancy and preterm labor; delayed wound healing; erythrocytosis; gestational diabetes; hirsutism; hyper-insulinemia including nesidio-blastosis; hyperandrogenism; hypercortisolism; Cushing's syndrome; hyperpilosity; infertility; malignant tumor cells containing the androgen receptor, such as is the case for breast, brain, skin, ovarian, bladder, lymphatic, liver and kidney cancers; menstrual irregularity; ovarian hyperandrogenism; polycystic ovarian syndrome; seborrhea; sleep disorders; sleep apnea; and visceral adiposity.

In some embodiments, the compounds provided herein have an agonistic activity on muscle and bone tissue, and have a neutral or antagonistic effect on prostate tissue. In some embodiments, such compounds are used to treat or prevent a condition selected from among muscle wasting, cachexia, frailty, sarcopenia, osteopenia, osteoporosis, hypogonadism and sexual dysfunction.

In some embodiments, the compounds provided herein have no effect on muscle and/or bone, and have neutral or antagonistic effect on prostate. In some embodiments, such compounds are used to treat or prevent a condition selected from among benign prostatic hyperplasia (BPH), prostate cancer and sexual dysfunction.

1. Muscle Wasting

Muscle wasting is associated with chronic, neurological, genetic or infectious pathologies, diseases, illnesses or conditions. In some embodiments, the pathology, illness, disease or condition is chronic. In some embodiments, the pathology, illness, disease or condition is genetic. In some embodiments, the pathology, illness, disease or condition is neurological. In some embodiments, the pathology, illness, disease or condition is infectious. As described herein, the pathologies, diseases, conditions or disorders for which the compounds and compositions provided herein are administered are those that directly or indirectly produce a loss of muscle mass, or that result in a muscle wasting disorder.

Muscle wasting infectious pathologies, diseases, illnesses or conditions include acquired immunodeficiency syndrome (AIDS); burns; cachexias, such as AIDS cachexia, cancer cachexia, and cardiac cachexia; cancer; cardiomyopathy; chronic kidney or heart failure; chronic obstructive pulmonary disease (COPD); denervation; diabetes; emphysema; end stage renal failure; frailty; HIV infection; inactivity; leprosy; malnutrition; muscle atrophies such as Post-Polio Muscle Atrophy (PPMA) or X-linked spinal-bulbar muscular atrophy (SBMA); muscular dystrophies, such as Duchenne Muscular Dystrophy, myotonic dystrophy, Becker's muscular dystrophy (benign pseudohypertrophic muscular dystrophy), limb-girdle muscular dystrophy, facioscapulohumeral muscular dystrophy (FSHD), congenital muscular dystrophy, Oculopharyngeal Muscular Dystrophy (OPMD), distal muscular dystrophy and Emery-Dreifuss muscular dystrophy; osteomalacia; renal disease; sarcopenia; sepsis; and tuberculosis. In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, microgravity, peripheral nerve damage, spinal cord damage, chemical damage, burns, disuse, deconditioning that occurs when a limb is immobilized, long term hospitalization due to illness or injury, and alcoholism. Muscle wasting, if left unabated, can have dire health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and AIDS.

Muscle wasting due to infectious pathologies include muscle wasting disorders due to infection with coxsackie virus, enterovirus, Epstein-Barr virus, herpes zoster, HIV, influenza, mycobacteria, rickettsia, schistosoma, trichinella or trypanosomes.

The loss of muscle mass that occurs during muscle wasting can be characterized by a breakdown or degradation of muscle protein, such as by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting.

Muscle wasting also is associated with advanced age. It is believed that general weakness in old age is due to muscle wasting. As the body ages, an increasing proportion of skeletal muscle is replaced by fibrous tissue. The result is a significant reduction in muscle power, performance and endurance. Long term hospitalization due to illness or injury, or muscle disuse that occurs, for example, when a limb is immobilized, also can lead to muscle wasting. Patients suffering injuries, chronic illnesses, burns, trauma or cancer, who are hospitalized for long periods of time, often exhibit a long-lasting unilateral muscle wasting.

Administration of anabolic steroids have demonstrated the ability to increase weight and muscle mass in some patients with muscle wasting, such as in cancer patients. However, administration of anabolic steroids can result in unwanted androgenic side effects, including development of oily skin or acne, as well as masculinization in women and prostate stimulation in men. SARMs have demonstrated efficacy for attenuating muscle wasting across a range of disorders (e.g., see Allen et al. Endocrine 32(1): 41-51 (2007); Lynch et al., Pharmacology & Therapeutics 113(3): 461-487 (2007); Gao et al., Endocrinology 146(11): 4887-4897 (2005); Lynch, Expert Opinion on Emerging Drugs 9(2): 345-361 (2004); U.S. Pat. Appl. Pub. No. 20060111441 and WO03049675). SARMs generally demonstrate predominantly anabolic activity in muscle and bone with minimal androgenic effects in most other tissues. In some embodiments, the compounds provided herein are useful for treating muscle wasting. In some embodiments, the compounds provided herein are useful for treating sarcopenia.

2. Muscle Tone and Strength

Androgen receptor agonists are known to have a beneficial effect on muscle tone and strength (e.g., see Gao et al., Endocrinology 146(11): 4887-4897 (2005), Jasuja et al, J Clin Endocrinol Metab. 90(2): 855-863 (2005) and Ferrando et al, Am J Physiol Endocrinol Metab. 282(3): E601-E607 (2002). Androgen replacement in healthy, hypogonadal men results in gains in fat-free mass, muscle size and maximal voluntary strength (e.g., see Bhasin et al., J. Endocrin. 170: 27-38 (2001)). Thus, the compounds provided herein can stimulate muscle growth and can be used for treatment of sarcopenia and frailty. In one embodiment, one or more compounds of formula I, II or III are used to enhance muscle tone in a subject. In another embodiment, one or more compounds of formula I, II or III are used to improve muscle strength in a subject.

3. Osteoporosis

Osteoporosis is a disease characterized by low bone mass and structural deterioration of bone tissue leading to bone fragility and an increased susceptibility to fractures of the hip, spine, ribs and wrist. Loss of estrogens or androgens causes an imbalance between resorption and formation of bone by prolonging the lifespan of osteoclasts and shortening the lifespan of osteoblasts. Loss of androgens also may induce bone loss by increasing the rate of bone remodeling (Lindberg et al., Minerva Endocrinol. 30(1): 15-25 (2005)). The beneficial effects of androgens on bone in postmenopausal osteoporosis are described in art (e.g., see Hofbauer et al., Eur. J. Endocrinol. 140: 271 286 (1999). Androgens also play an important role in bone metabolism in men (e.g., see Anderson et al., Bone 18: 171-177 (1996). Androgen receptor modulator compounds also have been shown to improve bone strength in a rat model of post-menopausal osteoporosis (e.g., see Martinborough et al., J Med Chem. 50(21): 5049-5052 (2007)). Osteoporosis can result from androgen deprivation. In one embodiment, the compounds provided herein can activate the function of the androgen receptor in a mammal, and in particular to activate the function of the androgen receptor in bone.

Methods for assessing osteoporosis and osteopenia are well known in the art. For example, a subject's bone mineral density (BMD), measured by densitometry and expressed in $g/cm^2$, is compared with a "normal value," which is the mean BMD of sex-matched young adults at their peak bone mass, yielding a "T-score." A score of 0 means the subject's BMD is equal to the norm for a healthy young adult. Differences between the BMD of a subject and that of the healthy young adult norm are measured in standard deviation units (SDs). A T-score between +1 and −1 is considered normal or healthy. A T-score between −1 and −2.5 indicates low bone mass and is indicative of osteopenia. A T-score of −2.5 or lower is indicative of osteoporosis. As the T-score number becomes more negative, the severity of the osteoporosis increases.

The compounds provided herein are useful for the treatment of osteoporosis in women and men as a monotherapy or in combination with inhibitors of bone resorption, such as bisphosphonates, estrogens, SERMs, cathepsin inhibitors, $\alpha_v\beta_3$ integrin receptor antagonists, calcitonin, and proton pump inhibitors. They also can be used with agents that stimulate bone formation, such as parathyroid hormone or analogs thereof.

In one embodiment, a compound provided herein is administered in combination with an effective amount of at least one bone-strengthening agent chosen from among estrogen and estrogen derivatives, alone or in combination with progestin or progestin derivatives; bisphosphonates; anti-estrogens; selective estrogen receptor modulators (SERMs); $\alpha_v\beta_3$ integrin receptor antagonists; cathepsin inhibitors; proton pump inhibitors; PPARγ inhibitors; calcitonin; and osteoprotegerin.

Exemplary estrogen and estrogen derivatives include 17β-estradiol, estrone, conjugated estrogen (PREMARIN®), equine estrogen and 17β-ethynyl estradiol. The estrogen or estrogen derivative can be used alone or in combination with a progestin or progestin derivatives. Exemplary progestin derivatives include norethindrone and medroxy-progesterone acetate. Other estrogen receptor modulators are known in the art (e.g., see U.S. Pat. Nos. 7,151,196, 7,157,604, 7,138,426).

Exemplary bisphosphonate compounds, which can be used in combination with a compound provided herein include alendronate (see U.S. Pat. Nos. 5,510,517, and 5,648,491), [(cycloheptylamino)-methylene]-bis-phosphonate (incadronate) (see U.S. Pat. No. 4,970,335); (dichloromethylene)-bis-phosphonic acid (clodronic acid) and the disodium salt (clodronate) (see Quimby et al., J. Org. Chem 32: 4111-4114 (1967)); (1-hydroxy-ethylidene)-bis-phosphonate (etidronate); [1-hydroxy-3-(methylpentyl-amino) propylidene]-bis-phosphonate (ibandronate) (see U.S. Pat. No. 4,927,814), (6-amino-1-hydroxy-hexylidene)-bis-phosphonate (neridronate); [3-(dimethyl-amino)-1-hydroxy-propylidene]-bis-phosphonate (olpadronate); (3-amino-1-hydroxy-propylidene)-bis-phosphonate (pamidronate); [2-(2-pyridinyl)ethylidene]-bis-phosphonate (piridronate) (see U.S. Pat. No. 4,761,406); [1-hydroxy-2-(3-pyridinyl)-ethylidene]-bis-phosphonate (risedronate); {[(4-chlorophenyl)-thio]methylene}-bis-phosphonate (tiludronate) (see U.S. Pat. No. 4,876,248); [1-hydroxy-2-(1H-imidazol-1-yl)-ethylidene]-bis-phosphonate (zoledronate); and [1-hydroxy-2-imidazopyridin-(1,2-a)-3-ylethylidene]-bis-phosphonate (minodronate). In one embodiment of the methods and compositions provided herein, the bisphosphonate is chosen from among alendronate, clodronate, etidronate, ibandronate, incadronate, minodronate, neridronate, olpadronate, pamidronate, piridronate, risedronate, tiludronate, zoledronate, and mixtures and pharmaceutically acceptable salts thereof.

SERMs, or selective estrogen receptor modulators, are agents known in the art to prevent bone loss by inhibiting bone resorption via pathways believed to be similar to those of estrogens (e.g., see Goldstein et al., Human Reproduction Update 6: 212-224 (2000); Lufkin et al., Rheumatic Disease Clinics of North America 27: 163-185 (2001), Chan, Semin Oncol. 29(3 Suppl 11): 129-133 (2002), Jordan, Cancer Research 61: 5683-5687 (2001) and Miller & Komm, Chapter 15, *"Targeting the Estrogen Receptor with SERMs"* in Ann. Rep. Med. Chem. 36: 149-158 (2001)). Exemplary SERMs include arzoxifene, clomiphene, droloxifene, enclomiphene, idoxifene, lasofoxifene, levormeloxifene, nafoxidine, raloxifene, tamoxifen, toremifene, zuclomiphene, and salts thereof (see, e.g., U.S. Pat. Nos. 4,729,999, 4,894,373 and 5,393,763).

$\alpha_v\beta_3$ Integrin receptor antagonists suppress bone resorption and can be employed in combination with the SARMs provided herein for the treatment of bone disorders including osteoporosis. Antagonists of the $\alpha_v\beta_3$ integrin receptor are known in the art (e.g., see U.S. Pat. Nos. 5,204,350, 5,217,994, 5,639,754, 5,710,159, 5,723,480, 5,741,796, 5,760,028, 5,773,644, 5,773,646, 5,780,426, 5,843,906, 5,852,210, 5,919,792, 5,925,655, 5,929,120, 5,952,281, 5,952,341, 5,981,546, 6,008,213, 6,017,925, 6,017,926, 6,028,223, 6,040,311, 6,066,648, 6,069,158, 6,048,861, 6,159,964, 6,489,333, 6,784,190, 7,056,909, 7,074,930 and 7,153,862.

Cathepsin is a cysteine protease and is described in U.S. Pat. Nos. 5,501,969 and 5,736,357. Cysteine proteases, such as cathepsins, are linked to a number of disease conditions, including arthritis, bone remodeling, inflammation and tumor metastasis. Cathepsin protease inhibitors can inhibit osteoclastic bone resorption by inhibiting the degradation of collagen fibers and are thus useful in the treatment of bone resorption diseases, such as osteoporosis. Examples of cathepsin inhibitors are described in Deaton, Current Topics in Medicinal Chemistry 5(16): 1639-1675 (2005), in U.S. Pat. Nos. 7,279,478, 7,279,472, 7,112,589 and 7,012,075, and in WO 01/49288 and WO 01/77073.

Proton pump inhibitors, such as osteoclast vacuolar ATPase inhibitors, can be employed together with the SARMs provided herein. The proton ATPase found on the apical membrane of the osteoclast has been reported to play a significant role in the bone resorption process and is a target for the design of inhibitors of bone resorption, thereby useful for the treatment and prevention of osteoporosis and related metabolic diseases (e.g., see Niikura, Drug News Perspect. 19(3): 139-44 (2006), Visentin et al., J Clin Invest 106(2): 309-318 (2000) and Niikura et al., Br J of Pharmacology 142: 558-566 (2004)). Exemplary inhibitors include bafilomycin A1, SB242784, FR167356, FR177995, FR202126, FR133605 and NiK-12192 [4-(5,6-dichloro-1H-indol-2-yl)-3-ethoxy-N-(2,2,6,6-tetramethyl-piperidin-4-yl)-benzamide] (Petrangolini et al., J Pharmacol Exp Ther 318 (3): 939-946 (2006).

Activators of the peroxisome proliferator-activated receptor gamma (PPARγ) are known in the art inhibit osteoclast-like cell formation and bone resorption (e.g., see Okazaki et al., Endocrinology 140: 5060-5065 (1999)). Exemplary PPARγ activators include the glitazones, such as ciglitazone, darglitazone, englitazone, troglitazone, pioglitazone, rosiglitazone, and BRL 49653, the thiazolidinediones (see, e.g., Yki-Järvinen, New Eng J Med 351(11): 1106-1118 (2004), netoglitazone, 15-deoxy-$\Delta_{12,14}$-prostaglandin $J_2$ and analogs, derivatives, and pharmaceutically acceptable salts thereof.

In one embodiment, therapeutically effective amounts of a compound of Formula I, II or III alone or in combination with another active agent is administered to the mammal to treat a condition or disorder selected from among osteoporosis, osteopenia, glucocorticoid-induced osteoporosis and bone fracture.

4. Prostate Disease and Prostate Cancer

The compounds provided herein can be used for treatment of prostate disease, such as prostate cancer and benign prostatic hyperplasia (BPH). In one embodiment, compounds provided herein can block or inhibit (antagonize) the function of the androgen receptor in the prostate of a male individual.

For advanced prostate cancer, the standard treatment is androgen receptor-blockade, usually in combination with LHRH superagonists, which suppresses both adrenal and testicular testosterone. The rationale of this approach is that early prostate cancer usually depends on androgens for growth. The mechanism of clinically utilized anti-androgens is thought to involve blockade of the AR by binding to it and/or by interference with binding of the AR to the DNA. Anti-androgens (androgen receptor antagonists) have been shown to be effective for the treatment of prostate cancer. For example, flutamide, bicalutamide and nilutamide were found to completely block AR binding to the DNA. Bicalutamide, a non-steroidal anti-androgen, has be used to combat prostate cancer, and the properties and usefulness of bicalutamide as an anti-androgen are known in the art (e.g., see Furr et al., Urology 47 (Suppl. 1A): 13-25 (1996) and Kolvenbag et al., Urology 47 (Suppl. 1A): 70-79 (1996)). Other examples of anti-androgens used in the treatment of prostate cancer are flutamide and nilutamide (e.g., see U.S. Pat. No. 7,018,993). The properties and usefulness of these anti-androgens are known in the art (e.g., see Neri, J. Drug Develop. 1 (Suppl.): 5-9 (1987), Neri et al., *Urology* 34 (4 Suppl.): 19-21 and 46-56 (1989), Neri et al., J Steroid Biochem. 6(6): 815-819 (1975), Neri et al., Anticancer Res. 9(1): 13-16 (1989), Jackson et al., Anticancer Res. 27(3B): 1483-1488 (2007), Harris et al., Expert Opin Investig Drugs 10(3): 493-510 (2001), Shen et al., Endocrinology 141(5): 1699-1704 (2000), Harris et al., Drugs and Aging 3: 9-25 (1993) and U.S. Pat. No. 7,241,753). Animal models for determining the effectiveness of compounds for treatment of prostate cancer are known in the art (e.g., see U.S. Pat. No. 7,053,263).

In certain embodiments, compounds and/or compositions provided herein are therapeutically effective for treating prostate cancer. In certain instances, prostate cancer is dependant on androgens. Such androgen dependent prostate cancer is typically amenable to treatment by androgen receptor antagonists and/or androgen receptor partial agonists. In certain embodiments, the prostate cancer is androgen dependant prostate cancer. In certain embodiments, the prostate cancer is androgen independent prostate cancer. In certain embodiments, the prostate cancer is androgen independent, but androgen receptor dependant prostate cancer.

In some embodiments, the compounds provided herein are tissue selective AR modulators. In some embodiments, the compounds provided herein are tissue selective AR antagonists. Tissue selective AR antagonists in the prostate that lack antagonistic action in bone and muscle are known in the art to be useful agents for the treatment of prostate cancer, either alone or as an adjunct to traditional androgen deprivation therapy (see, e.g., Stoch et al., J. Clin. Endocrin. Metab. 86: 2787-2791 (2001)). Thus, compounds provided herein that are tissue selective AR antagonists in the prostate that lack antagonistic action in bone and muscle are useful agents for the treatment of prostate cancer, either alone or as an adjunct to traditional androgen deprivation therapy.

5. Hematopoietic Conditions and Disorders

Hematopoiesis is a constant process in which specialized blood cells, such as erythrocytes, B and T lymphocytes, platelets, granulocytes, monocytes, and macrophages, are generated from hematopoietic stem cells. A number of undesired hematopoietic conditions can occur in a subject. These include inadequate production of, or increased destruction of, platelets, red blood cells or white blood cells. For example, inadequate platelet or blood cell production or destruction can result in aplastic anemia, refractory anemias, idiopathic thrombocytopenia purpura, immune thrombocytopenias, leukemia, myelodysplastic and preleukemia syndromes, megaloblastic anemia and platelet deficiency, myeloproliferative disorders and uremia. Hematopoietic cytokines, such as erythropoietin, have been used to treat various diseases arising from imbalances between degradation and reconstitution of blood cells or from generation of inappropriate numbers of certain blood cells.

Androgens are known in the art to stimulate renal hypertrophy and erythropoietin (EPO) production. Androgens have been used to treat anemia caused by chronic renal failure. In addition, androgens increase serum EPO levels in anemic patients with non-severe aplastic anemia and myelodysplastic syndromes. Thus, the selective androgen modulator compounds provided herein can be used to treat certain hematopoietic disorders including aplastic anemia, refractory anemias, idiopathic thrombocytopenia purpura, immune thrombocytopenias, leukemia, preleukemia/myelodysplastic syndromes, megaloblastic anemia and platelet deficiency, myeloproliferative disorders and uremia. In one embodiment, a compound of formula I, II or III is used to increase the number of blood cells, such as red blood cells and platelets in a subject.

6. Neurodegenerative Diseases and Disorders

The compounds described herein can be used in the treatment of neurodegenerative diseases, such as Alzheimer's disease. The art teaches that androgens and selective androgen receptor modulators can be useful in preventing the onset or delaying the progression of Alzheimer's disease in male patients (e.g., see Fuller et al., J Alzheimer's Dis. 12(2): 129-142 (2007)). It is known in the art that androgen receptor agonists have therapeutic value in the treatment of neurodegenerative diseases such as Alzheimer's disease (e.g., see Hammond et al., J. Neurochem. 77: 1319-1326 (2001)). Androgen receptor agonists, such as testosterone, have been shown to reduce secretion of β-amyloid peptides characteristic of Alzheimer's disease and can therefore be used in the treatment of Alzheimer's disease (Gouras et al., Proc. Nat. Acad. Sci. USA 97: 1202-1205 (2000)). Androgen receptor agonists also have been shown to inhibit hyperphosphorylation of proteins implicated in the progression Alzheimer's disease (e.g., see Papasozomenos, Proc. Nat. Acad. Sci. USA 99: 1140-1145 (2002)). Studies have shown that apoE4 contributes to cognitive decline in Alzheimer's disease by reducing AR levels in the brain, and that stimulating AR-dependent pathways can reverse apoE4-induced cognitive deficits (e.g., see Raber et al., J Neurosci. 22(12): 5204-5209 (2002). Thus, the compounds provided herein are useful in the treatment of Alzheimer's disease and other neurodegenerative disorders. Additionally, androgen receptor modulators can be useful in treating cognitive impairment (see Pfankuch et al., Brain Res. 1053(1-2): 88-96 (2005) and Wisniewski, Horm. Res. 58: 150-155 (2002)). Studies have shown that age-related decline in testosterone levels is associated with depression and that testosterone has been useful in the treatment of depression (e.g., see Carnahan et al., Drugs Aging 21(6): 361-376 (2004). Accordingly, the compounds provided herein are useful in the treatment of cognitive impairment and depression.

7. Obesity

Obesity has been associated with alterations in androgen secretion, transport, metabolism, and action, with obese men displaying a decrease of testosterone levels with increasing body weight and obese women, especially those with abdominal obesity, displaying a condition of functional hyperandrogenism (e.g., see Pasquali, Fertil Steril. 85(5): 1319-1340 (2006). It has been demonstrated in the art that androgen administration reduces subcutaneous and visceral fat in obese patients (e.g., see Lovejoy et al., Int. J. Obesity 19: 614-624 (1995) and Lovejoy et al., J. Clin. Endocrinol. Metab. 81: 2198-2203 (1996)). Therefore, the SARMs provided herein can be beneficial in the treatment of obesity. In one embodiment, the compounds provided herein that are AR agonists are used to treat a male subject with abdominal adiposity. In one embodiment, the compounds provided herein that are AR antagonists are used to treat a female subject with abdominal obesity.

8. Insulin Disorders and Diabetes

In vivo studies have shown that the androgen receptor plays a key role in the development of insulin resistance, which may contribute to the development of type 2 diabetes and cardiovascular disease (e.g., see Lin et al., Diabetes 54(6): 1717-1725 (2005). Androgen receptor agonists also can have therapeutic value against metabolic syndrome (insulin resistance syndrome, syndrome X), particularly in men. Low levels of total and free testosterone in men have been associated with type 2 diabetes, visceral obesity, insulin resistance (hyperinsulinemia, dyslipidemia) and metabolic syndrome (e.g., see Laaksonen et al., Diabetes Care 27(5): 1036-1041 (2004), Marin et al., *Obesity Res.* 1(4): 245-251 (1993) and Laaksonen et al., Euro. J Endocrin 149: 601-608 (2003)) and, in women, there is a correlation between high androgen levels and insulin resistance (e.g., see Corbould, J Endocrinol. 192(3): 585-594 (2007). Accordingly, the compounds provided herein can be used to treat insulin resistance and type II diabetes.

9. Sexual Dysfunction

Testosterone is used as a treatment for sexual dysfunction in hypogonadal patients (Yassin et al., World Journal of Urology 24: 6: 639 (2006). It is known in the art that androgen deficiency in women is clinically often associated with a loss of libido and energy (e.g., Arlt, Eur J Endocrinol 154(1): 1-11 (2006) and Rivera-Woll et al., Human Reproduction Update 10(5): 421 (2004)). Low androgen levels have been shown to contribute to the decline in sexual interest in many women during their later reproductive years (Davis, Clin. Endocrinol. Metab. 84: 1886-1891 (1999)). In clinical trials, women treated with the androgen DHEA exhibited an increase in the frequency of sexual thoughts, interest, and satisfaction compared to women taking a placebo (e.g., see Arlt et al., N Engl. J. Med. 341: 1013-1020 (1999) and Miller, J. Clin. Endocrinol. Metab. 86: 2395-2401 (2001)). Androgen deficiency in men is related to diminished libido (e.g., see Fine, JAOA Supplement 1 Vol 104(1): S9-S15 (2004)). It also is known in the art that erectile response is centrally and peripherally regulated by androgens. Studies have shown that treatment with testosterone positively impacts the tissues of the penis involved in the mechanism of erection, and that testosterone deficiency impairs the anatomical and physiological erectile capacity, which is reversible upon androgen replacement (e.g., see Gooren et al., Asian Journal of Andrology 8(1): 3-9 (2006). Thus, the compounds provided herein can be useful in the treatment of sexual dysfunction. For example, the compounds provided herein are useful for hormone replacement therapy in hypogonadic (androgen deficient) men.

In one embodiment, compounds provided herein are useful in activating the function of the androgen receptor in bone and/or muscle tissue and blocking or inhibiting the function of the androgen receptor in the prostate of a male individual or in the uterus of a female individual.

In one embodiment, the compounds provided herein are used to attenuate or block the function of the androgen receptor in the prostate of a male individual or in the uterus of a female individual induced by AR agonists without effecting hair-growing skin or vocal cords. In one embodiment, the compounds provided herein are used to activate the function of the androgen receptor in bone and/or muscle tissue, but not in organs which control blood lipid levels (e.g., the liver).

10. Arthritic Conditions and Inflammatory Disorders

Androgen receptor modulators are known in the art to be useful in the treatment of arthritic conditions or inflammatory disorders (e.g., see Cutolo et al., Ann. N.Y. Acad. Sci. 966: 131-142 (2002); Cutolo, Rheum Dis Clin North Am 26(4): 881-895 (2000); Bijlsma et al., Am J Reprod Immunol 28(34): 231-234 (1992); Jansson et al., Arthritis Rheum 44(9): 2168-2175 (2001); and Purdie, Br Med Bull 56(3): 809-823 (2000). Also, see Merck Manual, 17th edition, pp. 449-451.)

The compounds provided herein also are used, alone or in combination, to treat or prevent arthritic conditions, such as Behcet's disease, bursitis, tendonitis, CPPD deposition disease, carpal tunnel syndrome, Ehlers-Danlos syndrome, fibromyalgia, gout, infectious arthritis, inflammatory bowel disease, juvenile arthritis, lupus erythematosus, Lyme disease, Marfan syndrome, myositis, osteoarthritis, osteogenesis imperfecta, osteonecrosis, polyarteritis, polymyalgia rheumatica, psoriatic arthritis, Raynaud's phenomenon, reflex sympathetic dystrophy syndrome, Reiter's syndrome, rheumatoid arthritis, scleroderma and Sjogren's syndrome. Provided herein are methods for the treatment or prevention of an arthritic condition, the method including administering a therapeutically effective amount of a compound of any of Formulae I, II or III in an amount effective for the treatment or prevention of an arthritic condition or an inflammatory disorder. In one embodiment, the method is for the treatment or prevention of osteoarthritis, which includes administering a therapeutically effective amount of a compound of any of Formulae I, II or III in an amount effective for the treatment or prevention of osteoarthritis.

11. Modifying Lipid Profile

High doses of testosterone and other anabolic steroids have the ability to reduce cholesterol and to reduce HDL, often greater that 60%, 65%, 70%, 75% and 80%. In one embodiment, a compound of formula I, II or III is used to reduce total cholesterol, LDL, HDL, VLDL, and/or triglycerides. In some embodiments, administration of a compound of formula I, II or III can be used to reduce levels of total cholesterol, LDL, VLDL, triglycerides and/or HDL, while the LDL/HDL ratio remains in the normal range.

12. Contraception

Hormonal contraception is known in the art. For example, hormonal male contraceptive methods provide pregnancy protection by means of spermatogenic suppression or inhibition, generally by the suppression of gonadotropins (e.g., see Pasqualotto et al., Rev Hosp Clin Fac Med Sao Paulo 58(5): 275-283 (2003), Ly et al., Hum Reprod. 20(6): 1733-1740 (2005) and Brady et al., Hum Reprod. 19(11): 2658-2667 (2004)). This can be accomplished by administration of an androgen receptor modulator alone, or in combination with other androgens, such as 19-nortestosterone, 7α-methyl-19-nortestosterone (MENT) and 5α-dihydrotestosterone, or administration of testosterone in combination with an anti-androgen, (e.g., see Turner et al., J Clin Endocrinol Metab 88(10): 4659-4667 (2003). Hormonally mediated suppression of ovulation in women using synthetic androgens is known in the art, but their use is limited because of adverse effects, including weight gain, decreased high-density lipoprotein cholesterol, and in some instances, facial hair growth and acne (e.g., see Johnson, Clin Obstet Gynecol. 41: 405-421 (1998) and Sulak, Am J Manag Care 11: S492-S497 (2005). The selective androgen modulating compounds provided herein are useful for providing contraception while minimizing adverse side effects associated with steroidal androgens.

13. Postmenopausal Conditions

Reduced levels of testosterone in postmenopausal women are associated with loss of libido, decreased sexual activity, diminished feelings of physical well-being and fatigue (e.g., see Kingsberg, J Sex Med. 4 Suppl 3: 227-234 (2007). The compounds disclosed herein can exhibit androgen agonism in the central nervous system and can be used to treat vasomotor symptoms, such as hot flashes, and other postmenopausal conditions, and to increase energy. There is evidence in the art that hot flashes decrease in women treated with androgens (e.g., see Notelovitz, Mayo Clin Proc. 79(4 Suppl): S8-S13 (2004)). Tissue-selective AR antagonists also can treat polycystic ovarian syndrome in postmenopausal women (Eagleson et al., J. Clin. Endocrinol. Metab. 85: 4047-4052 (2000)). In one embodiment, a compound of formula I, II or III is used to treat a postmenopausal condition in a female subject. In one embodiment, the postmenopausal condition is selected from among hot flashes, loss of libido, decreased feelings of well being and fatigue. In one embodiment, a compound of formula I, II or III is used to treat hot flashes in a female subject. In one embodiment, a compound of formula I, II or III is used to treat hypoactive sexual desire disorder in a postmenopausal female subject.

E. FORMULATION OF PHARMACEUTICAL COMPOSITIONS

The compounds of Formula I, II or III or pharmaceutically acceptable salts or prodrugs thereof can be provided as combinations with other therapeutic agents or in pharmaceutical compositions. The pharmaceutical compositions provided herein include therapeutically effective amounts of one or more of the selective androgen receptor activity modulators provided herein that are useful in the prevention, treatment, or amelioration of one or more of the symptoms of diseases or disorders associated with androgen receptor activity.

The compositions include one or more compounds provided herein. The compositions are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel, *Introduction to Pharmaceutical Dosage Forms*, 4$^{th}$ Edition (1985), 126).

In certain embodiments, a pharmaceutical composition including one or more compounds provided herein is prepared using known techniques, including, but not limited to, mixing, dissolving, granulating, dragée-making, levigating, emulsifying, encapsulating, entrapping or tabletting processes.

In the compositions, effective concentrations of one or more compounds or pharmaceutically acceptable derivatives is (are) mixed with a suitable pharmaceutical carrier or vehicle. The compounds can be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with androgen activity or in which androgen activity is implicated.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, such as tumor-targeted liposomes, also can be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

One or more than one of the compounds provided herein is included in the pharmaceutically acceptable carrier in an amount sufficient to exert a therapeutically useful effect in the absence of undesirable side effects on the subject treated.

The concentration of the one or more than one compounds provided herein in the pharmaceutical composition will depend on absorption, inactivation and excretion rates of the compound, the physicochemical characteristics of the compound, the dosage schedule, and amount administered as well as other factors known to those of skill in the art. For example, the amount that is delivered is sufficient to ameliorate one or more of the symptoms of diseases or disorders associated with androgen activity or in which androgen activity is implicated, as described herein.

The effective amount of a compound provided herein can be determined by one of ordinary skill in the art, and includes exemplary dosage amounts for a mammal of from about 0.05 to 100 mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. In some embodiments, the daily dosage of a compound provided herein can be varied over a wide range from about or 0.01 to about or 1000 mg per adult human per day. For example, dosages can range from about or 0.1 to about or 200 mg/day. In some embodiments, the dosage can range from 0.2 mg to 20 mg per day. In some embodiments, the dosage can range from 0.5 mg to 10 mg per day. In some embodiments, the daily dosage can be 0.1 mg, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8 mg, 8.25 mg, 8.5 mg, 8.75 mg, 9 mg, 9.25 mg, 9.5 mg, 9.75 mg, 10 mg. For oral administration, the compositions can be provided in the form of unit dosages such as tablets or capsules or liquids including from about or 0.01 to about or 1000 mg, such as for example, 0.01, 0.05, 0.075, 0.1, 0.25, 0.5, 0.75, 1, 2, 2.5, 3, 4, 5, 6, 7, 8, 9, 10, 15, 20, 25, 50, 75, 100, 125, 150, 175, 180, 190, 200, 225, 250, 300, 400, 500, 750, 800, 850, 900, 950 and 1000 milligrams of the active ingredient for the symptomatic adjustment of the dosage to the subject to be treated. In some embodiments, the compositions can be provided in the form of unit dosages such as tablets or capsules or liquids including from about or 0.01 to about or 1000 such as for example, 0.01, 0.05, 0.075, 0.1, 0.25, 0.5, 0.75, 1, 2.5, 3, 4, 5, 6, 7, 8, 9, 10, 15, 20, 25, 50, 75, 100, 125, 150, 175, 180, 190, 200, 225, 250, 300, 350, 400, 450, 500, 550, 600, 650, 700, 750, 800, 850, 900, 950 and 1000 micrograms of the active ingredient for the symptomatic adjustment of the dosage to the subject to be treated.

The pharmaceutical composition including one or more than one compound provided herein can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compounds, compositions, methods and other subject matter provided herein.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives or prodrugs thereof are mixed with a suitable pharmaceutical carrier or vehicle for systemic, topical or local administration to form pharmaceutical compositions. One or more than one compound provided herein is/are included in an amount effective for ameliorating one or more symptoms of, or for treating or preventing diseases or disorders associated with androgen receptor activity or in which androgen receptor activity is implicated, as described herein. The concentration of the one or more than one compound in the composition will depend on absorption, inactivation, excretion rates of the active compound, the dosage schedule, amount administered, particular formulation as well as other factors known to those of skill in the art.

The compositions are intended to be administered by a suitable route, including orally in the form of capsules, tablets, granules, powders or liquid formulations including syrups; parenterally, such as subcutaneously, intravenously, intramuscularly, with intersternal injection or infusion techniques (as sterile injectable aqueous (aq.) or non-aqueous solutions or suspensions); nasally, such as by inhalation spray; topically, such as in the form of a cream or ointment; rectally, such as in the form of suppositories; liposomally; and locally. The compositions can be in liquid, semi-liquid or solid form and are formulated in a manner suitable for each route of administration. In certain embodiments, administration of the formulation includes parenteral and oral modes of administration. In one embodiment, the compositions are administered orally.

In certain embodiments, the pharmaceutical compositions provided herein including one or more compounds provided herein is a solid (e.g., a powder, tablet, and/or capsule). In certain of such embodiments, a solid pharmaceutical composition including one or more compounds provided herein is prepared using ingredients known in the art, including, but not limited to, starches, sugars, diluents, granulating agents, gums, lubricants, binders, and disintegrating agents.

In certain embodiments, a pharmaceutical composition including one or more compounds provided herein is formulated as a depot preparation. Certain of such depot preparations are typically longer acting than non-depot preparations. In certain embodiments, such preparations are administered by implantation (for example, subcutaneously or intramuscularly) or by intramuscular injection. In certain embodiments, depot preparations are prepared using suitable polymeric or hydrophobic materials (for example, an emulsion in an acceptable oil) or ion exchange resins, or as sparingly soluble derivatives, for example, as a sparingly soluble salt.

In certain embodiments, a pharmaceutical composition including one or more compounds provided herein includes a delivery system. Examples of delivery systems include, but are not limited to, liposomes and emulsions. Certain delivery systems are useful for preparing certain pharmaceutical compositions including those including hydrophobic compounds. In certain embodiments, certain organic solvents such as dimethylsulfoxide are used.

In certain embodiments, a pharmaceutical composition including one or more compounds provided herein (active ingredient) includes one or more tissue-specific delivery molecules designed to deliver the pharmaceutical composition to specific tissues or cell types. For example, in certain embodiments, pharmaceutical compositions include liposomes coated with a tissue-specific antibody.

In certain embodiments, a pharmaceutical composition including one or more compounds provided herein includes a co-solvent system. Certain of such co-solvent systems include, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol including 3% w/v benzyl alcohol, 8% w/v of the nonpolar surfactant Polysorbate 80™, and 65% w/v polyethylene glycol 300. The proportions of such co-solvent systems can be varied considerably without significantly altering their solubility and toxicity characteristics. Furthermore, the identity of co-solvent components can be varied: for example, other surfactants can be used instead of Polysorbate 80™; the fraction size of polyethylene glycol can be varied; other biocompatible polymers can replace polyethylene glycol, e.g., polyvinyl pyrrolidone; and other sugars or polysaccharides can substitute for dextrose.

In certain embodiments, solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediamine-tetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as surfactants that include polyoxyethylene derivatives of sorbitan monolaurate, such as TWEEN® or polysorbate surfactants, or dissolution in aqueous sodium bicarbonate. Derivatives of the compounds, such as prodrugs of the compounds also can be used in formulating effective pharmaceutical compositions.

In certain embodiments, a pharmaceutical composition including one or more compounds provided herein includes a sustained release system. A non-limiting example of such a sustained-release system is a semipermeable matrix of solid hydrophobic polymers. In certain embodiments, sustained release systems can, depending on their chemical nature, release compounds over a period of hours, days, weeks or months.

In certain embodiments, upon mixing or addition of the compound(s), the resulting mixture can be a solution, suspension or emulsion. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions including suitable quantities of the compounds or pharmaceutically acceptable derivatives thereof. The pharmaceutically active compounds and derivatives thereof are typically formulated and administered in unit dosage forms.

The composition can include in addition to the one or more than one compound provided herein other ingredients, such as, but not limited to, a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols and ethanol, to thereby form a solution or suspension. If desired, the pharmaceutical composition to be administered also can include minor amounts of nontoxic auxiliary substances such as wetting agents, emulsifying agents, or solubilizing agents, or pH buffering agents, for example, acetate or sodium citrate, or cyclodextrin derivatives, sorbitan monolaurate, triethanolamine sodium acetate, triethanolamine oleate. Actual methods of preparing such dosage forms are known, or will be apparent, to those skilled in this art; for example, see *Remington's Pharmaceutical Sciences*, Mack Publishing Company, Easton, Pa., 15$^{th}$ edition (1975). The composition or formulation to be administered will, in any event, include a quantity of the active compound in an amount sufficient to alleviate the symptoms of the treated subject.

Dosage forms or compositions can be prepared to include one or more than one compound provided herein in the range of 0.005% to 100% with the balance made up from non-toxic carrier. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium croscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can include 0.001%-100% active ingredient, in one embodiment 0.1-85%, in another embodiment 75-95%. In some embodiments, the compositions include 1-10% active ingredient. In some embodiments, the compositions include 10-25% active ingredient. In some embodiments, the compositions includes 15-35% active ingredient. In some embodiments, the compositions include 40-60% active ingredient. In some embodiments, the compositions include 50-75% active ingredient. In some embodiments, the active ingredient is present at 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In certain embodiments, the compounds can be administered in a form suitable for immediate release or extended release. Immediate release or extended release can be achieved with suitable pharmaceutical compositions or, particularly in the case of extended release, with devices such as subcutaneous implants or osmotic pumps. Exemplary compositions for topical administration include a topical carrier such as a mineral oil gelled with polyethylene (e.g., PLASTIBASE®).

In certain embodiments, compounds provided herein used in the pharmaceutical compositions can be provided as pharmaceutically acceptable salts with pharmaceutically compatible counter-ions. Pharmaceutically compatible salts can be formed with many acids, including, but not limited to, hydrochloric, sulfuric, acetic, citric, ascorbic, butyric, lactic, tartaric, malic, fumaric, succinic and valeric.

In certain embodiments, the pharmaceutical compositions include one or more than one compound provided herein in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The compositions can include in addition to the one or more than one compound provided herein other active compounds to obtain desired combinations of properties.

The compounds provided herein, or pharmaceutically acceptable derivatives or prodrugs thereof as described herein, also can be advantageously administered for therapeutic or prophylactic purposes together with another pharmacological agent known in the general art to be of value in treating one or more of the diseases or medical conditions referred to hereinabove, such as diseases or disorders associated with androgen receptor activity or in which androgen receptor activity is implicated. It is to be understood that such combination therapy constitutes a further aspect of the compositions and methods of treatment provided herein.

In certain embodiments, a pharmaceutical composition including one or more compounds provided herein is formulated as a prodrug. In certain embodiments, prodrugs are useful because they are easier to administer than the corresponding active form. For example, in certain instances, a prodrug can be more bioavailable (e.g., through oral administration) than is the corresponding active form. In certain instances, a prodrug can have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain embodiments, a prodrug includes a short peptide (polyamino acid) bound to an acid group. In certain of such embodiments, the peptide is metabolized to form the corresponding active form.

In certain embodiments, a pharmaceutical composition including one or more compounds provided herein is useful for treating a conditions or disorder in a mammalian, and particularly in a human subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical compositions are administered to achieve local rather than systemic exposures. For example, pharmaceutical compositions can be injected directly in the area of desired effect (e.g., in the renal or cardiac area). In certain embodiments in which the pharmaceutical composition is administered locally, the dosage regimen is adjusted to achieve a desired local concentration of a compound provided herein.

In certain embodiments, a pharmaceutical composition including one or more compounds provided herein is administered in the form of a dosage unit (e.g., tablet, capsule, pill, injection, bolus). In certain embodiments, such dosage units include a selective androgen receptor modulator provided herein in a dose from about or 0.01 µg/kg of body weight to about or 50 mg/kg of body weight. In certain embodiments, such dosage units include a selective androgen receptor modulator in a dose from about or 0.05 µg/kg of body weight to about or 40 mg/kg of body weight. In certain embodiments, such dosage units include a selective androgen receptor modulator in a dose from about or 0.1 µg/kg of body weight to about or 30 mg/kg of body weight. In certain embodiments, such dosage units include a selective androgen receptor modulator in a dose from about or 0.5 µg/kg of body weight to about or 25 mg/kg of body weight. In certain embodiments, such dosage units include a selective androgen receptor modulator in a dose from about or 1 µg/kg of body weight to about or 20 mg/kg of body weight. In certain embodiments, such dosage units include a selective androgen receptor modulator in a dose from about or 2 µg/kg of body weight to about or 15 mg/kg of body weight. In certain embodiments, such dosage units include a selective androgen receptor modulator in a dose from about or 10 µg/kg of body weight to about or 5 mg/kg of body weight. In certain embodiments, such dosage units include a selective androgen receptor modulator provided herein in a dose from about or 0.01 mg/kg of body weight to about or 1 mg/kg of body weight. In certain embodiments, such dosage units include a selective androgen receptor modulator in a dose from about or 0.05 mg/kg of body weight to about or 0.1 mg/kg of body weight. In certain embodiments, such dosage units include a selective androgen receptor modulator in a dose from about or 0.001 µg/kg of body weight to about or 100 µg/kg of body weight. In certain embodiments, such dosage units include a selective androgen receptor modulator in a dose from about or 0.01 µg/kg of body weight to about or 10 µg/kg of body weight. In certain embodiments, such dosage units include a selective androgen receptor modulator in a dose from about or 0.1 µg/kg of body weight to about or 1 µg/kg of body weight. An approximate average adult body weight is 70 kg. Thus, for an adult of average body weight, a dose of 0.1 µg/kg of body weight is equivalent to 7 µg, a dose of 1 µg/kg of body weight is equivalent to 70 µg, a dose of 10 µg/kg of body weight is equivalent to 700 µg or 0.7 mg and a dose of 0.1 mg/kg of body weight is equivalent to 7 mg.

In certain embodiments, pharmaceutical compositions are administered as needed, once per day, twice per day, three times per day, or four or more times per day. It is recognized by those skilled in the art that the particular dose, frequency, and duration of administration depends on a number of factors, including, without limitation, the biological activity desired, the condition of the subject, and tolerance for the pharmaceutical composition.

In certain embodiments, a pharmaceutical composition provided herein is administered for a period of continuous therapy. For example, a pharmaceutical composition provided herein can be administered over a period of days, weeks, months, or years.

Dosage amount, interval between doses, and duration of treatment can be adjusted to achieve a desired effect. In certain embodiments, dosage amount and interval between doses are adjusted to maintain a desired concentration of compound in a subject. For example, in certain embodiments, dosage amount and interval between doses are adjusted to provide plasma concentration of a compound provided herein at an amount sufficient to achieve a desired effect. In certain of such embodiments the plasma concentration is maintained above the minimal effective concentration (MEC). In certain embodiments, pharmaceutical compositions provided herein are administered with a dosage regimen designed to maintain a concentration above the MEC for 10-90% of the time, between 30-90% of the time, or between 50-90% of the time.

1. Compositions for Oral Administration

In certain embodiments, oral pharmaceutical dosage forms are either solid, gel or liquid. The solid dosage forms are tablets, capsules, granules, and bulk powders. Types of oral tablets include compressed, chewable lozenges and tablets which can be enteric coated, sugar coated or film coated. Capsules can be hard or soft gelatin capsules, while granules and powders can be provided in non-effervescent or effervescent form with the combination of other ingredients known to those skilled in the art.

In certain embodiments, the formulations are solid dosage forms, such as capsules or tablets. The tablets, pills, capsules, troches and other solid dosage forms can include any of the following ingredients, or compounds of a similar nature: a binder; a diluent; a disintegrating agent; a lubricant; a glidant; a sweetening agent; and a flavoring agent.

In certain embodiments, pharmaceutical compositions for oral administration are push fit capsules made of gelatin. Certain of such push fit capsules include one or more compounds provided herein in admixture with one or more fillers such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds provided are be dissolved or suspended in suitable liquids, such as fatty oils, liquid paraffin, or liquid polyethylene glycols. In addition, stabilizers can be added.

In certain embodiments, pharmaceutical compositions are prepared for buccal administration. Certain of such pharmaceutical compositions are tablets or lozenges formulated in conventional manner. In some embodiments, the compositions are formulated as dissolvable films, such as those made with pullulan or described in the art (e.g., see U.S. Pat. Nos. 6,596,298, 7,067,116, 7,182,964 and 7,241,411).

Examples of binders for use in the compositions provided herein include microcrystalline cellulose, gum tragacanth, glucose solution, gum arabic, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol, xylitol and artificial sweetening agents such as saccharin. Flavoring agents include natural flavors extracted from plants such as fruits and synthetic blends of compounds which produce a pleasant sensation, such as, but not limited to peppermint and methyl salicylate, including spray dried natural and artificial flavors. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound can be provided in a composition that protects it from the acidic environment of the stomach. For example, the composition can be formulated in an enteric coating that maintains its integrity in the stomach and releases the active compound in the intestine. The composition also can be formulated in combination with an antacid or other such ingredient.

When the dosage unit form is a capsule, it can include, in addition to material of the above type, a liquid carrier such as a fatty oil. In addition, dosage unit forms can include various other materials which modify the physical form of the dosage unit, for example, coatings of sugar and other enteric agents. The compounds also can be administered as a component of an elixir, suspension, syrup, wafer, sprinkle or chewing gum. A syrup can include, in addition to the active compounds, sucrose as a sweetening agent and certain preservatives, dyes and colorings and flavors.

The active materials also can be mixed with other active materials which do not impair the desired action, or with materials that supplement the desired action, such as antacids, H2 blockers (acid reducers), and diuretics.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents also can be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and can include a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, gum arabic, gum tragacanth, xanthan gum, propylene glycol alginate, bentonite, and surfactants such as polyoxyethylene sorbitan monooleate. Suspending agents include xanthan gum, sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, e.g., in propylene carbonate, vegetable oils or triglycerides, can be encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those including a compound provided herein, a dialkylated mono- or poly-alkylene glycol, including, but not limited to, 1,2-dimethoxy-methane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Exemplary compositions can include fast-dissolving diluents such as mannitol, lactose, sucrose, and/or cyclodextrins. Also included in such formulations can be high molecular weight excipients such as celluloses and microcrystalline celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers also can be added for ease of fabrication and use.

In certain of such embodiments, a pharmaceutical composition for oral administration is formulated by combining one or more compounds provided herein with one or more pharmaceutically acceptable carriers. Certain of such carriers enable compounds provided herein to be formulated in dosage forms, such as tablets, pills, dragees, capsules, liquids, gels, syrups, slurries and suspensions, for oral ingestion by a subject. In certain embodiments, pharmaceutical compositions for oral use are obtained by mixing one or more compounds provided herein and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross linked polyvinyl pyrrolidone, agar, or alginic acid or a salt thereof, such as sodium alginate) are added.

In certain embodiments, dragee cores are provided with coatings. In certain of such embodiments, concentrated sugar solutions can be used, which can optionally include gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to tablets or dragee coatings.

In certain embodiments, a daily dosage regimen for a subject includes an oral dose of between 0.1 µg and 2000 mg of a compound provided herein. In certain embodiments, a daily dosage regimen for a subject includes an oral dose of between 1 µg and 500 mg of a compound provided herein. In certain embodiments, a daily dosage regimen for a subject includes an oral dose of between 10 µg and 100 mg of a compound provided herein. In certain embodiments, a daily dosage regimen for a subject includes an oral dose selected from among 0.01, 0.05, 0.075, 0.1, 0.25, 0.5, 0.75, 1, 2, 2.5, 3, 4, 5, 6, 7, 8, 9, 10, 15, 20, 25, 50, 75, 100, 125, 150, 175, 180, 190, 200, 225, 250, 300, 400, 500, 750, 800, 850, 900, 950 and 1000 milligrams of a compound provided herein. In certain embodiments, a daily dosage regimen is administered as a single daily dose. In certain embodiments, a daily dosage regimen is administered as two, three, four, or more than four doses.

2. Injectables, Solutions and Emulsions

In certain embodiments, the pharmaceutical composition is prepared for transmucosal administration. In certain of such embodiments penetrants appropriate to the barrier to be permeated are used in the formulation. Such penetrants are generally known in the art.

Parenteral administration, generally characterized by injection, either subcutaneously, intramuscularly or intravenously also is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, mannitol, 1,3-butanediol, Ringer's solution, an isotonic sodium chloride solution or ethanol. In addition, if desired, the pharmaceutical compositions to be administered also can include minor amounts of non-toxic auxiliary substances such as wetting or emulsifying agents, pH buffering agents, stabilizers, solubility enhancers, and other such agents, such as for example, mono- or diglycerides, fatty acids, such as oleic acid, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. Briefly, a compound provided herein is dispersed in a solid inner matrix, e.g., polymethyl-methacrylate, polybutylmethacrylate, plasticized or unplasticized polyvinylchloride, plasticized nylon, plasticized polyethylene-terephthalate, natural rubber, polyisoprene, polyisobutylene, polybutadiene, polyethylene, ethylene-vinylacetate copolymers, silicone rubbers, polydimethyl-siloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxy-ethanol copolymer, that is insoluble in body fluids. The compound diffuses through the outer polymeric membrane in a release rate controlling step. The percentage of active compound included in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions including thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Anti-oxidants include sodium bisulfate. Local anesthetics include procaine hydrochloride. Suspending and dispersing agents include sodium carboxymethylceluose, hydroxy-propyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit dosage parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution including an active compound is an effective mode of administration. Another embodiment is a sterile aqueous or oily solution or suspension including an active material injected as necessary to produce the desired pharmacological effect.

Injectables are designed for local and systemic administration. Typically a therapeutically effective dosage is formulated to include a concentration of at least about 0.1% w/w up to about 90% w/w or more, in some embodiments more than 1% w/w, of the active compound to the treated tissue(s). The active ingredient can be administered at once, or can be divided into a number of smaller doses to be administered at intervals of time. The precise dosage and duration of treatment is a function of the tissue being treated and can be determined empirically using known testing protocols or by extrapolation from in vivo or in vitro test data. It is to be noted that concentrations and dosage values also can vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of formulations provided herein.

The compounds can be formulated in any suitable vehicle or form. For example, they can be in micronized or other suitable form and/or can be derivatized to produce a more soluble active product or to produce a prodrug or for other purposes. The form of the resulting mixture depends upon a number of factors, including, for example, an intended mode of administration and the solubility of the compound in the selected carrier or vehicle. The effective concentration is sufficient for ameliorating the symptoms of the condition and can be empirically determined.

In certain embodiments, a pharmaceutical composition is prepared for administration by injection wherein the pharmaceutical composition includes a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers and/or suspending agents. Certain pharmaceutical compositions for injection are presented in unit dosage form, e.g., in ampules or in multi dose containers. Certain pharmaceutical compositions for injection are suspensions, solutions or emulsions in oily or aqueous vehicles, and can include formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions can include substances that increase the viscosity of the suspension, such as sodium carboxymethyl cellulose, sorbitol, or dextran. Optionally, such suspensions also can include suitable stabilizers or agents that increase the solubility of the compounds to allow for the preparation of highly concentrated solutions.

In certain embodiments, the pharmaceutical composition is prepared for administration by inhalation. Certain of such pharmaceutical compositions for inhalation are prepared in the form of an aerosol spray in a pressurized pack or a nebulizer. Certain of such pharmaceutical compositions include a propellant, e.g., dichlorodifluoromethane, trichlorofluoromethane, dichlorotetrafluoroethane, carbon dioxide or other suitable gas. In certain embodiments using a pressurized aerosol, the dosage unit can be determined with a valve that delivers a metered amount. In certain embodiments, capsules and cartridges for use in an inhaler or insufflator can be formulated. Certain of such formulations include a powder mixture of a compound provided herein and a suitable powder base such as lactose or starch.

In certain embodiments, the pharmaceutical compositions provided are administered by continuous intravenous infusion. In certain of such embodiments, from 0.01 μg to 500 mg of the composition is administered per day.

3. Lyophilized Powders

Of interest herein also are lyophilized powders, which can be reconstituted for administration as solutions, emulsions and other mixtures. They also can be reconstituted and formulated as solids or gels.

The sterile, lyophilized powder is prepared by dissolving a compound provided herein, or a pharmaceutically acceptable derivative thereof, in a suitable solvent. The solvent can include an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent also can include a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. In some embodiments, each vial includes a single dosage of from 10 μg to 1000 mg. In another embodiment, each vial includes a single dosage of from 100 μg to 500 mg. In another embodiment, each vial includes a single dosage of from 0.1 mg to 50 mg. In another embodiment, each vial includes a single dosage of from 0.5 mg to 20 mg. In another embodiment, each vial includes a single dosage of 1 mg, 2 mg, 3 mg, 4 mg, 5 mg, 6 mg, 7 mg, 8 mg, 9 mg or 10 mg. In another embodiment, each vial includes multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1 mg to 50 mg is added per mL of sterile water or other suitable carrier. In some embodiments, 5 mg to 35 mg is added per mL of sterile water or other suitable carrier. In other embodiments, 10 mg to 30 mg of lyophilized powder is added per mL of sterile water or other suitable carrier. The precise amount depends upon the selected compound. Such amount can be empirically determined.

4. Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration. Transdermal skin patches useful for administering the compounds disclosed herein include those well known to those of ordinary skill in that art.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflation, alone or in combination with an inert carrier such as lactose. In such a case, the particles of the formulation will typically have diameters of less than 50 microns, in some embodiments less than 10 microns.

In certain embodiments, the pharmaceutical compositions for inhalation are prepared in the form of an aerosol spray in a pressurized pack or a nebulizer. Certain of such pharmaceutical compositions include a propellant, e.g., dichlorodifluoro-methane, trichlorofluoromethane, dichlorotetrafluoroethane, carbon dioxide or other suitable gas. In certain embodiments using a pressurized aerosol, the dosage unit can be determined with a valve that delivers a metered amount. In certain embodiments, capsules and cartridges for use in an inhaler or insufflator can be formulated. Certain of such formulations include a powder mixture of a compound provided herein and a suitable powder base such as lactose or starch.

Exemplary compositions for nasal aerosol or inhalation administration include solutions that can include, for example, benzyl alcohol or other suitable preservatives, absorption promoters to enhance absorption and/or bioavailability, and/or other solubilizing or dispersing agents such as those known in the art.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients also can be administered. These solutions, particularly those intended for ophthalmic use, can be formulated as 0.01%-10% isotonic solutions, pH about 5-7, with appropriate salts. In certain embodiments in which the compositions is administered locally, the dosage regimen is adjusted to achieve a desired local concentration of a compound provided herein.

In certain embodiments, the pharmaceutical composition is prepared for topical administration. Certain of such pharmaceutical compositions include bland moisturizing bases, such as ointments or creams. Any of the ointment bases known in the art, including water in oil emulsion bases, oil in water emulsion bases, absorption bases, oleaginous bases and water soluble or water miscible bases can be used (e.g., see *Remington: The Science and Practice of Pharmacy*, 19th Ed. (Easton, Pa.: Mack Publishing Co., 1995) at pages 1399-1404). Oleaginous ointment bases are generally anhydrous and include, for example, vegetable oils, animal fats, and semisolid petroleum-based hydrocarbons. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, stearic acid and polyethylene glycols of varying molecular weight. Creams are viscous liquids or semi-solid emulsions, and can be either oil-in-water or water-in-oil emulsions. Cream bases are water-washable, and contain an oil phase, an emulsifier, and an aqueous phase, which can include a fatty alcohol. The emulsifier in a cream formulation is generally a nonionic, anionic, cationic, or amphoteric surfactant. Lotions are preparations to be applied to the skin surface without friction, and often include a water or alcohol base, and include an emulsion and often solid particles (such as cocoa butter or fatty acid alcohols).

Exemplary suitable ointment bases include, but are not limited to, petrolatum, petrolatum plus volatile silicones, and lanolin. Cream bases, such as those including an emulsion of water, a mineral oil or petrolatum, one or more fatty alcohols or fatty esters, a polyoxyethylene ether or ester surfactant or polysorbate surfactant, also can be used. Exemplary suitable cream bases include, but are not limited to, cold cream (USP), hydrous lanolin and hydrophilic ointment (USP). The moisturizing bases can further contain various other emollients, emulsifiers, perfumes, colorants and preservatives.

Suitable water-in-oil emulsions are commercially available, e.g., blends of petrolatum, mineral oil, ceresin, lanolin alcohol, panthenol, glycerin and bisabolol under the designation Aquaphor™, available from Beiersdorf Futuro Inc. (Cincinnati, Ohio); blends of water, glycerin, panthenol, caprylic/capric triglyceride, dicaprylyl carbonate, octyl-dodecanol, C12-15 alkyl benzoate, dimethicone, squalane, tapioca starch, cetearyl alcohol, glyceryl stearate citrate, myristyl myristate, butylene glycol, benzyl alcohol, carbomer, phenoxyethanol, ammonium acryloyldimethyltaurate/VP copolymer, sodium hydroxide, methylparaben, propylparaben, iodopropynl butylcarbamate, such as Eucerin™, available from Beiersdorf Futuro Inc. (Cincinnati, Ohio), blends of water, mineral oil, petrolatum, glycerin, isohexadecane, microcrystalline wax, lanolin alcohol, paraffin, panthenol, magnesium sulfate, decyl oleate, octyldodecanol, aluminum stearate, methylchloroisothiazolinone, methylisothiazolinone, citric acid and magnesium stearate, such as Nivea™ Cream, available from Beiersdorf Futuro Inc. (Cincinnati, Ohio).

Suitable oil-in-water emulsions are commercially available, e.g., water, mineral oil, petrolatum; sorbitol, stearic acid, lanolin, lanolin alcohol, cetyl alcohol, glyceryl stearate/PEG-100 stearate, triethanolamine, dimethicone, propylene glycol, microcrystalline wax, tri(PPG-3 myristyl ether) citrate, disodium EDTA, methylparaben, ethylparaben, propylparaben, xanthan gum, butylparaben and methyldibromo glutaronitrile, such as Lubriderm™ Cream, available from Pfizer (Morris Plains, N.J.); a blend of purified water, petrolatum, mineral oil, cetostearyl alcohol, propylene glycol, sodium laurel sulfate, isopropyl palmitate, imidazolidinyl urea, methylparaben and propylparaben, such as Dermabase™ cream, available from Paddock Industries, Inc. (Minneapolis, Minn.); and a blend of purified water, glycerin, hydrogenated polyisobutene, cetearyl alcohol and ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium Hydroxide and citric acid, such as Cetaphil™ lotion, available from Galderma Laboratories (Ft. Worth, Tex.).

In certain embodiments, the formulation, route of administration and dosage for the pharmaceutical composition provided herein can be chosen in view of a particular subject's condition (see e.g., Fingl et al., "The Pharmacological Basis of Therapeutics", Chapter 1, p. 1 (1975)). In certain embodiments, the pharmaceutical composition is administered as a single dose. In certain embodiments, a pharmaceutical composition is administered as a series of two or more doses administered over one or more days.

5. Compositions for Other Routes of Administration

In certain embodiments, the pharmaceutical composition is prepared for topical administration such as rectal administration. The pharmaceutical dosage forms for rectal administration include, but are not limited to rectal suppositories, capsules and tablets for systemic effect. In certain embodiments, a pharmaceutical agent is prepared for rectal administration, such as a suppositories or retention enema. Certain of such pharmaceutical agents include known ingredients, such as cocoa butter and/or other glycerides. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, Carbowax (polyoxyethylene glycol) and appropriate mixtures of mono-, di- and triglycerides of fatty acids. Combinations of the various bases can be used. In certain embodiments, the pharmaceutical compositions include moisturizing bases, such as ointments or creams. Agents to raise the melting point of suppositories include spermaceti and wax. Rectal suppositories can be prepared either by the compressed method or by molding. The typical weight of a rectal suppository is about 2 to 3 gm.

Tablets and capsules for rectal administration are manufactured using the same pharmaceutically acceptable substances and by the same methods as for formulations for oral administration.

F. ARTICLES OF MANUFACTURE

The compounds provided herein or pharmaceutically acceptable derivatives or prodrugs, or pharmaceutical compositions that include such compounds, can be packaged as articles of manufacture including packaging material, within the packaging material a compound or pharmaceutically acceptable derivative thereof provided herein, which is effective for modulating the activity of androgen receptor, or for treatment, prevention or amelioration of one or more symptoms of androgen receptor mediated diseases or disorders, or diseases or disorders in which androgen receptor activity is implicated, and a label that indicates that the compound or composition is used for modulating the activity of androgen receptor or for treatment, prevention or amelioration of one or more symptoms of androgen receptor mediated diseases or disorders, or diseases or disorders in which androgen receptor activity is implicated.

The articles of manufacture provided herein include packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes and any packaging material suitable for a selected formulation and intended mode of administration and treatment. A wide array of formulations of the compounds and compositions provided herein are contemplated as are a variety of treatments for any disease or disorder in which androgen receptor activity is implicated as a mediator or contributor to the symptoms or cause.

In certain embodiments, the pharmaceutical compositions can be presented in a pack or dispenser device which can include one or more unit dosage forms including a compound provided herein. The pack can for example include metal or plastic foil, such as a blister pack. The pack or dispenser device can be accompanied by instructions for administration. The pack or dispenser also can be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions including a compound provided herein formulated in a compatible pharmaceutical carrier also can be prepared, placed in an appropriate container, and labeled for treatment of an indicated condition.

G. KITS

The compounds provided herein and compositions that include the provided compounds also can be provided as kits. Kits can include a pharmaceutical composition described herein and an item for administration. For example, a selective androgen receptor modulator provided herein can be supplied with a device for administration, such as a syringe, an inhaler, a dosage cup, a dropper, or an applicator. The kit can, optionally, include instructions for application including dosages, dosing regimens and instructions for modes of administration. Kits also can include a pharmaceutical composition described herein and an item for diagnosis. For example, such kits can include an item for measuring the concentration, amount or activity of androgen receptor of a subject.

H. EVALUATION OF THE ACTIVITY OF THE COMPOUNDS

Standard physiological, pharmacological and biochemical procedures are available for testing the compounds provided herein to identify those that possess activity as selective androgen receptor modulators. In vitro and in vivo assays known in the art can be used to evaluate the activity of the compounds provided herein as selective androgen receptor modulators. Exemplary assays include, but are not limited to, fluorescence polarization assay, luciferase assay and co-transfection assay. For example, SARMs can be identified using a series of in vitro cell-assays that profiles ligand mediated activation of AR (e.g., see U.S. Pat. No. 7,196, 076). AR agonistic activity can be determined by monitoring the ability of the SARM compounds to maintain and/or stimulate the growth of AR-containing tissue such as prostate and seminal vesicles, as measured by weight. AR antagonistic activity can be determined by monitoring the ability of the SARM compounds to inhibit the growth of AR-containing tissue.

The agonist and antagonist effects of SARMs can be measured in non-tumor tissues via a series of in vivo rat models in which surrogate endpoints are measured in tissues including, but not limited to, the prostate, seminal vesicle, and levitor ani muscle, as well as the hypothalamic axis via measurement of plasma luteinizing hormone (LH) levels. The Sprague-Dawley rat model has been used extensively as a model for identifying selective androgen receptor modulators (SARMs) with in vivo pharmacological activity, thereby identifying active, non-steroidal selective androgen receptor modulators that can be useful therapeutics, such as for enhancing muscle, bone, and sexual function and treating prostate cancer (e.g., see Yin et al., J Pharmacol Exp Ther 304(3): 1334-1340 (2003), Jasuja et al., Endocrinology 146(10): 4472-4478 (2005), Miner et al., Endocrinology 148(1): 363-373 (2007), Morrissey et al., Journal of Andrology 23(3): 341-351 (2002), Adesanya et al., Scientific Research and Essay 2(8): 309-314 (2007).

The agonist or antagonist activity of a potential SARM also can be measured in a normal, non-tumor cell line. Examples of normal, non-tumor cells lines include, but are not limited to, primary rat prostate epithelial and stromal cells, murine muscle cell line C2C12, primary guinea pig smooth muscle cells, primary smooth-muscle cells from immature (I-PSMC) or adult (A-PSMC) rat penis, primary rabbit smooth muscle cell line, prostatic smooth muscle cell line PS-1, prostatic smooth muscle cell line PSMC1, mouse bone cell cultures and osteoblasts cells and primary rat seminal vesicle lines SVC-1 and SCV-2 (e.g., see Chen et al., FEBS Letters 491: 91-93 (2001), Gerdes et al., Endocrinology 139: 3569-3577 (1998), Gonzalez-Cadavid et al., Mol. Cell. Endocrinol. 90: 219-229 (1993), Nemeth et al., J. Andrology 19: 718-724 (1998), Ricciardelli I., J. Endocrinol. 140: 373-383 (1994), Sadeghi-Nejad et al., Int. J. Impotence Res. 10: 165-169 (1998), Sarah et al., J. Cell. Physiol. 185: 416-424 (2000), and Tajana et al., EMBO J. 3: 637-644 (1984) Zhang et al., Prostate 30: 117-129 (1997) and Zhuang et al., J. Steroid Biochem. Mol. Biol. 41: 693-696 (1992).

Several surrogate endpoint in vivo assays also can be used to examine the effects of a potential SARM on the AR pathway. These assays measure the effects of a potential SARM on normal androgen dependent tissues and functions, such as, but not limited to, prostate, seminal vesicle, levator ani muscle, bone, libido, fertility and hypothalamus (measurement of blood LH levels). These assays are widely recognized as having a direct correlation to the effects of a potential SARM on the AR pathways in humans. Exemplary surrogate endpoint in vivo assays are described in Ashby et al., J. Appl. Tox. 20: 35-47 (2000), Chen et al., WET #75424 (2004), Yamada et al., Tox. Sciences 53: 289-296 (2000), Hamann et al., J. Med. Chem. 41: 623-639 (1998), Furr et al., Eur. Urol 29: 83-95 (1996), Broulik et al., Bone 20: 473-475 (1997), Maucher et al., J. Cancer Res. Clin. Oncol. 119: 669-674(1993), Higuchi et al., Bioorganic & Medicinal Chemistry Letters 17(19): 5442-5446 (2007); Arjan van Oeveren et al., Bioorganic & Medicinal Chemistry Letters 17(6): 1527-1531 (2007); and Vanderschueren et al., Endocrine Reviews 25(3): 389-425 (2004).

Animal models bearing a hormone-dependent tumor also can be used to assess the antagonist activity of a potential SARM against the tumor and the agonist or antagonist activity against AR-containing normal non-tumor tissues in the animal. For example, the above surrogate endpoint in vivo assays can be run using a rat bearing an androgen-dependent rat prostate tumor, such as Dunning R-3327. In this manner, effects of a SARM on a rat androgen-dependent prostate tumor can be determined while simultaneously examining the effects of the SARM agent on AR-containing normal non-tumor tissues such as, but not limited to, prostate, seminal vesicle, and levitor ani muscle as well as effects on the hypothalamic axis via measurements of plasma LH levels. In a similar fashion, immune compromised nude rats bearing human androgen-dependent prostate tumors can be used. In this manner, effects of a SARM on a human androgen-dependent prostate tumor can be determined while simultaneously examining the effects of the SARM agent on normal tissues such as, but not limited to, prostate, seminal vesicle, and levitor ani muscle as well as effects on the hypothalamic axis via measurements of plasma LH levels. In addition, in vivo rat assays can be used to determine the effect of SARMs on libido and reproduction.

In certain embodiments, the compounds provided herein are capable of modulating activity of androgen receptor in a "co-transfection" assay (also called a "cis-trans" assay), which is known in the art (see e.g., Evans et al., Science 240: 889-95 (1988); U.S. Pat. Nos. 4,981,784 and 5,071,773; and Pathirana et al., "Nonsteroidal Human Progesterone Receptor Modulators from the Marie Alga Cymopolia Barbata," Mol. Pharm. 47: 630-35 (1995)). Modulating activity in a co-transfection assay has been shown to correlate with in vivo modulating activity. Thus, in certain embodiments, such assays are predictive of in vivo activity (see, e.g., Berger et al., J. Steroid Biochem. Molec. Biol. 41: 773 (1992)). The in vitro biology of the compounds provided herein can be determined using any assay known in the art. For example, the co-transfection assay, as described herein or in the art, can be used. The co-transfection assay provides functional activity expressed as agonist $EC_{50}$ and antagonist $IC_{50}$ values.

In certain co-transfection assays, two different co-transfection plasmids are prepared. In the first co-transfection plasmid, cloned cDNA encoding an intracellular receptor (e.g., androgen receptor) is operatively linked to a constitutive promoter (e.g., the SV 40 promoter). In the second co-transfection plasmid, cDNA encoding a reporter protein, such as firefly luciferase (LUC), is operatively linked to a promoter that is activated by a receptor-dependant activation factor. Both co-transfection plasmids are co-transfected into the same cells. Expression of the first co-transfection plasmid results in production of the intracellular receptor protein. Activation of that intracellular receptor protein (e.g., by binding of an agonist) results in production of a receptor-dependant activation factor for the promoter of the second co-transfection plasmid. That receptor-dependant activation factor in turn results in expression of the reporter protein encoded on the second co-transfection plasmid. Thus, reporter protein expression is linked to activation of the receptor. Typically, that reporter activity can be conveniently measured (e.g., as increased luciferase production).

Certain co-transfection assays can be used to identify agonists, partial agonists, and/or antagonists of intracellular receptors. In certain embodiments, to identify agonists, co-transfected cells are exposed to a test compound. If the test compound is an agonist or partial agonist, reporter activity is expected to increase compared to co-transfected cells in the absence of the test compound. In certain embodiments, to identify antagonists, the cells are exposed to a known agonist (e.g., androgen for the androgen receptor) in the presence and absence of a test compound. If the test compound is an antagonist, reporter activity is expected to decrease relative to that of cells exposed only to the known agonist.

An exemplary co-transfection assay is the luciferase reporter assay (Evans, Science 240: 889-895 (1988), Berger et al., J Steroid Biochem Mol Biol 41: 733-738 (1992)) can be used to establish the ability of a compound of formulae I, II or III to activate (agonist activity) or repress (antagonist activity) the ability of the human androgen receptor (hAR) to induce gene expression. A human cell line containing endogenously expressed hAR (e.g., MDA-MB-453 cells, derived from a human mammary carcinoma, American Tissue Type Culture Collection [ATCC] HTB 131) can be transfected with an androgen responsive luciferase reporter plasmid to measure the level of cross-reactivity of the compound on other nuclear receptors (such as the glucocorticoid receptor (GR), estrogen receptor (ER), mineralocorticoid receptor (MR), progesterone receptor (PR), retinoid receptor (RAR), retinoid X receptor (RXR), peroxisome proliferator activating receptors alpha (PPARα), gamma (PPARγ) and delta (PPARδ), liver X receptor (LXR), farnesyl X receptor (FXR) and the pregnane X receptor (PXR)). In the assay, luciferase reporter plasmids containing the cDNA for firefly luciferase (LUC) under the control of a conditional promoter containing hormone response elements recognized by the appropriate nuclear receptor are co-transfected into cells with the nuclear receptor expression plasmid. Any appropriate nuclear receptor expression plasmid known in the art can be used. Exemplary of such plasmids are the reporter plasmid MMTV-LUC, which contains the mouse mammary tumor virus (MTV) long terminal repeat (LTR), which is a conditional promoter containing hormone response elements recognized by AR, GR, MR and PR (Giguere et al., Cell 46: 645-652 (1986)). The reporter plasmid MTV-ERES-LUC contains the mouse MTV LTR in which the hormone response elements have been deleted and replaced with five copies of a 33-base pair estrogen response element (ERE) recognized by ER (McDonnell et al., J Biol Chem 269: 11945-11949 (1994)). The reporter plasmid MTV-TREp-LUC contains two copies of a thyroid hormone response element (TRE) sequence, recognized by RAR (Bissommette et al., Mol Cell Biol 15(10): 5576-5585 (1995), Umesono et al., Nature 336(6196): 262-265 (1988)). The reporter plasmid CRBP-(2)-tk-LUC contains two copies of a response element sequence from the cellular retinoid binding protein (CRBP) promoter, recognized by RXR, linked to the tk promoter (Mangelsdorf et al., Cell 66(3): 555-561 (1991)). The promoter plasmid pPREA3-tk-LUC contains a response element sequence from the acyl CoA oxidase gene, recognized by PPARγ, linked to the tk promoter (Kliewer et al., Nature 355(6359): 446-449 (1992)). The reporter plasmid LXRE-tk-LUC contains a response element sequence recognized by LXR, linked to the tk promoter (Willy et al., Genes Dev 9(9): 1033-1045 (1995)). The reporter plasmid EcRE7-tk-LUC contains a response element sequence recognized by FXR, linked to the tk promoter (Forman et al., Cell 81(5): 687-693 (1995)). The reporter plasmid CYP3A1-tk-LUC contains a response element from the CYP3A1 promoter that is recognized by PRX, linked to the tk promoter.

Any receptor plasmid expression plasmid known in the art can be used in the assay. Exemplary receptor expression plasmids include pRShGR (Giguere et al., Cell 46: 645-652 (1986)), pRShMR (Arriza et al., Science 237: 268-275 (1987)), pSVhPR-B (Vegeto et al., Cell 69: 703-713 (1992)), pRShRXRα (Boehm et al., J Med Chem 37(18): 2930-2941 (1994)), pCMVhPPARγ (Willy et al., Genes Dev 9(9): 1033-1045 (1995)), pCMVGAL4hPPARα, pCMVGAL4hPPARδ, pCMV-LXRα and pCMV-FXRα (Cesario et al., Mol Endocrinol 15(8): 1360-1369 (2001)).

The cotransfections are performed using known methods (Berger et al., J Steroid Biochem Mol Biol 41: 733-738 (1992)). The appropriate recombinant DNA receptor expression plasmid and the luciferase reporter plasmid for the GR, MR, PR, PAP, RXR, PPARα, PPARγ, PPARδ, LXRα, FXRα and PXRα assays are transiently transfected into cells using a non-liposomal formulation (e.g., the FuGENE 6 transfection reagent, Roche, Indianapolis, Ind., according to manufacturer's specifications).

Tissue selective androgen receptor agonists provided herein typically have $EC_{50}$ values of 1 micromolar or less and efficacy values greater than about 50% in a standard AR assay, such as the co-transfection assay described herein. In some embodiments, the $EC_{50}$ is in the range of 1 to 1000 μM. In some embodiments, the $EC_{50}$ is in the range of 1 to 500 μM. In some embodiments, the $EC_{50}$ is in the range of 1 to 100 μM. In some embodiments, the $EC_{50}$ is less than 100 μM. In some embodiments, the $EC_{50}$ is less than 75, 70, 65, 60, 55, 50, 45, 40, 35, 30, 25, 20, 15, 10, 5 or 1 μM. In some embodiments, the efficacy values are greater than about or at 55%, 50%, 65%, 70%, 75%, 80%, 85%, 90%, 95%, 100%, 105%, 110%, 115%, 120%, 125% or greater. In some embodiments, the compounds provided herein have an $EC_{50}$ value of 10 μM or less and an efficacy value greater than 50%, 55%, 60%, 65%, 70%, 75%, 80%, 85%, 90%, 95% or 100%. In some embodiments, the compounds provided herein have an $EC_{50}$ value of about or 1 μM to about or 5 μM and an efficacy value greater than 50%, 55%, 60%, 65%, 70%, 75%, 80%, 85%, 90%, 95% or 100%. In some embodiments, the compounds provided herein exhibit an $EC_{50}$ value of no greater than 10 micromolar, or no greater than 1 micromolar, or no greater than 100 nanomolar, or no greater than 10 nanomolar or no greater than 1 nanomolar in an assay for determination of AR receptor antagonist activity.

Tissue selective androgen receptor antagonists provided herein typically have $IC_{50}$ values of 1 micromolar or less and efficacy values greater than about or 50% in a standard AR assay, such as the co-transfection assay described herein. In some embodiments, the $IC_{50}$ is in the range of 1 to 1000 μM. In some embodiments, the $IC_{50}$ is in the range of 1 to 500 μM. In some embodiments, the $IC_{50}$ is in the range of 1 to 100 μM. In some embodiments, the $IC_{50}$ is less than 100 μM. In some embodiments, the $IC_{50}$ is less than 75, 70, 65, 60, 55, 50, 45, 40, 35, 30, 25, 20, 15, 10, 5 or 1 μM. In some embodiments, the efficacy values are greater than about or at 55%, 50%, 65%, 70%, 75%, 80%, 85%, 90%, 95%, 100%, 105%, 110%, 115%, 120%, 125% or greater. In some embodiments, the compounds provided herein have an $IC_{50}$ value of 10 μM or less and an efficacy value greater than 50%, 55%, 60%, 65%, 70%, 75%, 80%, 85%, 90%, 95% or 100%. In some embodiments, the compounds provided herein have an $IC_{50}$ value of about or at 1 μM to about or at 5 μM and an efficacy value greater about 50%, 55%, 60%, 65%, 70%, 75%, 80%, 85%, 90%, 95% or 100%. In some embodiments, the compounds provided herein exhibit an $IC_{50}$ value of no greater than 10 micromolar, or no greater than 1 micromolar, or no greater than 100 nanomolar, or no greater than 10 nanomolar or no greater than 1 nanomolar in an assay for determination of AR receptor antagonist activity.

The compounds provided herein exert their receptor-modulatory effects with high selectivity. This means that they do not bind to certain other receptors (other than AR receptors) with high affinity, but rather only bind to, activate, or inhibit the activity of other receptors with affinity constants of greater than 1 micromolar (μM). In some embodiments, the compounds only bind to, activate, or inhibit the activity of other receptors with affinity constants of greater than 100 μM. In some embodiments, the compounds only bind to, activate, or inhibit the activity of other receptors with affinity constants of greater than 1000 μM. Because side effects are often due to undesirable receptor activation or antagonism, the high selectivity of the compounds provided herein can reduce the incidence of side effects caused by undesirable activation or antagonism of other one or more other receptor(s). The compounds provided herein activate AR-induced gene expression. This was demonstrated in the cotransfection assay in MDA-MB-453 cells.

In assays measuring the affinity and functional activation of AR by compounds provided herein, compounds of formula I activated AR-dependent gene expression. For example, Compound 102 demonstrated consistently higher potency than other tested androgen modulator compounds in binding to AR protein, in activating AR in a functional assay, in stimulating expression of a key gene in muscle cells, and in repressing a key inflammatory modulator in bone cells. Higher potency indicates that a substance can be administered at a lower dose to achieve equal therapeutic effect. Use of a lower dose is beneficial because it reduces the size of the oral dosage form or the number of capsules or tablets required to administer an effective dose, thereby improving patient convenience and comfort, and lower dose improves the safety of a drug by reducing the amount of drug undergoing metabolism, which can yield products that produce off-target side effects.

1. Effect on Muscle

Skeletal α-actin is a major component of skeletal muscle. Androgens play a role in increasing muscle mass and strength (Mooradian et al., Endocr Rev 8: 1-28 (1987); Bhasin et al., J Clin Endocrinol Metab 82: 407-413 (1997); and Bhasin et al., N Engl J Med 335: 1-7 (1996)). Androgens up-regulate α-actin mRNA in rat levator ani skeletal muscle and hence AR-mediated modulation of skeletal α-actin promoter activity is a marker for studying androgen regulation of gene expression in muscle. The effect the compounds provided herein on muscle can be tested by any method known in the art. Such methods include increases in the weight of the levator ani muscle, which are indicative of anabolic activity, and are accepted in the art as a reliable index of anabolic activity (e.g., see Antonio et al., J Appl Physiol 87: 2016-2019 (1999)) and the expression of myosin heavy chain (MHC) subtypes in skeletal muscle. MHC is the predominant protein in skeletal muscle and is expressed in a tissue-specific and developmentally regulated manner (Adams et al., Am J Physiol. 276(4 Pt 2): R954-961 (1999)). Expression of MHC subtypes can be examined using RT-PCR of masseter muscle tissue of female rats by the method of Wright et al. (J Appl Physiol. 83(4): 1389-96 (1997)). At steady state, mRNA expression parallels the pattern of MHC protein expression. Because transcription of MHC mRNA occurs in advance of MHC protein translation, and the increased sensitivity of RT-PCR compared to western blotting, rapid changes in mRNA expression can be detected and used to analyze the subtle dynamic effects on muscle metabolism. An anabolic effect on masseter muscle is demonstrated increasing transcription of MHC, such as MHC type as compared to the untreated control. Other assays are known in the art (e.g., see Miner et al., Endocrinology 148(1): 363-373 (2007); Eisenberg et al., Journal of Pharmacology and Experimental Therapeutics 99(1): 38-44 (1950); Labrie et al., J Endocrinology 184: 427-433 (2005)).

An exemplary assay for measuring AR-mediated gene expression in mouse muscle cells is the human skeletal α-actin assay. A mouse muscle cell line (C2C12, obtained from American Type Cell Culture (ATCC, Rockville, Md.)) can be used in the luciferase reporter assay. An SK α-actin-LUC reporter plasmid is constructed by inserting the skeletal α-actin promoter sequence into a luciferase reporter vector (e.g., by cloning the human skeletal α-actin promoter region from −77 to +202 bp from human liver genomic DNA (Clontech, Palo Alti, Calif.) and inserting the sequence into a pGL3-Basic reporter plasmid (Promega, Madison, Wis.)). The C2C12 cell line can be transiently transfected with a human AR expression plasmid and a luciferase reporter plasmid containing the skeletal α-actin promoter upstream of the luciferase cDNA. The compounds to be tested are added to the cells after transfection and after 24 hours of incubation, the cells are lysed with a detergent-containing buffer and assayed for luciferase activity. The $EC_{50}$ is determined from the concentration response curve for the compound, and efficacy is calculated by comparison with the standard androgen agonist, dihydrotestosterone.

2. Effect on Bone

Anabolic activity of the compounds provided herein on bone can be tested by any method known in the art. Such methods include bone formation rate, which can be assessed by osteocalcin level measurement. Plasma osteocalcin levels can be determined using any method known in the art (e.g., see Koyama et al., J Immunol Methods 139(1): 17-23 (1991)). A commercially available rat osteocalcin EIA kit is available from Biomedical Technologies Inc. (Stoughton, Mass.). Additional assays include bone nodule formation assays (Vanderschueren et al., Endocrine Reviews 25(3): 389-425 (2004), Beresford et al., 45(2): 163-178 (2005) and use of rodent models of osteoporosis (e.g., see Gowen et al., J Clin Invest. 105: 1595-604 (2000); Pietschmann et al., Exp Gerontol. 42(11): 1099-1108 (2007); and Wang et al, Bone. 29(2): 141-148 (2001)). Bone turnover markers also have been demonstrated to be an effective, validated tool for monitoring bone activity. For example, bone alkaline phosphatase, urinary hydroxyproline, serum alkaline phosphatase, tartrate-resistant acid phosphatase, osteocalcin levels, and urinary calcium-creatinine ratio, are used as bone turnover markers (e.g., Sit et al., Adv Ther. 24(5): 987-995 (2007); Szulc et al., Osteoporos Int. 18(11): 1451-61 (2007); and Hannon et al., Cancer Treat Rev. 32 Suppl 1: 7-14 (2006)). C-telopeptide is used as a bone resorption marker (e.g., see Srivastava et al., Calcified Tissue International 66(6): 435-442 (2000)).

An exemplary cotransfection assay for measuring AR-mediated effects on bone measures the modulation of IL-6 promoter activity. IL-6 is an important bone resorption factor (Jilka et al, Science 257: 88-91 (1992); Bellido et al., J Clin Invest 95: 2886-2895 (1995)). Overexpression of IL-6 can cause severe bone loss in vivo. In vitro studies have indicated that cytokines, such as TNFα and IL-1β strongly stimulate IL-production through the induction of NFκB (Kurokouchi et al., J Bone Mineral Res 13: 1290-1299 (1998); Ng et al., J Biol Chem 269: 19021-19027 (1994)). It has been reported that androgens regulate IL-6 mRNA by suppressing NFKB binding to its response element (Keller et al., J Biol Chem 271: 26267-26275 (1996)). Thus, the AR-mediated modulation of IL-6 promoter activity provides an excellent marker for studying androgen action in bone. The assay is a cotransfection assay that measures the ability of compound to repress gene expression via the human androgen receptor from the IL-6 promoter using a luciferase reporter assay in human osteoblast cells.

A human osteoblast cell line (Saos-2, available from American Type Cell Culture (ATCC, Rockville, Md.)) can be used in the luciferase reporter assay. An IL-6-LUC reporter plasmid can be constructed by inserting the IL-6 promoter sequence into a luciferase reporter vector (e.g., by cloning the human IL-6 promoter region from −232 to +17 bp from human liver genomic DNA (Clontech, Palo Alti, Calif.) and inserting the sequence into a pGL2-enhancer reporter plasmid (Promega, Madison, Wis.)). The Saos-2 cell line can be transiently transfected with a human AR expression plasmid and a luciferase reporter plasmid containing the IL-6 promoter upstream of the luciferase cDNA. The compounds to be tested are added to the cells after transfection and after 24 hours of incubation, the cells are lysed with a detergent-containing buffer and assayed for luciferase activity. The $EC_{50}$ is determined from the concentration response curve for the compound, and the inhibitory effect on TNFα/IL-1β induction (% inhibition) can be calculated according to the equation:

$$\% \text{ Inhibition} = \frac{[(TNF\alpha/IL-1\beta \text{ control} - \text{basal}) - (\text{androgen treatment} - \text{basal})]}{[(TNF\alpha/IL-1\beta \text{ control} - \text{basal})]} \times 100$$

where
  TNFα/IL-1β control=mean luciferase response measured in cells treated with media containing TNFα and IL-1β without test compound;
  basal=mean luciferase response measured in cells treated with media alone; and
  androgen treatment=mean luciferase response measured in cells treated with media containing TNFα and IL-1β with test compound.

3. Antagonist Activity Against Hormone-Dependent Tumors

Various methods for identifying SARMs having antagonist activity against hormone-dependent tumors while exhibiting no activity, or agonist activity against other non-tumor tissues containing the androgen receptor, can be used. For example, antagonist activity in hormone-dependent tumors can be ascertained by screening the compounds in hormone-dependent tumor cell lines for inhibition of growth, either in vitro or in vivo. Examples of hormone-dependent tumor cell lines that can be used for screening potential SARMs include, but are not limited to, human breast tumor cell line MDA MB453, human breast tumor cell line ZR-75-1, murine breast line Shionogi, rat prostate adenocarcinoma line Dunning R-3327, human prostate tumor cell line MDA PCa 2a and PCa 2b, human prostate cell line LNCap, human prostate tumor cell line CWR22, human prostate tumor cell line LuCaP 35 and LuCaP 23.12, human prostate cell line LAPC-4 and LAPC-9, human prostate tumor cell line PC-295, human prostate tumor cell line PC-310, and human osteosarcoma cell line MG-63. These human and murine prostate and breast cell lines and the tumor model systems derived therein are well accepted by those of skill in the art as indicative of the pharmacology of human hormone-dependent tumors, such as prostate cancer. Examples of the relationship of such models to the human disease state is discussed in the art (e.g., see Jacques et al., Endocrinology 140: 416-421 (1999); Yeap et al. Endocrinology 140: 3282-3291 (1999), Sharma et al., Oncogene 18: 5349-5355 (1999), Bentei et al., In Vitro Cell Dev. Biol. 35: 655-662 (1999), Suzuki et al., J. Steroid Biochem. Mol. Biol. 37: 559-567 (1990), Peehl, Urol. Oncol. 2: 100-102 (1996), Wytske et al., Urol. Oncol. 2: 122-125

(1996), Leland, Urol. Oncol. 2: 126-128 (1996), Buhler et al., The Prostate 43: 63-70 (2000), Navone et al., Clin. Cancer Res. 6: 1190-1197 (2000), Etreby et al., The Prostate 42: 99-106 (2000), Jongsma et al., Cancer Res. 60: 741-748 (2000), Jongsma et al., Amer. J. Path. 154: 543-551 (1999), Ye et al., Clin. Cancer Res. 5: 2171-2177 (1999), Navone et al., Clin. Cancer Res. 3: 2493-2500 (1997), Chen et al., Cancer Res. 58: 2777-2783 (1998), and Craft et al., Cancer Res. 59: 5030-5036 (1999).

4. Efficacy and Toxicity

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a bacterial or mammalian, including human, cell line. The results of such studies are often predictive of toxicity in animals, such as mammals, or more specifically, humans. Exemplary assays include bacterial reverse mutation assays (e.g., see Ames et al., Mutation Research 31: 347-364 (1975); Green et al., Mutation Research 38: 3-32 (1976); and Maron et al., Mutation Research 113: 173-215 (1983), cytological methods for detecting chemical mutagens (Evans, *Chemical Mutagens, Principles and Methods for their Detection*, Vol. 4 (Plenum Press, New York, N.Y. (1976))), chromosomal aberration assays (Galloway et al., Mutation Research 312(3): 241-261 (1994)), genotoxicity assays (Federal Register 61: 18198-18202 (1996) and Federal Register 62: 16026-16030 (1997)) and cytogenetic assays (Preston et al., Mutation Research 87: 143-188 (1981)).

Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Non-limiting examples of appropriate in vivo animal models include castrated male rats or aged male orchidectomized rats. When selecting a model to determine efficacy, the skilled artisan can be guided by the state of the art to choose an appropriate model, dose, and route of administration, and regime. Human clinical trials also can be used to determine the efficacy of a compound in humans.

5. Receptor Binding Assays

The binding of the compounds provided herein to androgen receptor can be assessed using any method known in the art. For example, a baculovirus expression plasmid including cDNA encoding the human steroidal hormone receptor protein (AR, PR, GR, MR, or ER) can be prepared using standard techniques. See e.g., Allegretto et al., *J. Biol. Chem.* 268: 26625 (1993); Srinivasan and Thompson, *Mol. Endo.* 4: 209 (1990); and D. R. O'Reilly et al., in "Baculovirus Expression Vectors", D. R. O'Reilly et al., eds., W.H. Freeman, New York, N.Y., pp. 139-179 (1992). In an exemplary method, the expression plasmid is infected together with wild type *Autographa californica* multiple nuclear polyhedrosis virus DNA into *Spodopter frupperda*-21 (Sf-21) cells to generate recombinant virus including AR cDNA. See, e.g., O'Reilly et al., "Regulation of expression of a baculovirus ecdysteroid UDP glucosyltransferase gene" in *Baculovirus Expression Vectors*, WH Freeman, NY, 139-179 (1992) and the recombinant virus including receptor cDNA collected.

The recombinant virus then can be used to infect cells, such as Sf-21 cells. The infected Sf-21 cells are incubated for 48 hours and then collected by centrifugation, resuspended in lysis buffer (50 mM potassium phosphate buffer, pH 7.0, 10 mM monothioglycerol, 5 mM DTT, 20 mM sodium molybdate, 1 mM PMSF, 1 µg/mL aprotinin, and 10 µg/mL leupeptin) and homogenized. The resulting receptor lysates are used in the binding assays. Binding assay samples can be prepared in separate mini-tubes in a 96-well format using Receptor-Assay Buffer (10% glycerol, 25 mM sodium phosphate, 10 mM potassium fluoride, 10 mM sodium molybdate, 0.25 mM CHAPS, 2 mM DTT and 1 mM EDTA, (adjusted to pH 7.5)) containing 50 µg of receptor lysate; 2-4 nM of [$^3$H]-steroid (dihydrotestosterone, progesterone, dexamethasone, aldosterone, or estradiol) at 50-100 Ci/mmol; and either a reference compound or a test compound. Test compounds included selective androgen receptor binding compounds as provided herein. Reference compounds were unlabeled steroids, which have been previously shown to bind to the steroid hormone receptors, such as dihydrotestosterone for androgen receptors. Each reference compound and test compound are assayed at varying concentrations, e.g., ranging from $3.2 \times 10^{-10}$ to $10^{-5}$ M and the assay samples are incubated, e.g., for 16-24 hours at 4° C.

After incubation, 200 µL of 6.25% hydroxylapatite in assay buffer is added to each assay sample to precipitate the protein. The assay samples then are centrifuged, the resulting pellets washed twice with assay buffer lacking DTT and the radioactivity in counts per minute (CPM) of each washed pellet is determined by liquid scintillation counter (MicroBeta™, Wallach).

Specific binding for a particular sample is calculated using the equation:

(Sample CPM)–(Average Non-specific CPM)

"Average Non-specific CPM" is the amount of radioactivity from samples including an excess (e.g., 1000 nM) of unlabeled steroid, such as dihydrotestosterone. $IC_{50}$ values (the concentration of test compound required to decrease specific binding by 50%) were determined using the log-logit (Hill) method.

In some embodiments, the compounds provided herein exhibit a $K_i$ of no greater than 10 micromolar, or no greater than 5 micromolar, or no greater than 1 micromolar, or no greater than 100 nanomolar, or no greater than 10 nanomolar or no greater than 1 nanomolar in an AR receptor binding assay.

6. In Vivo Assay—Sprague-Dawley Rat Model

The Sprague-Dawley rat model is used in the art as a model for identifying selective androgen receptor modulators (SARMs) that exhibit in vivo pharmacological activity, thereby identifying active, nonsteroidal selective androgen receptor modulators. In the rat, the effects of androgens in skeletal muscle can be assessed by monitoring the weight of the levator ani muscle (Herschberger et al., Proc Soc Exp Biol Med 83: 175-180 (1981)), a muscle that expresses high levels of androgen receptor (Max et al., Biochem J 200: 77-82 (1981)). Under androgen treatment, the weight of the levator ani muscle markedly increases, providing a reliable endpoint to study the anabolic effect of androgens in skeletal muscle (Herschberger et al., Proc Soc Exp Biol Med 83: 175-180 (1981)).

Androgens also stimulate sebaceous gland secretions in the skin and have been linked with increased sebum production and acne (Boudou et al., J Clin Endocrinol Metab 80(4): 1158-1161 (1995)). The preputial gland in rodents is a modified sebaceous gland and has been used as an indicator of sebum production (Miyake et al., J Invest Dermatol 103: 721-725 (1994); Nickerson et al., Acta Anat (Basel) 94:

481-489 (1976); and Deplewski et al., Endocrinology 138: 4416-4420 (1997)). Androgen supplementation increases the weight of sebaceous glands and their secretions.

Male steroid hormones also have been found to be critical for maintenance and growth of bone. For example, osteopenia often occurs in hypogonadism in men, a condition that results in reduced circulating testosterone levels (Devogelaer et al., Maturitas 15: 17-23 (1992)). Osteopenia is a degenerative process that can be reversed with testosterone supplementation (Finkelstein et al., J Clin Endocrinol & Metabolism 69: 776-783 (1989); Behre et al., J Clin Endocrinol & Metabolism 82: 2386-2390 (1997); and Katznelson et al., J Clin Endocrinol & Metabolism 81: 4358-4365 (1996)). A similar phenomenon can be observed in male rats in which bone loss due to castration can be restored by administering androgen (Wakley et al., J Bone & Mineral Research 6: 325-330 (1991)). In order to assess bone loss in rats, biochemical markers, such as serum osteocalcin, can be measured. Osteocalcin is a bone matrix protein component that is synthesized and deposited by bone-forming osteoblasts and it is also released from the bone during bone resorption by osteoclasts (Ivaska et al., J Biol Chem 279: 18361-18369 (2004)). During both processes, this protein and its breakdown products are released into the circulation and can served as biochemical markers. Measurement of circulating osteocalcin levels in the serum of rats can by used to assess bone turnover or metabolism (Vanderschueren et al., Endocrinology 141(5): 1642-1647 (2000); Vanderschueren et al., Bone Miner 26(2): 123-131 (1994); and Hunter et al., Arthritis Res Ther 10(4): R102 (2008)).

Mature male Sprague-Dawley rats of approximately 2 months of age generally are used. After a one-week acclimation period, they are castrated under isoflurane anesthesia. One group of animals is sham-operated and treated with vehicle and serves as a control. After surgery, the rats are sorted into groups so that no statistically significant differences in body weight are observed. Treatment generally begins the same day of the surgery after the surgical procedure. Animals are treated either orally (4 mL/kg) or subcutaneously (0.4 mL/kg) each morning for 14 consecutive days with vehicle or various compound solutions of different strengths. Approximately 24 hours after the last dose, rats are sacrificed by decapitation and organs and blood collected. Trunk blood is collected and then the ventral prostate, seminal vesicles and levator ani muscle are dissected out, blotted dry and weighed individually. The blood is allowed to clot at room temperature and the serum separated by centrifugation. The serum is then collected and kept frozen until processed for measurement of LH levels by radioimmunoassay (MA).

The compound of interest is suspended in a vehicle, such as a solution of 9.995% polyethylene glycol (average molecular weight 400; PEG-400; Sigma, St. Louis, Mo.), 0.005% Tween 80 (polyoxyethylene sorbitan monooleate; Sigma, St. Louis, Mo.), and 90.0% of a 1% carboxymethylcellulose (CMC; Sigma, St. Louis, Mo.) solution in NanoPure water. The compound is suspended in the vehicle and can be homogenized in a blender for 4 minutes. The suspension also can be sonicated for 2 minutes. The high concentration formulation was then diluted using vehicle to obtain the proper volume and concentrations of the dosing materials.

Testosterone is dissolved in a 30:70 mixture of PEG-400 and DMSO and administered subcutaneously.

Serum samples are assayed for LH with a double antiserum procedure using reagents from the National Institute of Diabetes and Digestive and Kidney Diseases (NIDDK). In brief, samples and standards (NIDDK-rLH-RP-3) in a total volume of 200 µl are incubated at room temperature for 2-3 days with 100 µl primary antiserum (rabbit NIDDK-anti-rLH-S-11) diluted 1:100,000. Thereafter, 100 µl of iodinated LH (Covance Laboratories Inc.) diluted to 200,000-300,000 cpm/ml is added to the tubes and incubation continued for an additional 24 hour period. Bound hormone is separated from free hormone by precipitation with a specific goat anti-rabbit serum (GARS; Antibodies Inc). For this purpose, 50 µl of 4% normal rabbit serum is added to each incubation tube, after which an additional 50 µl of a 1:10 GARS solution is added. The tubes are vortexed and incubated overnight at 4° C. The assay is terminated by centrifugation at 2,500 rpm for 30 min in a centrifuge at 4° C. The supernatants are decanted and discarded and the pellets are counted in a 10-channel gamma-counter. The assay has a minimal detectable amount of 0.001 ng/tube and the intra- and inter-assay variability is less than 10%. In order to minimize interassay variability, all samples from a single study are run in the same assay.

Results are analyzed by analysis of variance on Box-Cox transformed data (Box and Cox, J Roy Statist Soc Series B 26: 211-252 (1964), Box and Hill, Technometrics 16: 385-389 (1974) and Peltier et al., J. Anim. Sci. 76: 847-849 (1998)). For ventral prostate and LH levels the logarithm of the data are used for statistical analysis. Seminal vesicle and levator ani muscle data are elevated to 0.2 and 0.6, respectively. These transformations are performed to ensure that variances are homogeneous among groups and that the residuals of the one-way analysis of variance model followed a Gaussian (normal) distribution. When the analyses of variance reach significance, data are further evaluated by the Dunnett's test. A $P<0.05$ is considered as the minimum criterion to declare statistically significant differences.

In addition, efficacy data are calculated as percentage of the response observed in the sham-operated group. In this respect, the orchidectomized, vehicle-treated group is considered as 0% efficacy, whereas the sham-operated group represented 100% efficacy. This conversion allows direct comparison of data independently of having different controls as is the case in experiments using subcutaneously and orally administered compounds.

Potencies are estimated on the transformed data using a four-parameter logistic equation. The model estimates $EC_{50}$'s in a logarithmic scale, since log $EC_{50}$ is a more robust estimate of the potency (Ghosh et al., J Biopharm Stat 8: 645-665 (1998)). The model also provides a SE for the estimate that is used to calculate 95% confidence limits of the estimated potencies. The following equation exemplifies the basic, reparametrized four parameter logistic equation used in estimating potencies in these studies:

$$\frac{A-D}{1+e^{B \cdot (\log C - \log x)}} + D$$

where A is the maximum, D is the minimum, B is the slope, C is either the $EC_{50}$ or the $IC_{50}$ depending on the direction of the response, and x is the dose of the compound used.

I. METHODS OF USE OF THE COMPOUNDS AND COMPOSITIONS

Methods of use of the compounds and compositions provided herein also are provided. The methods include in vitro and in vivo uses of the compounds and compositions for altering androgen receptor activity and for treatment, prevention, or amelioration of one or more symptoms of diseases or disorder that are modulated through androgen receptor activity, or in which androgen receptor activity is implicated. In certain embodiments, provided herein are methods of treating a subject by administering a compound provided herein. In certain embodiments, such subject exhibits symptoms or signs of a androgen receptor mediated condition. In certain embodiments, a subject is treated prophylactically to reduce or prevent the occurrence of a condition.

The compounds provided herein can be used in the treatment of a variety of conditions. For example, a compound of Formula I, II or III or pharmaceutically acceptable salts or prodrugs thereof can be used to treat a condition including, but not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondro-dysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD); reducing cachexia and protein loss due to chronic illness such as cancer or AIDS; treatment of hyperinsulinemia including nesidioblastosis; treatment of immunosuppressed subjects; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in subjects taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

In certain embodiments, provided are methods for treating a subject by administering one or more than one compound of Formula I, II or III or pharmaceutically acceptable salts or prodrugs thereof. Exemplary conditions that can be treated with the selective androgen receptor modulators provided herein include, but are not limited to, hypogonadism, wasting diseases, cancer cachexia, frailty, infertility, osteoporosis, hirsutism, acne, male-pattern baldness, prostatic hyperplasia, and cancer, including, but not limited to, various hormone-dependent cancers, including, without limitation, prostate and breast cancer. In certain embodiments, a selective androgen receptor agonist or partial agonist is used for male hormone replacement therapy. In certain embodiments, one or more selective androgen receptor agonists and/or partial agonists are used to stimulate hematopoiesis. In certain embodiments, a selective androgen receptor agonist or partial agonist is used as an anabolic agent. In certain embodiments, a selective androgen receptor agonist and/or partial agonist is used to improve athletic performance.

In another embodiment, a compound of Formula I, II or III or pharmaceutically acceptable salts or prodrugs thereof is administered to a subject in order to treat a condition responsive to an AR modulator compound. The method includes administering to a subject having a condition responsive to an AR modulator compound a therapeutically effective amount of one or more than one compound provided herein to treat the condition responsive to an AR modulator compound. In some embodiments, the condition is treated by agonizing the androgen receptor. In some embodiments, the condition is treated by antagonizing the androgen receptor. In various embodiments, the condition treated is selected from among hypogonadism, lower than normal testosterone plasma levels, infertility, sexual arousal disorder, disorders of libido, muscle wasting, cachexia, sarcopenia, frailty, bone density loss, mood disorders (including lack of well being, lack of vigor, anger, irritability, sadness, tiredness, nervousness and depression), impaired cognitive function (including verbal fluency and spatial memory), neurodegenerative disorders, including Alzheimer's disease, mild cognition impairment, Lewis body dementia, and frontal temporal dementia, xerophthalmia, metabolic disorders, including dyslipidemia, atherosclerosis, and non-insulin dependent diabetes (NIDDM), cardiovascular disorders including but not limited to hypertension, coronary artery disease, and myocardial perfusion, obesity, anemia, prostate cancer, and schizophrenia. In other embodiments, a compound of Formula I, II or III or pharmaceutically acceptable salts or prodrugs thereof can be administered to a subject in order to prevent a condition in the subject. In various embodiments, the condition prevented includes bone density loss, xerophthalmia, metabolic disorders, including dyslipidemia, atherosclerosis, and non-insulin dependent diabetes (NIDDM), cardiovascular disorders including hypertension, coronary artery disease, and myocardial perfusion, obesity and prostate cancer.

In certain embodiments, one or more than one compound of Formula I, II or III or pharmaceutically acceptable salts or prodrugs thereof is used to treat acne, male-pattern baldness, wasting diseases, hirsutism, hypogonadism, osteoporosis, infertility, impotence, obesity, and cancer. In certain embodiments, one or more compounds provided herein are used to stimulate hematopoiesis. In certain embodiments, one or more compounds provided herein are used for contraception.

In certain embodiments, provided herein are methods for treating a subject having a condition caused by androgen deficiency or a condition ameliorated by androgen replacement. The methods include administering to the subject a therapeutically effective amount of one or more than one compound of Formula I, II or III or pharmaceutically acceptable salts or prodrugs thereof, and thereby treating the condition. In certain embodiments, the condition is selected from among abdominal obesity, Alzheimer's disease, anemia, an arthritic condition, atherosclerosis, benign prostatic hyperplasia (BPH), cancer cachexia, cognitive decline, depression, metabolic syndrome, a muscular dystrophy, obesity, osteopenia, osteoporosis, a periodontal disease, prostate cancer, sexual dysfunction, sleep apnea, type II diabetes, bone fracture, frailty, wasting, aging skin, hypogonadism, post-menopausal symptoms in women, female sexual dysfunction, premature ovarian failure, atherosclerosis, hypercholesterolemia, hyperlipidemia, aplastic anemia and other hematopoietic disorders, pancreatic cancer, renal cancer, arthritis and joint repair.

1. Methods of Treating Muscle Wasting

In certain embodiments, provided herein are methods of treating, preventing, suppressing, inhibiting or reducing the incidence of muscle wasting in a subject. The methods include administering to the subject one or more than one compound of Formula I, II or III or pharmaceutically acceptable salts or prodrugs thereof, in an amount effective to treat, prevent, suppress, inhibit or reduce muscle wasting in the subject. In some embodiments, the muscle wasting is caused by a condition selected from among andropause, a spinal muscular atrophy, a muscular dystrophy, myasthenia gravis, AIDS cachexia, cardiac cachexia, cancer cachexia, cancer, Chronic Obstructive Pulmonary Disease (COPD), emphysema, diabetes, HIV infection, acquired immunodeficiency syndrome (AIDS), sepsis, tuberculosis, renal failure, heart failure, cardiomyopathy, bed rest, disuse, inactivity, microgravity, malnutrition, sarcopenia and aging. In some embodiments, the one or more than one compound of Formula I, II or III or pharmaceutically acceptable salts or prodrugs thereof is orally administered to the subject. In one method, the compounds provided herein are used in a method for the treatment of muscular dystrophy, sarcopenia and frailty. In one embodiment, the methods include co-administering one or more than one compound provided herein with one or more agents selected from among interleukin-10 (IL-10), interleukin-4 (IL-4), a TNF inhibitor, fluorinated 4-azasteroid derivatives, glial growth factors, acetylcholine receptor inducing activity (ARIA), heregulins, neu differentiation factor, and neuregulins (e.g., see U.S. Pat. Nos. 6,444,642 and 7,037,888).

In one embodiment, provided herein are methods of treating a muscle-wasting condition associated with chronic illness. The methods include administering to the subject one or more than one compound of Formula I, II or III or pharmaceutically acceptable salts or prodrugs thereof, in an amount effective to treat the muscle-wasting condition. In one embodiment, provided herein are methods for preventing a muscle wasting disorder in a subject, which include administering to the subject one or more than one compound of Formula I, II or III or pharmaceutically acceptable salts or prodrugs thereof, in an amount effective to preventing a muscle wasting disorder in the subject. In one embodiment, provided herein are methods for suppressing a muscle wasting disorder in a subject, which include administering to the subject one or more than one compound of Formula I, II or III or pharmaceutically acceptable salts or prodrugs thereof, in an amount effective to suppress the muscle wasting disorder in a subject. In one embodiment, provided herein are methods for reducing the incidence of a muscle wasting disorder in a subject, which include administering to the subject one or more than one compound of Formula I, II or III or pharmaceutically acceptable salts or prodrugs thereof, in an amount effective to suppress the muscle wasting disorder in a subject.

Methods for identifying a subject in need of treatment for a muscular wasting disease are known in the art. For example, a subject in need of treatment for a muscular wasting disease will often generate less electrical activity during muscle contraction as compared to a healthy subject and this can be detected by electromyography. Alternative methods for diagnosis include, for example, blood tests and muscle biopsies. Suitably, blood tests can be run to determine the levels of various constituents of muscle and muscle fibers. For example, many muscular wasting diseases can be diagnosed by conducting a blood test to measure the level of creatinine in the blood. Creatinine is a breakdown product of creatine, which is an important constituent of muscle. Blood tests for determining the amount of creatine phosphokinase (CPK), which is an enzyme found predominantly in the heart, brain, and skeletal muscle, can be conducted to diagnose a subject in need for treatment of a muscular wasting disease. Specifically, when the total CPK level is substantially elevated, it usually indicates injury or stress to one or more of the heart, brain, and skeletal muscle. Subjects that may be affected by either Duchenne muscular dystrophy or Becker muscular dystrophy can be diagnosed by measuring the level of dystrophin. Typically, in subjects with either Duchenne muscular dystrophy or Becker muscular dystrophy, the level of dystrophin is deficient; but, in a subject with Duchenne muscular dystrophy, the level is more severely deficient.

Muscle biopsies also can be used to identify a subject in need of treatment for a muscular wasting disease. Generally, during a muscle biopsy, a small piece of muscle tissue is removed surgically for laboratory analysis. The analysis can reveal abnormalities in the muscle, such as inflammation, damage, or infection. The subject also can be diagnosed for a muscular wasting disease using magnetic resonance imagining (MRI). During an MRI, cross-sectional images of muscle are generated by a magnetic field and radio waves. Similar to the muscle biopsy analysis, the image generated by an MRI can reveal abnormalities in the muscle, such as inflammation, damage, or infection.

2. Methods of Improving Muscle Performance, Size and/or Strength

In certain embodiments, provided herein are methods of increasing muscle performance, muscle size, muscle strength, or any combination thereof in a subject. The methods include administering to the subject one or more than one compound of Formula I, II or III or pharmaceutically acceptable salts or prodrugs thereof, in an amount effective to increase muscle performance, muscle size, and/or muscle strength in the subject.

In some embodiments, provided herein are methods of activating the function of the androgen receptor muscle tissue and blocking or inhibiting the function of the androgen receptor in the prostate of a male individual or in the uterus of a female individual. The methods include administering to the subject one or more than one compound of Formula I, II or III or pharmaceutically acceptable salts or prodrugs thereof, in an amount effective to activate the function of the androgen receptor in muscle tissue and to block or inhibit the function of the androgen receptor in the prostate of a male individual or in the uterus of a female individual.

3. Methods of Improving Athletic Performance

In certain embodiments, one or more than one compound of Formula I, II or III or pharmaceutically acceptable salts or prodrugs thereof is used to improve athletic performance. The methods include administering one or more than one compound of Formula I, II or III or pharmaceutically acceptable salts or prodrugs thereof in a therapeutically effective amount to improve athletic performance. In some embodiments, one or more compounds provided herein are used, for example, to shorten the time normally needed to recover from physical exertion or to increase muscle strength. Athletes to whom one or more compounds provided herein can be administered include, but are not limited to, horses, dogs and humans. In certain embodiments, one or more than one compound of Formula I, II or III or pharmaceutically acceptable salts or prodrugs thereof is administered to an athlete engaged in a professional or recreational competition, including, but not limited to weight-lifting, body-building, track and field events, and any of various team sports.

4. Methods of Treating Bone-Related Conditions

In certain embodiments, provided herein are methods of treating, preventing, suppressing, inhibiting or reducing the incidence of osteoporosis, osteopenia, gluco-corticoid-induced osteoporosis or bone fracture in a subject. The methods include administering to the subject one or more than one compound of Formula I, II or III or pharmaceutically acceptable salts or prodrugs thereof, in an amount effective to treat osteoporosis, osteopenia, glucocorticoid-induced osteoporosis or bone fracture in the subject. In one embodiment, the one or more than one compound of Formula I, II or III or pharmaceutically acceptable salts or prodrugs thereof is co-administered with an effective amount of at least one other therapeutic agent, such as an estrogen or estrogen derivatives, alone or in combination with progestin or progestin derivatives; a bisphosphonate; an anti-estrogen; a selective estrogen receptor modulators (SERM); an $\alpha_v\beta_3$ integrin receptor antagonist; a cathepsin inhibitor; a proton pump inhibitor; a PPARγ inhibitor; calcitonin; and osteoprotegerin. In one embodiment, the method is for the treatment of osteoporosis. In one embodiment, the method is for the treatment of osteopenia. In one embodiment, the method is for the treatment of glucocorticoid-induced osteoporosis. In one embodiment, the method is for the treatment of bone fracture.

In some embodiments, provided herein are methods of activating the function of the androgen receptor in bone tissue and blocking or inhibiting the function of the androgen receptor in the prostate of a male individual or in the uterus of a female individual. The methods include administering to the subject one or more than one compound of Formula I, II or III or pharmaceutically acceptable salts or prodrugs thereof, in an amount effective to activate the function of the androgen receptor in bone tissue and to block or inhibit the function of the androgen receptor in the prostate of a male individual or in the uterus of a female individual.

In certain embodiments, provided herein are methods of increasing the strength of, or mass of a bone of a subject, or for promoting bone formation in a subject. The methods include administering one or more than one compound of Formula I, II or III or pharmaceutically acceptable salts or prodrugs thereof in an amount effective to increase the strength of, or mass of a bone of a subject, or to promote bone formation in a subject.

In some embodiments, provided herein are methods for preventing a bone-related disorder in a subject, which include administering one or more than one compound of Formula I, II or III or pharmaceutically acceptable salts or prodrugs thereof in an amount effective to prevent the bone-related disorder in the subject. In some embodiments, provided herein are methods for suppressing a bone-related disorder in a subject, which include administering one or more than one compound of Formula I, II or III or pharmaceutically acceptable salts or prodrugs thereof in an amount effective to suppress the bone-related disorder in the subject. In some embodiments, provided herein are methods for inhibiting a bone-related disorder in a subject, which include administering one or more than one compound of Formula I, II or III or pharmaceutically acceptable salts or prodrugs thereof in an amount effective to inhibit the bone-related disorder in the subject.

In one embodiment, the bone-related disorder is osteoporosis. In another embodiment, the bone-related disorder is osteopenia, In another embodiment, the bone-related disorder is increased bone resorption. In another embodiment, the bone-related disorder is bone fracture. In another embodiment, the bone-related disorder is bone frailty. In another embodiment, the bone-related disorder is any combination of osteoporosis, osteopenia, increased bone resorption, bone fracture and bone frailty.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

5. Methods of Treating Cancer

In certain embodiments, one or more than one compound of Formula I, II or III or pharmaceutically acceptable salts or prodrugs thereof is used for treating, preventing, suppressing, inhibiting or reducing the incidence of cancer in a subject. Certain exemplary cancers include, but are not limited to, breast cancer, colorectal cancer, gastric carcinoma, glioma, head and neck squamous cell carcinoma, skin cancer, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer, including, but not limited to prostatic hyperplasia. The methods include administering one or more compounds provided herein in a therapeutically effective amount to treat the cancer. In one embodiment, administration of the one or more than one compound provided herein to a subject afflicted with a cancerous condition alleviates the cancerous condition by killing the cancerous cells. In one embodiment, administration of the one or more than one compound provided herein to a subject afflicted with a cancerous condition results in the inhibition of growth and/or metastasis of the cancer.

In some embodiments, one or more than one compound of Formula I, II or III or pharmaceutically acceptable salts or prodrugs thereof is administered in combination with one or more other therapeutic agents, such as, but not limited to, anti-proliferative agents, such as paclitaxel, a paclitaxel derivative, taxanes and *vinca* alkaloids, anti-tumor agents, such as mitomycin C or doxorubicin, hormones and antagonists, such as adreno-corticosteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone), radionuclides, toxins and cytotoxic drugs, boron addends, chemotherapy agents, photodynamic therapy dyes, and antibiotics or combinations thereof to treat cancer. Many toxins and cytotoxic drugs are known in the art that have cytotoxic effects on cells, any of which can be used in connection with the methods provided herein. Examples of known cytotoxic agents useful in the present methods are listed, for example, in Goodman et al., "The Pharmacological Basis of Therapeutics," Sixth Edition, A. G. Gilman et al., eds., Macmillan Publishing Co., New York (1980). These include, but are not limited to, adrenocortical suppressants, such as mitotane; alkyl sulfonates, such as busulfan; ethylenimine derivatives, such as thiotepa; nitrosoureas, such as carmustine, lomustine, semustine and streptozocin; folic acid analogs, such as methotrexate; methyl hydrazine derivatives, such as procarbazine; nitrogen mustards, such as mechlorethamine, cyclophosphamide, melphalan, uracil mustard and chlorambucil; purine analogs, such as mercaptopurine and thioguanine; pyrimidine analogs, such as fluorouracil, cytarabine and azaribine; substituted urea compounds, such as hydroxyurea; taxol; triazenes, such as dacarbazine; and vinca alkaloids, such as vinblastine and vincristine.

Any antibiotic known in the art, such as aminoglycosides, bleomycin, cephalosporins and other beta-lactam antibiotics, chloramphenicol, clindamycin, dactinomycin, daunorubicin, doxorubicin, fusidic acid, macrolides, metronidazole, mithramycin, mitomycin, mupirocin, penicillins, rifamycins, sulfonamides, tetracyclines, trimethoprim and beta-lactam inhibitors, can be included in the formulation. Drugs that interfere with intracellular protein synthesis also can be used in the methods provided herein; such drugs are known to those skilled in the art and include puromycin, cycloheximide, and ribonuclease.

The methods provided herein also can include administration of one or more than one compound of Formula I, II or III or pharmaceutically acceptable salts or prodrugs thereof in combination with dyes used photodynamic therapy for the treatment of cancer, and used in conjunction with appropriate non-ionizing and ionizing radiation. The use of porphyrins and other dyes used in photodynamic therapy can be used in the methods herein. Photodynamic therapy for the treatment of cancer is well known in the art (e.g., see U.S. Pat. Nos. 7,018,395, 7,011,812, 6,806,284, 6,723,750, 6,710,066, 6,630,128 and 6,622,729).

6. Methods of Treating Prostate Cancer

In certain embodiments, provided herein are methods for treating, preventing, suppressing, inhibiting or reducing the incidence of prostate cancer in a subject. The methods include administering one or more than one compound of Formula I, II or III or pharmaceutically acceptable salts or prodrugs thereof in a therapeutically effective amount to treat the cancer. In some embodiments, the prostate cancer is androgen dependant prostate cancer. In certain embodiments, the prostate cancer is androgen independent prostate cancer. In certain embodiments, the prostate cancer is androgen independent, but androgen receptor dependant prostate cancer. In some embodiments, administration of the one or more than one compound provided herein to a subject afflicted with prostate cancer alleviates the prostate cancer by killing the cancerous cells. In one embodiment, administration of the one or more than one compound provided herein to a subject afflicted with prostate cancer results in the inhibition of growth and/or metastasis of the prostate cancer. In some embodiments, the one or more than one compound of Formula I, II or III or pharmaceutically acceptable salts or prodrugs thereof is co-administered with another therapeutic agent, including, but not limited to, flutamide, bicalutamide and nilutamide, anti-tumor agent, such as toxins and cytotoxic drugs, which can be selectively targeted to react with prostate tumors by conjugating to a prostate tumor antigen, and radionuclides.

In certain embodiments, methods are provided for delaying the progression of prostate cancer in a subject suffering from prostate cancer. The methods include administering to the subject one or more than one compound of Formula I, II or III or pharmaceutically acceptable salts or prodrugs thereof, in an amount effective to delay the progression of prostate cancer in the subject.

7. Methods of Contraception

In certain embodiments, provided herein are methods for providing contraception in a subject. The methods include administering to the subject one or more than one compound of Formula I, II or III or pharmaceutically acceptable salts or prodrugs thereof, in an amount effective to provide contraception in the subject. In some embodiments, provided herein are methods for providing contraception in a male subject. The methods include administering to the subject one or more than one compound of Formula I, II or III or pharmaceutically acceptable salts or prodrugs thereof, in an amount effective to suppress sperm production in the subject, thereby effecting contraception in the subject. In one embodiment, the compounds provided herein inhibit spermatogenesis in a subject. In one embodiment, the method includes co-administering one or more than one compound of Formula I, II or III or pharmaceutically acceptable salts or prodrugs thereof with an androgen, such as 19-nortestosterone, 7α-methyl-19-nortestosterone and 5α-dihydro-testosterone. In one embodiment, the method includes co-administration of a compound of Formula I, II or III or pharmaceutically acceptable salts or prodrugs thereof that is an AR antagonist with testosterone.

8. Methods of Providing Hormone Therapy

In certain embodiments, provided herein are methods for providing hormone therapy to a subject. The method includes administering to the subject one or more than one compound of Formula I, II or III or pharmaceutically acceptable salts or prodrugs thereof, in an amount effective to modulate androgen receptor activity, and thereby effect a change in an androgen-dependent condition.

9. Methods of Treating Postmenopausal Conditions

In certain embodiments, provided herein are methods for treating, preventing, suppressing, inhibiting or reducing the incidence of postmenopausal conditions in a subject. The methods include administering to the subject one or more than one compound of Formula I, II or III or pharmaceutically acceptable salts or prodrugs thereof, in an amount effective to treat the postmenopausal condition. In one embodiment, the postmenopausal condition treated by the method includes, but is not limited to, loss of libido, decreased sexual activity, diminished feelings of physical well-being, fatigue and hot flashes. In one embodiment, the method includes co-administering one or more than one compound of Formula I, II or III or pharmaceutically acceptable salts or prodrugs thereof with one or more estrogens, such as estrone, 2-hydroxyestrone, 2-methoxyestrone, 4-hydroxyestrone, 15-α-hydroxyestrone, 16-α-hydroxy estrone, 16-β-hydroxyestrone, estradiol (17β-estradiol), 2-hydroxy-estradiol, 2-methoxy-estradiol, 4-hydroxy-estradiol, 16-oxoestradiol, estriol, 16-epiestriol and 17-epiestriol or combinations thereof. In one embodiment, the method includes co-administering one or more than one compound of Formula I, II or III or pharmaceutically acceptable salts or prodrugs thereof with one or more estrogenic compound, such as estradiol valerate, estrone, estrone sulfate, an estrone sulfate piperazine salt or an ester thereof, or a synthetic estrogen. In one embodiment, the method includes co-administering one or more than one compound of Formula I, II or III or pharmaceutically acceptable salts or prodrugs thereof with one or more agents selected from among alendronate, calcitonin, clodronate, clomiphene, clomiphene citrate, clonidine, conjugated estrogen, natural estrogen, synthetic estrogen, ethinyl estradiol, estradiol, enclomiphene, enclomiphene citrate, etidronate, ibandronate, medroxyprogesterone acetate, megestrol acetate, norethindrone acetate, pamidronate, progesterone, risedronate, tiludronate, zuclomiphene, zuclomiphene citrate and combinations thereof.

10. Methods of Treating Hematopoietic Disorders

Also provided herein are methods of treating, preventing, suppressing, inhibiting or reducing the incidence of a hematopoietic disorder in a subject. The methods include administering to the subject one or more than one compound of Formula I, II or III or pharmaceutically acceptable salts or prodrugs thereof, in an amount effective to treat the hematopoietic disorder. In some embodiments, the hematopoietic disorder includes, but not limited to, anemia, leukemia, and hematopoietic conditions caused by bone marrow transplantation or chemo-/radiation therapy. Also provided are methods of increasing the number of red blood cells in a mammal in need thereof. The method includes administering a therapeutically effective amount of one or more than one compound of Formula I, II or III or pharmaceutically acceptable salts or prodrugs thereof, in an amount effective to increase the number of red blood cells in a subject. Also provided are methods of treating anemia, thrombocytopenia or neutropenia in a subject. The methods include administering to the subject in need of such treatment one or more than one compound of Formula I, II or III or pharmaceutically acceptable salts or prodrugs thereof, in an amount effective to treat anemia, thrombocytopenia or neutropenia in the mammal. In some embodiments of these methods, one or more than one compound of Formula I, II or III or pharmaceutically acceptable salts or prodrugs thereof is co-administered with a therapeutically effective amount of at least one hematopoietic cytokine. In some embodiments, the hematopoietic cytokine is selected from among erythropoietin, granulocyte-colony stimulating factor, granulocyte-macrophage-colony stimulating factor, interleukin-1, interleukin-3, interleukin-4, interleukin-5, interleukin-7, interleukin-9, interleukin-11, macrophage-colony stimulating factor, stem cell factor and thrombopoietin.

Also provided are methods of increasing serum EPO levels in a subject. The methods include administering a therapeutically effective amount of one or more than one compound of Formula I, II or III or pharmaceutically acceptable salts or prodrugs thereof, in an amount effective to increase the serum EPO levels in the subject.

11. Methods of Treating Neurodegenerative Diseases and Disorders

In some embodiments, provided herein are methods of treating, preventing, suppressing, inhibiting or reducing the incidence of a neurodegenerative disease or disorder in a subject. The methods include administering to a subject having a neurodegenerative disease or disorder, one or more than one compound of Formula I, II or III or pharmaceutically acceptable salts or prodrugs thereof, in an amount effective to treat the neurodegenerative disease or disorder. In some embodiments, the neurodegenerative disorder is Alzheimer's disease. In some embodiments, methods for preventing the onset or delaying the progression of Alzheimer's disease in patients are provided. The method includes administering to a subject one or more than one compound of Formula I, II or III or pharmaceutically acceptable salts or prodrugs thereof, in an amount effective to prevent the onset or delay the progression of Alzheimer's disease in a subject. The method can include co-administering an effective amount of one or more than one compound of Formula I, II or III or pharmaceutically acceptable salts or prodrugs thereof with a therapeutically-effective amount of a compound that inhibits the formation or release of β-amyloid.

Any of the known inhibitors of the formation or release of β-amyloid can be used in the methods, including, but not limited to, compounds described in U.S. Pat. App. Pub. Nos. U.S. 2002/0025955, 2002/0022621 and U.S. 2003/0114496 and in WO 03/018543, WO 01/53255, WO 01/66564, WO 01/70677, WO 01/90084, WO 01/77144, WO 02/30912, WO 02/36555, WO 02/081435, WO 02/081433, WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391 and WO 02/057252.

12. Methods of Treating Cognitive Impairment

Also provided herein are methods for treating, preventing, suppressing, inhibiting or reducing the incidence of cognitive impairment in a subject. The methods include administering to a subject having cognitive impairment one or more than one compound of Formula I, II or III or pharmaceutically acceptable salts or prodrugs thereof, in an amount effective to treat the cognitive impairment.

13. Methods of Treating Depression

Also provided herein are methods for treating, preventing, suppressing, inhibiting or reducing the incidence of depression in a subject. The methods include administering to a subject having cognitive impairment one or more than one compound of Formula I, II or III or pharmaceutically acceptable salts or prodrugs thereof, in an amount effective to treat depression.

14. Methods of Treating Obesity

Also provided herein are methods of treating, preventing, suppressing, inhibiting or reducing the incidence of obesity in a subject. The methods include administering to a subject one or more than one compound of Formula I, II or III or pharmaceutically acceptable salts or prodrugs thereof, in an amount effective to treat obesity. In one embodiment, a compound of Formula I, II or III or pharmaceutically acceptable salts or prodrugs thereof that is an AR agonist is used to treat a male subject with abdominal adiposity. In one embodiment, a compound of Formula I, II or III or pharmaceutically acceptable salts or prodrugs thereof that is an AR antagonist is used to treat a female subject with abdominal obesity.

15. Methods of Treating Insulin Resistance and Diabetes

Provided herein are methods of treating, preventing, suppressing, inhibiting or reducing the incidence of insulin resistance in a subject. The methods include administering to a subject one or more than one compound of Formula I, II or III or pharmaceutically acceptable salts or prodrugs thereof, in an amount effective to treat insulin resistance. Also provided herein are methods of treating, preventing, suppressing, inhibiting or reducing the incidence of type 2 diabetes in a subject. The methods include administering to a subject one or more than one compound of Formula I, II or III or pharmaceutically acceptable salts or prodrugs thereof, in an amount effective to treat type 2 diabetes. In some embodiments, the method for treating diabetes includes co-administering an effective amount of one or more than one compound of Formula I, II or III or pharmaceutically acceptable salts or prodrugs thereof with an effective amount of an anti-diabetic drug, such as, but not limited to, thiazolidinedione-type drugs such as pioglitazone or rosiglitazone, sulfonylurea-type drugs, such as chlorpropamide, glimepiride, glipizide, glyburide or tolbutamide, a biguanide-type drug such as metformin, exenatide, acarbose, repaglinide, nateglinide, tolazamide or combinations thereof.

Also provided herein are methods of treating, preventing, suppressing, inhibiting or reducing the incidence of arterial hypertension, hyper-insulineamia, hyperglycaemia or dyslipidaemia characteristically appearing with insulin resistance. The methods include administering to a subject one or more than one compound of Formula I, II or III or pharmaceutically acceptable salts or prodrugs thereof, in an amount effective to treat arterial hypertension, hyperinsulinemia, hyperglycaemia, type 2 diabetes or dyslipidaemia characteristically appearing with insulin resistance.

16. Methods of Treating Sexual Dysfunction

In certain embodiments, provided herein are methods of treating, preventing, suppressing, inhibiting or reducing the incidence of sexual dysfunction in a subject. The methods include administering to the subject one or more than one compound of Formula I, II or III or pharmaceutically acceptable salts or prodrugs thereof, in an amount effective to treat or prevent sexual dysfunction in the subject. In some embodiments, the sexual dysfunction is male erectile dysfunction. In some embodiments, the sexual dysfunction is impotence.

In certain embodiments, provided herein are methods of increasing the libido of a male or female subject. The methods include administering to the subject in need thereof one or more than one compound of Formula I, II or III or pharmaceutically acceptable salts or prodrugs thereof in an amount that is effective to increase the libido of the subject.

17. Methods of Treating Arthritic Conditions and Inflammatory Disorders

Also provided herein are methods for treating, preventing, suppressing, inhibiting or reducing the incidence of an arthritic condition or inflammatory disorder. The methods include administering one or more than one compound of Formula I, II or III or pharmaceutically acceptable salts or prodrugs thereof in an amount effective for the treatment or prevention of an arthritic condition or an inflammatory disorder. In one embodiment, the arthritic condition or inflammatory disorder is selected from among osteoarthritis, Behcet's disease, bursitis, tendonitis, CPPD deposition disease, carpal tunnel syndrome, Ehlers-Danlos syndrome, fibromyalgia, gout, infectious arthritis, inflammatory bowel disease, juvenile arthritis, lupus erythematosus, Lyme disease, Marfan syndrome, myositis, osteoarthritis, osteogenesis imperfecta, osteonecrosis, polyarteritis, polymyalgia rheumatica, psoriatic arthritis, Raynaud's phenomenon, reflex sympathetic dystrophy syndrome, Reiter's syndrome, rheumatoid arthritis, scleroderma and Sjogren's syndrome. In one embodiment, the method is for treating, preventing, suppressing, inhibiting or reducing the incidence of osteoarthritis, which includes administering one or more than one compound of Formula I, II or III or pharmaceutically acceptable salts or prodrugs thereof in an amount effective for the treatment or prevention of osteoarthritis. In certain embodiments of these methods, the one or more than one compound of Formula I, II or III or pharmaceutically acceptable salts or prodrugs thereof is co-administered with one or more drugs or agents known to treat or prevent arthritic conditions, such as corticosteroids, cytotoxic drugs (or other disease modifying or remission inducing drugs), gold treatment, methotrexate, aspirin, NSAIDs, COX-2 inhibitors and DMARDs (Disease-Modifying Anti-Rheumatic Drugs).

Exemplary DMARDs include, but are not limited to, leflunomide, auranofin, sulfasalazine, mycophenolate, myochrysine, cyclosporine, cyclophosphamide, azathioprine, chlorambucil, methotrexate, minocycline, penicillamine and hydroxychloroquine. Exemplary NSAIDs include, but are not limited to, diclofenac/misoprostol, diclofenac potassium, diclofenac, diflunisal, etodolac, fenoprofen, flurbiprofen, ibuprofen, indomethacin, ketoprofen, meclofenamate, mefanamic acid, meloxicam, nabumetone, naproxen and naproxen sodium, oxaprozin, piroxicam, sodium sulindac and tolmetin. Exemplary COX-2 inhibitors include, but are not limited to, celecoxib, rofecoxib and valdecoxib.

18. Methods of Improving Lipid Profile

In certain embodiments, provided herein are methods of improving the lipid profile in a subject. The methods include administering to the subject one or more than one compound of Formula I, II or III or pharmaceutically acceptable salts or prodrugs thereof in an amount effective to effect the lipid profile in the subject. In one embodiment, the one or more than one compound of Formula I, II or III or pharmaceutically acceptable salts or prodrugs thereof is co-administered with another agent, such as an anti-cholesterol agent or lipid-lowering agent, such as, but not limited to, β-hydroxy-β-methylbutyric acid, lactoferrin, cholestyramine, colestipol, colesevelam, nicotinic acid, fibric acids (gemfibrozil, fenofibrate and clofibrate) and HMG-coA reductase inhibitors (lovastatin, pravastatin, simvastatin, fluvastatin, atorvastatin and cerivastatin).

In certain embodiments, provided herein are methods of reducing circulating lipid levels in a subject. The method includes administering to the subject one or more than one compound of Formula I, II or III or pharmaceutically acceptable salts or prodrugs thereof in an amount effective to reduce circulating lipid levels in the subject.

19. Methods of Treating Atherosclerosis

In certain embodiments, provided herein are methods of treating, preventing, suppressing, inhibiting or reducing the incidence of atherosclerosis and its associated diseases including cardiovascular disorders, cerebrovascular disorders, peripheral vascular disorders, and intestinal vascular disorders in a subject. The methods include administering to the subject one or more than one compound of Formula I, II or III or pharmaceutically acceptable salts or prodrugs thereof, alone or in combination with a selective estrogen receptor modulator (SERM) compound.

20. Methods of Treating Conditions Related to Androgen Decline

In certain embodiments, provided herein are methods of treating, preventing, suppressing, inhibiting or reducing the incidence of a condition related to androgen decline, such as in a male subject. The methods include administering to the subject one or more than one compound of Formula I, II or III or pharmaceutically acceptable salts or prodrugs thereof in an amount effective to treat the condition related to androgen decline in the subject. In some embodiments, the condition is selected from among fatigue, depression, decreased libido, sexual dysfunction, erectile dysfunction, hypogonadism, osteoporosis, hair loss, obesity, sarcopenia, osteopenia, benign prostate hyperplasia, anemia, alterations in mood and cognition, and prostate cancer.

21. Methods of Treating Conditions Related to Androgen Deficiency

In certain embodiments, provided herein are methods of treating, preventing, suppressing, inhibiting or reducing the incidence of a condition related to androgen deficiency, such as in a female subject. The methods include administering to the subject one or more than one compound of Formula I, II or III or pharmaceutically acceptable salts or prodrugs thereof, in an amount effective to treat the condition related to androgen decline in the subject. In one embodiment, the condition is selected from among sexual dysfunction, decreased sexual libido, sarcopenia, osteopenia, osteoporosis, alterations in cognition and mood, depression, anemia, hair loss, obesity, endometriosis, breast cancer, uterine cancer and ovarian cancer.

J. COMBINATION THERAPIES

In certain embodiments, one or more compounds or compositions provided herein can be co-administered with one or more other therapeutic agents. In certain embodiments, such one or more other therapeutic agents are designed to treat the same disease or condition as the one or more compounds or pharmaceutical compositions provided herein. In certain embodiments, such one or more other therapeutic agents are designed to treat a different disease or condition as the one or more compounds or compositions provided herein. In certain embodiments, such one or more other therapeutic agents are designed to treat an undesired effect of one or more compounds or compositions provided herein. In certain embodiments, one or more compounds or compositions provided herein is co-administered with another therapeutic agent to treat an undesired effect of that other agent.

In certain embodiments, compounds or compositions provided herein and one or more other therapeutic agents are administered at the same time. In some embodiments, compounds or compositions provided herein and one or more other therapeutic agents are administered at the different times. In certain embodiments, compounds or compositions provided herein and one or more other therapeutic agents are prepared together in a single formulation. In certain embodiments, compounds or compositions provided herein and one or more other therapeutic agents are prepared separately.

Examples of therapeutic agents that can be co-administered with compounds or compositions provided herein include, but are not limited to, analgesics (e.g., acetaminophen); anti-inflammatory agents, including, non-steroidal anti-inflammatory drugs (e.g., ibuprofen, COX-1 inhibitors and COX-2, inhibitors); salicylates; anti-biotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immuno-modulators; muscle relaxants; anti-histamines; osteoporosis agents (e.g., bisphosphonates, calcitonin, and estrogens); prostaglandins, antineoplastic agents; psychotherapeutic agents; sedatives; antibodies; and vaccines.

In other embodiments, therapeutic agents that can be co-administered with compounds or compositions provided herein include, but are not limited to, other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralo-corticoid receptor antagonists; phosphodiesterase inhibitors; protein tyrosine kinase inhibitors; thyroid mimetics (including thyroid receptor agonists); anabolic agents; HIV or AIDS therapies; therapies used in the treatment of Alzheimer's and other cognitive disorders; therapies used in the treatment of sleeping disorders; anti-proliferative agents; anti-tumor agents; bisphosphonates; estrogens; SERMs; anti-estrogens; cathepsin inhibitors; $\alpha_v\beta_3$ integrin receptor antagonists; calcitonin; PPARγ inhibitors; osteoprotegerin; and proton pump inhibitors.

K. EXAMPLES

The following examples, including experiments and results achieved, are provided for illustrative purposes only and are not to be construed as limiting the claimed subject matter.

Example 1

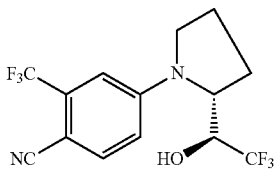

101

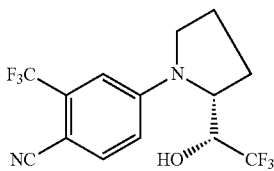

102

4-(2(R)-(1(S)-hydroxyl-2,2,2-trifluoroethyl)-pyrrolidinyl)-2-trifluoromethyl-benzonitrile (Compound 101) and R,R-4-(2-(1-Hydroxyl-2,2,2-trifluoroethyl)-pyrrolidinyl)-2-trifluoromethyl-benzonitile (Compound 102)

A mixture of D-prolinol, 4-fluoro-2-trifluoromethylbenzonitrile, and triethylamine in THF was stirred over night at 60° C. Standard work-up of the reaction mixture provided R-4-(2-hydroxylmethylpyrrolidinyl)-2-trifluoromethyl-benzonitrile in moderate yield. The intermediate alcohol was oxidized by sulfur trioxide pyridine complex to give R-4-(2-formyl-pyrrolidinyl)-2-trifluoromethyl-benzonitrile. The aldehyde intermediate was treated with trimethyl(trifluoromethyl)-silane to provide a mixture of two diastereomers. HPLC separation generated pure forms of Compounds 101 and 102.

Compound 101: $^1$H-NMR (500 MHz, CDCl$_3$) 7.59 (d, J=8.8, 1H), 7.07 (d, J=2.9, 1H), 6.92 (dd, J=8.8 and 2.9, 1H), 4.24 (t, J=7.5, 1H), 3.91 (t, J=6.3, 1H), 3.63 (dd, J=7.8 and 9.3, 1H), 3.29 (td, J=6.9 and 9.7, 1H), 2.55 (s, 1H), and 2.05-2.23 (m, 4H).

Compound 102: $^1$H-NMR (500 MHz, acetone-d$_6$) 7.78 (d, J=8.8, 1H), 7.01 (d, J=2.9, 1H), 6.94 (dd, J=8.8 and 2.9, 1H), 5.68 (bd, J=3.3, 1H), 4.44-4.50 (m, 1H), 4.36 (d, J=8.3, 1H), 3.64-3.77 (m, 1H), 3.44 (td, J=9.8 and 7.8, 1H), 2.30-2.47 (m, 2H), and 2.07-2.17 (m, 2H).

Example 2

R,R,R-4-(2-(1-Hydroxyl-2,2,2-trifluoroethyl)-5-methylpyrrolidinyl)-2-trifluoro-methylbenzonitrile (Compound 103) and 4-(2(R)-(1(S)-hydroxyl-2,2,2-trifluoroethyl)-5(R)-methylpyrrolidinyl)-2-trifluoromethylbenzonitrile (Compound 104)

Compounds 103 and 104 can be prepared in a similar fashion as described in Example 1 by using D-pyroglutamic acid as a starting material.

Compound 103: $^1$H-NMR (500 MHz, CDCl$_3$) 7.54 (d, 1H, J=8.5), 6.88 (d, 1H, J=2.3), 6.68 (dd, 1H, J=8.5 and 2.3), 4.41-4.32 (m, 1H), 4.19-4.15 (m, 1H), 3.98-3.93 (m, 1H), 2.79 (d, 1H, J=5.6), 2.59-2.49 (m, 1H), 2.17-1.98 (m, 2H), 1.93-1.85 (m, 1H), 1.35 (d, 3H, J=6.1).

Compound 104: $^1$H-NMR (500 MHz, CDCl$_3$) 7.62 (d, 1H, J=8.8), 7.16 (d, 1H, J=2.3), 6.99 (dd, 1H, J=8.8 and 2.3), 4.21-4.15 (m, 1H), 3.95-3.84 (m, 2H), 2.60 (d, 1H, J=3.5), 2.43-2.34 (m, 1H), 2.04-1.99 (m, 2H), 1.94-1.72 (m, 1H), 1.40 (d, 3H, J=6.1).

Example 3

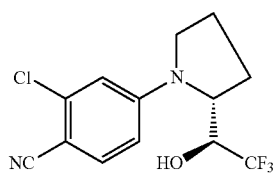

105

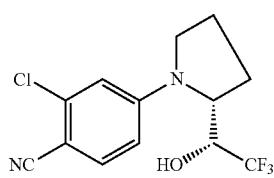

106

R,R-4-(2-(1-Hydroxyl-2,2,2-trifluoroethyl)pyrrolidinyl)-2-chlorobenzonitrile (Compound 105) and 4-(2(R)-(1(S)-hydroxyl-2,2,2-trifluoroethyl)pyrrolidinyl)-2-chlorobenzonitrile (Compound 106)

Compounds 105 and 106 can be prepared in a similar fashion as described in Example 1 by using 2-chloro-4-fluorobenzonitrile as a starting material.

Example 4

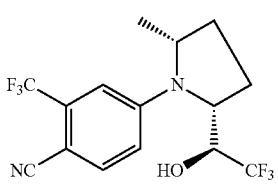

103

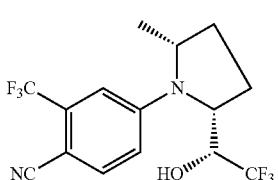

104

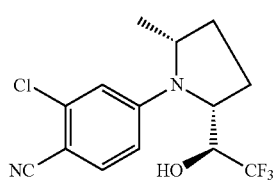

107

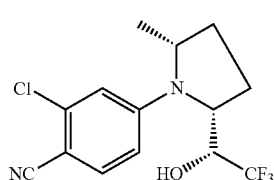

108

R,R,R-4-(2-(1-Hydroxyl-2,2,2-trifluoroethyl)-5-methylpyrrolidinyl)-2-chlorobenzonitrile (Compound 107) and 4-(2(R)-(1(S)-hydroxyl-2,2,2-trifluoroethyl)-5(R)-methylpyrrolidinyl)-2-chlorobenzonitrile (Compound 108)

Compounds 107 and 108 can be prepared in a similar fashion as described in Example 1 by using 2-chloro-4-fluorobenzonitrile as a starting material.

Compound 107: $^1$H-NMR (500 MHz, CDCl$_3$) 7.39 (d, 1H, J=8.8), 6.61 (d, 1H, J=2.3), 6.46 (dd, 1H, J=8.8 and 2.3), 4.41-4.36 (m, 1H), 4.14-4.09 (m, 1H), 3.93-3.88 (m, 1H), 2.78 (d, 1H, J=5.6), 2.55-2.49 (m, 1H), 2.13-1.98 (m, 2H), 1.88-1.81 (m, 1H), 1.33 (d, 3H, J=6.4).

Compound 108: $^1$H-NMR (500 MHz, CDCl$_3$) 7.45 (d, 1H, J=9.1), 6.89 (d, 1H, J=2.3), 6.76 (dd, 1H, J=9.1 and 2.3), 4.15-4.09 (m, 1H), 3.89-3.80 (m, 2H), 2.66 (d, 1H, J=2.6), 2.41-2.31 (m, 1H), 2.03-1.96 (m, 2H), 1.82-1.69 (m, 1H), 1.38 (d, 3H, J=6.2).

Example 5

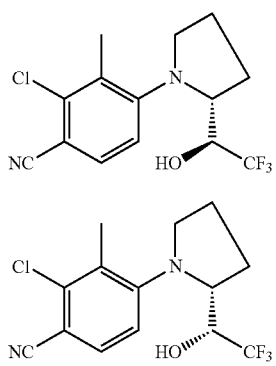

R,R-4-(2-(1-Hydroxyl-2,2,2-trifluoroethyl)pyrrolidinyl)-2-chloro-3-methyl-benzonitrile (Compound 109) and 4-(2(R)-(1(S)-hydroxyl-2,2,2-trifluoroethyl)-pyrrolidinyl)-2-chloro-3-methylbenzonitrile (Compound 110)

Compounds 109 and 110 can be prepared in a similar fashion as described in Example 1 by using 2-chloro-4-fluoro-3-methylbenzonitrile as a starting material.

Compound 109: $^1$H-NMR (500 MHz, CDCl$_3$) 7.43 (d, 1H, J=8.5), 6.92 (d, 1H, J=8.5), 4.19-4.14 (m, 1H), 4.00-3.95 (m, 1H), 3.71-3.63 (m, 1H), 3.02-2.95 (m, 1H), 2.39 (d, 1H, J=4.4), 2.34 (s, 3H), 2.32-2.21 (m, 1H), 2.17-2.00 (m, 2H), 1.93-1.80 (m, 1H).

Compound 110: $^1$H-NMR (500 MHz, CDCl$_3$) 7.45 (d, 1H, J=8.5), 7.10 (d, 1H, J=8.5), 4.30-4.25 (m, 1H), 3.80-3.78 (m, 1H), 3.61-3.53 (m, 1H), 3.10 (bs, 1H), 2.91-2.84 (m, 1H), 2.40 (s, 3H), 2.43-2.32 (m, 1H), 2.14-1.90 (m, 2H), 1.89-1.81 (m, 1H).

Example 6—Co-Transfection Assay—AR Agonist/Antagonist Activity

The ability of Compound 102 (4-(2(R)-(1(R)-hydroxyl-2,2,2-trifluoroethyl)-pyrrolidinyl)-2-trifluoromethylbenzonitrile) to activate or repress the ability of AR to induce gene expression was assessed using the cotransfection assay.

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

The CV-1 cells were transiently transfected by calcium phosphate coprecipitation according to the procedure of Berger et al., J. Steroid Biochem. Mol. Biol. 41: 733 (1992) with the following plasmids: pShAR (5 ng/well), MTV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in J. A. Simental et al., "Transcriptional activation and nuclear targeting signals of the human androgen receptor", J. Biol. Chem. 266: 510 (1991). The reporter plasmid, MTV-LUC, contains the cDNA for firefly luciferase (LUC) under control of the mouse mammary tumor virus (MTV) long terminal repeat, a conditional promoter containing an androgen response element. See e.g., Berger et al. supra. In addition, pRS-β-Gal, coding for constitutive expression of E. coli β-galactosidase (β-Gal), was included as an internal control for evaluation of transfection efficiency and compound toxicity.

Six hours after transfection, media was removed and the cells were washed with phosphate-buffered saline (PBS). Media containing reference compounds (e.g., progesterone as a PR agonist, mifepristone ((11β,17β)-11-[4-(dimethylamino)-phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)-phenyl]-pronanamide; Schering-Plough) as an AR antagonist; estradiol (Sigma) as an ER agonist and ICI 164,384 (N-butyl-3,17-dihydroxy-N-methyl-(7-alpha,17-beta)-estra-1,3,5(10)-triene-7-undecanamide; ICI Americas) as an ER antagonist; dexamethasone (Sigma) as a GR agonist and RU486 as a GR antagonist; and aldosterone (Sigma) as an MR agonist and spironolactone ((7-alpha-[acetylthio]-17-alpha-hydroxy-3-oxopregn-4-ene-21-carboxylic acid gamma-lactone; Sigma) as an MR antagonist) and/or Compound 102 in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

$$\frac{LUC \text{ response}}{\beta\text{-Gal rate}}$$

where β-Gal rate=β-Gal·1×$10^{-5}$/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response (EC$_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist were quantified ($IC_{50}$). In addition, the efficacy of antagonists was determined as a function (%) of maximal inhibition.

Compound 102 produced a concentration-dependent increase in luciferase activity in MDA-MB-453 cells that have endogenous expression of hAR. Compound 102 did not produce a concentration-dependent decrease in luciferase activity when tested in the presence of an $EC_{50}$ concentration of DHT (1 nM). Compound 102 was found to be a potent activator of hAR with an $EC_{50}$ of 3.1 nM and an efficacy of 59% when expressed relative to dihydrotestosterone (DHT, $EC_{50}$ of 2 nM and an efficacy of 100%), a natural ligand for AR. The ability of Compound 102 to activate transcription by other nuclear receptors also was evaluated. Agonist efficacy was determined relative to the appropriate reference agonist for each nuclear receptor. Compound 102 did not transactivate (demonstrate agonist activity) through the other nuclear receptors evaluated (hPR-B, hGR, hMR, hERα, hRARα, hLXRα, hFRα, hPPARα, hPPARγ, hPPARδ), except it very weakly activated hRXRα. Compound 102 antagonized dexamethasone-induced activation of hGR (60% with an $IC_{50}$ of 1.6 μM) and progesterone-induced activation of hPR-B (74% with $IC_{50}$ of 280 nM), but not activation of hERα or hMR.

Example 7—Receptor Binding Assays

Preparation of Receptor Proteins

A baculovirus expression plasmid including cDNA encoding the human androgen receptor (hAR) was prepared using standard techniques. The expression plasmid was used to transfect *Spodopter frugiperda*-21 (Sf-21) cells. A suspension culture of uninfected Sf-21 cells was grown to a density of $1.2 \times 10^6$ cells/mL and then infected with the recombinant virus including hAR cDNA at a multiplicity of infection of 2. The infected Sf-21 cells were incubated for 48 hours and then collected by centrifugation at 1000×g for 10 minutes at 4° C. The resulting cell pellets were resuspended in lysis buffer (50 mM potassium phosphate buffer, pH 7.0, 10 mM monothioglycerol, 5 mM DTT, 20 mM sodium molybdate, 1 mM PMSF, 1 μg/mL aprotinin, and 10 μg/mL leupeptin) and incubated for 15 minutes on ice. The resuspended cell pellets were homogenized using a Dounce homogenizer and a B pestle. A volume of 2 M KCl was added to the homogenized cell pellets to a final concentration of 0.4 M. The resulting receptor lysates were centrifuged at 100,000×g for 60 min at 4° C. and stored for use in binding assays.

Binding Assays

Binding assay samples were prepared in separate mini-tubes in a 96-well format at 4° C. Each binding assay sample was prepared in a volume of 250 μL of Receptor-Assay Buffer (10% glycerol, 25 mM sodium phosphate, 10 mM potassium fluoride, 10 mM sodium molybdate, 0.25 mM CHAPS, 2 mM DTT and 1 mM EDTA, (adjusted to pH 7.5)) containing 50 μg of receptor lysate; 2-4 nM of [$^3$H]-dihydrotestosterone at 50-100 Ci/mmol; and either a reference compound or a test compound. Each reference compound and test compound was assayed at varying concentrations, ranging from $3.2 \times 10^{-10}$ to $10^{-5}$ M. Each concentration of each reference compound and each test compound was assayed in triplicate. The assay samples were incubated for 16 hours at 4° C.

After incubation, 200 μL of 6.25% hydroxylapatite in assay buffer was added to each assay sample to precipitate the protein. The assay samples were then centrifuged and the supernatants were discarded. The resulting pellets were washed twice with assay buffer lacking DTT. Radioactivity in counts per minute (CPM) of each washed pellet was determined by liquid scintillation counter (MicroBeta™, Wallach).

After correcting for nonspecific binding, $IC_{50}$ values were determined using a 4-parameter fit, such as provided in commercially available software for curve fitting (e.g., Xlfit curve fitting software, IDBS Scientific Products, Guildford, UK). Typically all 4 parameters were floated to allow the best fit to converge. The $K_i$ values were determined by application of the Cheng-Prusoff equation to the $IC_{50}$ values using previously determined $K_d$ values for each specific ligand.

Compound 102 and other androgen modulating compounds, including R,R-2,2,2-trifluoro-1-[1-(4-nitro-3-trifluoromethyl-phenyl)-pyrrolidin-2-yl]-ethanol (LG0893410) and S,R-2,2,2-trifluoro-1-[1-(4-nitro-3-trifluoromethyl-phenyl)-pyrrolidin-2-yl]-ethanol (LG0893411):

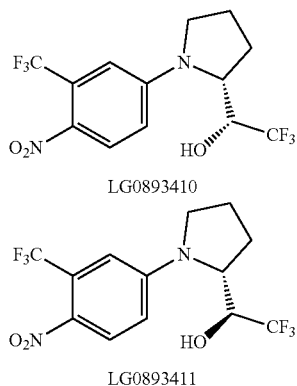

LG0893410

LG0893411 were tested for their ability to bind to hAR. Compound 102 demonstrated consistently higher potency, with a $K_i$ of 0.9 nM, by 3-6 fold than LG0893410 ($K_i$ of 2.5 nM) and LG0893411 ($K_i$ of 5.7 nM) for binding to baculovirus expressed hAR protein. Higher potency indicates that Compound 102 can be administered at a lower dose to achieve equal therapeutic effect.

Example 8—Activation of hAR-Responsive Luciferase Reporter

A functional assay was conducted to determine the ability of test substances to modulate gene expression via endogenous human androgen receptor (hAR) in a human cell line. A luciferase reporter assay was utilized to establish the ability of test compounds to activate hAR-regulated gene expression in a human cell line containing endogenously expressed hAR (MDAMB-453 cells) transfected with an androgen-responsive luciferase reporter plasmid containing the cDNA for firefly luciferase. MBA-MB-453 cells were transfected with a plasmid containing the cDNA for firefly luciferase (LUC) under the control of a conditional promoter containing hormone response elements recognized by AR (MMTV-LUC) and a P-galactosidase expression plasmid (pRS-(3-Gal) for normalization of transfection efficiency. The reporter plasmid MMTVLUC contains the mouse Mammary Tumor Virus (MMTV) Long Terminal Repeat (LTR)

conditional promoter containing hormone response elements recognized by hAR. The luciferase response was calculated as:

Luciferase response/β-gal rate where
Luciferase response=Relative Luciferase Units (RLU) and
β-gal rate=β-gal $0.D_{.415}$/β-Gal incubation time in minutes.

The mean of the normalized response at each concentration of compound was calculated. The effective concentration that produced 50% of the maximum response ($EC_{50}$) was determined for each compound by interpolation between two concentrations spanning the midpoint of the concentration-response curve. Agonist efficacy for test compounds was calculated as a percent of normalized response relative to the maximum normalized response by the reference agonist DHT.

Each of Compound 102, LG0893410 and LG0893411 activated AR-dependent gene expression. Compound 102, having an $EC_{50}$ of 2.8 nM, was 8.5 to 12.5 times more potent in activating hAR-responsive luciferase reporter than LG0893410 ($EC_{50}$ of 24.2 nM) and LG0893411 ($EC_{50}$ of 35.0 nM). Higher potency indicates that Compound 102 can be administered at a lower dose to achieve equal therapeutic effect.

Example 9—Activation of hAR in a Co-Transfection Assay

A luciferase reporter co-transfection assay also was used to evaluate the ability of compounds provided herein to activate hAR regulated gene expression. Compound 102 and other androgen receptor modulators, including LG0893410 and LG0893411, were assayed to assess their ability to activate hAR regulated gene expression by transfecting CV-1 cells, derived from African monkey kidney and lacking endogenous AR, with an expression plasmid containing the cDNA for the human AR (pRShAR) and the androgen-responsive luciferase reporter plasmid (MMTV-LUC). CV-1 cells were transiently transfected with pRShAR, a P-galactosidase expression plasmid (pRS-(3-Gal) for normalization of transfection efficiency, and the reporter plasmid MMTV-LUC using a non-liposomal formulation, the FuGENE 6 transfection reagent.

The mean of the normalized response at each concentration of compound was calculated. The $EC_{50}$ was determined for each compound and agonist efficacy for test compounds was calculated as a percent of normalized response relative to the maximum normalized response by the reference agonist DHT.

Each of Compound 102, LG0893410 and LG0893411 activated hAR in the co-transfection assay. Compound 102, having an $EC_{50}$ of 4.4 nM, was 3 to 5 times more potent in activating hAR than LG0893410 ($EC_{50}$ of 13.0 nM) and LG0893411 ($EC_{50}$ of 23.3 nM). Higher potency indicates that Compound 102 can be administered at a lower dose to achieve equal therapeutic effect.

Example 10—Skeletal α-Actin Promoter Assay

Compound 102 was tested to determine its ability to activate human skeletal α-actin using the skeletal α-actin promoter assay. A mouse muscle cell line (C2C12) was transiently transfected with a human AR expression plasmid and a luciferase reporter plasmid containing the skeletal α-actin promoter upstream of the luciferase cDNA. C2C12 cells (at a concentration of $5 \times 10^5$) were seeded in a T25 flask and cultured for 24 hours. The cells were harvested by using trypsin and seeded at 6000 cells/well in 96-well plates. The same day, a non-liposomal formulation, FuGENE 6 reagent (Roche, Indianapolis, Ind.) was used for transfection of the cells. To each well was added 45.5 ng of the skeletal α-actin-LUC reporter plasmid, 4.55 ng pRShAR and 5 ng pRS-BG as carrier DNA. Twenty-four hours after transfection, different concentrations of the solvated compound ($10^{-10}$ to $10^{-6}$ M) were added in triplicate to the cells and the cells were incubated for 24 hours. The medium was aspirated and the cells were lysed with a detergent-containing buffer. After addition of Luciferase Assay Buffer to each well, the cells were assayed for luciferase activity using a luminometer to determine the level of transcriptional activation. The effective concentration that produced 50% of the maximum response ($EC_{50}$) was determined from the concentration-response curve for the compound by interpolation between two concentrations spanning the midpoint of the concentration response curve. Agonist efficacy for the test compound was calculated as a percent of luciferase response relative to the maximum luciferase response by the reference agonist DHT.

Compound 102 stimulated skeletal α-actin promoter activity in a concentration-dependent manner. At a concentration of $1 \times 10^{-7}$ M, Compound 102 increased the promoter activity about 17.5-fold compared to vehicle control. Compound 102 was not as potent as DHT but was equally efficacious. Compound 102 activated the skeletal α-actin promoter with an average $EC_{50}$ of 8.7 nM (DHT≈1 nM) and efficacy of 93% of DHT. Compound 102 showed a strong AR-mediated stimulation of skeletal α-actin promoter activity in muscle cells, indicating that this compound likely up-regulated skeletal α-actin production at the transcription level. Compound 102 stimulates α-actin promoter activity in muscle cells in a manner similar to that of DHT, is highly potent (8.7 nM) and efficacious (93% compared to DHT).

The ability of Compound 102 to stimulate muscle cells was compared to other androgen modulating compounds, including LG0893410 and LG0893411. Compound 102 was found to be 5-10 fold more potent in stimulating muscle cells than LG0893410 and LG0893411, having an $EC_{50}$ of 8.7 nM compared to 45.2 nM for LG0893410 and 85.6 nM for LG0893411. Compound 102 also was nearly as effective as the androgen agonist DHT in stimulating muscle cells (93% of DHT), while LG0893410 and LG0893411 were much less effective (having an efficacy of 43% and 59%, respectively) in stimulating α-actin gene transcription in muscle cells.

Example 11—IL-6 Promoter Repression Assay

IL-6 is an important bone resorption factor. Over-expression of IL-6 can cause severe bone loss in vivo. Reducing IL-6 production by bone cells would be therapeutically beneficial by reducing bone resorption. Compound 102 and the androgen receptor modulators LG0893410 and LG0893411 were tested to determine their ability to suppress TNFα-IL-1β-induced IL-6 promoter activity in Saos-2 human osteoblast cells using a cotransfection assay. A human osteoblast cell line (Saos-2) was transiently transfected with a human AR expression plasmid and a luciferase reporter plasmid containing the IL-6 promoter upstream of the luciferase cDNA. Saos-2 cells were seeded at 6000 cells/well in 96-well plates. The same day, a non-liposomal formulation, FuGENE 6 reagent (Roche, Indianapolis, Ind.)

was used for transfection of the cells. To each well was added 3.6 µg of the IL-6-LUC reporter plasmid and 0.7 µg of pCMV-hAR. Twenty-four hours after transfection, different concentrations of the solvated compound ($10^{-11}$ to $10^{-6}$ M) in DMEM (Dulbecco's Minimal Essential Media) were added in triplicate to the cells and the cells were incubated for 24 hours. The expression of luciferase was stimulated by the cytokines Tumor Necrosis Factor α (TNFα, 10 ng/mL) and Interleukin-1 beta (IL-1β, 1 ng/mL). The medium was aspirated and the cells were lysed with a detergent-containing buffer. After addition of Luciferase Assay Buffer to each well, the cells were assayed for luciferase activity using a luminometer to determine the level of transcriptional activation. The effective concentration that produced 50% of the maximum response ($EC_{50}$) was determined from the concentration-response curve for the compound by interpolation between two concentrations spanning the midpoint of the concentration response curve. Agonist efficacy for the test compound was calculated as a percent of luciferase response relative to the maximum luciferase response by the reference agonist DHT.

All three test substances were full agonists compared to DHT in suppressing IL-6 production by human bone cells. The addition of Compound 102 in concentrations from $10^{-11}$ to $10^{-6}$ M resulted in a concentration-dependent suppression of IL-6 promoter activity to the level seen in the absence of TNFα and IL-1β. Compound 102 displayed potent and efficacious AR-mediated suppression of TNFα-IL-1β-induced IL-6 promoter activity in Saos-2 human osteoblast cells. Compound 102 was found to be highly potent, having an average $IC_{50}$ of 0.41 nM (DHT had an average $IC_{50}$ of 0.03 nM, LG0893410 had an average $IC_{50}$ of 1.20 nM and LG0893411 had an average $IC_{50}$ of 1.50 nM) and Compound 102 was found to have an efficacy of 97% of DHT. Compound 102 suppresses IL-6 promoter activity in a manner similar to that of DHT, and is 3-4 fold more potent than LG0893410 and LG0893411. These results suggest that Compound 102 down-regulates IL-6 production at the transcriptional level. Because Compound 102 suppresses IL-6 production by osteoblasts, it is expected to have a beneficial in vivo effect on bone by reducing bone resorption.

Example 12—Metabolic Stability in Liver Microsomes

Liver microsomes are subcellular fractions that contain drug-metabolizing enzymes, such as cytochrome P450, flavin monooxygenases and UDP glucuronyl transferases. When the elimination of a drug occurs primarily by metabolism, the route of metabolism can significantly affect the drug's safety and efficacy, hence affecting the directions for use of the drug. Rat liver microsomes are a commonly used animal model for determination of drug metabolism (e.g., see Shayeganpour et al., Drug Metab Dispos 34 (1): 43-50 (2006)).

The metabolism of Compound 102 was evaluated in rat liver microsomes. The metabolism was initiated by adding 25 µL of cofactor (100 mM of glucose 6-phosphate, 20 mM of NADP, 20 mM of glucose-6-phosphate dehydrogenase, and 63 mM of UDPGA) to wells containing 50 µL of 5 mg/mL of rat liver microsomes and 425 µL of 0.59 mM of Compound 102 made in 100 mM phosphate buffer (pH 7.4) at 37° C. At 0, 5, 10 and 20 minutes, a 60 µL aliquot of the sample was withdrawn. The unmetabolized test substance remaining in the sample was determined using HPLC and mass spectrometry and the half-life for degradation of the compound was calculated in minutes using curve fitting. For Compound 102, the half-life was determined to be 44.5 minutes (average value determined in 2 experiments with each experiment using triplicate measurements), demonstrating that Compound 102 has high metabolic stability, since it is only slowly metabolized.

High metabolic stability promotes oral bioavailability and reduces the burden of xenobiotic metabolites generated after administration of a therapeutically effective dose. High metabolic stability is preferred for drugs that are intended for systemic administration, such as would be the case for treating diseases or conditions such as aplastic anemia; anorexia; arthritis, including inflammatory arthritis, rheumatoid arthritis, osteoarthritis and gout; arteriosclerosis; atherosclerosis; bone disease, including metastatic bone disease; bone damage or fracture, such as by accelerating bone fracture repair and/or stimulation of osteoblasts and/or stimulation of bone remodeling and/or stimulation of cartilage growth; distraction osteogenesis; reduced bone mass, density or growth; bone weakening, such as induced by glucocorticoid administration; musculoskeletal impairment (e.g., in the elderly); cachexia; cancer, including breast cancer and osteosarcoma; cardiac dysfunction (e.g., associated with valvular disease, myocardial infarction, cardiac hypertrophy or congestive heart failure); cardiomyopathy; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; chronic obstructive pulmonary disease (COPD); chronic bronchitis; decreased pulmonary function; emphysema; decreased libido in both men and women; depression; nervousness, irritability and/or stress; reduced mental energy and low self-esteem (e.g., motivation/assertiveness); dyslipidemia; erectile dysfunction; frailty; age-related functional decline ("ARFD") in the elderly; growth hormone deficiency; hematopoietic disorders; hormone replacement (male and female); hypercholesterolemia; hyperinsulinemia; hyperlipidemia; hypertension; hyperandrogenemia; hypogonadism (including primary and secondary); hypothermia (including hypothermia following anesthesia); impotence; insulin resistance; type 2 diabetes; lipodystrophy (including in subjects taking HIV or AIDS therapies such as protease inhibitors); male menopause; metabolic syndrome (syndrome X); loss of muscle strength and/or function (e.g., in the elderly); muscular dystrophies; muscle loss following surgery (e.g., post-surgical rehabilitation); muscular atrophy (e.g., due to physical inactivity, bed rest or reduced weight-bearing conditions such as microgravity); neuro-degenerative diseases; neuro-muscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction (e.g., erectile dysfunction, decreased sex drive, sexual well-being, decreased libido); physiological short stature, including growth hormone deficient children and short stature associated with chronic illness and growth retardation associated with obesity; tooth damage (such as by acceleration of tooth repair or growth); thrombocytopenia; vaginal dryness; atrophic vaginitis; ventricular dysfunction; wasting, including wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia), chemotherapy, multiple sclerosis or other neurodegenerative disorders.

Example 13—In Vivo Assay—Orchidectomized Mature Male Rats

The orchidectomized male Sprague-Dawley rat model was used to assess the effects of Compound 102 on various reproductive, gonadotropin and musculoskeletal endpoints, including sex accessory organs, bone, serum gonadotropin levels and striated muscle in mature male rats.

In this assay, two-month old rats were acclimated in a vivarium for one week. After this acclimation period, rats were surgically orchidectomized under isoflurane anesthesia and left untreated for 14 days. After 14 days, animals were sorted into groups such that no statistically significant differences in mean body weights were observed. Rats began receiving treatment 14 days after the day of surgery. Sham-operated and orchidectomized rats, treated with vehicle, served as controls. The different test groups were treated with various doses of Compound 102 (0.03 to 100 mg/kg/day per os (by mouth)). Dosages included 0.03, 0.1, 0.3, 1, 3, 10, 30 and 100 mg/kg/day. Ostarine, a non-steroidal androgenic drug (Evans et al., J Clin Oncology 25: 9119 (2007)) was dosed at dosages similar to other test groups as a comparison. After the 14$^{th}$ dose, venous blood was collected at 0, 1, 2, 4 and 6 hours after dosing. The blood samples were collected in EDTA-containing tubes (Becton Dickinson, Franklin Lakes, N.J.). Approximately 24 hours after the last dose, animals were euthanized and seminal vesicle weights, ventral prostate weights, levator ani weights, preputial gland weights and blood samples were collected on necropsy.

A. Serum and Plasma Collection

For serum, whole blood (5 mL) was collected in vacutainer tubes (Becton Dickinson) and the blood samples were allowed to clot at room temperature for about 2 hours. Serum was separated by centrifugation at 2500 rpm for 30 minutes, collected and frozen (−80° C.). For plasma, whole blood was collected in EDTA-containing tubes by centrifugation at 1000×g for 5 minutes at 4° C. Plasma samples were stored at −20° C.

B. Sample Preparation

For the preparation of all dose formulations, the appropriate amount of test compound (Compound 102) for the highest concentration to be administered was weighed. The compound was suspended in the formulation vehicle (5% Tween®-80 polysorbate, 90% PEG-400 polyethylene glycol and 5% PVP-K30 polyvinyl-pyrrolidone). The suspension was sonicated for 15 minutes, and the resulting formulation was diluted using vehicle to obtain the proper volume and concentrations of the dosing materials to achieve a dosing volume of 1 mL/kg body weight.

C. Luteinizing Hormone (LH) Radioimmunoassay

Serum samples were assayed with a double anti-serum procedure using reagents from the National Institute of Diabetes and Digestive and Kidney Diseases (NIDDK). Sample compounds and standards (NIDDK-rLH-RP-3) in a total volume of 200 μL were incubated at room temperature for 2 to 3 days with 100 μL primary anti-serum (rat LH antiserum: rabbit NIDDK-anti-rLH-S-11) diluted 1:100,000. Then, 100 μL of $^{125}$I-labeled LH (Covance Laboratories Madison, Wis.) diluted 200,000-300,000 cpm/mL was added to the tubes and incubation continued for an additional 24 hour period.

Bound hormone was separated from free hormone by precipitation with a specific goat ant-rabbit serum (GARS from Antibodies, Inc., Davis, Calif.). An aliquot of 50 μL of 4% normal rabbit serum was added to each incubation tube, after which an additional 50 μL of a 1:10 GARS solution was added. The tubes were vortexed and incubated overnight at 4° C.

The assay was terminated by centrifugation at 2,500 rpm for 30 minutes in a Sorvall RC 3C Plus centrifuge (rotor #H2000B) at 4° C. The supernatants were decanted and discarded and the pellets were counted in a 10-channel gamma-counter.

D. Osteocalcin Immunoradiometric Assay (IRMA)

Serum osteocalcin, a vitamin K-dependent, calcium binding protein, is a biochemical marker that reflects bone formation activity (Gundberg, J Clin Ligand Assay 21: 128-138 (1998)). Serum osteocalcin was quantitated using an IRMA kit from Immutopics, Inc. (#50-1500, San Clemente, Calif.). The procedures were performed following the protocols supplied by the vendor (Rat Osteocalcin IRMA Kit Cat. #50-1500, 2005) except that 25 μL of sample was used instead of 5 μL of sample as suggested. The test uses two different antibodies to measure the serum osteocalcin. The sample is incubated simultaneously with a bead-immobilized goat antibody that recognizes the mid-region C-terminal portion of the osteocalcin molecule and an $^{125}$I-labeled goat antibody that recognizes the amino terminal portion of the molecule. Osteocalcin present in the sample binds to the antibody immobilized on the bead and the radiolabeled antibody binds to the osteocalcin.

For sample dilution, 25 μL of sample and 400 μL of zero standard were dispensed into appropriately labeled tubes and vortexed. A 100 μL aliquot of standard, diluted control or diluted sample was dispensed into appropriately labeled tubes. 200 μL of $^{125}$I-labeled Rat Osteocalcin Antibody was dispensed into all tubes followed by vortex mixing. One bead including the goat antibody was added to each tube, tilting the tube to prevent splashing of the tube contents by the addition of the bead. The tubes were sealed with Parafilm® and incubated at room temperature for 18 to 24 hours. After the incubation period, the contents of each tube was aspirated, leaving the bead in the tube. The bead in each tube was washed three times by dispensing 2 mL of wash solution into each tube and then completely removing the wash solution by aspiration. Each tube was counted in a gamma counter for one minute and the counts recorded. A standard curve was generated using the rat osteocalcin standards provided in the kit. The rat osteocalcin concentration (in ng/mL) of the diluted controls and diluted samples were read directly from the standard curve.

E. Quantitation of Compound 102 in Plasma Samples

The determination of plasma concentration was done by an LC-MS/MS method.

The standard solution of each drug was spiked in blank rat plasma, calibration standards were constructed from 0.0001 μg/mL to 10 μg/mL; and 50 μL of each calibration standard was extracted with 250 μL of acetonitrile containing 10 ng/mL of internal standard in a 96-well plate. Also, 50 μL of plasma sample was extracted with 250 μL of acetonitrile containing internal standard in a 96-well plate.

The Q1/Q3 mass was 337.1/267.3 amu for Compound 102 in a negative mode and 338.0/269.1 amu for ostarine in a negative mode.

F. Pharmacokinetic Analysis

Plasma concentration time data for each animal were analyzed using WinNonlin (version 5.0, Pharsight WinNolin copyright© 1998-2005) by con-compartmental PK methods (Gibaldi et al., *Pharmokinetics* (2$^{nd}$ ed., Marcel Dekker, New York, N.Y., pp. 271-318 and 409-417 (1982)). The elimination half life ($t_{1/2}$) was not estimated in this study due to the fact that plasma samples were collected at four time points (1, 2, 4 and 6 hours postdose). The area under the plasma concentration curve (AUC) was calculated by the trapezoidal method. The 0 hour plasma concentration was considered as the 24 hour plasma concentration at Day 14, assuming steady state, and used to estimate $AUC_{24}$. Peak pharmacokinetic (PK) parameters were calculated and rounded to three decimal places.

G. Data Analysis

Results were analyzed by analysis of transformed data (Box et al, J Roy Soc Series B 26: 211-252 (1964) and Box et al., Technometrics 16: 385-389 (1974). When necessary, transformations were performed to ensure that variances were homogeneous among groups and that the residuals of the one-way analysis of variance model followed a Gaussian (normal) distribution. When the analysis of variance reached significance, data were further evaluated by the Fisher's LSD test. A P value lee than 0.05 was considered as the minimum criterion to declare statistically significant differences. When possible, data were fitted to a modified four-parameter logistic equation (Ghosh et al., J Biopharm Stat 8: 645-665 (1998). The model estimates $ED_{50}$s in a logarithmic scale, since log $ED_{50}$ is a more robust estimate of the potency. The model also provides an SE for the estimate that is used to calculate 95% confidence limits of the estimated potencies. The following equation exemplifies the basic, reparametrized four-parameter logistic equation used in these studies:

$$Y=(A-D)/(1+e^{B} \cdot (\log C - \log x))+D$$

where A is the maximum, D is the minimum, B is the slope factor, C is either the $EC_{50}$ of the $IC_{50}$, depending on the direction of the response and x is the dose of the compound used.

Results

The 14-day rat model is a short term in vivo model used to demonstrate the selectivity of androgen modulator compounds. Orchidectomy removes almost all of the endogenous circulating androgens in the rat. When Compound 102 was orally administered at levels of about 1.5 mg/kg/day, Compound 102 was able to maintain levator ani weight at sham-equivalent levels, while the same dose did not maintain the growth of ventral prostate or seminal vesicle at sham-equivalent level. At the highest tested dose (100 mg/kg/day), Compound 102 significantly increased levator ani weight above sham-equivalent levels, but still only restored the ventral prostate or seminal vesicles to approximately 50% of sham levels. These findings suggest that Compound 102 when administered orally can sustain levator ani weight similar to or greater than intact counterparts while maintaining androgen-sensitive sex accessory glands at weights lower than intact male rats.

Compound 102 had an inhibitory effect on serum LH and was able to maintain sham-equivalent levels at a dose of 10 mg/kg/day. Compound 102 significantly decreased serum LH below sham equivalent levels at the highest tested dose (100 mg/kg/day).

Preputial gland weight, measured as a marker of sebaceous gland activity, remained below vehicle equivalent levels for all doses of Compound 102 less than 10 mg/kg/day PO. Compound 102 increased preputial gland weight above the sham level at the 30 mg/kg/day dose. The effect was statistically significant at this dose.

Serum osteocalcin tended to decrease with increasing dose of Compound 102, but the effects were not statistically significant at any tested dose. Orchidectomy has been reported to increase serum osteocalcin in male rats 2 weeks post-surgery (Ivaska et al., J Biol Chem 279: 18361-18369 (2004)).

The test compound was quantified in most of the plasma samples collected, although Compound 102 was below the limit of quantitation (BLQ) in a few plasma samples at 0.03 mg/kg/day and 0.1 mg/kg/day doses. The mean PK parameters for Compound 102 are shown below in Table 1:

TABLE 1

Pharmacokinetic Parameters at Day 14 (Mean ± SD).

| Parameter | 0.03 mg/kg | 0.01 mg/kg | 0.3 mg/kg | 1 mg/kg | 3 mg/kg | 10 mg/kg | 30 mg/kg | 100 mg/kg |
|---|---|---|---|---|---|---|---|---|
| $AUC_6$ (µg · hr/ml) | 0.002 ± 0.001 | 0.004 ± 0.005 | 0.018 ± 0.008 | 0.063 ± 0.037 | 0.113 ± 0.069 | 0.370 ± 0.141 | 0.645 ± 0.406 | 0.998 ± 0.480 |
| $AUC_{24}$* (µg · hr/ml) | 0.005 ± 0.007 | 0.015 ± 0.012 | 0.042 ± 0.029 | 0.123 ± 0.063 | 0.234 ± 0.140 | 0.764 ± 0.315 | 1.881 ± 1.120 | 4.053 ± 1.987 |
| $C_{MAX}$ (µg/ml) | 0.001 ± 0.001 | 0.002 ± 0.001 | 0.012 ± 0.012 | 0.018 ± 0.010 | 0.036 ± 0.019 | 0.111 ± 0.050 | 0.205 ± 0.169 | 0.321 ± 0.112 |
| $t_{MAX}$ (hr) | 2.0 ± 1.6 | 2.8 ± 2.2 | 1.3 ± 1.0 | 2.5 ± 1.7 | 1.3 ± 0.5 | 1.8 ± 1.5 | 4.3 ± 2.4 | 3.5 ± 2.9 |

*The 0 hr plasma concentration was substituted for the 24 hr plasma concentration in order to estimate $AUC_{24}$.

The systemic exposures, as measured by $AUC_{24}$ and $C_{MAX}$, increased as the dose level increased and were roughly dose proportional. The peak plasma concentrations were observed between 1 hour and 5 hour postdose.

Pharmacokinetic analysis indicated that exposure of Compound 102 increased with dose up to 100 mg/kg/day PO. Expressed relative to exposure ($AUC_{24}$), levator ani and ventral prostate weights increased with Compound 102 exposure in a dose dependent manner. Compound 102 increased levator ani to sham equivalent levels at an exposure of approximately 0.2 µg·/mL. At exposures of 1 µg·/mL or greater, Compound 102 stimulated muscle mass above sham equivalent levels yet restored the ventral prostate to less than 50% of sham equivalent levels. Ostarine was not as potent as Compound 102, restoring levator ani weight to sham equivalent levels at an exposure of 4 µg·/mL. At exposures greater than 10 µg·/mL, ostarine stimulated muscle mass above sham levels but did not restore ventral prostate to sham equivalents at any dose.

Thus, in orchidectomized male rats, Compound 102 exhibited positive activity in musculoskeletal endpoints. Compound 102 had dose proportional exposure and maintained levator ani weight at sham-equivalent levels at a dose of 2 mg/kg/day ($AUC_{24}$: 0.2 µg·/mL). At doses that maintained levator ani weights at sham equivalent levels, Compound 102 had lower efficacy (relative to sham) in sex accessory and sebaceous glands. In this model, Compound 102 showed tissue selective activity toward the muscle endpoint. Compound 102 showed lower potency for reducing the elevated LH levels in castrate rats (≥10 mg/kg/day) compared to increasing the reduced levator ani skeletal muscle mass in these animals (2 mg/kg/day). Compound 102 suppressed serum LH below sham-equivalent levels at high doses. The comparator compound, ostarine (a known non-steroidal selective androgen receptor modulator (SARM)), had similar efficacy relative to Compound 102 and also demonstrated high tissue selectivity.

The finding that Compound 102 increases the levator ani skeletal muscle in rats with abnormally low muscle mass suggests that the compound can be used for treating sarcopenia in humans (e.g., see Joseph et al., Mol Aspects Med 26: 181-201 (2005)). Based on the ≈2 mg/kg/day dose in rats for restoration of skeletal muscle mass (equivalent to 14 mg/m$^2$ body surface area), the dose for therapeutic effect in humans would target systemic exposure of about 0.1-0.5 μg·hr/mL, such as 0.2 μg·hr/mL in patients with sarcopenia.

Example 14—In Vivo Assay—Ovariectomized Mature Female Rats

In animal models of osteoporosis, androgens increase bone density and strength in male rats (Wakely et al., J Bone & Mineral Research 6: 325-330 (1991) and Vandenput et al., Calcified Tissue International 70: 170-175 (2002)) and female rats (Tobias et al., Am J Physiology 267: E853-E859 (1994) and Coxam et al., Bone 19: 107-114 (1996)). The ovariectomized mature female rat model was used to assess the effects of orally administered compounds provided herein, such as Compound 102, on bone as well as other efficacy and side-effect endpoints including muscle mass, fat mass and clitoral gland weight.

In this assay, approximately three-month old rats were acclimated in a vivarium for one week. After acclimation, rats were anesthetized with Avertin and the ovariectomy (OVX) was performed using the dorsal approach. For the sham procedure, the surgical procedure was conducted per protocol, and the ovaries exteriorized but not removed. After recovery, no further experimental manipulations were performed for seven weeks, at which point the rats were scanned by dual energy x-ray absorptiometry and sorted into experimental groups based upon femoral bone mineral content (BMC). Three dosages of Compound 102 were tested (0.03, 0.3 and 3 mg/kg/day PO). For comparison, ostarine, a known non-steroidal SARM, was tested at the same dosages (0.03, 0.3 and 3 mg/kg/day PO). In addition, reference compounds estradiol and testosterone were administered. Estradiol was administered subcutaneously to one ovariectomized group at a dose of 0.1 mg/kg/day and testosterone propionate was administered subcutaneously to another ovariectomized group at a dose of 1 mg/kg/day.

Treatment continued once daily for 12 weeks, at which point animals were euthanized and tissues were collected for further analysis. Animals received subcutaneous injections of fluorochrome markers for bone histomorphometric analysis. Alizarian Red S was prepared as a 3% solution and given at a dose of 30 mg/kg at the time of the baseline scan. Calcein was administered 10 days and 3 days prior to necropsy.

After the 14$^{th}$ dose, approximately 250 μL venous blood was collected via percutaneous jugular puncture from the rats at 0, 0.5, 1, 2, 4 and 6 hours post-dosing. The blood samples were collected into lithium-heparin tubes (Becton Dickinson, Franklin Lakes, N.J.). Plasma fractions were collected for pharmacokinetic analysis. Approximately 24 hours after the last dose, rats were sacrificed by cardiac exsanguination, and blood was collected into serum separator tubes (Becton Dickinson), and the gastrocnemius muscle, plantaris muscle, uterus, clitoral glands, clitoris and inguinal fat pads were isolated, blotted and weighed individually. Uterine weight measurements can be inaccurate in surgically ovariectomized rats due to the potential loss of uterine tissue at the tips of the uterine horns during removal of the ovaries. To minimize this variability, the length of the uterine horns was measured and the uterine weight was reported normalized to uterine length. The left femur and lumbar vertebra L5 were wrapped in saline-soaked gauze and stored at −20° C. for biochemical analysis. The right femur and lumbar vertebrae L3-L4 were collected and stored in 70% ethanol for histomorphometry. The right tibia was collected in formalin for histological analysis. The left tibia was collected on dry ice and stored at −20° C. for measurement of alkaline phosphatase activity.

A. Sample Preparation

Compound 102 and ostarine individually were formulated in a solution containing 5% Tween-80 polysorbate, 90% PEG-400 polyethylene glycol, and 5% polyvinyl-pyrrolidone K30. The mixture was stirred and sonicated in a water bath for 30 minutes until the compound dissolved into a solution. After sonication, 1% carboxymethyl cellulose (CMC) in water was added to the solution in a 9:1 ratio (9 parts CMC/water solution to 1 part PEG-400/Tween-80/PVP). Compound 102 and ostarine were administered orally in a volume of 4 mL/kg.

Reference compounds estradiol and testosterone propionate were formulated in a vehicle containing 70% polyethylene glycol and 30% DMSO (dimethyl sulfoxide) by volume. Compounds were weighed and added to the appropriate volume of vehicle. The mixture was sonicated for several minutes to ensure that the compounds were thoroughly dissolved. The reference compounds were administered subcutaneously in a volume of 0.4 mL/kg.

B. Dual Energy X-Ray Absorptiometry (DEXA)

Dual X-ray absorptivity (DEXA) was performed on a Norland Peripheral Dual Energy X-Ray Absorptiometer (pDEXA Sabre, Norland Medical Systems, Orthmetrix, White Plains, N.Y.). Prior to each use, the machine was calibrated using two phantoms supplied by the manufacturer. The machine calculated a coefficient of variation over the prior 16 calibrations to determine the measurement precision. The coefficient of variation for the quality control phantoms was between 0.47% to 0.57% during the course of the study.

For in vivo DEXA measurements, the rats were anesthetized with isoflurane (Hospira, Inc., Lake Forrest, Ill.) and placed prone on the bed of the scanner. A scan that encompassed the lumbar spine and the right femur was performed and collected. Regional analysis were performed on the whole femur, the mid-diaphyseal femoral shaft and the lumbar spine. The mid-femur measurement included 3.5 mm on either side of the mid-length of the femur and included the entire cortical width. The lumbar spine was defined as L3-L5 as defined by the intervertebral disk and included the entire spine width. The bone mineral content (BMC), projected bone area and the areal bone mineral density (BMD) were measured for each region, described above. BMD was calculated as the BMC divided by projected bone area. The coefficient of variations on repeated scans on live rats was determined to by less than 1.6% for measurements of the BMC and 2.5% for measurements of the BMD for the femur and vertebral bodies.

BMC, BMD and bone length were measured by pDEXA on an entire femur after it was removed from the animal at the end of the experiment. The coefficients of variation for the phantom standards were as described above for the in vivo measurements. The coefficient of variation for repeated measurement of the isolated femur was less than 0.4% for the BMC and the BMD measurements.

C. Osteocalcin IRMA

Serum osteocalcin was quantitated using a kit from Immutopics (#50-1500, San Clemente, Calif.), using the procedures described above in Example 13.

D. Alkaline Phosphatase Derived from the Tibial Periosteum

The whole, intact tibias were manually cleaned of muscle and other adherent soft tissue. Whole tibias were enzymatically digested with 0.2% SigmaBlend collagenase Type F (Sigma-Aldrich) for 1 hour at 37° C. The periosteal isolate was then sonicated for 20 seconds at 30 A with a Kontes Micro Ultrasonic Cell Disrupter Model #KT50 (Vineland, N.J.). Total alkaline phosphatase activity of the homogenate was quantified on an ACE Clinical Chemistry Analyzer (Alfa Wassermann, Fairfield, N.J.) following the manufacturer's protocols.

E. Biomechanical Testing

All biomechanical testing was performed on a QTest2/L materials testing system with a 2 kN load cell (MTS, Eden Prairie, Minn.). Data was collected at 10 Hz from the load cell and the crosshead displacement and analyzed using software designed for materials testing (TestWorks 4, MTS).

Whole femurs were collected for biomechanical analysis and thawed at room temperature prior to testing. Femurs were kept moist with saline throughout the preparation and testing. Total femoral length was measured with handheld digital calipers (Mitutoyo, Japan) and the midpoint of the femur was identified. The medial-lateral and anterior-posterior diameters were measured at the mid-femur with calipers. The whole femur was placed on a custom-designed 3-point bending fixture, consisting of stainless steel pins, 0.63 mm in diameter, with a span of 15 mm between the lower supports. A 5N preload was applied to the femurs at the mid-femur prior to the start of testing. Testing was performed with a constant crosshead displacement rate of 20 mm/minute until failure, which was defined as a 50% reduction in load. After failure, cortical thickness was measured at each quadrant of the mid-femur using handheld digital calipers. Peak load and peak displacement were measured directly from the load cell and the crosshead, respectively. Stiffness was calculated from the slope of the linear region of the load/displacement curve. Energy absorption (EnergyToPeak) was calculated as the area under the load/displacement curve. All of the measurements listed above describe structural or organ level properties. In an effort to distinguish overall structural and geometric changes from intrinsic tissue level changes, additional endpoints were calculated. These endpoints represent each of the above described endpoints normalized to the tissue volume and geometry. Peal stress (a), strain (c), modulus of elasticity (Young's modulus—E) and modulus of toughness were calculated using standard equations (e.g., see Turner et al., Bone 14: 595-608 (1993) and Gere et al., *Mechanics of Materials* (PWS-Kent, Boston (1984)).

Lumbar vertebra L5 were thawed at room temperature prior to testing and were kept moist with saline throughout the preparation and mechanical testing. The lateral and dorsal spinous processes were removed with a handheld grinding/cutting tool (Dremel, Mount Prospect, Ill.) and the cranial end of the vertebral body was mounted on an aluminum slab with a cyanoacrylate glue. The stub was mounted in the grips of a low speed saw (Isomet, Buehler Ltd., Lake Bluff, Ill.) and two plane-parallel section were cut at 4 mm intervals, effectively removing the growth plates and primary spongiosa from the ends of the vertebral body. The resultant cylinder of bone was measured with handheld digital calipers in the cranial/caudal, medial/lateral and dorsal/ventral directions. Specimens were placed on the loading platen and a compressive load was applied at 20 mm/minute in the cranial/caudal direction until failure of the vertebral body. Peak load and peak displacement were measured directly from the load cell and the crosshead, respectively. Stiffness was calculated from the slope of the linear region of the load/displacement curve. Energy absorption was calculated as the area under the load/displacement curve. As with the femur, the organ level properties described above were normalized to yield intrinsic of material properties of the lumbar spine using standard engineering equations.

F. Bone Histomorphometry

The lumbar vertebral bodies were trimmed, dehydrated and embedded in polymethyl methacrylate. The femur were trimmed into thirds (proximal, mid-shaft and distal). All were dehydrated in ethanol and the distal and mid-shaft were embedded in polymethyl methacrylate. The proximal portion of the femur was dried and stored. Section of the vertebral bodies and femur mid-shaft were cut with precision bone saws, the section mounted on plastic slides and the sections were ground to about 30-40 μm in thickness using a bone grinding system. The sections were polished and the fluoro-chrome makers were viewed in the unstained section. The section from the lumbar vertebral bodies were used for histomorphometric indices of cancellous bone, while the sections of the femur mid-shafts were used for histomorphometric indices of cortical bone.

Indices of cortical bone were measured at the mid-diaphyseal shaft of the femur. Measurements were made on a BioQuant Nova Prime image analysis system interface with a fluorescence microscope. All measurements were made using the calcein labels. These labels were given near the end of the study. The following measurements were made: cortical area, marrow area, periosteal and endocortical surface perimeter, periosteal and endocortical percent double labeled surface (% dLS), periosteal and endocortical percent single-labeled surface (% sLS), periosteal and endocortical percent mineralization surface (% MS), periosteal and endocortical new bone area, periosteal and endocortical mineral appositional rate (MAR), periosteal and endocortical bone formation rate, surface referent (BFRs), volume referent (BFRv) and endocortical eroded surface (% ES). Indices of cancellous bone structure were measured in the lumbar vertebral bodies. The measures were made in a central region that was bordered by the primary spongiosas at both ends. The indices of cancellous bone structure included: bone area, percent bone or trabecular bone volume (%), bone perimeter, bone surface/volume ration and trabecular thickness.

G. Pharmacokinetic Analysis

Pharmacokinetic analysis was performed as described in Example 13.

H. Data Analysis

Results were analyzed by analysis of transformed or ultratransformed data (Box et al., J Roy Statist Soc Series B 26: 211-252 (1964) and Box et al., Technometrics 16: 385-389 (1974). When necessary, transformations were performed to ensure that variances were homogeneous among groups, and that the residuals of the one-way analysis of variance model followed a Gaussian (normal) distribution. When the analysis of variance reached significance, data were further evaluated by the Fisher's LSD test. A P value less than 0.05 was considered as the minimum criterion to declare statistically significant differences.

i. Body and Organ Weights

Compound 102 significantly increased body weight, gastrocnemius weight and plantaris weight, indicating anabolic activity on skeletal muscle. At the dose tested, testosterone tended to increase body weight gain more than vehicle, but this increase did not achieve statistical significance. Compound 102 significantly increased weight gain from baseline compared to vehicle at all the doses tested. Ostarine significantly increased weight gain compared to vehicle at the mid and high dose levels, but at the low dose there was no significant difference from vehicle. At the maximally effective does for Compound 102 (0.3 mg/kg) and ostarine (0.3 mg/kg), the increased change in body weight was similar (mean change of +66 grams and +65 grams, respectively). The increase in body weight resulted from an increase in lean tissue mass rather than in increase in fat mass. Inguinal fat pad weight was used as a representative fat pad to assess the effects of drug on body fat. Inguinal fat pad weight was increased by ovariectomy (OVX+vehicle vs. Sham, $P<0.01$) and treatment with either estradiol or testosterone reduced the elevated fat pad weight due to ovariectomy. However, neither Compound 102 nor ostarine significantly affected inguinal fat pad weight at any dose. The weights of two skeletal muscles, gastrocnemius and plantaris, were measured to assess the effects of drugs on lean body mass. Compound 102 had equal or greater efficacy on muscle endpoints in comparison to testosterone or ostarine. At the maximally effective dose for each drug (0.3 mg/kg Compound 102 or ostarine), the gastrocnemius muscle mass was increased by 17% and 10% by Compound 102 and ostarine, respectively. At the dose administered in this experiment, testosterone tended to increase muscle weight, but the increase did not achieve statistical significance for either gastrocnemius or plantaris muscles.

Clitoral gland weight was measured to assess the effect of drugs on sebaceous glands. Testosterone significantly increased clitoral gland weight at the dose tested. Neither Compound 102 nor ostarine affected clitoral gland weight at the low dose tested. Both Compound 102 and ostarine increased clitoral gland weight at the high dose tested. At the mid dose (0.3 mg/kg), which was maximally effective for increasing body weight and skeletal muscle mass, Compound 102 and ostarine had similar activity which was only slightly above the sham level. The relatively small increase versus sham was statistically significant ($P<0.05$) for mid dose ostarine whereas Compound 102 did not quite achieve statistical significance versus sham at the mid dose ($P>0.05$).

Clitoral weight was measured to assess the virilizing effects of drugs. Testosterone had a large impact on clitoral weight in spite of its lack of activity on muscle. Compound 102 and ostarine did not affect clitoral weight at the low dose tested. Both Compound 102 and ostarine significantly increased clitoral weight at the high dose, but to a slightly lesser extent than testosterone ($P>0.05$ testosterone verus high dose Compound 102 or ostarine). At mid dose (0.3 mg/kg), which was maximally effective for increasing body weight and skeletal mass, Compound 102 had significantly less activity versus testosterone ($P<0.01$) whereas ostarine was not significantly different from testosterone ($P>0.05$).

Uterine weight measurements can be inaccurate in surgically ovariectomized rats due to the potential loss of uterine tissue at the tips of the uterine horns during removal of the ovaries. To minimize this variability uterine weight was normalized to uterine length. Both Compound 102 and ostarine increased uterine weight to length ratio above estrogen deficient OVX controls in a dose dependent manner. Uterine weight to length ratio was significantly ($P<0.01$) less than sham operated controls at both the low and mid dose of Compound 102. Uterine weight to length ratio was significantly ($P<0.01$) less than sham operated controls for low dose ostarine but not for mid dose ostarine ($P>0.05$). Compound 102 increased uterine weight to length ratio significantly less than ostarine ($P<0.01$) at both the low and mid dose. At the high dose (3 mg/kg) uterine weight to length ratio was significantly ($P<0.01$) increased above sham levels for Compound 102 and ostarine but the compounds were not significantly different from each other ($P>0.05$ high dose ostarine versus high dose Compound 102).

ii. Dual Energy X-Ray Absorptiometry

Compound 102 significantly increased bone mineral density (BMD) and bone mineral content (BMC) at the lumbar spine after 12 weeks of dosing. At the 0.3 mg/kg dose, Compound 102 was the most efficacious treatment in this experiment. Testosterone, in particular, did not significantly increase lumbar spine BMD or BMC. Estradiol increased spinal bone density but did not alter bone mineral content, which is consistent with a different mechanism of action. Ostarine had similar activity relative to Compound 102. Compound 102 also was effective at the femur, a site comprised of both cortical and cancellous bone. Compound 102 significantly increased femur BMD and BMC and was the most efficacious compound tested in this experiment. Ostarine had similar activity as Compound 102, while testosterone was less efficacious and did not significantly increase BMD or BMC above vehicle levels. Similar to the results at the lumbar spine, estradiol significantly increased femur BMD but not BMC.

iii. Biochemical Assays

Serum osteocalcin, a marker for bone turnover, was significantly suppressed by Compound 102 and ostarine in a dose-dependent manner. Estradiol and testosterone also suppressed osteocalcin below the levels of vehicle-treated OVX controls. Alkaline phosphatase activity from isolated tibiae was significantly increased by Compound 102 and ostarine treatment. In contrast, estradiol significantly suppressed tibial alkaline phosphatase activity. Testosterone tended to increase alkaline phosphatase activity, but the differences were not significantly significant.

iv. Biomechanical Testing

Compound 102 significantly increased whole femur bending strength and bending stiffness. Ostarine had similar activity, increasing femur bending strength slightly less effectively than Compound 102 but increasing bending stiffness slightly more effectively than Compound 102. The difference between Compound 102 and ostarine were not significantly significant at equivalent doses. Testosterone increased bending stiffness but did not significantly increase bending strength. Estradiol did not have a significant effect on biomechanical properties at the femur.

Compression testing of the lumbar spine revealed very minor differences among treatment groups. None of the treatments significantly increased peak stress or stiffness compared to vehicle controls. These findings are inconsistent with the DEXA and histomorphometry data. Previous experiments have consistently demonstrated a correlation between DEXA, histomorphometry and biomechanics. Furthermore, in multiple studies using this experimental paradigm, significant effect of estradiol on lumbar spine compressive strength and stiffness was observed. The lack of activity with estradiol in the present experiment is anomalous.

v. Histomorphometry

A greater proportion of bone formation was double-labeled with fluorochrome markers as opposed to single-labeled, indicating a more rapid deposition of new bone. Mineral apposition rates were similarly increased by Compound 102. The periosteal surface of the mid-femur is a site with negligible bone resorption rats of this age; hence the increase in bone formation indicates anabolic activity. Ostarine and testosterone displayed similar anabolic activity on the periosteal surface, although ostarine, but not testosterone, increased cortical bone area. This is consistent with the DEXA and biomechanical testing data. Estradiol, in contrast, suppressed bone formation rate and cortical bone cross sectional area. There was minimal effect of any compound on bone histomorphometry at the endosteal surface in this experiment. There was a tendency for decreased endosteal mineral apposition rate (MAR) and bone formation rate; however, there was insufficient double-labeled surface to provide quantitative data for statistical analysis. No statistical comparisons were made for these endpoints due to the absence of double-labeled surface throughout the experimental groups.

At a trabecular bone site (lumbar spine), Compound 102 significantly suppressed mineralizing surface and bone formation rates in a does-dependent manner. This decrease indicates a suppression of bone remodeling consistent with changes in serum osteocalcin. The net effect was an increase in trabecular bone volume with the 0.3 mg/kg dose of Compound 102. Ostarine and estradiol had similar activity on trabecular bone remodeling and bone volume. Testosterone had qualitatively similar effects, but the changes were small and only achieved statistical significance for the mineralizing surface measurement.

vi. Pharmacokinetic Parameters

The mean PK parameters for Compound 102 and the comparator compound ostarine are shown below in Table 2:

cortical bone sites and are inconsistent with a compound that predominately inhibits resorption, such as estradiol. Compound 102 suppressed cancellous bone turnover while increasing trabecular bone volume and increasing bone mineral density at the lumbar spine. In addition to the effects on bone, Compound 102 increased gastrocnemius muscle weight, plantaris muscle weight and body weight without affecting inguinal fat pad weight. Compound 102 demonstrated some tissue selectivity, as it was more efficacious on muscle and bone at the 0.3 mg/kg dose than testosterone, yet has reduced activity on the clitoral gland, clitoris or uterus relative to testosterone. The effects of Compound 102 on bone and muscle were similar to the comparator compound ostarine, although Compound 102 had increased potency, reaching maximal efficacy at an exposure substantially lower than that of ostarine. The data indicate that Compound 102 has beneficial effects in an animal model of osteoporosis.

Example 17—Pharmacokinetics of Compound 102 in Sprague Dawley Rats

The pharmacokinetics of Compound 102 following repeat oral administration for 15 days was evaluated in Sprague-Dawley rats. A total of 30 rats (15 males and 15 females) were divided into three dose groups (5 males/5 females). Compound 102 was suspended in a vehicle of 2% Tween 90: 0.5% carboxymethyl cellulose (high viscosity) (50:50, v/v) at concentrations of 0.25, 0.75 and 2.5 mg/mL and animals were dosed via oral gavage at 1, 3 and 10 mg/kg once daily for 15 days. Tap water and a diet of rodent chow were provided to the animals ad libitum.

Blood samples were collected on Day 1 and Day 15. Approximately 0.25 mL of blood was collected from each animal via jugular cannula on Day 1 and from tail vein on Day 15. Blood samples were taken 1, 2, 4, 8, 12 and 24 hr

TABLE 2

Pharmacokinetic Parameters at Day 14 (Mean ± SD of n = 4)

| Compound (mg/kg) | $AUC_6$ (µg · hr/ml ± SD) | $AUC_{24}$ * (µg · hr/ml ± SD) | $C_{MAX}$ (µg/ml ± SD) | $t_{MAX}$ (hr ± SD) |
|---|---|---|---|---|
| Compound 102 (0.03) | 0.056 ± 0.056 | 0.119 ± 0.090 | 0.039 ± 0.028 | 3.5 ± 1.9 |
| Compound 102 (0.3) | 0.051 ± 0.041 | 0.229 ± 0.289 | 0.040 ± 0.034 | 0.5 ± 0.4 |
| Compound 102 (3) | 0.404 ± 0.199 | 0.880 ± 0.326 | 0.207 ± 0.087 | 0.5 ± 0.0 |
| Ostarine (0.03) | 0.125 ± 0.022 | 0.552 ± 0.118 | 0.035 ± 0.007 | 2.6 ± 2.4 |
| Ostarine (0.3) | 1.083 ± 0.105 | 4.138 ± 0.448 | 0.332 ± 0.040 | 0.6 ± 0.2 |
| Ostarine (3) | 5.043 ± 1.301 | 20.644 ± 3.645 | 1.476 ± 0.429 | 1.1 ± 0.6 |

* The 0 hr plasma concentration was substituted for the 24 hr plasma concentration in order to estimate $AUC_{24}$.

The systemic exposure, as measured by $AUC_6$, $AUC_{24}$ and $C_{MAX}$, increased as the dose level increased. Ostarine showed significantly higher exposure that Compound 102. Overall, the peal plasma concentrations of each test article were observed between 0.5 hours and 3.5 hour postdose.

Conclusions

Compound 102 is a selective androgen receptor modulator that has beneficial effects on bone and muscle in a model of postmenopausal osteoporosis. Compound 102 significantly increased cortical bone mass, density, strength, stiffness and periosteal bone formation rates when orally administered to osteopenic female rats. These changes demonstrate that Compound 102 has anabolic activity at postdose. Each blood sample was collected into tubes containing lithium heparin and kept on wet ice pending centrifugation (max 2 hrs). Samples were centrifuged under refrigeration (2°-8° C. at 3000 g) for 10 minutes. Plasma was transferred into a pre-labeled tube (approximately 125 µL) placed on dry ice and stored frozen at −70° C. until analysis.

50 µL of plasma was extracted with 250 µL of acetonitrile and the plasma concentration of Compound 102 was determined by an LC-MS/MS method. The plasma concentration time data were analyzed by a non-compartmental pharmacokinetic method using WinNonlin. The results for pharmacokinetics (Mean±SD, n=5) is shown in Table 3 (Day 1) and Table 4 (Day 15).

TABLE 3

Pharmacokinetic Parameters on Day 1.

| Parameter | 1 mg/kg | | 3 mg/kg | | 10 mg/kg | |
|---|---|---|---|---|---|---|
| | Male | Female | Male | Female | Male | Female |
| $AUC_{24}$ (µg · hr/ml) | 0.104 ± 0.010 | 0.413 ± 0.042 | 0.318 ± 0.053 | 1.209 ± 0.391 | 1.288 ± 0.452 | 3.965 ± 0.334 |
| $AUC_{inf}$ (µg · hr/ml) | 1.109 ± 0.012 | 0.436 ± 0.036 | 0.341 ± 0.080 | 1.256 ± 0.406 | 1.301 ± 0.459 | 4.206 ± 0.384 |
| $C_{MAX}$ (µg/ml) | 0.014 ± 0.005 | 0.041 ± 0.006 | 0.051 ± 0.009 | 0.129 ± 0.054 | 0.176 ± 0.069 | 0.366 ± 0.052 |
| $t_{max}$ (hours) | 1.2 ± 0.4 | 1.4 ± 0.5 | 1.2 ± 0.4 | 2.6 ± 1.3 | 1.2 ± 0.4 | 1.4 ± 0.5 |
| $t^{1/2}$ (hours) | 5.2 ± 0.8 | 5.4 ± 1.2 | 4.6 ± 2.1 | 4.8 ± 0.7 | 3.5 ± 0.3 | 5.6 ± 0.7 |

TABLE 4

Pharmacokinetic Parameters on Day 15.

| Parameter | 1 mg/kg | | 3 mg/kg | | 10 mg/kg | |
|---|---|---|---|---|---|---|
| | Male | Female | Male | Female | Male | Female |
| $AUC_{24}$ (µg · hr/ml) | 0.288 ± 0.076[1] | 0.428 ± 0.179 | 0.876 ± 0.141 | 1.003 ± 0.464[2] | 2.623[3] | 4.285 ± 0.632[1] |
| $AUC_{inf}$ (µg · hr/ml) | 0.297 ± 0.082[1] | 0.443 ± 0.186 | 0.893 ± 0.148 | 1.156 ± 0.504[2] | 2.668[3] | 4.535 ± 0.504[1] |
| $C_{MAX}$ (µg/ml) | 0.052 ± 0.021[1] | 0.045 ± 0.015 | 0.133 ± 0.020 | 0.139 ± 0.035[2] | 0.345[3] | 0.389 ± 0.089[1] |
| $t_{max}$ (hours) | 1.3 ± 0.5[1] | 1.8 ± 1.3 | 1.2 ± 0.4 | 1.8 ± 0.5[2] | 1.5[3] | 2.0 ± 0.0[1] |
| $t^{1/2}$ (hours) | 4.6 ± 0.4[1] | 4.6 ± 0.2 | 4.1 ± 0.5 | 3.7 ± 0.8[2] | 3.9[3] | 5.4 ± 1.5[1] |

[1] n = 4: 1 animal death due to gavage error.
[2] n = 3: 2 animal deaths due to gavage error.
[3] n = 2: 3 animal deaths due to gavage error.

Compound 102 showed dose proportional increase of systemic exposure at 1, 3 and 10 mg/kg dose levels. Female rats showed higher systemic exposure than male rats on Day 1 and Day 15. The systemic exposure of Compound 102 did not decrease with repeat administration. The systemic exposure in male rats was higher on Day 15 than on Day 1, while that in female rats remained similar between the two days.

Conclusions

The repeat administration of Compound 102 at pharmacologic doses (1, 3 and 10 mg/kg) for 15 days resulted in dose proportional increase of systemic exposure and similar (females) or higher (males) systemic exposure compared to single dose administration. At equal doses, systemic exposure of Compound 102 was higher in females than males.

Example 18—Oral Toxicity and Toxicokinetic Study in Sprague Dawley Rats

A Sprague Dawley Rat model was used to study oral toxicity and toxicokinetics. Animals were assigned to groups by a stratified randomization scheme designed to achieve similar group mean body weights and the groups were randomly assigned to a dosing to provide control of bias. A total of 154 Sprague-Dawley rats were assigned to dose groups as shown in Table 5 below.

TABLE 5

Dose groups.

| Group | Test Material | No. of Males | No. of Females | Total per Group | Dose level (mg/kg/day) |
|---|---|---|---|---|---|
| Main Study Group | | | | | |
| 1 | Vehicle Control | 10 | 10 | 20 | 0 |
| 2 | Low | 10 | 10 | 20 | 10 |
| 3 | Low-Mid | 10 | 10 | 20 | 100 |
| 4 | High-Mid | 10 | 10 | 20 | 300 |
| 5 | High | 10 | 10 | 20 | 700 |
| Toxicokinetic Groups | | | | | |
| 6 | Vehicle Control | 3 | 3 | 6 | 0 |
| 7 | Low | 6 | 6 | 12 | 10 |
| 8 | Low-Mid | 6 | 6 | 12 | 100 |
| 9 | High-Mid | 6 | 6 | 12 | 300 |
| 10 | High | 6 | 6 | 12 | 700 |

All animals were dosed via oral gavage once daily for 14 days. The animals were evaluated for changes in clinical signs (mortality/morbidity observations, twice daily), cage side observations (general appearance and behavior), food consumption (quantitatively measured by weighing), body weights, clinical pathology indices including serum chemistry, hematology, coagulation and urinalysis, and other parameters. Blood samples were collected for toxicokinetics analysis from Groups 6-10 at various time points on Days 1 and 14 (Group 6 4 hours post dose; Groups 7-10 at 1, 4 and 12 hours or 2, 8 and 24 hours). The animals were fasted for at least 8 hours prior to blood collections for serum chemistry and urine collection. Serum chemistry parameters tested included alanine aminotransferase, total protein, aspartate aminotransferase, albumin, alkaline phosphatase, globulin, gamma-glutamyl-transferase, albumin/globulin ratio, lactate dehydrogenase, glucose, total bilirubin, cholesterol, urea nitrogen, triglycerides, creatinine, sodium, calcium, potassium, phosphorus and chloride. Hematology parameters analyzed included red blood cell count, reticulocyte count, hemoglobin concentration, red blood cell distribution width, mean corpuscular volume, mean platelet volume, mean corpuscular hemoglobin concentration, white blood cell count and differentials and mean corpuscular hemoglobin. Urinalysis parameters included color/character, ketones, specific gravity, bilirubin, pH, occult blood, protein, glucose and microscopics. Main study animals were euthanized on Day 15. At termination, a full necropsy was conducted and all tissues were collected, preserved, processes and examined microscopically from Groups 1 and 5, and target organs (liver and kidney) from Groups 2-4, by a veterinary pathologist certified by the American College of Veterinary Pathologists.

Control vehicle included Peg-400 (Sigma P-3265), Tween 80 (Sigma P-8074) and PVP-K30 (polyvinyl pyrrolidone or povidone K-30, Spectrum PN P1454) at a ratio of 90:5:5, w/w/w. Appropriate amounts of Compound 102 were added to the control vehicle to produce homogeneous dosing solutions/suspensions.

Results

Once daily, oral gavage administration of Compound 102 for 14 days to Sprague-Dawley rats at 10, 100, 300 or 700 mg/kg/day was not associated with test article-related morbidity or early death. There were only two 700 mg/kg/day female animals that died early on Days 3 and 9, but gross and microscopic findings indicate that each death was the result of esophageal perforation during dosing.

Clinical observation data indicated an increased incidence and frequency in rough hair coat and nasal discharge for animals dosed with Compound 102 (particularly for the female animals at ≥100 mg/kg/day). Male and female animals dosed with Compound 102 exhibited an increased weight gain compared to control animals, which was an anticipated pharmacological effect of this class of compounds.

Clinical pathology alterations attributed to administration of Compound 102 included minimal changes in alkaline phosphatase (ALP), phosphorus, triglycerides, potassium, reticulocyte counts, red cell distribution width, platelet counts and mean platelet volume at doses ≥10 mg/kg/day. A minimal prolongation in prothrombin time was also noted for male and female animals dosed with Compound 102 at 300 and 700 mg/kg/day. Because of the small magnitude of change, none of these alterations were considered to be adverse. There were no test article-related findings in the urinalysis data. There were no macroscopic or microscopic changes that were considered to be related to Compound 102. Dose-dependent liver weight increases were not correlated with appreciable increases in hepatocellular size or liver pathology.

On Day 1, systemic exposure of Compound 102 increased with increasing dose up to 300 mg/kg/day in both male and female rats. At 700 mg/kg/day, Compound 102 systemic exposure was not increased, indicating that absorption was saturated. There was a noticeable sex difference in Day 1 toxicokinetic samples, with higher systemic exposure in females across all dose levels. Repeat administration of Compound 102 decreased systemic exposure, and the decrease in systemic exposure was more pronounced in the high dose groups.

Serum Chemistry

In female rats dosed at ≥10 mg/kg/day alkaline phosphatase values and phosphorus concentrations were minimally higher. These changes were not accompanied by increases in bilirubin or GGT. Due to the alterations noted in phosphorus and ALP, it appears that Compound 102 may have an effect on bone; however, no histological changes were noted. Thus, while these changes are attributed to administration of Compound 102, they are not considered to be adverse, and may reflect the anabolic nature of Compound 102.

Triglyceride concentrations were minimally lower in male rats dosed at ≥100 mg/kg/day and in female rats dosed at ≥300 mg/kg/day (changes were statistically significant). Potassium levels were minimally higher in male rats dosed at ≥300 mg/kg/day and in female rats dosed at ≥100 mg/kg/day. These minimal changes in potassium and triglycerides were not considered to be adverse. Intergroup differences in other serum chemistry parameters were sporadic or of a magnitude of change commonly observed in laboratory rats undergoing similar study procedures and were not considered to the test article-related.

Hematology

Female rats dosed with ≥10 mg/kg/day Compound 102 had higher reticulocyte counts and red cell distribution width. These changes were not accompanied by decreased indicators of circulating erythrocyte mass (i.e., red blood cells, hemoglobin or hematocrit) nor were the changes noted in male animals. Platelet counts also were increased with statistical significance for female animals dosed at ≥100 mg/kg/day and for males dosed at 10 mg/kg/day and 700 mg/kg/day. Increases in mean platelet count also were noted for the female animals (statistically significant for Groups 3 and 5). The test article increases in reticulocyte counts, RDW, platelets and MPV were minimal and not considered to be adverse. Intergroup differences in the hematology chemistry parameters were sporadic or of a magnitude of change commonly observed in laboratory rats undergoing similar study procedures and were not considered to the test article-related.

Coagulation

A minimal prolongation in prothrombin time was noted for male and female animals dosed with Compound 102 at 300 and 700 mg/kg/day. The magnitude of this change was not considered to be adverse.

Urinalysis

There were no alterations in the urinalysis parameters that were attributed to administration of Compound 102.

Postmortem Observations

There were no macroscopic or microscopic changes that were considered related to Compound 102. Dose-dependent liver weight increases were not correlated with appreciable increases in hepatocellular size and the liver pathology was negligible. There were, compared to concurrent controls, several statistically significant increases in group mean absolute organ weights. Those absolute organ weights with dose-dependent increases were limited to the liver of both sexes. The group mean body weights were increased compared to the controls at every dose level. Despite the increased body weights, liver to body weight ratios were increased in a doe-dependent manner for males and females at 100 mg/kg/day and above (statistically significant at 300 and 700 mg/kg/day). Liver to brain weight ratios also were increased in a dose dependent manner.

Conclusions

Once daily oral gavage administration of Compound 102 for 14 days to Sprague-Dawley rats at 10, 100, 200 or 700 mg/kg/day was not associated with test article-related moribundity or early death. A statistically significant increase in food consumption was noted for female animals dosed with Compound 102 (all dose levels), which correlates with an increased weight gain in these animals. No such change was noted for male animals. A dose independent test article-related increase in body weight occurred for male and female animals (of statistical significance between Days 8 and 14). The mean body weight gain in the high dose group appeared less than that noted in the lower dose groups for male and female animals. There were no macroscopic or microscopic changes that were considered to be related to Compound 102. Dose-dependent liver weight increases were not correlated with appreciable increases in hepatocellular size or liver pathology.

Test article-related clinical signs included increased observations of rough hair coat and nasal discharge for animals dosed at ≥100 mg/kg/day. Increases in body weight also were observed for male and female animals dosed with Compound 102. Non-adverse clinical pathology alterations related to administration of ≥10 mg/kg/day Compound 102 were noted for alkaline phosphatase, phosphorus, triglyceride, potassium, reticulocyte counts, red cell distribution width, platelet counts, mean platelet volume and prothrombin time.

On Day 1, systemic exposure of Compound 102 increased with increasing dose up to 300 mg/kg/day in both male and female rats. At 700 mg/kg/day, Compound 102 showed a saturated absorption without further increase of systemic exposure. There was a noticeable sex difference in Day 1 toxicokinetic sample, with higher systemic exposure in females across all dose levels. Repeat administration of Compound 102 decreased systemic exposure, and the decrease in systemic exposure was more pronounced in the high dose groups.

Based on the overall findings, and as the clinical observations of rough hair coat and nasal discharge (indications of stress) noted for animals dosed at ≥100 mg/kg/day were not associated with additional clinical findings, the No-observed-adverse-effect level (NOAEL) for this study was considered to be 700 mg/kg/day.

Example 19—14-Day Oral Toxicity and Toxicokinetic Study in Cynomolgus Monkeys

A study was performed to determine any potential toxicity and the toxicokinetic profile of Compound 102 when administered orally (via nasal gavage) to cynomolgus monkeys for at least 14 days. The cynomolgus monkey was chosen for this study as it is a non-rodent species that is commonly used for non-clinical toxicity evaluations. Use of the monkey model maximized the likelihood of identifying toxicological responses that may occur in humans. Ten experimentally naïve cynomolgus monkeys (5 male and 5 female) from about 2.5 to 3 years of age and weighing between about 2.3 to about 2.8 kg at Day −1 of the study were assigned to dose groups as shown in Table 6 below.

TABLE 6

| Group No. | No. of Males/ Females | Dose Level (mg/kg) | Dose Volume (mL/kg) | Dose Solution Conc. (mg/ml) | No. Necropsied on Day 15 |
| --- | --- | --- | --- | --- | --- |
| 1 | 1/1 | 0 (control) | 2 | 0 | 1/1 |
| 2 | 1/1 | 5 | 2 | 2.5 | 1/1 |
| 3 | 1/1 | 50 | 2 | 25 | 1/1 |

TABLE 6-continued

| Group No. | No. of Males/ Females | Dose Level (mg/kg) | Dose Volume (mL/kg) | Dose Solution Conc. (mg/ml) | No. Necropsied on Day 15 |
| --- | --- | --- | --- | --- | --- |
| 4 | 1/1 | 150 | 2 | 75 | 1/1 |
| 5 | 1/1 | 450 | 2 | 225 | 1/1 |

All animals were dosed via nasal gavage once daily for 14 consecutive days. The first day of dosing was designated Day 1 for all animals. The animals were evaluated for clinical signs (evaluation of mortality and morbidity, twice daily), cage side observations and food consumption (once daily), body weight (Days 1, 8 and 14), physical examination (Day −5 and post dosing following the 13/24 hour toxicokinetic collection on Day 14), ophthalmic examination (prestudy and owing the Day 13/24 hour toxicokinetic collection on Day 14), and clinical pathology parameters (serum chemistry, hematology and coagulation on Days −3 and 14), urine samples were collected during necropsy (Day 15) for urinalysis. Blood samples were collected for toxicokinetic analysis at 1, 2, 4, 8, 12 and 24 hours post dose on Days 1 and 13.

All ten animals were euthanized one day after the last dose. At termination, a full necropsy was conducted on all animals, and tissues were collected, preserved, processed and examined microscopically by an American College of Veterinary Pathologists (ACVP) certified pathologist.

Vehicle was composed of PEG 400/Tween® 80/PVP-K30 (90/5/5, w/w/w). Appropriate amounts of Compound 102 were added to vehicle to prepare the suspension of test compound administered to the animals.

Blood samples for evaluation of serum chemistry, hematology and coagulation parameters were collected from all animals on Days −3 and 14. Urine samples were obtained by bladder puncture during necropsy. The animals were fasted for at east 8 hours prior to blood collections for serum chemistry. Serum chemistry parameters included alanine aminotransferase (ALT), total protein, aspartate aminotransferase (AST), alkaline phosphatase (ALP), gamma-glutamyltransferase (GGT), albumin, globulin, albumin/globulin ratio, lactate dehydrogenase (LD), glucose, total bilirubin, cholesterol, urea nitrogen (BUN), creatinine, triglycerides, sodium, calcium, potassium, phosphorus, chloride and carbon dioxide. Hematology parameters included red blood cell count, hemoglobin concentration, hematocrit, mean corpuscular volume (MCV), mean corpuscular hemoglobin concentration (MCHC), mean corpuscular hemoglobin (MCH), red cell distribution width, reticulocyte count, platelet count, mean platelet volume (MPV) and white blood cell count. Coagulation parameters included prothrombin time (PT) and activated partial thromboplastin time. Urinalysis parameters included color/character, specific gravity, pH, protein, glucose, ketones, bilirubin, occult blood and microscopics.

Results

All animals survived until scheduled necropsy. There were no Compound 102-related clinical signs or effects on food consumption. Watery feces was observed frequently for all study animals beginning on Day 1. The watery feces were attributed to the PEG400 component of the vehicle, which is known to produce gastrointestinal disturbances, including diarrhea, following ingestion.

There was a dose-independent increase in body weight in all of the Compound 102-dosed animals relative to controls. The magnitude of the increases to individual animal body weight during the study was considered notable and consistent with the expected pharmacological activity of the class of compound (i.e., SARMs are known to be androgenic and increase bone and muscle mass; see Shalender et al., Nature Clinical Practice Endocrinology & Metabolism 2: 146-159 (2006)). There were no Compound 102-related findings identified during ophthalmic examinations.

Serum Chemistry

Serum cholesterol concentration was decreased on Day 14 in all animals receiving Compound 102. The reductions in cholesterol did not appear to be adverse. Ater 14 days of dosing, the female animal dosed with 450 mg/kg had elevated serum alanine aminotransferase (ALT) and aspartate aminotransferase (AST) activity, without increased lactate dehydrogenase (LD). This animal also had barely noticeable minimal single cell hepatocellular necrosis in the liver. Taken together, these changes affecting a high-dose animal suggested a possible relationship with the test article. Other changes in serum chemistry parameters including small increases in gamma-glutamyltransferase on Day 14 in several animals in dosed groups were attributed to biological variability commonly observed in laboratory-housed cynomolgus monkeys undergoing similar study procedures.

Hematology

There was a dose-independent decrease in platelet count at all Compound 102 dose levels. On Day 14, platelet counts were lower (approximately 14% to 38%) relative to Day −3 in both male and female animals in the 5, 50 and 150 mg/kg-dosed groups and the female high-dose animal (450 mg/kg). Platelet count on Day 14 was marginally increased for the high-dose and control males and reduced approximately 5% for the control female relative to Day −3. Although the platelet counts were lower for 7 of 8 Compound 102-dosed animals on Day 14 (relative to Day −3) and to the control animals, the clinical significance of this finding was not considered adverse.

The indicators of circulating erythrocyte mass were mildly reduced on Day 14 (relative to Day −3) in all 5 groups, due to toxicokinetic blood sample collection on Day 13. Red cell distribution width and reticulocyte counts were mildly increased on Day 14 (relative to Day −3) in all 5 groups; these changes reflect regenerative erythropoiesis resulting from blood collections on Day −3 (for clinical pathology) and Day 1 (for toxicokinetics). Fluctuations in total leukocyte (WBC), neutrophil, lymphocyte and monocyte counts which were most consistent in both Group 4 animals were dose-independent and likely incidental.

Coagulation

On Day 14, all animals in Compound 102-dosed groups, except for the 5 mg/kg-dosed female, had minimally prolonged (1.8 to 3.5 seconds longer than Day −3) prothrombin time (PT); PT in the control animals was similar to Day −3. The changes did not exhibit a dose response and were not considered adverse.

Urinalysis

There were no Compound 102-related effects on urinalysis parameters.

Macroscopic Observations

Gross necropsy findings suggestive of a relationship to Compound 102 administration were limited to decreased thymus size and brown discoloration of the adrenals in both sexes at 150 and 450 mg/kg. Decreased thymus size correlated microscopically with minimal to mild lymphoid depletion on the thymic cortex. There was no microscopic correlate to the brown adrenal discoloration.

Histopathology

There were no direct Compound 102-related microscopic findings. Minimal to mild lymphoid cortical depletion of the thymus was present in males at 150 mg/kg and above and at 50 mg/kg and above in females. This observation, however, was considered secondary to stress and not a direct toxicologic effect. Most microscopic findings were randomly distributed in control and dosed animals or were considered common incidental findings in cynomolgus monkeys and not believed to be related to Compound 102 dosing.

Conclusions

Daily administration of 5, 50, 150 and 50 mg/kg Compound 102 for 14 days did not result in mortality, adverse clinical signs or changes in food consumption or histologic effects. There were no abnormal findings identified during physical or ophthalmic examinations, or from urinalysis.

Compound 102-related effects were identified at the 5, 50, 150 and 450 m/kg dose levels in both sexes, including increased body weight (consistent with the expected pharmacological activity of this class of compounds), decreased serum cholesterol concentration and platelet count, and prolonged prothrombin time. These changes were generally dose-independent and considered non-adverse.

Macroscopic (gross necropsy) observations possibly related to Compound 102 were limited to brown discoloration of the adrenals and decreased thymus size at 150 and 450 mg/kg in both sexes. There was no apparent microscopic correlate to the brown adrenals. Minimal to mild lymphoid cortical depletion of the thymus in males at 150 mg/kg and above and in females at 50 mg/kg and above and decreased thymus size were considered secondary to stress and not a direct toxicologic effect.

The systemic exposure of Compound 102 increased with increasing dose up to 450 mg/kg in both sexes. Following repeat administration of Compound 102 the systemic exposure was decreased on Day 13 (relative to Day 1 exposure), and the decrease in systemic exposure was more pronounced in the high-dose groups. There was no noticeable sex difference in the Day 1 and Day 13 toxicokinetic parameters.

Under the conditions of this study, the NOAEL was 450 mg/kg for the males and 150 mg/kg for the females (based on findings that in the 450 mg/kg-dosed female ALT and AST were elevated and there were histologic changes to the liver). A NOEL was not achieved as a result of increased body weight, decreased serum cholesterol concentration and platelet count, and prolonged prothrombin time present in all Compound 102-dosed groups.

Since modifications will be apparent to those of skill in this art, it is intended that this invention be limited only by the scope of the appended claims.

The invention claimed is:

1. A method of promoting tissue formation or growth, or a combination thereof, in a subject comprising:
   administering to the subject a therapeutically effective amount of a compound of formula

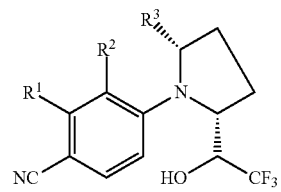

R¹ is CF₃, F or Cl;
R² is H or methyl; and
R³ is H or methyl,
or a pharmaceutically acceptable salt or ester thereof,
thereby promoting tissue formation or growth, or a combination thereof, in the subject.

2. The method of claim 1, wherein the tissue is muscle tissue.

3. The method of claim 2, wherein the compound of formula I is R,R-4-(2-(1-Hydroxyl-2,2,2-trifluoroethyl)-pyrrolidinyl)-2-trifluoromethyl-benzonitrile, or a pharmaceutically acceptable salt thereof.

4. The method of claim 3, wherein the subject does not suffer an adverse androgenic effect.

5. The method of claim 4, wherein R¹ is CF₃, R² is H and R³ is H.

6. The method of claim 1, wherein R¹ is CF₃, R² is H and R³ is methyl.

7. The method of claim 1, wherein R¹ is CF₃, R² is methyl and R³ is hydrogen.

8. The method of claim 1, wherein R¹ is F or Cl, R² is H and R³ is H.

9. The method of claim 1, wherein R¹ is F or Cl, R² is H and R³ is methyl.

10. The method of claim 1, wherein R¹ is F or Cl, R² is methyl and R³ is hydrogen.

11. The method of claim 4, wherein the compound of formula I is selected from among:
R,R-4-(2-(1-Hydroxyl-2,2,2-trifluoroethyl)pyrrolidinyl)-2-trifluoromethyl-benzonitrile;
4-(2(R)-(1(S)-hydroxyl-2,2,2-trifluoroethyl)pyrrolidinyl)-2-trifluoromethyl-benzonitrile;
R,R,R-4-(2-(1-Hydroxyl-2,2,2-trifluoroethyl)-5-methyl-pyrrolidinyl)-2-trifluoromethyl-benzonitrile;
4-(2(R)-(1(S)-hydroxyl-2,2,2-trifluoroethyl)-5(R)-methylpyrrolidinyl)-2-trifluoromethyl-benzonitrile;
R,R-4-(2-(1-Hydroxyl-2,2,2-trifluoroethyl)pyrrolidinyl)-2-chlorobenzonitrile;
4-(2(R)-(1(S)-hydroxyl-2,2,2-trifluoroethyl)pyrrolidinyl)-2-chlorobenzonitrile;
R,R,R-4-(2-(1-hydroxyl-2,2,2-trifluoroethyl)-5-methyl-pyrrolidinyl)-2-chlorobenzonitrile;
4-(2(R)-(1(S)-hydroxyl-2,2,2-trifluoroethyl)-5(R)-methylpyrrolidinyl)-2-chlorobenzonitrile;
R,R-4-(2-(1-hydroxyl-2,2,2-trifluoroethyl)pyrrolidinyl)-2-chloro-3-methylbenzonitrile;
4-(2(R)-(1(S)-hydroxyl-2,2,2-trifluoroethyl)-pyrrolidinyl)-2-chloro-3-methylbenzonitrile;
3-methyl-4-((R)-2-((R)-2,2,2-trifluoro-1-hydroxyethyl)pyrrolidin-1-yl)-2-(trifluoromethyl)-benzonitrile;
3-methyl-4-((R)-2-((S)-2,2,2-trifluoro-1-hydroxyethyl)pyrrolidin-1-yl)-2-(trifluoromethyl)-benzonitrile;
3-methyl-4-((2R,5R)-2-methyl-5-((S)-2,2,2-trifluoro-1-hydroxyethyl)-pyrrolidin-1-yl)-2-(trifluoromethyl)benzonitrile;
2-fluoro-4-((2R,5R)-2-methyl-5-((S)-2,2,2-trifluoro-1-hydroxyethyl)-pyrrolidin-1-yl)-benzonitrile;
2-fluoro-3-methyl-4-((2R,5R)-2-methyl-5-((S)-2,2,2-trifluoro-1-hydroxyethyl)-pyrrolidin-1-yl)benzonitrile;
2-fluoro-3-methyl-4-((R)-2-((S)-2,2,2-trifluoro-1-hydroxyethyl)pyrrolidin-1-yl)-benzonitrile;
2-fluoro-4-((R)-2-((S)-2,2,2-trifluoro-1-hydroxyethyl)pyrrolidin-1-yl)benzonitrile;
2-chloro-4-((2R,5R)-2-methyl-5-((S)-2,2,2-trifluoro-1-hydroxyethyl)-pyrrolidin-1-yl)-benzonitrile;
2-chloro-3-methyl-4-((2R,5R)-2-methyl-5-((S)-2,2,2-trifluoro-1-hydroxyethyl)-pyrrolidin-1-yl)benzonitrile;
2-chloro-3-methyl-4-((R)-2-((S)-2,2,2-trifluoro-1-hydroxyethyl)pyrrolidin-1-yl)-benzonitrile; and
2-chloro-4-((R)-2-((S)-2,2,2-trifluoro-1-hydroxyethyl)pyrrolidin-1-yl)-benzonitrile;
or a pharmaceutically acceptable salt thereof.

12. The method of claim 1, wherein the compound of formula I is R,R-4-(2-(1-Hydroxyl-2,2,2-trifluoroethyl)-pyrrolidinyl)-2-trifluoromethyl-benzonitrile, or a pharmaceutically acceptable salt thereof.

13. The method of claim 1, wherein the subject does not suffer an adverse androgenic effect.

* * * * *